Figure 14A:
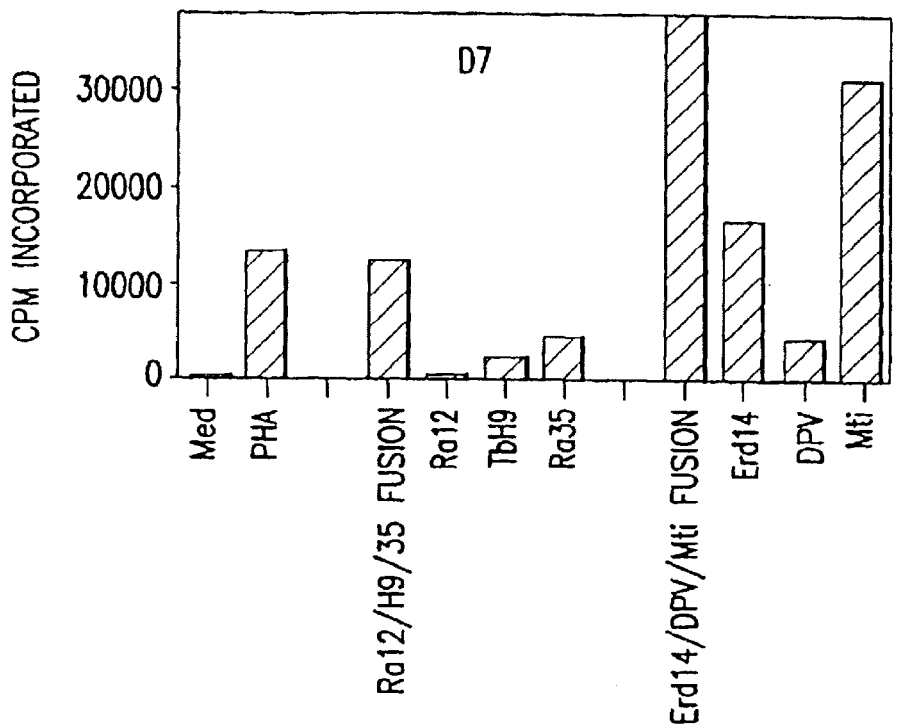

(12) United States Patent
Reed et al.

(10) Patent No.: US 6,977,069 B2
(45) Date of Patent: Dec. 20, 2005

(54) **FUSION PROTEINS OF *MYCOBACTERIUM TUBERCULOSIS* ANTIGENS AND THEIR USES**

(75) In

```
TCTAGAAATAATTTTGTTTACTTTAAGAANGANATATACATATGCATCACCATCACCATCACACGGCCCGCGTCCGATAACTTCCACCTGTCCCAGCGTGG
                                        M H H H H H H T A A S D N F Q L S Q G G
                                                      ├──Tb Ra12──
                                                                                                         100

GCAGCGATTCGCCCATTCCGATCGGGCAGCGGATGGCCGATCGCGGGCCAGATCCGATCGGGTGGGGGGTCACCCACCGTTCATATCGGCCCTACCCCCTTC
 Q G F A I P I G Q A M A I A G Q I R S G G G S P T V H I G P T A F
                                                Tb Ra12
                                                                                                         200

CTCGGCTTGGGTGTTGTCGACAACAACGGCAACGGCGCCACGAGTCCAACGCGTGGTCGGGAGCGCTCCGGCGGCAAGTCTCGGCATCTCCACCGGCGACG
 L G L G V V D N N G N G A R V Q R V V G S A P A A S L G I S T G D
                                                Tb Ra12
                                                                                                         300

TGATCACCGCCGGTCGACGGCGCCTCCGATCAACTCGGCCACCGGCGATGGCCGACGCGCCTTAACGGGCATCATCCCCGTGACGTCATCTCGGTGACCTGGCA
 V I T A V D G A P I N S A T A M A D A L N G H H P G D V I S V T W Q
                                                Tb Ra12
                                                                                                         400

AACCAAGTCGGCGGCCACCCCTACAGGGAACGTGACATTGGCCGAGGGACCCCCGGCCGAATTCATGGTGGATTTCGGGGCGTTACCACCGGAGATCAAC
 T K S G G T R T G N V T L A E G P P A E F M V D F G A L P P E I N
                    Tb Ra12                    ┤├         Tb H9
                                                                                                         500

TCCGCGAGGATGTACGCCGGCCCCGGGTTCGGCCTCGCTGGTGGCCGCGGGCTCAGATGTCGGACAGCGTGGCGACTGACCTGTTTTCGGCCGCGTCGGCGT
 S A R M Y A G P G S A S L V A A A C M W D S V A S D L F S A A S A
                            Tb H9
                                                                                                         600

TTCAGTCGGTGGTCTGGGGTCTCACGGTGCGGTCGTGGATAGGTTCGTCGGCCGGGTCTGATGGTGCCGGCGGCCTCCCCGTATGTGGCCTGGATGAGCGT
 F Q S V V W G L T V G S W I G S S A G L M V A A A S P Y V A W M S V
                              Tb H9
                                                                                                         700

CACCGCCGGGCAGGCCGAGCCTGACCCCCCCCCAGGTCCCGGTTGCTGCGGCGGCCCTACGACACGGCGTATGGGCTGACGGTGCCCCCGCCGGTGATCCCC
 T A G Q A E L T A A Q V R V A A A A Y E T A Y G L T V P P P V I A
                              Tb H9
                                                                                                         800

GAGAACCGTGCTGAACTGATGATTCTGATAGCGACCAACCTCTTGGGGCAAAACACCCCCGCGATCGCGGTCAACGAGCCCCAATACGGCCAGATGTGGG
 E N R A E L M I L I A T N L L G Q N T P A I A V N E A E Y G E M W
                              Tb H9
                                                                                                         900
```

FIG.1A

```
CCCAAGACGCCGCCGCGATGTTTGGCTACGCCGCGGCGACGGCGACGGCGACGGCGACGTTCCTGCCGTTCGAGGAGGCCCCGGAGATGACCAGCGCGGG
 A  Q  D  A  A  A  M  F  G  Y  A  A  A  T  A  T  A  T  L  L  P  F  E  E  A  P  E  M  T  S  A  G
                                          ── Tb H9 ──
```
1000

```
TGGGCTCCTCGAGCAGGCCCCCGCCGTCGAGGAGGCCTCCGACACCGCCCCGGCGAACCACTTGATGAACAATGTGCCCCAGGCGCTGCAACAGCTGGCC
 G  L  L  E  Q  A  A  A  V  E  E  A  S  D  T  A  A  A  N  Q  L  M  N  N  V  P  Q  A  L  Q  Q  L  A
                                          ── Tb H9 ──
```
1100

```
CAGCCCACCCAGGGCACCACGCCTTCTTCCAAGCTGGGCTGGCCTGTGGAAGACCGTCTCGCCCGCATCCGTCGCCCGATCAGCAACATGGTGTCGATGGCCA
 Q  P  T  Q  G  T  T  P  S  S  K  L  G  G  L  W  K  T  V  S  P  H  R  S  P  I  S  N  M  V  S  M  A
                                          ── Tb H9 ──
```
1200

```
ACAACCACATGTCGATGACCAACTCCGGTGTGTCCATGACCAACACCTTGAGCTCGATGTTGAAGGGCTTTGCTCCGGCGGCGGCCGCCCAGGCCGTGCA
 N  N  H  M  S  M  T  N  S  G  V  S  M  T  N  T  L  S  S  M  L  K  G  F  A  P  A  A  A  A  Q  A  V  Q
                                          ── Tb H9 ──
```
1300

```
AACCCCGGCGCAAAACGGGGTCCGGGCCGATGAGCTCGCTGGGCCAGCTCCCTGGGTTCTTCGGGTCTGGCGGTGGGGTGGCCGGCCAACTTGGGTCGGGCG
 T  A  A  Q  N  G  V  R  A  M  S  S  L  G  S  S  L  G  S  S  G  L  G  G  G  V  A  A  N  L  G  R  A
                                          ── Tb H9 ──
```
1400

```
GCCTCGGTCGGTTCGTTGTCGGTGCCGCAGCCCTGGGCCGCGCCCCAACCAGCCAGTGACCCCGGCGGCCCCGGGCGCTGCCGCTCGACCAGCCTGACCAGCG
 A  S  V  G  S  L  S  V  P  Q  A  W  A  A  A  N  Q  A  V  T  P  A  A  R  A  L  P  L  T  S  L  T  S
                                          ── Tb H9 ──
```
1500

```
CCGCGGAAAGAGGGCCCCGGCAGATGCTGGGCGGGCTGCCGGTGGGGCAGATGGGCGCCAGGGCCGGTGGTGGCCTCAGTGGTGTGCTGCGCGTTCCGCC
 A  A  E  R  G  P  G  Q  M  L  G  G  L  P  V  G  Q  M  G  A  R  A  G  G  G  L  S  G  V  L  R  V  P  P
                                          ── Tb H9 ──
```
1600

```
GCGACCCTATGTGATGCCGCATTCTCCGGCAGCCGGCCATATCGCCCCGCCCGGCCTTGTCGCAGGACCCGTTCGCCGACTTCCCCGCGCCTGCCCCTCGAC
 R  P  Y  V  M  P  H  S  P  A  A  G  D  I  A  P  P  A  L  S  Q  D  R  F  A  D  F  P  A  L  P  L  D
 ── Tb H9 ──────┤    ├────── Tb Ra35 ──────
```
1700

FIG.1B

```
CCGTCCGCGATGGTCGCCCAAGTGGGGCCACACGTGGTCAACATCAACACCAAACTGGGCTACAACAACGCCGTGGGCGCCGGGACCGGCATCGTCATCG
 P  S  A  M  V  A  Q  V  C  P  Q  V  V  N  I  N  T  K  L  G  Y  N  N  A  V  G  A  G  T  G  I  V  I
                                         Tb Ra35                                                          1800

ATCCCAACCGTGTCGTGCTGACCAACAACCACGTGATCGCGGCGCCCACCGACATCAATGCGTTCAGCGTCGGCTCCGGCCAAACCTACGGCGTCGATGT
 D  P  N  G  V  V  L  T  N  N  H  V  I  A  G  A  T  D  I  N  A  F  S  V  G  S  G  Q  T  Y  G  V  D  V
                                         Tb Ra35                                                          1900

GGTCGGCTATGACCGCACCCAGGATGTCGCCGTGCTGCAGCTCCGCGGTGCCGGTGGCCTACCATCGGCGGCGATCGGTGGCGGCGTCGCCGTTGGTGAG
 V  G  Y  D  R  T  Q  D  V  A  V  L  Q  L  R  G  A  G  G  L  P  S  A  A  I  G  G  G  V  A  V  G  E
                                         Tb Ra35                                                          2000

CCCTTCGTCGCCGATGGGCAACAGCGGTGGGCAGGCCGGAACGCCCCGTGCGGTGCCTGGCAGGCTGGTCCGCCTCCGCCCAAACCGTGCAGGCCTCCGATT
 P  F  V  A  M  G  N  S  G  G  Q  G  G  T  P  R  A  V  P  G  R  V  V  A  L  G  Q  T  V  Q  A  S  D
                                         Tb Ra35                                                          2100

CGCTGACCGGTGCCCAAGAGACATTGAACGGGTTGATCCAGTTCGATGCCGCGATCCAGCCCGGTGATTCGGGCGGGGCCGTCGTCAACGGCCTAGGACA
 S  L  T  G  A  E  E  T  L  N  G  L  I  Q  F  D  A  A  I  Q  P  G  D  S  G  G  P  V  V  N  G  L  G  Q
                                         Tb Ra35                                                          2200

GGTGGTCGGTATGAACACGGCCGCGTCCTAGGATATCCATCACACTGGCGGCCCGCTCGAGCAGATCCGGNTGTAACAAAGCCCGAAA
 V  V  G  M  N  T  A  A  S
 ─────── Tb Ra35 ──────▶                                                                                  2267
```

FIG.1C

```
CATATACATATCCATCACCATCACCATCACATGGCCACCACCCTTCCCGTTCAGCGCCACCCGCGGTCCCTCTTCCCCGAGTTTTCTGAGCTGTTCGCCG
|――――|――――|――――|――――|――――|――――|――――|――――|――――|――――| 100
    M  H  H  H  H  H  H  M  A  T  T  L  P  V  Q  R  H  P  R  S  L  F  P  E  F  S  E  L  F  A
        |―――――――――――――――――――――――― ERD 14 ――――――――――――――――――――――

CCTTCCCGTCATTCGCCGGACTCCGGCCCACCTTCGACACCCGGTTGATCCGGCTGGAAGACCGAGATGAAAGAGGGGCGCTACCGAGGTACGCGCCGGAGCT
|――――|――――|――――|――――|――――|――――|――――|――――|――――|――――| 200
 A  F  P  S  F  A  G  L  R  P  T  F  D  T  R  L  M  R  L  E  D  E  M  K  E  G  R  Y  E  V  R  A  E  L
――――――――――――――――――――――――――――――――― ERD 14 ―――――――――――――――――――――――――――――

TCCCGGGGTCGACCCCGACAAGGACGTCGACATTATGGTCCGCGATGGTCAGCTGACCATCAAGGCCGAGCGCACCGAGCAGAAGGACTTCGACGGTCGC
|――――|――――|――――|――――|――――|――――|――――|――――|――――|――――| 300
 P  G  V  D  P  D  K  D  V  D  I  M  V  R  D  G  Q  L  T  I  K  A  E  R  T  E  Q  K  D  F  D  G  R
――――――――――――――――――――――――――――――― ERD 14 ―――――――――――――――――――――――――――――

TCGGAATTCGCGTACCGTTCCTTCGTTCGCACCGTGTCGCTGCCGGTAGGTGCTGACGAGGACGACATTAAGGCCACCTACGACAAGGGCATTCTTACTG
|――――|――――|――――|――――|――――|――――|――――|――――|――――|――――| 400
 S  E  F  A  Y  G  S  F  V  R  T  V  S  L  P  V  G  A  D  E  D  D  I  K  A  T  Y  D  K  G  I  L  T
――――――――――――――――――――――――――――――― ERD 14 ―――――――――――――――――――――――

TGTCGGTGGCGGTTTCGGAAGGGAAGCCAACCGAAAAGCACATTCAGATCCCGTCCACCAACAAGCTTGATCCCGTGGACGCCGGTCATTAACACCACCTG
|――――|――――|――――|――――|――――|――――|――――|――――|――――|――――| 500
 V  S  V  A  V  S  E  G  K  P  T  E  K  H  I  Q  I  R  S  T  N  K  L  D  P  V  D  A  V  I  N  T  T  C
――――――――――――――― ERD 14 ―――――――――――――― [HindIII] ―――――――― DPV ――

CAATTACGGCCAGGTAGTAGCTGCGCTCAACGCGACGGATCCCGGGGCCTGCCGCACAGTTCAACGCCTCACCGGTGGCGCAGTCCTATTTGCGCAATTTC
|――――|――――|――――|――――|――――|――――|――――|――――|――――|――――| 600
 N  Y  G  Q  V  V  A  A  L  N  A  T  D  P  G  A  A  A  Q  F  N  A  S  P  V  A  Q  S  Y  L  R  N  F
―――――――――――――――――――――――――――― DPV ――――――――――――――――――――――――――

CTCGCCGCCACCGCCACCTCAGCGCCCTGCCATGGCCGCGGCAATTGCAAGCTGTGCCGGGCCGCCCACAGTACATCGGCCTTGTCGAGTCGGTTGCCGGCT
|――――|――――|――――|――――|――――|――――|――――|――――|――――|――――| 700
 L  A  A  P  P  P  Q  R  A  A  M  A  A  Q  L  Q  A  V  P  G  A  A  Q  Y  I  G  L  V  E  S  V  A  G
――――――――――――――――――――――――――― DPV ―――――――――――――――――――――――

CCTGCAACAACTATGAGCTCATGACGATTAATTACCAGTTCGGCGACGTCGACGCTCATGGCGCCATGATCCGCGCTCAGGCGGCGTCGCTTGAGGCCGA
|――――|――――|――――|――――|――――|――――|――――|――――|――――|――――| 800
 S  C  N  N  Y  E  L  M  T  I  N  Y  Q  F  G  D  V  D  A  H  G  A  M  I  R  A  Q  A  A  S  L  E  A  E
―― DPV ―― [Sac I] ―――――――――――――――――――――― MTI ―――――――――――
```

FIG.2A

```
GCATCAGGCCATCGTTCGTGATGTGTTGGCCGGCGGTGACTTTTGGGGCCGGCCCCGGTTCCGTGGCTTGCCAGGACTTCATTACCCAGTTGGGCCCGTAAC
|___|___|___|___|___|___|___|___|___|___|___|___|___|___|___|___|___|___|___| 900
  H  Q  A  I  V  R  D  V  L  A  A  G  D  F  W  G  G  A  C  S  V  A  C  Q  E  F  I  T  Q  L  G  R  N
                                              ———— MTI ————

TTCCAGGTGATCTACGAGCAGGCCAACGCCCACGGGCAGAAGGTGCAGGCTGCCGCCAACAACATGGCGCAAACCGACAGCGCCGTCGGCTCCAGCTGGG
|___|___|___|___|___|___|___|___|___|___|___|___|___|___|___|___|___|___|___|_ 1000
  F  Q  V  I  Y  E  Q  A  N  A  H  G  Q  K  V  Q  A  A  G  N  N  M  A  Q  T  D  S  A  V  G  S  S  W
                                              ———— MTI ————

CCACTAGTAACGGCCGCCAGTGTGCTGGAATTCTGCAGATATCCATCACACTGGCGGCCCCTCGAGCAGATCCGGCTGCTA
|___|___|___|___|___|___|___|___|___|___|___|___|___|___|___|__→ 1081

A[SpeI]
```

FIG.2B

TGTTCTTCGA CGGCAGGCTG GTGGAGGAAG GGCCCACCGA ACAGCTGTTC TCCTCGCCGA
   60

AGCATGCGGA AACCGCCCGA TACGTCGCCG GACTGTCGGG GGACGTCAAG GACGCCAAGC
   120

GCCGAAATTG AAGAGCACAG AAACGTATGG C GTG AAA ATT CGT TTG CAT ACG
   172
                                  Val Lys Ile Arg Leu His Thr
                                   1               5

CTG TTG GCC GTG TTG ACC GCT GCG CCG CTG CTG CTA GCA GCG GCG GGC
   220
Leu Leu Ala Val Leu Thr Ala Ala Pro Leu Leu Leu Ala Ala Ala Gly
         10              15                  20

TGT GGC TCG AAA CCA CCG AGC GGT TCG CCT GAA ACG GGC GCC GGC GCC
   268
Cys Gly Ser Lys Pro Pro Ser Gly Ser Pro Glu Thr Gly Ala Gly Ala
         25              30              35

GGT ACT GTC GCG ACT ACC CCC GCG TCG TCG CCG GTG ACG TTG GCG GAG
   316
Gly Thr Val Ala Thr Thr Pro Ala Ser Ser Pro Val Thr Leu Ala Glu
 40              45              50              55

ACC GGT AGC ACG CTG CTC TAC CCG CTG TTC AAC CTG TGG GGT CCG GCC
   364
Thr Gly Ser Thr Leu Leu Tyr Pro Leu Phe Asn Leu Trp Gly Pro Ala
                 60              65              70
TTT CAC GAG AGG TAT CCG AAC GTC ACG ATC ACC GCT CAG GGC ACC GGT
   412
Phe His Glu Arg Tyr Pro Asn Val Thr Ile Thr Ala Gln Gly Thr Gly
             75              80              85

TCT GGT GCC GGG ATC GCG CAG GCC GCC GCC GGG ACG GTC AAC ATT GGG
   460
Ser Gly Ala Gly Ile Ala Gln Ala Ala Ala Gly Thr Val Asn Ile Gly
         90              95             100

FIG.3A

```
GCC TCC GAC GCC TAT CTG TCG GAA GGT GAT ATG GCC GCG CAC AAG GGG
    508
Ala Ser Asp Ala Tyr Leu Ser Glu Gly Asp Met Ala Ala His Lys Gly
    105                 110                 115

CTG ATG AAC ATC GCG CTA GCC ATC TCC GCT CAG CAG GTC AAC TAC AAC
    556
Leu Met Asn Ile Ala Leu Ala Ile Ser Ala Gln Gln Val Asn Tyr Asn
120                 125                 130                 135

CTG CCC GGA GTG AGC GAG CAC CTC AAG CTG AAC GGA AAA GTC CTG GCG
    604
Leu Pro Gly Val Ser Glu His Leu Lys Leu Asn Gly Lys Val Leu Ala
                    140                 145                 150

GCC ATG TAC CAG GGC ACC ATC AAA ACC TGG GAC GAC CCG CAG ATC GCT
    652
Ala Met Tyr Gln Gly Thr Ile Lys Thr Trp Asp Asp Pro Gln Ile Ala
                155                 160                 165

GCG CTC AAC CCC GGC GTG AAC CTG CCC GGC ACC GCG GTA GTT CCG CTG
    700
Ala Leu Asn Pro Gly Val Asn Leu Pro Gly Thr Ala Val Val Pro Leu
            170                 175                 180

CAC CGC TCC GAC GGG TCC GGT GAC ACC TTC TTG TTC ACC CAG TAC CTG
    748
His Arg Ser Asp Gly Ser Gly Asp Thr Phe Leu Phe Thr Gln Tyr Leu
185                 190                 195

TCC AAG CAA GAT CCC GAG GGC TGG GGC AAG TCG CCC GGC TTC GGC ACC
    796
Ser Lys Gln Asp Pro Glu Gly Trp Gly Lys Ser Pro Gly Phe Gly Thr
200                 205                 210                 215

ACC GTC GAC TTC CCG GCG GTG CCG GGT GCG CTG GGT GAG AAC GGC AAC
    844
Thr Val Asp Phe Pro Ala Val Pro Gly Ala Leu Gly Glu Asn Gly Asn
                220                 225                 230

GGC GGC ATG GTG ACC GGT TGC GCC GAG ACA CCG GGC TGC GTG GCC TAT
    892
Gly Gly Met Val Thr Gly Cys Ala Glu Thr Pro Gly Cys Val Ala Tyr
                    235                 240                 245
```

FIG.3B

```
ATC GGC ATC AGC TTC CTC GAC CAG GCC AGT CAA CGG GGA CTC GGC GAG
    940
Ile Gly Ile Ser Phe Leu Asp Gln Ala Ser Gln Arg Gly Leu Gly Glu
        250                 255                 260

GCC CAA CTA GGC AAT AGC TCT GGC AAT TTC TTG TTG CCC GAC GCG CAA
    988
Ala Gln Leu Gly Asn Ser Ser Gly Asn Phe Leu Leu Pro Asp Ala Gln
    265                 270                 275

AGC ATT CAG GCC GCG GCG GCT GGC TTC GCA TCG AAA ACC CCG GCG AAC
    1036
Ser Ile Gln Ala Ala Ala Ala Gly Phe Ala Ser Lys Thr Pro Ala Asn
280                 285                 290                 295

CAG GCG ATT TCG ATG ATC GAC GGG CCC GCC CCG GAC GGC TAC CCG ATC
    1084
Gln Ala Ile Ser Met Ile Asp Gly Pro Ala Pro Asp Gly Tyr Pro Ile
            300                 305                 310

ATC AAC TAC GAG TAC GCC ATC GTC AAC AAC CGG CAA AAG GAC GCC GCC
    1132
Ile Asn Tyr Glu Tyr Ala Ile Val Asn Asn Arg Gln Lys Asp Ala Ala
        315                 320                 325

ACC GCG CAG ACC TTG CAG GCA TTT CTG CAC TGG GCG ATC ACC GAC GGC
    1180
Thr Ala Gln Thr Leu Gln Ala Phe Leu His Trp Ala Ile Thr Asp Gly
    330                 335                 340

AAC AAG GCC TCG TTC CTC GAC CAG GTT CAT TTC CAG CCG CTG CCG CCC
    1228
Asn Lys Ala Ser Phe Leu Asp Gln Val His Phe Gln Pro Leu Pro Pro
        345                 350                 355

GCG GTG GTG AAG TTG TCT GAC GCG TTG ATC GCG ACG ATT TCC AGC
    1273
Ala Val Val Lys Leu Ser Asp Ala Leu Ile Ala Thr Ile Ser Ser
360                 365                 370

TAGCCTCGTT GACCACCACG CGACAGCAAC CTCCGTCGGG CCATCGGGCT GCTTTGCGGA
    1333

GCATGCTGGC CCGTGCCGGT GAAGTCGGCC GCGCTGGCCC GGCCATCCGG TGGTTGGGTG
    1393
```

FIG.3C

GGATAGGTGC GGTGATCCCG CTGCTTGCGC TGGTCTTGGT GCTGGTGGTG CTGGTCATCG
1453

AGGCGATGGG TGCGATCAGG CTCAACGGGT TGCATTTCTT CACCGCCACC GAATGGAATC
1513

CAGGCAACAC CTACGGCGAA ACCGTTGTCA CCGACGCGTC GCCCATCCGG TCGGCGCCTA
1573

CTACGGGGCG TTGCCGCTGA TCGTCGGGAC GCTGGCGACC TCGGCAATCG CCCTGATCAT
1633

CGCCGGTGCCG CTCTCTGTAG GAGCGGCGCT GGTGATCGTG GAACGGCTGC CGAAACGGTT
1693

GGCCCAGGCT GTGGGAATAG TCCTGGAATT GCTCGCCGGA ATCCCCAGCG TGGTCGTCGG
1753

TTTGTGGGGG GCAATGACGT TCGGGCCGTT CATCGCTCAT CACATCGCTC CGGTGATCGC
1813

TCACAACGCT CCCGATGTGC CGGTGCTGAA CTACTTGCGC GGCGACCCGG GCAACGGGGA
1873

GGGCATGTTG GTGTCCGGTC TGGTGTTCGC GGTGATGGTC GTTCCCATTA TCGCCACCAC
1933

CACTCATGAC CTGTTCCGGC AGGTGCCGGT GTTGCCCCGG GAGGGCGCCA TCGGGAATTC
1993

FIG.3D

```
GGTCTTGACC ACCACCTGGG TGTCGAAGTC GGTGCCCGGA TTGAAGTCCA GGTACTCGTG    60
GGTGGGGCGG GCGAAACAAT AGCGACAAGC ATGCGAGCAG CCGCGGTAGC CGTTGACGGT   120
GTAGCGAAAC GGCAACGCGG CCGCGTTGGG CACCTTGTTC AGCGCTGATT TGCACAACAC   180
CTCGTGGAAG GTGATGCCGT CGAATTGTCG CGCGCGAACG CTGCCGACCA GGCCGATCCG   240
CTGCAACCCG GCAGCGCCCG TCGTCAACGG GCATCCCGTT CACCGCGACG GCTTGCCGGG   300
CCCAACGCAT ACCATTATTC GAACAACCGT TCTATACTTT GTCAACGCTG GCCGCTACCG   360
AGCGCCGCAC AGGATGTGAT ATGCCATCTC TGCCCGCACA GACAGGAGCC AGGCCTTATG   420
ACAGCATTCG GCGTCGAGCC CTACGGGCAG CCGAAGTACC TAGAAATCGC CGGGAAGCGC   480
ATGGCGTATA TCGACGAAGG CAAGGGTGAC GCCATCGTCT TTCAGCACGG CAACCCCACG   540
TCGTCTTACT TGTGGCGCAA CATCATGCCG CACTTGGAAG GGCTGGGCCG GCTGGTGGCC   600
TGCGATCTGA TCGGGATGGG CGCGTCGGAC AAGCTCAGCC ATCGGGACC CGACCGCTAT   660
AGCTATGGCG AGCAACGAGA CTTTTTGTTC GCGCTCTGGG ATGCGCTCGA CCTCGGCCAC   720
CACGTGGTAC TGGTGCTGCA CGACTGGGGC TCGGCGCTCG GCTTCGACTG GGCTAACCAG   780
CATCGCGACC GAGTGCAGGG GATCGCGTTC ATGGAAGCGA TCGTCACCCC GATGACGTGG   840
GCGGACTGGC CGCCGGCCGT GCGGGGTGTG TTCCAGGGTT TCCGATCGCC TCAAGGCGAG   900
CCAATGGCGT TGGAGCACAA CATCTTTGTC GAACGGGTGC TGCCCGGGGC GATCCTGCCA   960
CAGCTCAGCG ACGAGGAAAT GAACCACTAT CGGCGGCCAT TCGTGAACGG CGGCGAGGAC  1020
CGTCGCCCCA CGTTGTCGTG GCCACGAAAC CTTCCAATCG ACGGTGAGCC CGCCGAGGTC  1080
GTCGCGTTGG TCAACGACTA CCGGACCTGG CTCGAGGAAA CCGACATGCC GAAACTGTTC  1140
ATCAACGCCG AGCCCGGCGC GATCATCACC GGCCGCATCC GTGACTATGT CAGGAGCTGG  1200
CCCAACCAGA CCGAAATCAC AGTGCCCGGC GTGCATTTCG TTCAGGAGGA CAGCGATGGC  1260
```

FIG.4A

```
GTCGTATCGT GGGCGGGCGC TCGGCAGCAT CGGCGACCTG GGAGCGCTCT CATTTCACGA    1320

GACCAAGAAT GTGATTTCCG GCGAAGGCGG CGCCCTGCTT GTCAACTCAT AAGACTTCCT    1380

GCTCCGGGCA GAGATTCTCA GGGAAAAGGG CACCAATCGC AGCCGCTTCC TTCGCAACGA    1440

GGTCGACAAA TATACGTGGC AGGACAAAGG TCTTCCTATT TGCCCAGCGA ATTAGTCGCT    1500

GCCTTTCTAT GGGCTCAGTT CGAGGAAGCC GAGCGGATCA CGCGTATCCG ATTGGACCTA    1560

TGGAACCGGT ATCATGAAAG CTTCGAATCA TTGGAACAGC GGGGGCTCCT GCGCCGTCCG    1620

ATCATCCCAC AGGGCTGCTC TCACAACGCC CACATGTACT ACGTGTTACT AGCGCCCAGC    1680

GCCGATCGGG AGGAGGTGCT GGCGCGTCTG ACGAGCGAAG GTATAGGCGC GGTCTTTCAT    1740

TACGTGCCGC TTCACGATTC GCCGGCCGGG CGTCGCT                             1777
```

FIG.4B

TbH-9: protein sequence

Val Ala Trp Met Ser Val Thr Ala Gly Gln Ala Glu Leu Thr Ala Ala
1               5                   10                  15
Gln Val Arg Val Ala Ala Ala Ala Tyr Glu Thr Ala Tyr Gly Leu Thr
            20                  25                  30
Val Pro Pro Pro Val Ile Ala Glu Asn Arg Ala Glu Leu Met Ile Leu
            35                  40                  45
Ile Ala Thr Asn Leu Leu Gly Gln Asn Thr Pro Ala Ile Ala Val Asn
        50                  55                  60
Glu Ala Glu Tyr Gly Glu Met Trp Ala Gln Asp Ala Ala Ala Met Phe
65                  70                  75                  80
Gly Tyr Ala Ala Ala Thr Ala Thr Ala Thr Ala Thr Leu Leu Pro Phe
                85                  90                  95
Glu Glu Ala Pro Glu Met Thr Ser Ala Gly Gly Leu Leu Glu Gln Ala
            100                 105                 110
Ala Ala Val Glu Glu Ala Ser Asp Thr Ala Ala Ala Asn Gln Leu Met
            115                 120                 125
Asn Asn Val Pro Gln Ala Leu Lys Gln Leu Ala Gln Pro Thr Gln Gly
    130                 135                 140
Thr Thr Pro Ser Ser Lys Leu Gly Gly Leu Trp Lys Thr Val Ser Pro
145                 150                 155                 160
His Arg Ser Pro Ile Ser Asn Met Val Ser Met Ala Asn Asn His Met
                165                 170                 175
Ser Met Thr Asn Ser Gly Val Ser Met Thr Asn Thr Leu Ser Ser Met
                180                 185                 190
Leu Lys Gly Phe Ala Pro Ala Ala Ala Ala Gln Ala Val Gln Thr Ala
        195                 200                 205
Ala Gln Asn Gly Val Arg Ala Met Ser Ser Leu Gly Ser Ser Leu Gly
    210                 215                 220

FIG.4C

```
Ser Ser Gly Leu Gly Gly Gly Val Ala Ala Asn Leu Gly Arg Ala Ala
225             230             235             240
Ser Val Arg Tyr Gly His Arg Asp Gly Gly Lys Tyr Ala Xaa Ser Gly
            245             250             255
Arg Arg Asn Gly Gly Pro Ala
            260         Tb38-1: protein sequence Thr Asp Ala Ala Thr Leu Ala Gln Glu Ala Gly Asn Phe Glu Arg Ile
    1               5               10              15
        Ser Gly Asp Leu Lys Thr Gln Ile Asp Gln Val Glu Ser Thr Ala Gly
                    20              25              30
        Ser Leu Gln Gly Gln Trp Arg Gly Ala Ala Gly Thr Ala Ala Gln Ala
                    35              40              45
        Ala Val Val Arg Phe Gln Glu Ala Ala Asn Lys Gln Lys Gln Glu Leu
                    50              55              60
        Asp Glu Ile Ser Thr Asn Ile Arg Gln Ala Gly Val Gln Tyr Ser Arg
        65              70              75              80

Ala Asp Glu Glu Gln Gln Gln Ala Leu Ser Ser Gln Met Gly Phe
                        85              90              95
```

FIG.4D

```
TGGCGAATGG GACGCGCCCT GTAGCGGCGC ATTAAGCGCG GCGGGTGTGG TGGTTACGCG    60

CAGCGTGACC GCTACACTTG CCAGCGCCCT AGCGCCCGCT CCTTTCGCTT TCTTCCCTTC   120

CTTTCTCGCC ACGTTCGCCG GCTTTCCCCG TCAAGCTCTA AATCGGGGGC TCCCTTTAGG   180

GTTCCGATTT AGTGCTTTAC GGCACCTCGA CCCCAAAAAA CTTGATTAGG GTGATGGTTC   240

ACGTAGTGGG CCATCGCCCT GATAGACGGT TTTTCGCCCT TTGACGTTGG AGTCCACGTT   300

CTTTAATAGT GGACTCTTGT TCCAAACTGG AACAACACTC AACCCTATCT CGGTCTATTC   360

TTTTGATTTA TAAGGGATTT TGCCGATTTC GGCCTATTGG TTAAAAAATG AGCTGATTTA   420

ACAAAAATTT AACGCGAATT TTAACAAAAT ATTAACGTTT ACAATTTCAG GTGGCACTTT   480

TCGGGGAAAT GTGCGCGGAA CCCCTATTTG TTTATTTTTC TAAATACATT CAAATATGTA   540

TCCGCTCATG AATTAATTCT TAGAAAAACT CATCGAGCAT CAAATGAAAC TGCAATTTAT   600

TCATATCAGG ATTATCAATA CCATATTTTT GAAAAAGCCG TTTCTGTAAT GAAGGAGAAA   660

ACTCACCGAG GCAGTTCCAT AGGATGGCAA GATCCTGGTA TCGGTCTGCG ATTCCGACTC   720

GTCCAACATC AATACAACCT ATTAATTTCC CCTCGTCAAA AATAAGGTTA TCAAGTGAGA   780

AATCACCATG AGTGACGACT GAATCCGGTG AGAATGGCAA AAGTTTATGC ATTTCTTTCC   840

AGACTTGTTC AACAGGCCAG CCATTACGCT CGTCATCAAA ATCACTCGCA TCAACCAAAC   900

CGTTATTCAT TCGTGATTGC GCCTGAGCGA GACGAAATAC GCGATCGCTG TTAAAAGGAC   960

AATTACAAAC AGGAATCGAA TGCAACCGGC GCAGGAACAC TGCCAGCGCA TCAACAATAT  1020

TTTCACCTGA ATCAGGATAT TCTTCTAATA CCTGGAATGC TGTTTTCCCG GGGATCGCAG  1080

TGGTGAGTAA CCATGCATCA TCAGGAGTAC GGATAAAATG CTTGATGGTC GGAAGAGGCA  1140

TAAATTCCGT CAGCCAGTTT AGTCTGACCA TCTCATCTGT AACATCATTG GCAACGCTAC  1200

CTTTGCCATG TTTCAGAAAC AACTCTGGCG CATCGGGCTT CCCATACAAT CGATAGATTG  1260
```

FIG.5A

```
TCGCACCTGA TTGCCCGACA TTATCGCGAG CCCATTTATA CCCATATAAA TCAGCATCCA    1320

TGTTGGAATT TAATCGCGGC CTACAGCAAG ACCTTTCCCG TTGAATATGG CTCATAACAC    1380

CCCTTGTATT ACTGTTTATG TAAGCAGACA GTTTTATTGT TCATGACCAA AATCCCTTAA    1440

CGTGAGTTTT CGTTCCACTG AGCGTCAGAC CCCGTAGAAA AGATCAAAGG ATCTTCTTGA    1500

GATCCTTTTT TTCTGCGCGT AATCTGCTGC TTGCAAACAA AAAAACCACC GCTACCAGCG    1560

GTGGTTTGTT TGCCGGATCA AGAGCTACCA ACTCTTTTTC CGAAGGTAAC TGGCTTCAGC    1620

AGAGCGCAGA TACCAAATAC TGTCCTTCTA GTGTAGCCGT AGTTAGGCCA CCACTTCAAG    1680

AACTCTGTAG CACCGCCTAC ATACCTCGCT CTGCTAATCC TGTTACCAGT GGCTGCTGCC    1740

AGTGGCGATA AGTCGTGTCT TACCGGGTTG GACTCAAGAC GATAGTTACC GGATAAGGCG    1800

CAGCGGTCGG GCTGAACGGG GGGTTCGTGC ACACAGCCCA GCTTGGAGCG AACGACCTAC    1860

ACCGAACTGA GATACCTACA GCGTGAGCTA TGAGAAAGCG CCACGCTTCC CGAAGGGAGA    1920

AAGGCGGACA GGTATCCGGT AAGCGGCAGG GTCGGAACAG GAGAGCGCAC GAGGGAGCTT    1980

CCAGGGGGAA ACGCCTGGTA TCTTTATAGT CCTGTCGGGT TTCGCCACCT CTGACTTGAG    2040

CGTCGATTTT TGTGATGCTC GTCAGGGGGC GGAGCCTAT GCAAAAACGC CAGCAACGCG    2100

GCCTTTTTAC GGTTCCTGGC CTTTTGCTGG CCTTTTGCTC ACATGTTCTT TCCTGCGTTA    2160

TCCCCTGATT CTGTGGATAA CCGTATTACC GCCTTTGAGT GAGCTGATAC CGCTCGCCGC    2220

AGCCGAACGA CCGAGCGCAG CGAGTCAGTG AGCGAGGAAG CGGAAGAGCG CCTGATGCGG    2280

TATTTTCTCC TTACGCATCT GTGCGGTATT TCACACCGCA TATATGGTGC ACTCTCAGTA    2340

CAATCTGCTC TGATGCCGCA TAGTTAAGCC AGTATACACT CCGCTATCGC TACGTGACTG    2400

GGTCATGGCT GCGCCCCGAC ACCCGCCAAC ACCCGCTGAC GCGCCCTGAC GGGCTTGTCT    2460

GCTCCCGGCA TCCGCTTACA GACAAGCTGT GACCGTCTCC GGGAGCTGCA TGTGTCAGAG    2520

GTTTTCACCG TCATCACCGA AACGCGCGAG GCAGCTGCGG TAAAGCTCAT CAGCGTGGTC    2580

GTGAAGCGAT TCACAGATGT CTGCCTGTTC ATCCGCGTCC AGCTCGTTGA GTTTCTCCAG    2640

AAGCGTTAAT GTCTGGCTTC TGATAAAGCG GGCCATGTTA AGGGCGGTTT TTTCCTGTTT    2700
```

FIG.5B

```
GGTCACTGAT GCCTCCGTGT AAGGGGGATT TCTGTTCATG GGGGTAATGA TACCGATGAA    2760

ACGAGAGAGG ATGCTCACGA TACCGGTTAC TGATGATGAA CATGCCCGGT TACTGGAACG    2820

TTGTGACGGT AAACAACTGG CGGTATGGAT GCGGCGGGAC CAGAGAAAAA TCACTCAGGG    2880

TCAATGCCAG CGCTTCGTTA ATACAGATGT AGGTGTTCCA CAGGGTAGCC AGCAGCATCC    2940

TGCGATGCAG ATCCGGAACA TAATGGTGCA GGGCGCTGAC TTCCGCGTTT CCAGACTTTA    3000

CGAAACACGG AAACCGAAGA CCATTCATGT TGTTGCTCAG GTCGCAGACG TTTTGCAGCA    3060

GCAGTCGCTT CACGTTCGCT CGCGTATCGG TGATTCATTC TGCTAACCAG TAAGGCAACC    3120

CCGCCAGCCT AGCCGGGTCC TCAACGACAG GAGCACGATC ATGCGCACCC GTGGGGCCGC    3180

CATGCCGGCG ATAATGGCCT GCTTCTCGCC GAAACGTTTG GTGGCGGGAC CAGTGACGAA    3240

GGCTTGAGCG AGGGCGTGCA AGATTCCGAA TACCGCAAGC GACAGGCCGA TCATCGTCGC    3300

GCTCCAGCGA AAGCGGTCCT CGCCGAAAAT GACCCAGAGC GCTGCCGGCA CCTGTCCTAC    3360

GAGTTGCATG ATAAAGAAGA CAGTCATAAG TGCGGCGACG ATAGTCATGC CCCGCGCCCA    3420

CCGGAAGGAG CTGACTGGGT TGAAGGCTCT CAAGGGCATC GGTCGAGATC CCGGTGCCTA    3480

ATGAGTGAGC TAACTTACAT TAATTGCGTT GCGCTCACTG CCCGCTTTCC AGTCGGGAAA    3540

CCTGTCGTGC CAGCTGCATT AATGAATCGG CCAACGCGCG GGGAGAGGCG GTTTGCGTAT    3600

TGGGCGCCAG GGTGGTTTTT CTTTTCACCA GTGAGACGGG CAACAGCTGA TTGCCCTTCA    3660

CCGCCTGGCC CTGAGAGAGT TGCAGCAAGC GGTCCACGCT GGTTTGCCCC AGCAGGCGAA    3720

AATCCTGTTT GATGGTGGTT AACGGCGGGA TATAACATGA GCTGTCTTCG GTATCGTCGT    3780

ATCCCACTAC CGAGATATCC GCACCAACGC GCAGCCCGGA CTCGGTAATG GCGCGCATTG    3840

CGCCCAGCGC CATCTGATCG TTGGCAACCA GCATCGCAGT GGGAACGATG CCCTCATTCA    3900

GCATTTGCAT GGTTTGTTGA AAACCGGACA TGGCACTCCA GTCGCCTTCC CGTTCCGCTA    3960

TCGGCTGAAT TTGATTGCGA GTGAGATATT TATGCCAGCC AGCCAGACGC AGACGCGCCG    4020

AGACAGAACT TAATGGGCCC GCTAACAGCG CGATTTGCTG GTGACCCAAT GCGACCAGAT    4080

GCTCCACGCC CAGTCGCGTA CCGTCTTCAT GGGAGAAAAT AATACTGTTG ATGGGTGTCT    4140
```

FIG.5C

| | |
|---|---|
| GGTCAGAGAC ATCAAGAAAT AACGCCGGAA CATTAGTGCA GGCAGCTTCC ACAGCAATGG | 4200 |
| CATCCTGGTC ATCCAGCGGA TAGTTAATGA TCAGCCCACT GACGCGTTGC GCGAGAAGAT | 4260 |
| TGTGCACCGC CGCTTTACAG GCTTCGACGC CGCTTCGTTC TACCATCGAC ACCACCACGC | 4320 |
| TGGCACCCAG TTGATCGGCG CGAGATTTAA TCGCCGCGAC AATTTGCGAC GGCGCGTGCA | 4380 |
| GGGCCAGACT GGAGGTGGCA ACGCCAATCA GCAACGACTG TTTGCCCGCC AGTTGTTGTG | 4440 |
| CCACGCGGTT GGGAATGTAA TTCAGCTCCG CCATCGCCGC TTCCACTTTT TCCCGCGTTT | 4500 |
| TCGCAGAAAC GTGGCTGGCC TGGTTCACCA CGCGGGAAAC GGTCTGATAA GAGACACCGG | 4560 |
| CATACTCTGC GACATCGTAT AACGTTACTG GTTTCACATT CACCACCCTG AATTGACTCT | 4620 |
| CTTCCGGGCG CTATCATGCC ATACCGCGAA AGGTTTTGCG CCATTCGATG GTGTCCGGGA | 4680 |
| TCTCGACGCT CTCCCTTATG CGACTCCTGC ATTAGGAAGC AGCCCAGTAG TAGGTTGAGG | 4740 |
| CCGTTGAGCA CCGCCGCCGC AAGGAATGGT GCATGCAAGG AGATGGCGCC CAACAGTCCC | 4800 |
| CCGGCCACGG GGCCTGCCAC CATACCCACG CCGAAACAAG CGCTCATGAG CCCGAAGTGG | 4860 |
| CGAGCCCGAT CTTCCCCATC GGTGATGTCG GCGATATAGG CGCCAGCAAC CGCACCTGTG | 4920 |
| GCGCCGGTGA TGCCGGCCAC GATGCGTCCG GCGTAGAGGA TCGAGATCTC GATCCCGCGA | 4980 |
| AATTAATACG ACTCACTATA GGGGAATTGT GAGCGGATAA CAATTCCCCT CTAGAAATAA | 5040 |
| TTTTGTTTAA CTTTAAGAAG GAGATATACA TATGGGCCAT CATCATCATC ATCACGTGAT | 5100 |
| CGACATCATC GGGACCAGCC CCACATCCTG GAACAGGCG GCGGCGGAGG CGGTCCAGCG | 5160 |
| GGCGCGGGAT AGCGTCGATG ACATCCGCGT CGCTCGGGTC ATTGAGCAGG ACATGGCCGT | 5220 |
| GGACAGCGCC GGCAAGATCA CCTACCGCAT CAAGCTCGAA GTGTCGTTCA AGATGAGGCC | 5280 |
| GGCGCAACCG AGGGGCTCGA AACCACCGAG CGGTTCGCCT GAAACGGGCG CCGGCGCCGG | 5340 |
| TACTGTCGCG ACTACCCCCG CCTCGTCGCC GGTGACGTTG GCGGAGACCG GTAGCACGCT | 5400 |
| GCTCTACCCG CTGTTCAACC TGTGGGGTCC GGCCTTTCAC GAGAGGTATC CGAACGTCAC | 5460 |
| GATCACCGCT CAGGGCACCG GTTCTGGTGC CGGGATCGCC CAGGCCGCCG CCGGGACGGT | 5520 |
| CAACATTGGG GCCTCCGACG CCTATCTGTC GGAAGGTGAT ATGGCCGCGC ACAAGGGGCT | 5580 |

```
GATGAACATC GCGCTAGCCA TCTCCGCTCA GCAGGTCAAC TACAACCTGC CCGGAGTGAG    5640
CGAGCACCTC AAGCTGAACG GAAAAGTCCT GGCGGCCATG TACCAGGGCA CCATCAAAAC    5700
CTGGGACGAC CCGCAGATCG CTGCCCTCAA CCCCGGCGTG AACCTGCCCG GCACCGCGGT    5760
AGTTCCGCTG CACCGCTCCG ACGGGTCCGG TGACACCTTC TTGTTCACCC AGTACCTGTC    5820
CAAGCAAGAT CCCGAGGGCT GGGGCAAGTC GCCCGGCTTC GGCACCACCG TCGACTTCCC    5880
GGCCGTGCCG GGTGCGCTGG GTGAGAACGG CAACGGCGGC ATGGTGACCG GTTGCGCCCA    5940
GACACCGGGC TGCGTGGCCT ATATCGGCAT CAGCTTCCTC GACCAGGCCA GTCAACGGGG    6000
ACTCGGCGAG GCCCAACTAG GCAATAGCTC TGGCAATTTC TTGTTGCCCG ACGCGCAAAG    6060
CATTCAGGCC GCGGCGGCTG GCTTCGCATC GAAAACCCCG GCGAACCAGG CGATTTCGAT    6120
GATCGACGGG CCCGCCCCGG ACGGCTACCC GATCATCAAC TACGAGTACG CCATCGTCAA    6180
CAACCGGCAA AAGGACGCCG CCACCGCGCA GACCTTGCAG GCATTTCTGC ACTGGGCGAT    6240
CACCGACGGC AACAAGGCCT CGTTCCTCGA CCAGGTTCAT TTCCAGCCGC TGCCGCCCGC    6300
GGTGGTGAAG TTGTCTGACG CGTTGATCGC GACGATTTCC AGCGCTGAGA TGAAGACCGA    6360
TGCCGCTACC CTCGCGCAGG AGGCAGGTAA TTTCGAGCGG ATCTCCGGCG ACCTGAAAAC    6420
CCAGATCGAC CAGGTGGAGT CGACGGCAGG TTCGTTGCAG GGCCAGTGGC GCGGCGCGGC    6480
GGGGACGGCC GCCCAGGCCG CGGTGGTGCG CTTCCAAGAA GCAGCCAATA GCAGAAGCA    6540
GGAACTCGAC GAGATCTCCA CGAATATTCG TCAGGCCGGC GTCCAATACT CGACGGCCGA    6600
CGAGGAGCAG CAGCAGGCGC TGTCCTCGCA AATGGGCTTT GTGCCCACAA CGGCCGCCTC    6660
GCCCGCCGTCG ACCGCTGCAG CGCCACCCGC ACCGGCGACA CCTGTTGCCC CCCCACCACC    6720
GGCCGCCGCC AACACGCCGA ATGCCCAGCC GGGCGATCCC AACGCAGCAC CTCCGCCGGC    6780
CGACCCGAAC GCACCGCCGC CACCTGTCAT TGCCCCAAAC GCACCCCAAC CTGTCCGGAT    6840
CGACAACCCG GTTGGACGAT TCAGCTTCGC GCTGCCTGCT GGCTGGGTGG AGTCTGACGC    6900
CGCCCACTTC GACTACGGTT CAGCACTCCT CAGCAAAACC ACCGGGGACC GCCATTTCC    6960
CGGACAGCCG CGGCCGGTGG CCAATGACAC CCGTATCGTG CTCGGCCGGC TAGACCAAAA    7020
```
FIG.5E

```
GCTTTACGCC AGCGCCGAAG CCACCGACTC CAAGGCCGCG GCCCGGTTGG GCTCGGACAT    7080

GGGTGAGTTC TATATGCCCT ACCCGGGCAC CCGGATCAAC CAGGAAACCG TCTCGCTTGA    7140

CGCCAACGGG GTGTCTGGAA GCGCGTCGTA TTACGAAGTC AAGTTCAGCG ATCCGAGTAA    7200

GCCGAACGGC CAGATCTGGA CGGGCGTAAT CGGCTCGCCC GCGGCGAACG CACCGGACGC    7260

CGGGCCCCCT CAGCGCTGGT TTGTGGTATG GCTCGGGACC GCCAACAACC CGGTGGACAA    7320

GGGCCCGGCC AAGGCGCTGG CCGAATCGAT CCGGCCTTTG GTCGCCCCGC CGCCGGCGCC    7380

GGCACCGGCT CCTGCAGAGC CCGCTCCGGC GCCGGCGCCG GCCGGGGAAG TCGCTCCTAC    7440

CCCGACGACA CCGACACCGC AGCGGACCTT ACCGGCCTGA GAATTCTGCA GATATCCATC    7500

ACACTGGCGG CCGCTCGAGC ACCACCACCA CCACCACTGA GATCCGGCTG CTAACAAAGC    7560

CCGAAAGGAA GCTGAGTTGG CTGCTGCCAC CGCTGAGCAA TAACTAGCAT AACCCCTTGG    7620

GGCCTCTAAA CGGGTCTTGA GGGGTTTTTT GCTGAAAGGA GGAACTATAT CCGGAT       7676
```

FIG.5F

Met Gly His His His His His His Val Ile Asp Ile Ile Gly Thr Ser
1          5                       10             15
Pro Thr Ser Trp Glu Gln Ala Ala Ala Glu Ala Val Gln Arg Ala Arg
            20              25              30
Asp Ser Val Asp Asp Ile Arg Val Ala Arg Val Ile Glu Gln Asp Met
        35              40              45
Ala Val Asp Ser Ala Gly Lys Ile Thr Tyr Arg Ile Lys Leu Glu Val
    50              55              60
Ser Phe Lys Met Arg Pro Ala Gln Pro Arg Gly Ser Lys Pro Pro Ser
65              70              75              80
Gly Ser Pro Glu Thr Gly Ala Gly Ala Gly Thr Val Ala Thr Thr Pro
            85              90              95
Ala Ser Ser Pro Val Thr Leu Ala Glu Thr Gly Ser Thr Leu Leu Tyr
            100             105             110
Pro Leu Phe Asn Leu Trp Gly Pro Ala Phe His Glu Arg Tyr Pro Asn
            115             120             125
Val Thr Ile Thr Ala Gln Gly Thr Gly Ser Gly Ala Gly Ile Ala Gln
    130             135             140
Ala Ala Ala Gly Thr Val Asn Ile Gly Ala Ser Asp Ala Tyr Leu Ser
145             150             155             160
Glu Gly Asp Met Ala Ala His Lys Gly Leu Met Asn Ile Ala Leu Ala
            165             170             175
Ile Ser Ala Gln Gln Val Asn Tyr Asn Leu Pro Gly Val Ser Glu His
            180             185             190
Leu Lys Leu Asn Gly Lys Val Leu Ala Ala Met Tyr Gln Gly Thr Ile
            195             200             205
Lys Thr Trp Asp Asp Pro Gln Ile Ala Ala Leu Asn Pro Gly Val Asn
210             215             220

FIG.5G

Leu Pro Gly Thr Ala Val Val Pro Leu His Arg Ser Asp Gly Ser Gly
225                 230                 235                 240
Asp Thr Phe Leu Phe Thr Gln Tyr Leu Ser Lys Gln Asp Pro Glu Gly
            245                 250                 255
Trp Gly Lys Ser Pro Gly Phe Gly Thr Thr Val Asp Phe Pro Ala Val
            260                 265                 270
Pro Gly Ala Leu Gly Glu Asn Gly Asn Gly Gly Met Val Thr Gly Cys
            275                 280                 285
Ala Glu Thr Pro Gly Cys Val Ala Tyr Ile Gly Ile Ser Phe Leu Asp
            290                 295                 300
Gln Ala Ser Gln Arg Gly Leu Gly Glu Ala Gln Leu Gly Asn Ser Ser
305                 310                 315                 320
Gly Asn Phe Leu Leu Pro Asp Ala Gln Ser Ile Gln Ala Ala Ala Ala
            325                 330                 335
Gly Phe Ala Ser Lys Thr Pro Ala Asn Gln Ala Ile Ser Met Ile Asp
            340                 345                 350
Gly Pro Ala Pro Asp Gly Tyr Pro Ile Ile Asn Tyr Glu Tyr Ala Ile
            355                 360                 365
Val Asn Asn Arg Gln Lys Asp Ala Ala Thr Ala Gln Thr Leu Gln Ala
370                 375                 380
Phe Leu His Trp Ala Ile Thr Asp Gly Asn Lys Ala Ser Phe Leu Asp
385                 390                 395                 400
Gln Val His Phe Gln Pro Leu Pro Pro Ala Val Val Lys Leu Ser Asp
            405                 410                 415
Ala Leu Ile Ala Thr Ile Ser Ser Ala Glu Met Lys Thr Asp Ala Ala
            420                 425                 430
Thr Leu Ala Gln Glu Ala Gly Asn Phe Glu Arg Ile Ser Gly Asp Leu
            435                 440                 445
Lys Thr Gln Ile Asp Gln Val Glu Ser Thr Ala Gly Ser Leu Gln Gly
            450                 455                 460
Gln Trp Arg Gly Ala Ala Gly Thr Ala Ala Gln Ala Ala Val Val Arg
465                 470                 475                 480

FIG.5H

```
Phe Gln Glu Ala Ala Asn Lys Gln Lys Gln Glu Leu Asp Glu Ile Ser
                485                 490                 495
Thr Asn Ile Arg Gln Ala Gly Val Gln Tyr Ser Arg Ala Asp Glu Glu
            500                 505                 510
Gln Gln Gln Ala Leu Ser Ser Gln Met Gly Phe Val Pro Thr Thr Ala
            515                 520                 525
Ala Ser Pro Pro Ser Thr Ala Ala Ala Pro Pro Ala Pro Ala Thr Pro
    530                 535                 540
Val Ala Pro Pro Pro Pro Ala Ala Ala Asn Thr Pro Asn Ala Gln Pro
545             550                 555                 560
Gly Asp Pro Asn Ala Ala Pro Pro Pro Ala Asp Pro Asn Ala Pro Pro
            565                 570                 575
Pro Pro Val Ile Ala Pro Asn Ala Pro Gln Pro Val Arg Ile Asp Asn
            580                 585                 590
Pro Val Gly Gly Phe Ser Phe Ala Leu Pro Ala Gly Trp Val Glu Ser
        595                 600                 605
Asp Ala Ala His Phe Asp Tyr Gly Ser Ala Leu Leu Ser Lys Thr Thr
    610                 615                 620
Gly Asp Pro Pro Phe Pro Gly Gln Pro Pro Pro Val Ala Asn Asp Thr
625             630                 635                 640
Arg Ile Val Leu Gly Arg Leu Asp Gln Lys Leu Tyr Ala Ser Ala Glu
            645                 650                 655
Ala Thr Asp Ser Lys Ala Ala Ala Arg Leu Gly Ser Asp Met Gly Glu
            660                 665                 670
Phe Tyr Met Pro Tyr Pro Gly Thr Arg Ile Asn Gln Glu Thr Val Ser
        675                 680                 685
Leu Asp Ala Asn Gly Val Ser Gly Ser Ala Ser Tyr Tyr Glu Val Lys
    690                 695                 700
Phe Ser Asp Pro Ser Lys Pro Asn Gly Gln Ile Trp Thr Gly Val Ile
705                 710                 715                 720
Gly Ser Pro Ala Ala Asn Ala Pro Asp Ala Gly Pro Pro Gln Arg Trp
                725                 730                 735
```

FIG.5I

Phe Val Val Trp Leu Gly Thr Ala Asn Asn Pro Val Asp Lys Gly Ala
            740                 745                 750
Ala Lys Ala Leu Ala Glu Ser Ile Arg Pro Leu Val Ala Pro Pro Pro
        755                 760                 765
Ala Pro Ala Pro Ala Pro Ala Glu Pro Ala Pro Ala Pro Ala Pro Ala
        770                 775                 780
Gly Glu Val Ala Pro Thr Pro Thr Thr Pro Thr Pro Gln Arg Thr Leu
785                 790                 795                 800
Pro Ala
    802

```
ATGCCCGCAGGCCTCCTCAGCGGGATGGCCTTTGCCGCAGCCTCGCCCTGGCCGCCTGCCCGACCGCCCGGTGCCGCCAAGAGGACCGCCCGCAAACCC
---------+---------+---------+---------+---------+---------+---------+---------+---------+---------+   2520
TACGGGCGTCCGGAGGAGTCGCCCTACCGGAAACGGCCTCGGACCGGCGGCGCCGGGGCGGCACCCGGTGGTGCTGGTGACTGCCCGGTTCTCCTGCCCGGCGGTTTGGG

M  P  A  G  L  L  S  G  M  A  L  A  S  L  A  A  R  G  T  G  G  G  T  R  S  G  T  S  T  D  G  Q  E  D  G  R  K  P
─────────────────────────────────────────── mTCC2 ─────────────────────────────────────────────────

CCGGTAGTTGTGATTAGAGAGCAGCCCCCGCCCGGAAACCCCCCGCGGTAAGATATC
---------+---------+---------+---------+---------+------   2577
GGCCATCAACACTAATCTCTCGTCGGGGGCGGGCCCTTTGGGGGGCGCCATTCTATAG

P  V  V  V  I  R  E  Q  P  P  P  G  N  P  P  R      D  I
──── mTCC2 ────                                    ─ RV ─

FIG.6F
```

```
CATATGCATCACCATCACCATCACATGCCCACCACCCTTCCCGTTCAGCGCCACCCGCGGTCCCTCTTCCCCGAGTTTTCTGAGCCTGTTCGCGGCCTTCC
|++++++++|++++++++|++++++++|++++++++|++++++++|++++++++|++++++++|++++++++|++++++++|++++++++| 100
GTATACGTAGTGGTAGTGGTAGTGTACCCGTGGTGGGAAGGGCAAGTCGCCGTGGGCGCCCAGGGAGAAGCGCCTCAAAAGACTCGACAAGCGCCGGAAGG

H  M  H  H  H  H  H  H  M  A  T  T  L  P  V  Q  R  H  P  R  S  L  F  P  E  F  S  E  L  F  A  A  F

CGTCATTCGCCGGACTCCGGCCCACCTTCGACACCCGGTTGATGCGGCTGGAAGACGAGATGCCCGAGGGGCGCCTACGAGGTACGCGCGGAGCTTCCCGG
|++++++++|++++++++|++++++++|++++++++|++++++++|++++++++|++++++++|++++++++|++++++++|++++++++| 200
GCAGTAAGCGGCCTGAGGCCGGGTGGAAGCTGTGGGCCAACTACGCCGACCTTCTGCTCTACTTTCTCCCCGCGATGCTCCATGCGCGCCTCGAAGGGCC

P  S  F  A  G  L  R  P  T  F  D  T  R  L  M  R  L  E  D  E  M  K  E  G  R  Y  E  V  R  A  E  L  P  G

GGTCGACCCCGACAAGGACGTCGACATTATGGTCCGCGATGGTCAGCTGACCATCAAGGCCGAGCGCACCGAGCAGAAGGACTTCGACGGTCGCTCGGAA
|++++++++|++++++++|++++++++|++++++++|++++++++|++++++++|++++++++|++++++++|++++++++|++++++++| 300
CCAGCTGGGGCTGTTCCTGCAGCTGTAATACCAGGCGCTACCAGTCGACTGGTAGTTCCGGCTCCCGTGGCTCGTCTTCCTGAAGCTGCCAGCGAGCCTT

V  D  P  D  K  D  V  D  I  M  V  R  D  G  Q  L  T  I  K  A  E  R  T  E  Q  K  D  F  D  G  R  S  E

TTCGCGTACGGTTCCTTCGTTCGCACGGTGTCGCTGCCGGTAGGTGCTGACGAGGACGACATTAAGGCCACCTACGACAAGGGCATTCTTACTGTGTCGG
|++++++++|++++++++|++++++++|++++++++|++++++++|++++++++|++++++++|++++++++|++++++++|++++++++| 400
AAGCGCATGCCAAGGAAGCAAGCGTGCCACAGCGACGGCCATCCACCACTGCTCCTGCTGTAATTCCGGTGGATGCTGTTCCCGTAAGAATGACACAGCC

F  A  Y  G  S  F  V  R  T  V  S  L  P  V  G  A  D  E  D  D  I  K  A  T  Y  D  K  G  I  L  T  V  S

TGGCCGTTTCGGAAGGGAAGCCAACCGAAAAGCACATTCAGATCCGGTCCACCAACAAGCTTGATCCCGTGGACGCGGTCATTAACACCACCTGCAATTA
|++++++++|++++++++|++++++++|++++++++|++++++++|++++++++|++++++++|++++++++|++++++++|++++++++| 500
ACCGGCAAAGCCTTCCCTTCCGTTGGCTTTTCGTGTAAGTCTAGGCCAGGTGGTTGTTCGAACTAGGGCACCTGCGCCAGTAATTGTGGTGGACGTTAAT

V  A  V  S  E  G  K  P  T  E  K  H  I  Q  I  R  S  T  N  K  L  D  P  V  D  A  V  I  N  T  T  C  N  Y

CCGGCCAGGTAGTAGCTGCGCTCAACGCGACGGATCCGGCGGCTGCCGCACAGTTCAACCCCTCACCGGTGGCGCAGTCCTATTTGCGCAATTTCCTCGCC
|++++++++|++++++++|++++++++|++++++++|++++++++|++++++++|++++++++|++++++++|++++++++|++++++++| 600
GCCCGTCCATCATCGACGCGAGTTGCGCTGCCTAGGCCCCCGACGGCGTGTCAAGTTGCGGAGTGGCCACGCGTCAGGATAAACGCGTTAAAGGAGCGG

G  Q  V  V  A  A  L  N  A  T  D  P  G  A  A  A  Q  F  N  A  S  P  V  A  Q  S  Y  L  R  N  F  L  A

GCACCGCCACCTCAGCCGCGCTGCCATGGCCGCCGCAATTGCAAGCTGTGCCGGGGGCGGCACAGTACATCGGCCCTTGTCGAGTCGGTTCCCGGCTCCTGCA
|++++++++|++++++++|++++++++|++++++++|++++++++|++++++++|++++++++|++++++++|++++++++|++++++++| 700
CGTGGCGGTGGACTCGGCGCCACGGTACCGGCGCCTTAACGTTCGACACGGCCCCCCCGCGTGTCATGTAGCCGGAACAGCTCAGCCAACGGCCGAGGACGT

A  P  P  P  Q  R  A  A  M  A  A  Q  L  Q  A  V  P  G  A  A  Q  Y  I  G  L  V  E  S  V  A  G  S  C
```

FIG.7A

```
ACAACTATGAGCTCATGACGATTAATTACCAGTTCGGGGACGTCGACCCTCATGGCCCCATGATCCGCCCTCAGGCGGCGTCCCTTGAGGCGGAGCATCA
||||||||||||||||||||||||||||||||||||||||||||||||||||||||||||||||||||||||||||||||||||||||||||||||||| 800
TGTTGATACTCGAGTACTGCTAATTAATGGTCAAGCCCCTGCAGCTGCGAGTACCGGCGGTACTAGGCGCGAGTCCGCCGCAGCGAACTCCGCCTCGTAGT
  N  N  Y  E  L  M  T  I  N  Y  Q  F  G  D  V  D  A  H  G  A  M  I  R  A  Q  A  A  S  L  E  A  E  H  Q

GGCCATCGTTCGTCATCTCTTGCCGCCGCGGTGACTTTTCGGCCGGCCCCCGTTCGTGGCTTCCCAGGCAGTTCATTACCCAGTTGGGCCCGTAACTTCCAC
||||||||||||||||||||||||||||||||||||||||||||||||||||||||||||||||||||||||||||||||||||||||||||||||||| 900
CCGGTAGCAAGCACTAGACAACGGCGGCCCACTGAAAACCCGGCCGCGGCGCCAAGCCACCGAACGGTCCTCAAGTAATGGGTCAACCCGGCCATTGAAGGTC
  A  I  V  R  D  V  L  A  A  G  D  F  W  G  G  A  G  S  V  A  C  Q  E  F  I  T  Q  L  G  R  N  F  Q

GTGATCTACGAGCAGGCCAACGCCCACCGGCAGAAGGTGCAGGCTGCCCGCAACAACATGGCCCAAACCCGACAGCGCCGTCGCCTCCAGCTGGCCCACTA
||||||||||||||||||||||||||||||||||||||||||||||||||||||||||||||||||||||||||||||||||||||||||||||||||| 1000
CACTAGATGCTCGTCCGGTTGCGGGTGCCCGTCTTCCACGTCCGACGGCCGTTGTTGTACCGGGTTTGGCTGTCGCGGCAGCCGAGGTCGACCCGGTGAT
  V  I  Y  E  Q  A  N  A  H  G  Q  K  V  Q  A  A  G  N  N  M  A  Q  T  D  S  A  V  G  S  S  W  A  T

GTATGAGCCCTTTTGGATGCTCATATCCCACAGTTGGTGGCCTCCCAGTCGGCGGTTTGCCCGCCAAGCGGGGGCTGATGCGGCACACGATCCGTCAGGCCGA
||||||||||||||||||||||||||||||||||||||||||||||||||||||||||||||||||||||||||||||||||||||||||||||||||| 1100
CATACTCGGAAAACCTACGAGTATAGGGTGTCAACCACCGGAGGCGTCAGCCGCAAACGGCCGTTCCCCCCCGACTACCCCGTGTGCTAGCCAGTCCGGCT
  S  M  S  L  L  D  A  H  I  P  Q  L  V  A  S  Q  S  A  F  A  A  K  A  G  L  M  R  H  T  I  G  Q  A  E

GCAGGCGGCGATGTCGGCCTCAGGCGGTTTCACCAGGGGGAGTCGTCGGCGGCGTTTCAGGCCGCCCATGCCCGGTTTGTGGCGGCGGCCGGCCAAAGTCAAC
||||||||||||||||||||||||||||||||||||||||||||||||||||||||||||||||||||||||||||||||||||||||||||||||||| 1200
CGTCCGCCGCTACAGCCGAGTCCGCCAAAGTGGTCCCCCTCAGCAGCCGCCGCAAAGTCCGGCCGGGTACGGCCAAACACCGCCGCCGGCCGGCGTTTCAGTTG
  Q  A  A  M  S  A  Q  A  F  H  Q  G  E  S  S  A  A  F  Q  A  A  H  A  R  F  V  A  A  A  A  K  V  N

ACCTTGTTGGATGTCGGCGCAGGCGAATCTGGGTGAGGCCGCCCGGTACCTATGTGGCCGCCGATGCTGCGGCGCCGCTCGACCTATACCCGGTTCGATATC
|||||||||||||||||||||||||||||||||||||||||||||||||||||||||||||||||||||||||||||||||||||||||||||||----▶ 1299
TGGAACAACCTACAGCCGCGTCCCCTTAGACCCACTCCGGCGGCCATGGATACACCGGCGGCCTAGGACCCCGGCGCAGCCTGGCATATGGCCCAAGCCTATAG
  T  L  L  D  V  A  Q  A  N  L  G  E  A  A  G  T  Y  V  A  A  D  A  A  A  A  S  T  Y  T  G  F  D  I
```

```
CCTGGCCGCACGGCCGGCGGTGGCGGCACCCGTAGCCGGCACCACTGACCGGCCCAAGAGGACGGCCCAAACCCCCGTAGTTGTGATTAGA
                                                                                              2100
GGACCGGCGTGCCGGCCGTGCTGCCGCCATCGGCCATGGTGACTGGCCGGGTTCTCCTGCCGGCGTTTGGGGCCATCAACACTAATCT
```

` L  A  A  R  G  T  T  G  G  G  G  T  R  S  G  T  S  T  D  G  Q  E  D  G  R  K  P  P  V  V  V  I  R `

————————————— mTCC2 —————————————

```
GAGCAGCCGCCGCCCGGAAACCCCCGCGGTAAGATTTCTAAATCCATCACACTGGCGGCCCCTCGAG
                                                              2168
CTCGTCGGCGGCGGGCCCTTGGGGGCGCCATTCTAAAGATTTAGGTAGTGTGACCGCCGGGGAGCTC
```

`  E  Q  P  P  P  G  N  P  P  R    D  F    I  H  H  T  G  G  R  S  S`

————— mTCC2 —————     | pET polylinker | Xhol |

FIG. 8F

```
CATATGCATCACCATCACCATCACGATCCCGTGGACGCCGTCATTAACACCACCTGCAATTACGGGCACCTAGTAGCTGCGCTCAACGCGACGGATCCGG
|++++++++|++++++++|++++++++|++++++++|++++++++|++++++++|++++++++|++++++++|++++++++|++++++++| 100
GTATACGTAGTGGTAGTGGTAGTGCTAGGGCACCTGCGCCAGTAATTGTGGTGGACGTTAATGCCCGTCCATCATCGACGCGAGTTGCGCTGCCTAGGCC
  H  M  H  H  H  H  H  H  D  P  V  D  A  V  I  N  T  T  C  N  Y  G  Q  V  V  A  A  L  N  A  T  D  P
```

```
GGGCTGCCCCACAGTTCAACGCCTCACCGGTGGCCCAGTCCTATTTGCGCAATTTCCTCGCCGCACCGCCACCTCAGCGCGCTGCCATGCCCGCGCAATT
|++++++++|++++++++|++++++++|++++++++|++++++++|++++++++|++++++++|++++++++|++++++++|++++++++| 200
CCCGACGGGGTGTCAAGTTGCGGAGTGGCCACCGGGTCAGGATAAACGCGTTAAAGGAGCGGCGTGGCGGTGCAGTCGCGCGACCGTACCGGCGCGTTAA
  G  A  A  A  Q  F  N  A  S  P  V  A  Q  S  Y  L  R  N  F  L  A  A  P  P  P  Q  R  A  A  M  A  A  Q  L
```

```
GCAAGCTGTGCCGGGGCCGGCACAGTACATCGGCCTTGTCGAGTCGGTTGCCGGCTCCTGCAACAACTATGAGCTCATCACGATTAATTACCAGTTCGGG
|++++++++|++++++++|++++++++|++++++++|++++++++|++++++++|++++++++|++++++++|++++++++|++++++++| 300
CGTTCGACACGGCCCCGGCCGTGTCATGTAGCCGGAACAGCTCAGCCAACGGCCGAGGACGTTGTTGATACTCGAGTACTGCTAATTAATGGTCAAGCCC
  Q  A  V  P  G  A  A  Q  Y  I  G  L  V  E  S  V  A  G  S  C  N  N  Y  E  L  I  T  I  N  Y  Q  F  G
```

```
GACGTCGACGCTCATGGCGCCATGATCCGCGCTCAGGCGGCCTCCCTTGAGGCCGAGCATCAGGCCATCGTTCGTGATGTGTTGGCCGCCGGTGACTTTT
|++++++++|++++++++|++++++++|++++++++|++++++++|++++++++|++++++++|++++++++|++++++++|++++++++| 400
CTGCAGCTGCGAGTACCGCGGTACTAGGCGCGAGTCCGCCGCAGCCAACTCCGCCTCCTAGTCCGGTAGCAAGCACTACACAACCGGCGCCCACTGAAAA
  D  V  D  A  H  G  A  M  I  R  A  Q  A  A  S  L  E  A  E  H  Q  A  I  V  R  D  V  L  A  A  G  D  F
```

```
GGGCCGCGCCCGTTCGGTGGCTTGCCAGGAGTTCATTACCAGTTGGGCCGTAACTTCCAGGTGATCTACGAGCAGGCCAAGCGCCCACGGGCAGAAGGT
|++++++++|++++++++|++++++++|++++++++|++++++++|++++++++|++++++++|++++++++|++++++++|++++++++| 500
CCCGGCGCGGGCCAAGCCACCGAACGGTCCTCAAGTAATGGTCAACCCGGCATTGAAGGTCCACTAGATGCTCGTCCGGTTCGCGGGTGCCCGTCTTCCA
  W  G  G  A  G  S  V  A  Q  E  F  I  T  Q  L  G  R  N  F  Q  V  I  Y  E  Q  A  N  A  H  G  Q  K  V
```

```
GCAGCCTGCCGGCAACAACATGGCGCAAACCGACAGCGCCGTCGGCTCCAGCTGGGCCACTAGTATGAGCCTTTTGGATGCTCATATCCCACAGTTGGTG
|++++++++|++++++++|++++++++|++++++++|++++++++|++++++++|++++++++|++++++++|++++++++|++++++++| 600
CGTCGGACGGCCGTTGTTGTACCGCGTTTGGCTGTCGCGGCAGCCGAGGTCGACCCGGTGATCATACTCGGAAAACCTACGAGTATAGGGTGTCAACCAC
  Q  A  A  G  N  N  M  A  Q  T  D  S  A  V  G  S  S  W  A  T  S  M  S  L  L  D  A  H  I  P  Q  L  V
```

```
GCCTCCCAGTCGGCCGTTTGCCGCCAAGGCGGGGCTGATGCGGCACACGATCGGTCAGGCCGAGCAGCGGCGGATGTCGCCTGAGCCCTTTCACCAGGGC
|++++++++|++++++++|++++++++|++++++++|++++++++|++++++++|++++++++|++++++++|++++++++|++++++++| 700
CGGAGGGTCAGCCGGCAAACGGCGGTTCCGCCCCGACTACGCCGTGTGCTAGCCAGTCCGGCTCGTCGCCGCCTACCAGCGGACTCGGCAAAGTGGTCCCCG
  A  S  Q  S  A  F  A  A  K  A  G  L  M  R  H  T  I  G  Q  A  E  Q  A  A  M  S  A  Q  A  F  H  Q  G
```

FIG.9A

```
AGTCCTCGCCGCCGTTTCAGGCCGCCCATCCCCGGTTTGTCCGCGCCGCCGCCAAAGTCAACACCTTGTTGGATGTCGCGCAGGCGAATCTGGTTGAGGC
++++++++++|++++++++++|++++++++++|++++++++++|++++++++++|++++++++++|++++++++++|++++++++++|++++++++++| 800
TCAGGACCGCCGGCCCAAAGTCCGGCGGGTACGGGCCAAACACCGCCGCCGGCGGTTTCAGTTGTGGAACAACCTACAGCGCCTCCCCTTAGACCCACTCCG
 E  S  S  A  A  F  Q  A  A  H  A  R  I  V  A  A  A  A  K  V  N  T  L  L  D  V  A  Q  A  N  L  G  E  A
```

```
CCCCCGTACCTATGTGGCCGCCCGATGCTGCGGCCGCGTCGACCTATACCGGGTTCGATATCCATCACACTGGCCGGCCCCTCGAGCAGATCCGGCTCCTAA
++++++++++|++++++++++|++++++++++|++++++++++|++++++++++|++++++++++|++++++++++|++++++++++|++++++++++| 900
GCGGCCATGGATACACCGGCGGCTACGACGCCGGCGCAGCTGGATATGGCCCAAGCTATAGGTAGTGTGACCGGCCGGCGAGCTCGTATAGGCCGACGATT
  A  G  T  Y  V  A  A  D  A  A  A  A  S  T  Y  T  G  F  D  I  H  H  T  G  G  R  S  S  R  S  C  C
```

```
CAAAGCCCGAAAGGAAGCTGA
++++++++++|++++++++++|- 921
GTTTCGGGCTTTCCTTCGACT
  Q  S  P  K  G  S
```

FIG. 9B

```
CATATGCATCACCATCACCATCACATGGTGGATTTCGGGGCGTTACCACCGGAGATCAACTCCCCGACGATGTACGCCGGCCCCGGGTTCGGCCTCCCTGG
++++++++++|++++++++|++++++++|++++++++|++++++++|++++++++|++++++++|++++++++|++++++++|++++++++|  100
GTATACGTAGTGGTAGTGGTAGTGTACCACCTAAAGCCCCGCAATGGTGCCCTCTAGTTGAGGCGCTCCTACATGCGGCCGGGCCCAAGCCGGAGCGACC
  H  M  H  H  H  H  H  H  M  V  D  F  G  A  L  P  P  E  I  N  S  A  R  M  Y  A  G  P  G  S  A  S  L
```

```
TGCCCGCCGGCTCAGATGTGGGACAGCGTGGCCAGTGACCTGTTTTCGGCCGCGTCGGCGTTTCAGTCGGTGGTCTGGGGTCTGACGGTGGGGTCGTGGAT
++++++++++|++++++++|++++++++|++++++++|++++++++|++++++++|++++++++|++++++++|++++++++|++++++++|  200
ACCGGCGCCGAGTCTACACCCTGTCGCACCGGTCACTGGACAAAAGCCGGCGCAGCCGCAAAGTCAGCCACCAGACCCCAGACTGCCACCCCAGCACCTA
  V  A  A  A  Q  M  W  D  S  V  A  S  D  L  F  S  A  A  S  A  F  Q  S  V  V  W  G  L  T  V  G  S  W  I
```

```
AGGTTCGTCGGCGGGTCTGATGGTGGCGGCGGCCTCGCCGTATGTGGCGTGGATGAGCGTCACCGCGGGGCAGGCCGAGCTGACCGCCGCCCAGGTCCGG
++++++++++|++++++++|++++++++|++++++++|++++++++|++++++++|++++++++|++++++++|++++++++|++++++++|  300
TCCAAGCAGCCGCCCAGACTACCACCGCCGCCGGAGCGGCATACACCGCACCTACTCGCAGTGGCGCCCCGTCCGGCTCGACTGGCGGCGGGTCCAGGCC
   G  S  S  A  G  L  M  V  A  A  A  S  P  Y  V  A  W  M  S  V  T  A  G  Q  A  E  L  T  A  A  Q  V  R
```

```
GTTGCTGCCGCGGCCTACGAGACGGCGTATGGGCTGACCGTGCCCCCGCCGGTGATCGCCGAGAACCGTGCTGAACTGATGATTCTGATAGCGACCAACC
++++++++++|++++++++|++++++++|++++++++|++++++++|++++++++|++++++++|++++++++|++++++++|++++++++|  400
CAACGACGGCGCCGGATGCTCTGCCGCATACCCGACTGGCACGGGGGCGGCCACTAGCGGCTCTTGGCACGACTTGACTACTAAGACTATCGCTGGTTGG
   V  A  A  A  Y  E  T  A  Y  G  L  T  V  P  P  P  V  I  A  E  N  R  A  E  L  M  I  L  I  A  T  N
```

```
TCTTGGCGGCAAAACACCCCGGCCGATCGCGGTCAACGAGGCCGAATACGGCGAGATGTGGGCCCAAGACGCCGCCGCCATGTTTGGCTACGCCGCCGCCGAC
++++++++++|++++++++|++++++++|++++++++|++++++++|++++++++|++++++++|++++++++|++++++++|++++++++|  500
AGAACCCGGTTTTGTGGGGCCGCTAGCGCCAGTTGCTCCGGCTTATGCCGCTCTACACCCGGGTTCTGCGGCGGCGGTACAAACCGATGCGGCGGCGGCTG
   L  L  G  Q  N  T  P  A  I  A  V  N  E  A  E  Y  G  E  M  W  A  Q  D  A  A  A  M  F  G  Y  A  A  A  T
```

```
GGCGACGGCGACGGCCACGTTGCTGCCGTTCCAGGAGGCCCCGGAGATGACCAGCGCCGGGTGCCCTCCTCGAGCAGGCCGCCGCCCTCGACGAGGCCTCC
++++++++++|++++++++|++++++++|++++++++|++++++++|++++++++|++++++++|++++++++|++++++++|++++++++|  600
CCGCTGCCGCTGCCGCTGCAACGACGGCAAGCTCCTCCGGGGCCTCTACTGGTCGCGGCCCACCCGAGGAGCTCGTCCGGCGGCGGCCAGCTCCTCCGGAGG
    A  T  A  T  L  L  P  F  E  E  A  P  E  M  T  S  A  G  G  L  L  E  Q  A  A  A  V  E  E  A  S
```

```
GACACGGCCGCGGCGAACCAGTTGATGAACAATGTGCCCCAGGCGCTGCAACAGCTGGCCCAGCCCACGCAGGGCACCACGCCTTCTTCCAAGCTGGGTG
++++++++++|++++++++|++++++++|++++++++|++++++++|++++++++|++++++++|++++++++|++++++++|++++++++|  700
CTGTGCCGGCGCCGCTTGGTCAACTACTTGTTACACGGGGTCCGGCGACGTTGTCGACCGGGTCGGGTGCGTCCCGTGGTGCGGAAGAAGGTTCGACCCAC
   D  T  A  A  A  N  Q  L  M  N  N  V  P  Q  A  L  Q  Q  L  A  Q  P  T  Q  G  T  T  P  S  S  K  L  G
```

FIG.10A

```
GCCTGTGGAAGACGGTCTCGCCGCATCGGTCGCCGATCAGCAACATGGTCTCGATGGCCAACAACCACATGTCGATGACCAACTCGGGTGTGTCGATGAC
++++++++++|++++++++++|++++++++++|++++++++++|++++++++++|++++++++++|++++++++++|++++++++++|++++++++++| 800
CGGACACCTTCTGCCAGAGCGCCGTAGCCAGCGGCTAGTCGTTGTACCACAGCTACCGGTTGTTGGTGTACAGCTACTGGTTGAGCCCACACAGCTACTG
  G I W K T V S P H R S P I S N M V S M A N N H M S M T N S G V S M T
```

```
CAACACCTTGACCTCGATGTTGAAGGGCTTTGCTTCCGCGGGCGCCCGCCCACGGCCGTGCAAACCGCGCCGGCAAAAACGGGGGTCCCGGCCCATGACCTCCCTG
++++++++++|++++++++++|++++++++++|++++++++++|++++++++++|++++++++++|++++++++++|++++++++++|++++++++++| 900
GTTGTGGAACTCGAGCTACAACTTCCCGAAACGAGGCCGCCGCCGGCCGGGTCCGGCACGTTTGGCGCCGCCGTTTTGCCCCAGGCCCCCCTACTGGAGCGAC
  N T L S S M L K G F A P A A A A Q A V Q I A A Q N G V R A M S S L
```

```
GGCAGCTCGCTGGGTTCTTCGGGTCTGGGCGGTGGGGTGGCCGCCAACTTGGGTCGGGCGGCCTCGGTCGGTTCGTTGTCGGTGCCCCAGGCCTGGGCCG
++++++++++|++++++++++|++++++++++|++++++++++|++++++++++|++++++++++|++++++++++|++++++++++|++++++++++| 1000
CCGTCGAGCGACCCAAGAAGCCCAGACCCCGCCACCCCACCGGCGCGTTGAACCCAGCCCGCCCGAGCCCAGCCAAGCAACAGCCACGGCCTCCCGGACCCGGC
   G S S L G S S G L G G G V A A N L G R A A S V G S L S V P Q A W A
```

```
CGGCCAACCAGGCAGTCACCCCGGCGGCGCCGGGCGCTGCCGCTGACCAGCCTGACCAGCGCCGCGGAAAGAGGGCCCCGGCACATGCTGGGCGGCCTGCC
++++++++++|++++++++++|++++++++++|++++++++++|++++++++++|++++++++++|++++++++++|++++++++++|++++++++++| 1100
GCCGGTTGGTCCGTCAGTGGGGCCGCCGCGCCCGCGACGGCGACTGGTCGACTGGTCGCGGCGCCTTTCTCCCGGGCCCGTCTACGACCCGCCGACGG
  A A N Q A V T P A A R A L P L T S L T S A A E R G P G Q M L G G L P
```

```
GGTGGGCCAGATGGGCCCCAGGGCCGGTGGTGGCCTCAGTGGTGTGCTGCCTGTTCCCCCGCCCACCCTATGTGATGCCCCATTCTCCGGCAGCCCGCAAG
++++++++++|++++++++++|++++++++++|++++++++++|++++++++++|++++++++++|++++++++++|++++++++++|++++++++++| 1200
CCACCCGTCTACCCGGGGTCCCCGCCACCACCCGAGTCACCACACGACGCACAAGGCGGCGCCTGGGATACACTACGGCGTAACAGGCCGTCGGCCGTTC
   V G Q M G A R A G G L S G V L R V P P R P Y V M P H S P A A G K
```

```
CTTGATCCCGTGGACGCGGTCATTAACACCACCTGCAATTACGGGCAGGTAGTACCTGCCCTCAACGCGACGGATCCGGGGGCTGCCGCACAGTTCAACG
++++++++++|++++++++++|++++++++++|++++++++++|++++++++++|++++++++++|++++++++++|++++++++++|++++++++++| 1300
GAACTAGGGCACCTGCGCCAGTAATTGTGGTGGACGTTAATGCCCGTCCATCATGGACGCGAGTTGCGCTGCCTAGGCCCCCGACGGCGTCTCAAGTTGC
   L D P V D A V I N T T C N Y G Q V V A A L N A T D P G A A A Q F N
```

```
CCTCACCGGTGGCCCAGTCCTATTTGCCCAATTTCCTCGCCGCACCGCCACCTCAGCGCGCTGCCATGGCCGCGCAATTGCAAGCTGTGCCGGGGGCCGC
++++++++++|++++++++++|++++++++++|++++++++++|++++++++++|++++++++++|++++++++++|++++++++++|++++++++++| 1400
GGAGTGGCCACCGGGTCAGGATAAACGCGGTTAAAGGAGCGGCCGTGGCCGTGGAGTCGCGCGACGGTACCGGCGCCGTTAACGTTCGACACGGAAAAGCCG
   A S P V A Q S Y L R N F L A A P P P Q R A A M A A Q L Q A V P G A A
```

FIG.10B

```
ACAGTACATCGGCCTTGTCGAGTCGGTTGCCGGCTCCTGCAACAACTATGAGCTCATGACGATTAATTACCAGTTCGGGACGTCGACCCTCATGGCGCC
++++++++|++++++++|++++++++|++++++++|++++++++|++++++++|++++++++|++++++++|++++++++|++++++++| 1500
TGTCATGTAGCCCGAACAGCTCAGCCAACGGCCGAGGACGTTGTTGATACTCGAGTACTCCTAATTAATGGTCAAGCCCCTGCAGCTGCCAGTACGCGG
  Q  Y  I  G  L  V  E  S  V  A  G  S  C  N  N  Y  E  L  M  T  I  N  Y  Q  F  G  D  V  D  A  H  G  A
```

```
ATGATCCGCGCTCAGGCGGCGTCGCTTGAGGCGGAGCATCAGGCCATCGTTCGTGATGTGTTGGCCGCCGGTGACTTTTGGGGCGGCGCCGGTTCGGTCG
++++++++|++++++++|++++++++|++++++++|++++++++|++++++++|++++++++|++++++++|++++++++|++++++++| 1600
TACTAGGCGCGAGTCCGCCGCAGCGAACTCCGCCTCGTAGTCCGGTAGCAAGCACTACACAACCGGCGCCCACTGAAAACCCCGCCGCGGCCAAGCCACC
  M  I  R  A  Q  A  A  S  L  E  A  E  H  Q  A  I  V  R  D  V  L  A  A  G  D  F  W  G  G  A  G  S  V
```

```
CTTGCCAGGAGTTCATTACCCAGTTGGGCCGTAACTTCCAGGTGATCTACGAGCAGGCCAACGCCCACGGGCAGAAGGTGCAGGCTGCCGGCAACAACAT
++++++++|++++++++|++++++++|++++++++|++++++++|++++++++|++++++++|++++++++|++++++++|++++++++| 1700
GAACGGTCCTCAAGTAATGGGTCAACCGGCATTGAAGGTCCACTAGATGCTCGTCCGGTTGCGGGTGCCCGTCTTCCACGTCCGACGGCCGTTGTTGTA
  A  C  Q  E  F  I  T  Q  L  G  R  N  F  Q  V  I  Y  E  Q  A  N  A  H  G  Q  K  V  Q  A  A  G  N  N  M
```

```
GGCGCAAACCGACAGCGCCGTCGGCTCCACCTGGGCCACTAGTAACGGCCGCCAGTGTGCTGGAATTCTGCAGATATCCATCACACTGGCGGCCGCCTCGA
++++++++|++++++++|++++++++|++++++++|++++++++|++++++++|++++++++|++++++++|++++++++|++++++++| 1800
CCGCGTTTGGCTGTCGCGGCAGCCGAGGTGGACCCGGTGATCATTGCCGGCGGTCACACGACCTTAAGACGTCTATAGGTAGTGTGACCGCCGGCGGAGCT
  A  Q  T  D  S  A  V  G  S  S  W  A  T  S  N  G  R  Q  C  A  G  I  L  Q  I  S  I  T  L  A  A  A  R
```

FIG.10C

```
CATATGCATCACCATCACCATCACATGGCCACCACCCTTCCCGTTCAGCGCCACCGGCGGTCCCTCTTCCCCGAGTTTTCTGAGCTGTTCGCGGCCTTCC
++++++++++++++++++++++++++++++++++++++++++++++++++++++++++++++++++++++++++++++++++++++++++++++++++ 100
GTATACGTAGTGGTAGTGGTAGTGTACCGGTGGTGGCGAACGGCAAGTCGCGGTGGGCGCCCAGGGAGAAGCGGGCTCAAAAGACTCGACAAGCGCCGGAAGG
 H  M  H  H  H  H  H  H  H  M  A  T  T  I  P  V  Q  R  H  P  R  S  I  F  P  F  F  S  F  I  F  A  A  F
```

```
CGTCATTCCCCGGACTCCGGCCCACCTTCGACACCCGGTTGATGCGGCTGGAAGACCAGATGAAAGACGGGCGCCTACCGAGGTACGCGCCGAGCTTCCCGG
++++++++++++++++++++++++++++++++++++++++++++++++++++++++++++++++++++++++++++++++++++++++++++++++++ 200
GCAGTAAGCGGCCTGAGGCCGGGTGGAAGCTGTGGGCCAACTACGCCCGACCTTCTGCTCTACTTTCTCCCCGCGATGCTCCATGCGCGCCTCGAAGGGCC
 P  S  F  A  G  L  R  P  T  F  D  T  R  L  M  R  L  E  D  E  M  K  E  G  R  Y  E  V  R  A  E  L  P  G
```

```
GTCCACCCCCACAAGGACGTCGACATTATGGTCCGCGATGGTCAGCTGACCATCAAGGCCGAGCGCACCGAGCAGAAGGACTTCGACGGTCGCTCGGAA
++++++++++++++++++++++++++++++++++++++++++++++++++++++++++++++++++++++++++++++++++++++++++++++++++ 300
CCAGGTGGGGCTGTTCCTGCAGCTGTAATACCAGGCGCTACCAGTCGACTGTAGTTCCGGCTCCCGTGCCTCGTCTTCCTGAAGCTGCCAGCGAGCCTT
 V  D  P  D  K  D  V  D  I  M  V  R  D  G  Q  L  T  I  K  A  E  R  T  E  Q  K  D  F  D  G  R  S  E
```

```
TTCCGCTACCGTTCCTTCGTTCGCCACGGTGTCGCTGCCCGTACGTGCTGACGACGACGACATTAAGGCCACCTACGACAAGGGCATTCTTACTGTGTCGG
++++++++++++++++++++++++++++++++++++++++++++++++++++++++++++++++++++++++++++++++++++++++++++++++++ 400
AAGGCGCATGCCAAGGAAGCAAGCGTGCCACAGCGACGGCCATCCACGACTGCTCCTGCTGTAATTCCGGTGGATGCTGTTCCCGTAAGAATGACACAGCC
 F  A  Y  G  S  F  V  R  T  V  S  L  P  V  G  A  D  E  D  D  I  K  A  T  Y  D  K  G  I  L  T  V  S
```

```
TGCCCGTTTCGGAAGCGAACCCAACCGAAAAGCCACATTCAGATCCGGTCCACCAACAAGCTTGATCCCGTGGACGCCGTCATTAACACCACCTGCAATTA
++++++++++++++++++++++++++++++++++++++++++++++++++++++++++++++++++++++++++++++++++++++++++++++++++ 500
ACGGGCAAAGCCTTCGCTTGGGTTGGCTTTTCGTGTAAGTCTAGGCCAGGTGGTTGTTCGAACTAGGGCACCTGCCCCAGTAATTGTGGTGGACGTTAAT
 V  A  V  S  E  G  K  P  T  E  K  H  I  Q  I  R  S  T  N  K  L  D  P  V  D  A  V  I  N  T  T  C  N  Y
```

```
CGGCCACGTAGTACCTGCCCTCAACGCCACGGATCCGGGGGCTGCCGCAGAGTTCAACGCCTCACCGGTGGCCCAGTCCTATTTGCGCAATTTCCTCGCC
++++++++++++++++++++++++++++++++++++++++++++++++++++++++++++++++++++++++++++++++++++++++++++++++++ 600
GCCCGTCCATCATCGACGCGAGTTGCGCTGCCTAGGCCCCCGACGGCGTGTCAAGTTGCGGACTGCCCACCGCGTCAGGATAAACGCGTTAAAGGAGCGG
  G  Q  V  V  A  A  L  N  A  T  D  P  G  A  A  Q  F  N  A  S  P  V  A  Q  S  Y  L  R  N  F  L  A
```

```
GCACCGCCACCTCAGCCGCCTGCCATGGCCCCGCAATTGCAAGCTGTGCCGGGGGCCGCCACAGTACATCGGCCTTGTCGAGTCGGTTGCCGGCTCCTCCA
++++++++++++++++++++++++++++++++++++++++++++++++++++++++++++++++++++++++++++++++++++++++++++++++++ 700
CGTGGCGGTGGAGTCGGCGACGGTACCGGGCGCGTTAACGTTCGACACGGCCCCGGCGGTGTCATGTAGCCGGAACAGCTCAGCCAACGGCCGAGGACGT
  A  P  P  P  Q  R  A  A  M  A  A  Q  L  Q  A  V  P  G  A  A  Q  Y  I  G  L  V  E  S  V  A  G  S  C
```

FIG.11A

```
ACAACTATGAGCTCATGACGATTAATTACCAGTTCGGGGACGTCGACGCTCATGGCGCCATGATCCGCGCTCAGGCGGCGTCGCTTGAGGCGGACCATCA
++++++++|++++++++|++++++++|++++++++|++++++++|++++++++|++++++++|++++++++|++++++++|++++++++| 800
TGTTGATACTCGAGTACTGCTAATTAATGGTCAAGCCCCTGCAGCTGCGAGTACCCCCGTACTAGGCGCGAGTCCCCCCGCAGCGAACTCCGCCTCGTAGT
  N  N  Y  E  L  M  T  I  N  Y  Q  F  G  D  V  D  A  H  G  A  M  I  R  A  Q  A  A  S  L  E  A  E  H  Q
```

```
GCCCATCGTTCGTGATGTGTTGGGCGCGCGTGACTTTTCGGGCCGGCGCCCGTTCGGTGGCTTGCCAGGAGTTCATTACCCAGTTGGGCCGTAACTTCCAG
++++++++|++++++++|++++++++|++++++++|++++++++|++++++++|++++++++|++++++++|++++++++|++++++++| 900
CGGGTAGCAAGCACTACACAACCGGCGCCCCACTGAAAACCCCGCCGCGGGCCAAGCCACCCGAACCGTCCTCAAGTAATGGGTCAACCCGGCATTGAAGGTC
  A  I  V  R  D  V  L  A  A  G  D  F  W  G  G  A  G  S  V  A  C  Q  E  F  I  T  Q  L  G  R  N  F  Q
```

```
GTGATCTACGAGCAGGCCAACGCCCACGGCCAGAAGGTGCAGGCTGCCGGCAACAACATGGCGCAAACCGACAGCGCCGTCGGCTCCAGCTGGGCCACTA
++++++++|++++++++|++++++++|++++++++|++++++++|++++++++|++++++++|++++++++|++++++++|++++++++| 1000
CACTAGATGCTCGTCCGGTTGCCGGTGCCCGTCTTCCACGTCCGACGGCCGTGTTGTACCGCGTTTGGCTGTCGCGGCAGCCGAGGTCGACCCCGTGAT
  V  I  Y  E  Q  A  N  A  H  G  Q  K  V  Q  A  A  G  N  N  M  A  Q  T  D  S  A  V  G  S  S  W  A  T
```

```
GTAACGGCCGCCAGTGTGCCTGGAATTCTGCAGATATCCATCACACTGGCGGCCGCTCCAGCAGATCCGGCTGCTAACAAAGCCCGAAAGGAAGCTGAGTT
++++++++|++++++++|++++++++|++++++++|++++++++|++++++++|++++++++|++++++++|++++++++|++++++++| 1100
CATTGCCGGCGGTCACACCGACCTTAAGACGTCTATAGGTAGTGTGACCGCCGGCGAGGTCGTCTAGGCCGACGATTGTTTCGGGCTTTCCTTCGACTCAA
  S  N  G  R  Q  C  A  G  I  L  Q  I  S  I  T  L  A  A  A  R  A  D  P  A  A  N  K  A  R  K  E  A  E  L
```

```
CGCT
+++►1104
CCGA
  A
```

FIG.11B

```
CATATGCATCACCATCACCATCACATGGTGGATTTCCGGGCCCTTACCACCCGAGATCAACTCCGCGAGGATGTACGCCCGCCCGGGTTCGGCCTCGCTGG
++++++++++++++++++++++++++++++++++++++++++++++++++++++++++++++++++++++++++++++++++++++++++++++++++ 100
GTATACGTAGTGGTAGTGGTAGTGTACCACCTAAAGCCCCGGCAATGGTGGCCTCTAGTTGAGGCGCTCCTACATGCCGCCGGGCCCAAGCCGGACCGACC
  H  M  H  H  H  H  H  H  H  M  V  D  F  G  A  L  P  P  F  I  N  S  A  R  M  Y  A  G  P  G  S  A  S  L
```

```
TGGCCGCGGCTCAGATGTGGGACAGCGTGGCGAGTGACCTGTTTTCCGCCGCGTCGGCGTTTCAGTCGGTGGTCTGGGCTCTGACGGTGGGCTCGTGGAT
++++++++++++++++++++++++++++++++++++++++++++++++++++++++++++++++++++++++++++++++++++++++++++++++++ 200
ACCGGCGCCGAGTCTACACCCTGTCGCACCGCTCACTGGACAAAAGCCGGCGCCAGCCCGCAAAGTCAGCCACCAGACCCCAGACTGCCACCCCAGCACCTA
  V  A  A  A  Q  M  W  D  S  V  A  S  D  L  F  S  A  A  S  A  F  Q  S  V  V  W  G  L  T  V  G  S  W  I
```

```
AGGTTCCTCGGCGGGTCTGATGGTGGCGGCGGCCTCGCCGTATGTGGCGTGGATGAGCGTCACCGCGGGGCAGGCCGAGCTGACCGCCGCCCAGGTCCGG
++++++++++++++++++++++++++++++++++++++++++++++++++++++++++++++++++++++++++++++++++++++++++++++++++ 300
TCCAAGCAGCCGCCCAGACTACCACCGCCGCCGGAGCGGCATACACCGCCACCTACTCGCAGTGGCCGCCCCGTCCCGCTCGACTGGCGGCGGGTCCAGGCC
  G  S  S  A  G  L  M  V  A  A  A  S  P  Y  V  A  W  M  S  V  T  A  G  Q  A  E  L  T  A  A  Q  V  R
```

```
GTTGCTGCGGCGGCCTACGAGACGGCGTATGGGCTGACGGTGCCCCCGCCGGTGATCGCCGAGAACCGTGCTGAACTGATGATTCTGATAGCGACCAACC
++++++++++++++++++++++++++++++++++++++++++++++++++++++++++++++++++++++++++++++++++++++++++++++++++ 400
CAACGACGCCGCCGGATGCTCTGCCGCATACCCGACTGCCACGGGGGCGGCCACTAGCGGCTCTTGGCACGACTTGACTACTAAGACTATCGCTGGTTGG
  V  A  A  A  A  Y  E  T  A  Y  G  L  T  V  P  P  P  V  I  A  E  N  R  A  E  L  M  I  L  I  A  T  N
```

```
TCTTCGGGCAAAACACCCCGGCCATCGCCGTCAACGAGGCCGAATACGGCGAGATGTGGGCCCAAGACGCCGCCGCGATGTTTGGCTACGCCGCGGCGAC
++++++++++++++++++++++++++++++++++++++++++++++++++++++++++++++++++++++++++++++++++++++++++++++++++ 500
AGAACCCGTTTTGTGGGGCCGGTAGCGCCAGTTGCTCCGGCTTATGCCGCTCTACACCCGGGTTCTGCGGCGGCGCTACAAACCGATGCGGCGCCGCTG
  L  L  G  Q  N  T  P  A  I  A  V  N  E  A  E  Y  G  E  M  W  A  Q  D  A  A  A  M  F  G  Y  A  A  A  T
```

```
GGCCGACGGCGACGGCCAACGTTGCTGCCGGTTCGAGGAGGCGCCCGAGATGACCAGCGCGGTGGGCTCCTCGAGCAGGCCGCCGCCGGTCGAGGAGGCCTCC
++++++++++++++++++++++++++++++++++++++++++++++++++++++++++++++++++++++++++++++++++++++++++++++++++ 600
CCGGCTGCCCCTGCCGCTGCAACGACGGCAAGCTCCTCCGCGGCCTCTACTGGTCGCGCCCACCCGAGGAGCTCGTCCGGCGGCGCCCAGCTCCTCCGGAGG
     A  T  A  T  A  T  L  L  P  F  E  E  A  P  E  M  T  S  A  G  G  L  L  E  Q  A  A  A  V  E  F  A  S
```

```
GACACCCCCGCGGCGAACCAGTTGATGAACAATGTCCCCCAGGCGCTGCAACAGCTGGCCCAGCCCACGCAGGGCACCACGCCCTTCTTCCAAGCTGGGTG
++++++++++++++++++++++++++++++++++++++++++++++++++++++++++++++++++++++++++++++++++++++++++++++++++ 700
CTGTGGGGCGCGCCCTTGGTCAACTACTTGTTACAGGGGGTCGGCGACGTTGTCGACCGGGTCGGGTGCCTCCCGTGCTGCGGAAGAAGGTTCGACCCAC
     D  T  A  A  A  N  Q  L  M  N  N  V  P  Q  A  L  Q  Q  L  A  Q  P  T  Q  G  T  T  P  S  S  K  L  G
```

FIG.12A

```
GCCTGTGGAAGACGGTCTCGCCCGCATCGGTCGCCGATCAGCAACATGGTGTCCATGGCCAACAACCACATGTCGATGACCAACTCGGGTGTGTCCATGAC
++++++++|++++++++|++++++++|++++++++|++++++++|++++++++|++++++++|++++++++|++++++++|++++++++|  800
CGGACACCTTCTGCCAGAGCGGGCGTAGCCAGCGGCTAGTCGTTGTACCACAGCTACCGGTTGTTGGTGTACAGCTACTGGTTGAGCCCACACAGCTACTG
 G   W   K   T   V   S   P   H   R   S   P   I   S   N   M   V   S   M   A   N   N   H   M   S   M   T   N   S   G   V   S   M   T
```

```
CAACACCTTGAGCTCGATGTTGAAGGGCTTTGCCTCCGGCCGCGGCCGCCCAGGCCGTGCAAACCGCCGCCCAAAACGGGGTCCGGCCGATGAGCTCGCTC
++++++++|++++++++|++++++++|++++++++|++++++++|++++++++|++++++++|++++++++|++++++++|++++++++|  900
GTTGTGGAACTCGAGCTACAACTTCCCGAAACGGAGGCCGCCGCCGGCGGGTCCGGCACGTTTGGCGCCGCCGTTTTGCCCCAGGCCGGCTACTCGAGCGAC
  N   T   L   S   S   M   L   K   G   F   A   P   A   A   A   A   Q   A   V   Q   T   A   A   Q   N   G   V   R   A   M   S   S   L
```

```
GGCAGCTCCCTGGGTTCTTCGGGTCTCGGCCCGTGCGGTGGCCGGCCAACTTGGGTCGGCCGGCCTCCGTCGGTTCGTTGTCGGTGCCGCAGGCCTGGGCCG
++++++++|++++++++|++++++++|++++++++|++++++++|++++++++|++++++++|++++++++|++++++++|++++++++|  1000
CCGTCGAGGGACCCAAGAAGCCCAGACCCGCCACCCCACCGGCCGTTGAACCCAGCCGGCCGGAGCCAGCCAAGCAACAGCCACGGCGTCCGGACCCGGC
  G   S   S   L   G   S   S   G   L   G   G   G   V   A   A   N   L   G   R   A   A   S   V   G   S   L   S   V   P   Q   A   W   A
```

```
CGGCCAACCAGGCAGTCACCCCGGCGGCGCGGGCCCTGCCGCTGACCAGCCTGACCAGCGCCGCGGAAAGAGGGCCCGGGCAGATCCTGGGCGGCCTGCC
++++++++|++++++++|++++++++|++++++++|++++++++|++++++++|++++++++|++++++++|++++++++|++++++++|  1100
GCCGGTTGGTCCGTCAGTGGGGCCGCCGCGCCCGCGACGGCCGACTGGTCGGACTGGTCGCGGCGCCTTTCTCCCGGGCCCCTCTACGACCCGCCGACGG
  A   A   N   Q   A   V   T   P   A   A   R   A   L   P   L   T   S   L   T   S   A   A   E   R   G   P   G   Q   I   L   G   G   L   P
```

```
GGTGGGGCAGATGGGCGCCCAGGGCCGGTGCTGCGCCTCAGTGGTGTGCTGCCGTGTTCCGCCCCGACCCTATGTGATGCCGCATTCTCCGGCCAGCCGGCGAT
++++++++|++++++++|++++++++|++++++++|++++++++|++++++++|++++++++|++++++++|++++++++|++++++++|  1200
CCACCCCGTCTACCCGCGGGTCCCGGCCACCACCCGAGTCACCACACGACCCACAAGGCGGCGCTGGGATACACTACGGCCTAAGAGGCCGTCGGCCCCTA
  V   G   Q   M   G   A   R   A   G   G   G   L   S   G   V   L   R   V   P   P   R   P   Y   V   M   P   H   S   P   A   A   G   D
```

```
ATCGCCCCGCCGGCCCTTGTCGCAGGACCGGTTCGCCGACTTCCCCGCCTGCCCCTCGACCCGTCCGGGATGGTGGCCCCAAGTGGGGCCCACAGGTGGTCA
++++++++|++++++++|++++++++|++++++++|++++++++|++++++++|++++++++|++++++++|++++++++|++++++++|  1300
TAGCCGGCGGCCGGAACAGCGTCCTGGCCAAGCGGCTGAAGGGGCGCCCACGGGGAGCTGGGCCAGGGCCTACCAGCGGGTTCACCCCGGTGTCCACCAGT
  I   A   P   P   A   L   S   Q   D   R   F   A   D   F   P   A   L   P   L   D   P   S   A   M   V   A   Q   V   G   P   Q   V   V
```

```
ACATCAACACCAAAACTGGGCTACAACAACGCCGTGGGCGCCGGGACCGGCATCGTCATCGATCCCAACGGTGTCGTGCTGACCAACAACCACGTGATCGC
++++++++|++++++++|++++++++|++++++++|++++++++|++++++++|++++++++|++++++++|++++++++|++++++++|  1400
TGTAGTTGTGGTTTTGACCCGATGTTGTTGCGGCACCCGCGGCCCCTGGCCGTACCAGTAGCTAGGGTTGCCACAGCACCGACTGGTTGTTGGTGCACTAGCG
  N   I   N   T   K   L   G   Y   N   N   A   V   G   A   G   T   G   I   V   I   D   P   N   G   V   V   L   T   N   N   H   V   I   A
```

FIG.12B

```
GGGCGCCACCGACATCAATGCCTTCAGCGTCGCTCCGCCAAACCTACGGCGTCGATGTGGTCGGGTATGACCGCACCCAGCATGTCGCGGTGCTGCAG
+++++++++++++++++++++++++++++++++++++++++++++++++++++++++++++++++++++++++++++++++++++++++++++++++ 1500
CCCGCGGTGGCTGTAGTTACGCAAGTCGCAGCCGAGGCCGGTTTGGATGCCGGCAGCTACACCAGCCCATACTGGCGTGGGTCCTACAGCGCCACGACGTC
  G  A  T  D  I  N  A  F  S  V  G  S  G  Q  T  Y  G  V  D  V  V  G  Y  D  R  T  Q  D  V  A  V  L  Q
```

```
CTCCGCCGTGCCGGTGCCCTGCCGTCGGCGGCGATCGGTGCCGGCGTCCCGTTGGTGAGCCCGTCGTCGCGATGGGCAACAGCGGTGGGCAGGCGGGAA
++++++++++++++++++++++++++++++++++++++++++++++++++++++++++++++++++++++++++++++++++++++++++++++++++ 1600
GAGGCGGCACGGCCACCGGACGGCAGCCGCCCCTAGCCACGGCCGCAGCGCCAACCACTCGGGCAGCAGCGCTACCCGTTGTCGCCACCCGTCCCGCCTT
  L  R  G  A  G  G  L  P  S  A  A  I  G  G  G  V  A  V  G  E  P  V  V  A  M  G  N  S  G  G  Q  G  G
```

```
CGGCCCCGTGCCGTGCCCTGGCAGGGTGGTCCGCCTCGCCCAAACCGTGCAGGCGTCGGATTCGCTGACCGGTGCCCAAGAGACATTGAACGGGTTGATCCA
++++++++++++++++++++++++++++++++++++++++++++++++++++++++++++++++++++++++++++++++++++++++++++++++++ 1700
GCCGGGGCACGGCCACGGACCGTCCCACCAGGCCGGAGCGGGTTTGGCACGTCCGCAGCCTAAGCGACTGCCCACCGCCTTCTCTGTAACTTGCCCAACTAGGT
  T  P  R  A  V  P  G  R  V  V  A  L  G  Q  T  V  Q  A  S  D  S  L  T  G  A  E  E  T  L  N  G  L  I  Q
```

```
GGTCGATGCCGCGATCCAGCCCGGTGATTCGGGCGGCGCCCGTCGTCAACGGCCTAGGACAGGTGGTCGGTATGAACACCGCCGCGTCCTACGATATC
+++++++++++++++++++++++++++++++++++++++++++++++++++++++++++++++++++++++++++++++++++++++++++++++++- 1797
CAAGCTACGGCGCTAGGTCGGCGGCCACTAAGCCCGCCGCCGGGCCAGCAGTTGCCGGATCCTGTCCACCAGCCATACTTGTGCCGGCGGCAGGATCCTATAG
   F  D  A  A  I  Q  P  G  D  S  G  G  P  V  V  N  G  L  G  Q  V  V  G  M  N  T  A  A  S     D  I
```

FIG.12C

FIG.13A

```
                                                                    Cfr9 I
          Eco52 I                                                   Xma I
          Xma III                                                   | Sma I
          |        EcoR I        Bam HI                             | | Bgl I
          |        |             |                                  | | |
TGCCCGAGGGACCCCCGGCCCGAATTCGACGACGACGACAAGGATCCACCTGACCCCCATCAGCCGGACATGACGAAAGGCTATTGCCCGGGTGGCCCGATG
++++++++++|++++++++++|++++++++++|++++++++++|++++++++++|++++++++++|++++++++++|++++++++++|++++++++++| 500
ACCGGGCTCCCTGGGGGCCGGCTTAAGCTGCTGCTGCTGTTCCTAGGTGGACTGGGCGTAGTCGGCCCTGTACTGCTTTCCGATAACGGGCCCACCCGGCTAC

L A E G P P A E F D D D K D P P D P H Q P D M T K G Y C P G G R W
  W P R D P R P N S T T T R I H L T P I S R T   R K A I A R V A D
    G R G T P G R I R R R R Q G S T   P A S A G H D E R L L P G W P M
```

```
GGGTTTTGGCGACTTGGCCCGTGTGCGACGGCGAGAACTACCCCGACGGCTCGTTTTGGCACCAGTGGATGCAAACGTGGTTTACCGGCCCCACAGTTTTAC
++++++++++|++++++++++|++++++++++|++++++++++|++++++++++|++++++++++|++++++++++|++++++++++|++++++++++| 600
CCCAAAACCGCTGAACCGGCACACGCTGCCGCTCTTGATGGGGCTGCCGAGCCAAAACCGTGGTCACCTACGTTTGCACCAAATGGCCGGGGTGTCAAAATG

G F G D L A V C D G E K Y P D G S F W H Q W M Q T W F T G P Q F Y
   G V L A T W P C A T A R S I P T A R F G T S G C K R G L P A H S F T
     G F W R L G R V R R R E V P R R L V L A P V D A N V V Y R P T V L
```

```
                        Dra III
                        PflM I
       RleA I           Van91 I                                     EcoR I
       |                |                                           |
TTCGATTGTGTCAGCGGCCGGTGAGCCCCTCCCCGGCCCGCCGCCACCGGCTGGTTGCGGTGGGGCAATTCCGTCCGAGCAGCCCAACCCTCCCTGAGAAT
++++++++++|++++++++++|++++++++++|++++++++++|++++++++++|++++++++++|++++++++++|++++++++++|++++++++++| 700
AAGCTAACACAGTCGCCGGCCACTCGGGGAGGGGCCGGCCGGCGGCGGTGGCCCACCAACGCCACCCCGTTAAGGCAGGCTCGTCGGGTTGCCAGGGACTCTTA

F D C V S G G E P L P G P P P P G G C G A I P S E Q P N A P   E
   S I V S A A V S P S P A R R H R V V A V G Q F R P S S P T L P E N
     L R L C Q R R   A P P R P A A T G W L R W G N S V R A A Q R S L R I
```

TC
←702
AG

F
S
←

FIG.13B

FUSION PROTEINS OF *MYCOBACTERIUM TUBERCULOSIS* ANTIGENS AND THEIR USES

The present application is a continuation of application Ser. No. 09/287,849, filed Apr. 7, 1999 now U.S. Pat. No. 6,627,198 which is a continuation-in-part of application Ser. No. 09/223,040 filed Dec. 30, 1998, now U.S. Pat. No. 6,544,522 and of application Ser. No. 09/056,556 filed Apr. 7, 1998, now U.S. Pat. No. 6,350,456 which is a continuation-in-part of application Ser. No. 09/025,197 filed Feb. 18, 1998, abandoned, which is a continuation-in-part of application Ser. No. 08/942,578 filed Oct. 1, 1997, abandoned which is a continuation-in-part of application Ser. No. 08/818,112, filed Mar. 13, 1997, now U.S. Pat. No. 6,290,969, each of which is incorporated by reference herein in its entirety.

1. INTRODUCTION

The present invention relates to fusion proteins containing at least two *Mycobacterium tuberculosis* antigens. In particular, it relates to bi-fusion proteins which contain two individual *M. tuberculosis* antigens, tri-fusion proteins which contain three *M. tuberculosis* antigens, tetra-fusion proteins which contain four *M. tuberculosis* antigens, and penta-fusion proteins which contain five *M. tuberculosis* antigens, and methods for their use in the diagnosis, treatment and prevention of tuberculosis infection.

2. BACKGROUND OF THE INVENTION

Tuberculosis is a chronic infectious disease caused by infection with *M. tuberculosis*. It is a major disease in developing countries, as well as an increasing problem in developed areas of the world, with about 8 million new cases and 3 million deaths each year. Although the infection may be asymptomatic for a considerable period of time, the disease is most commonly manifested as an acute inflammation of the lungs, resulting in fever and a nonproductive cough. If untreated, serious complications and death typically result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistance.

In order to control the spread of tuberculosis, effective vaccination and accurate early diagnosis of the disease are of utmost importance. Currently, vaccination with live bacteria is the most efficient method for inducing protective immunity. The most common *Mycobacterium* employed for this purpose is *Bacillus* Calmette-Guerin (BCG), an avirulent strain of *M. bovis*. However, the safety and efficacy of BCG is a source of controversy and some countries, such as the United States, do not vaccinate the general public with this agent.

Diagnosis of tuberculosis is commonly achieved using a skin test, which involves intradermal exposure to tuberculin PPD (protein-purified derivative). Antigen-specific T cell responses result in measurable induration at the injection site by 48–72 hours after injection, which indicates exposure to Mycobacterial antigens. Sensitivity and specificity have, however, been a problem with this test, and individuals vaccinated with BCG cannot be distinguished from infected individuals.

While macrophages have been shown to act as the principal effectors of *M. tuberculosis* immunity, T cells are the predominant inducers of such immunity. The essential role of T cells in protection against *M. tuberculosis* infection is illustrated by the frequent occurrence of *M. tuberculosis* in Acquired Immunodeficiency Syndrome patients, due to the depletion of $CD4^+$ T cells associated with human immunodeficiency virus (HIV) infection. Mycobacterium-reactive $CD4^+$ T cells have been shown to be potent producers of gamma-interferon (IFN-γ), which, in turn, has been shown to trigger the anti-mycobacterial effects of macrophages in mice. While the role of IFN-γ in humans is less clear, studies have shown that 1,25-dihydroxy-vitamin D3, either alone or in combination with IFN-γ or tumor necrosis factor-alpha, activates human macrophages to inhibit *M. tuberculosis* infection. Furthermore, it is known that IFN-γ stimulates human macrophages to make 1,25-dihydroxy-vitamin D3. Similarly, interleukin-12 (IL-12) has been shown to play a role in stimulating resistance to *M. tuberculosis* infection. For a review of the immunology of *M. tuberculosis* infection, see Chan and Kaufmann, 1994, *Tuberculosis: Pathogenesis, Protection and Control*, Bloom (ed.), ASM Press, Washington, D.C.

Accordingly, there is a need for improved vaccines, and improved methods for diagnosis, preventing and treating tuberculosis.

3. SUMMARY OF THE INVENTION

The present invention relates to fusion proteins of *M. tuberculosis* antigens. In particular, it relates to fusion polypeptides that contain two or more *M. tuberculosis* antigens, polynucleotides encoding such polypeptides, methods of using the polypeptides and polynucleotides in the diagnosis, treatment and prevention of *M. tuberculosis* infection.

The present invention is based, in part, on the inventors' discovery that polynucleotides which contain two to five *M. tuberculosis* coding sequences produce recombinant fusion proteins that retain the immunogenicity and antigenicity of their individual components. The fusion proteins described herein induced both T cell and B cell responses, as measured by T cell proliferation, cytokine production, and antibody production. Furthermore, a fusion protein was used as an immunogen with adjuvants in vivo to elicit both cell-mediated and humoral immunity to *M. tuberculosis*. Additionally, a fusion protein was made by a fusion construct and used in a vaccine formulation with an adjuvant to afford long-term protection in animals against the development of tuberculosis. The fusion protein was a more effective immunogen than a mixture of its individual protein components.

In a specific embodiment of the invention, the isolated or purified *M. tuberculosis* polypeptides of the invention may be formulated as pharmaceutical compositions for administration into a subject in the prevention and/or treatment of *M. tuberculosis* infection. The immunogenicity of the fusion protein may be enhanced by the inclusion of an adjuvant.

In another aspect of the invention, the isolated or purified polynucleotides are used to produce recombinant fusion polypeptide antigens in vitro. Alternatively, the polynucleotides may be administered directly into a subject as DNA vaccines to cause antigen expression in the subject, and the subsequent induction of an anti-*M. tuberculosis* immune response.

It is also an object of the invention that the polypeptides be used in in vitro assays for detecting humoral antibodies or cell-mediated immunity against *M. tuberculosis* for diagnosis of infection or monitor of disease progression. Additionally, the polypeptides may be used as an in vivo diagnostic agent in the form of an intradermal skin test. Alternatively, the polypeptides may be used as immunogens to generate anti-*M. tuberculosis* antibodies in a non-human animal. The antibodies can be used to detect the target antigens in vivo and in vitro.

4. BRIEF DESCRIPTION OF THE DRAWINGS

FIGS. 1A–1C: The nucleotide sequence (SEQ ID NO:1) and amino acid sequence (SEQ ID NO:2) of tri-fusion protein Ra12-TbH9-Ra35 (designated Mtb32–Mtb39 fusion).

FIG. 2A and 2B: The nucleotide sequence (SEQ ID NO:3) and amino acid sequence (SEQ ID NO:4) of tri-fusion protein Erd14-DPV-MTI.

FIGS. 3A–3D: The nucleotide sequence (SEQ ID NO:5) and amino acid sequence (SEQ ID NO:6) of tri-fusion protein TbRa3-38kD-Tb38-1.

FIGS. 4A–4D: The nucleotide sequence (SEQ ID NO:7) and amino acid sequence (SEQ ID NO:8) of bi-fusion protein TbH9-Tb38-1.

FIGS. 5A–5J: The nucleotide sequence (SEQ ID NO:9) and amino acid sequence (SEQ ID NO:10) of tetra-fusion protein TbRa3-38kD-Tb38-1-DPEP (designated TbF-2).

Figure 6A:
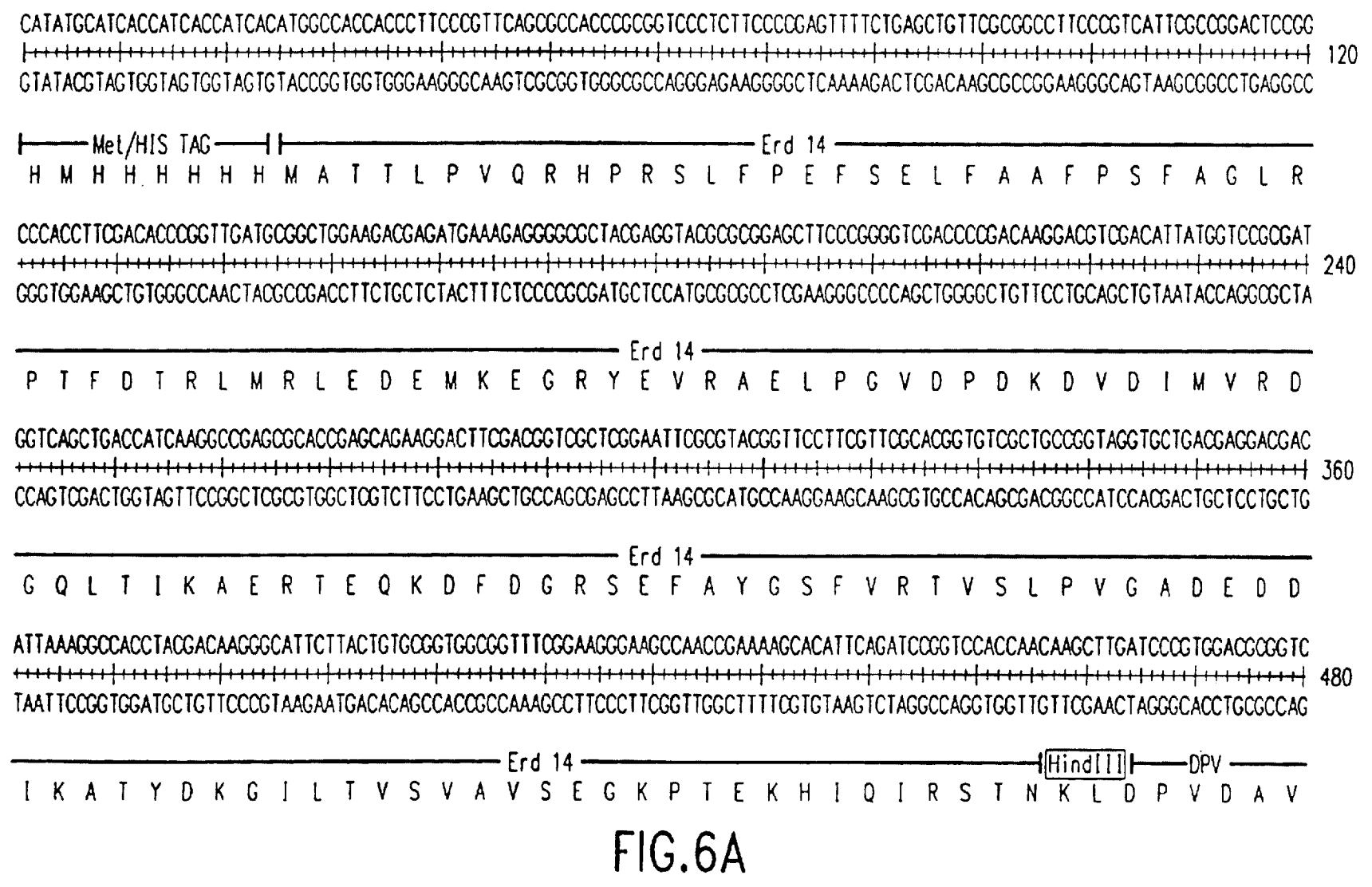

FIGS. 6A–6F: The nucleotide sequence (SEQ ID NO:11) and amino acid sequence (SEQ ID NO:12) of penta-fusion protein Erd14-DPV-MTI-MSL-MTCC2 (designated Mtb88f).

FIGS. 7A and 7B: The nucleotide sequence (SEQ ID NO:13) and amino acid sequence (SEQ ID NO:14) of tetra-fusion protein Erd14-DPV-MTI-MSL (designated Mtb46f).

Figure 8B:
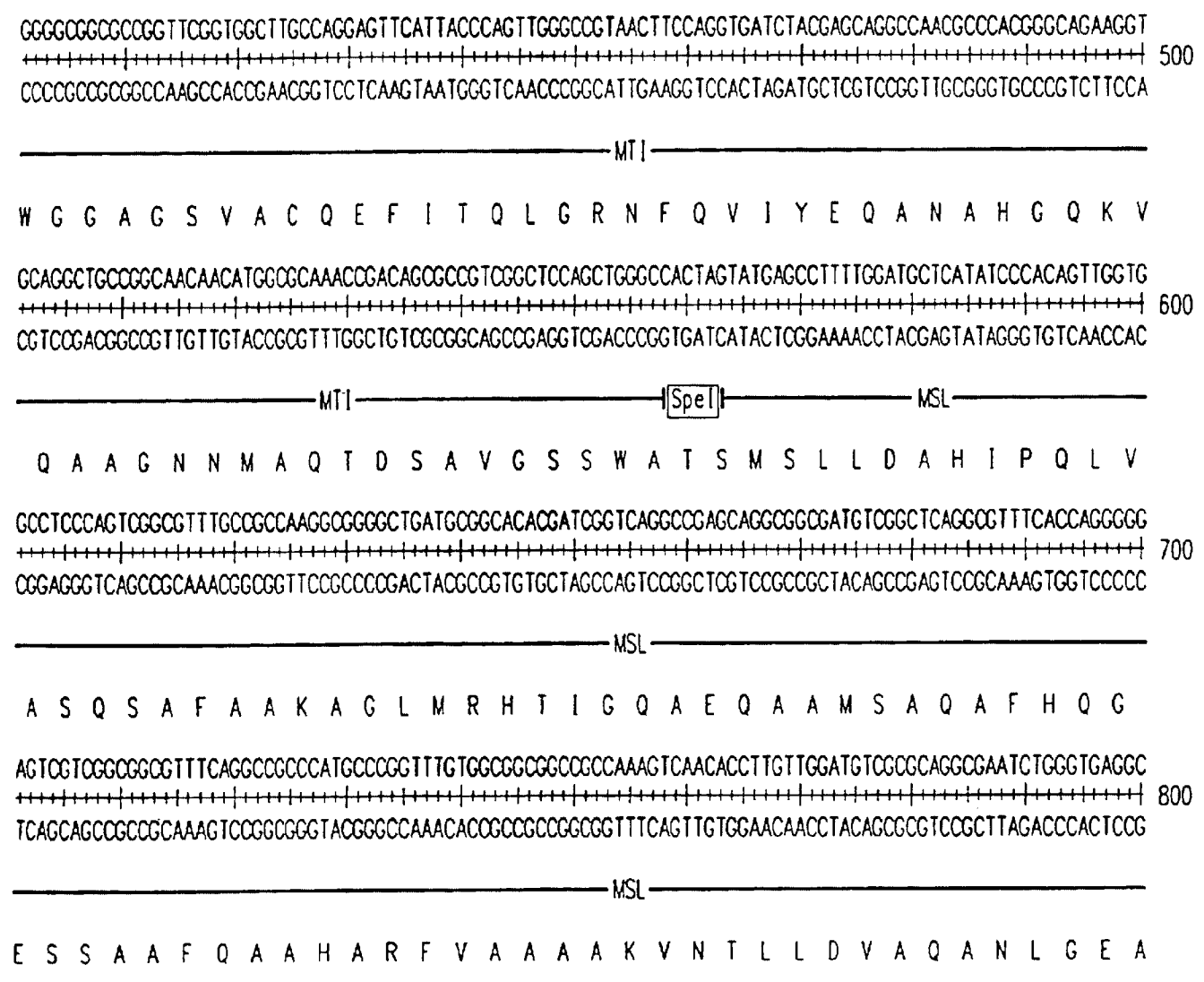
Figure 8C:
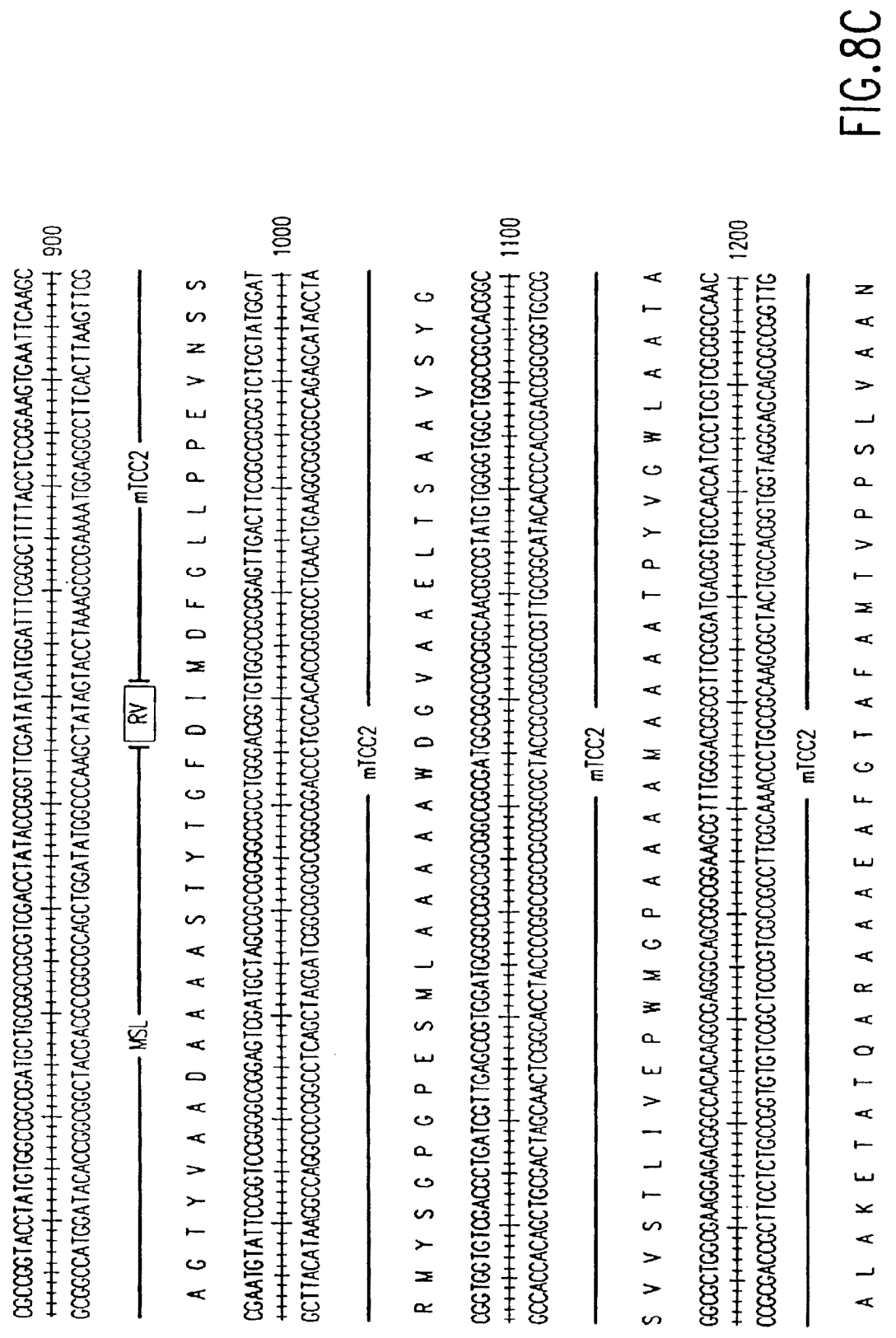
Figure 8E:
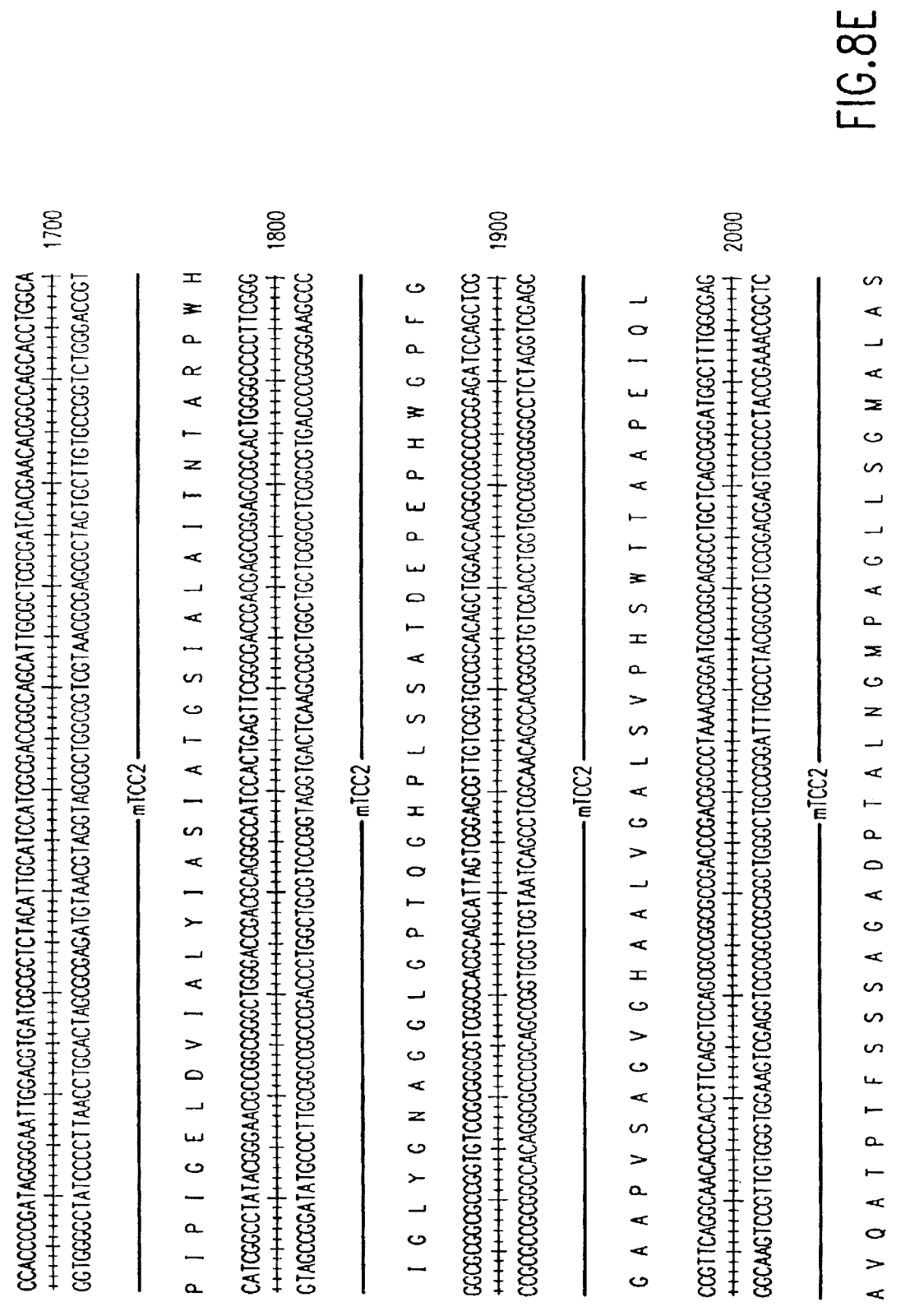

FIGS. 8A–8F: The nucleotide sequence (SEQ ID NO:15) and amino acid sequences (SEQ ID NOS:16 and 17) of tetra-fusion protein DPV-MTI-MSL-MTCC2 (designated Mtb71f).

FIGS. 9A and 9B: The nucleotide sequence (SEQ ID NO:18) and amino acid sequences (SEQ ID NOS:19 and 20) of tri-fusion protein DPV-MTI-MSL (designated Mtb31f).

FIGS. 10A–10C: The nucleotide sequence (SEQ ID NO:21) and amino acid sequence (SEQ ID NO:22) of tri-fusion protein TbH9-DPV-MTI (designated Mtb61f).

FIGS. 11A and 11B: The nucleotide sequence (SEQ ID NO:23) and amino acid sequence (SEQ ID NO:24) of tri-fusion protein Erd14-DPV-MTI (designated Mtb36f).

FIGS. 12A–12C: The nucleotide sequence (SEQ ID NO:25) and amino acid sequence (SEQ ID NO:26) of bi-fusion protein TbH9-Ra35 (designated Mtb59f).

Figure 13A:
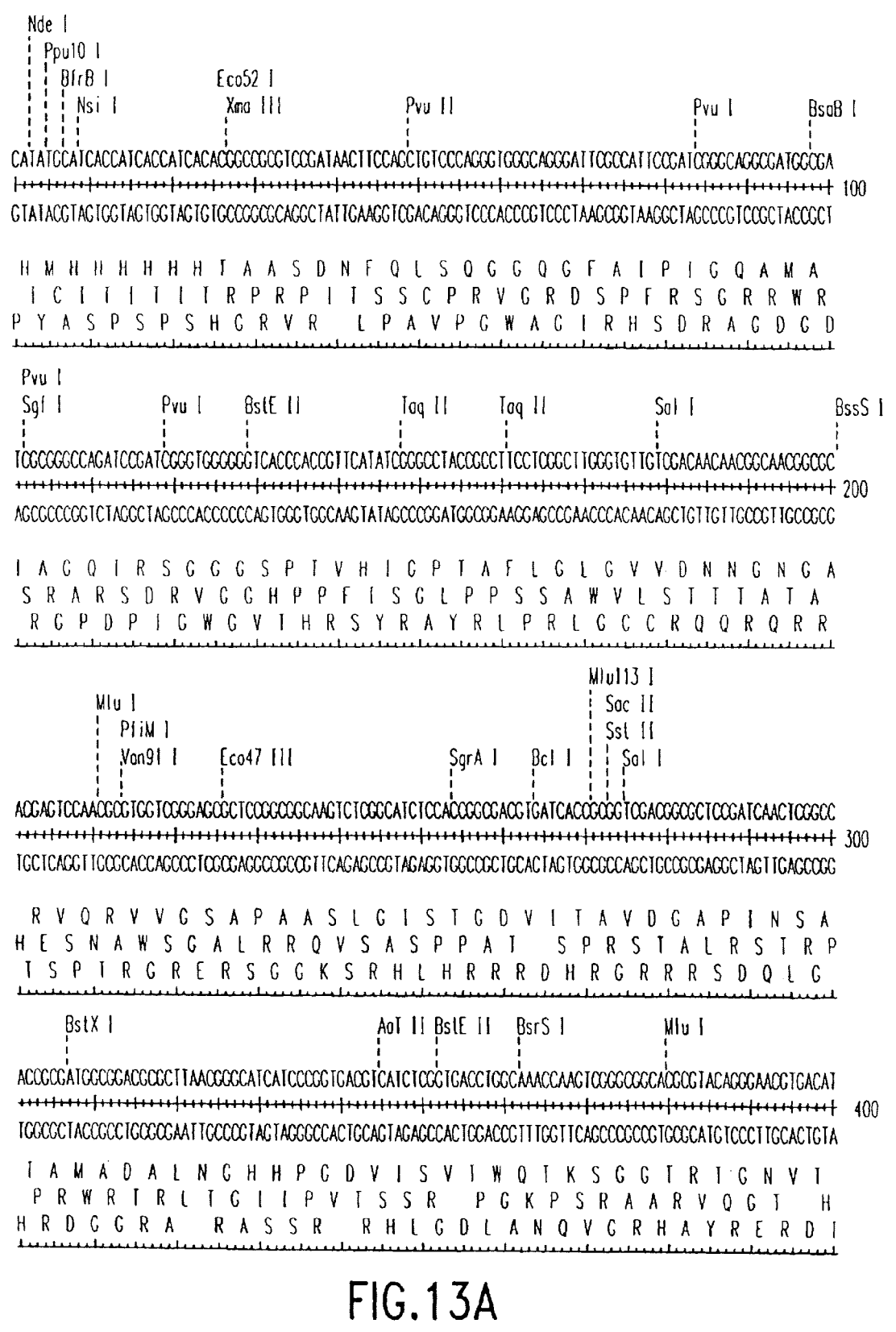

FIGS. 13A and 13B: The nucleotide sequence (SEQ ID NO:27) and amino acid sequences from three reading frames (SEQ ID NOS:28, 29–33 and 34–39, respectively) of bi-fusion protein Ra12-DPPD (designated Mtb24).

FIGS. 14A–14F: T cell proliferation responses of six PPD+ subjects when stimulated with two fusion proteins and their individual components.

FIGS. 15A–15F: IFN-γ production of six PPD+ subjects when stimulated with two fusion proteins and their individual components.

FIGS. 16A–16F: T cell proliferation of mice immunized with a fusion protein or its individual components and an adjuvant.

Figure 17:
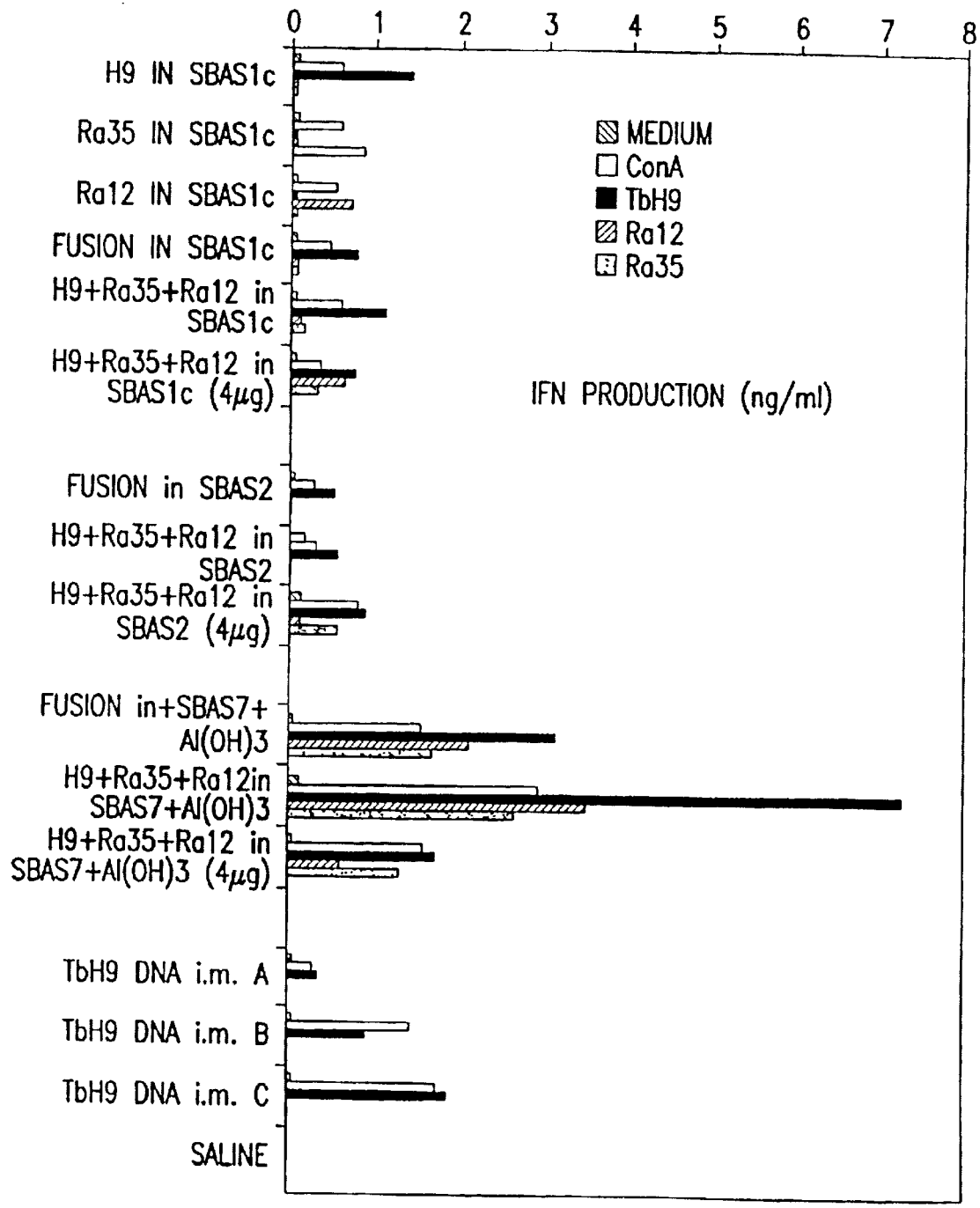

FIG. 17: IFN-γ production of mice immunized with a fusion protein or its individual components and an adjuvant.

Figure 18:
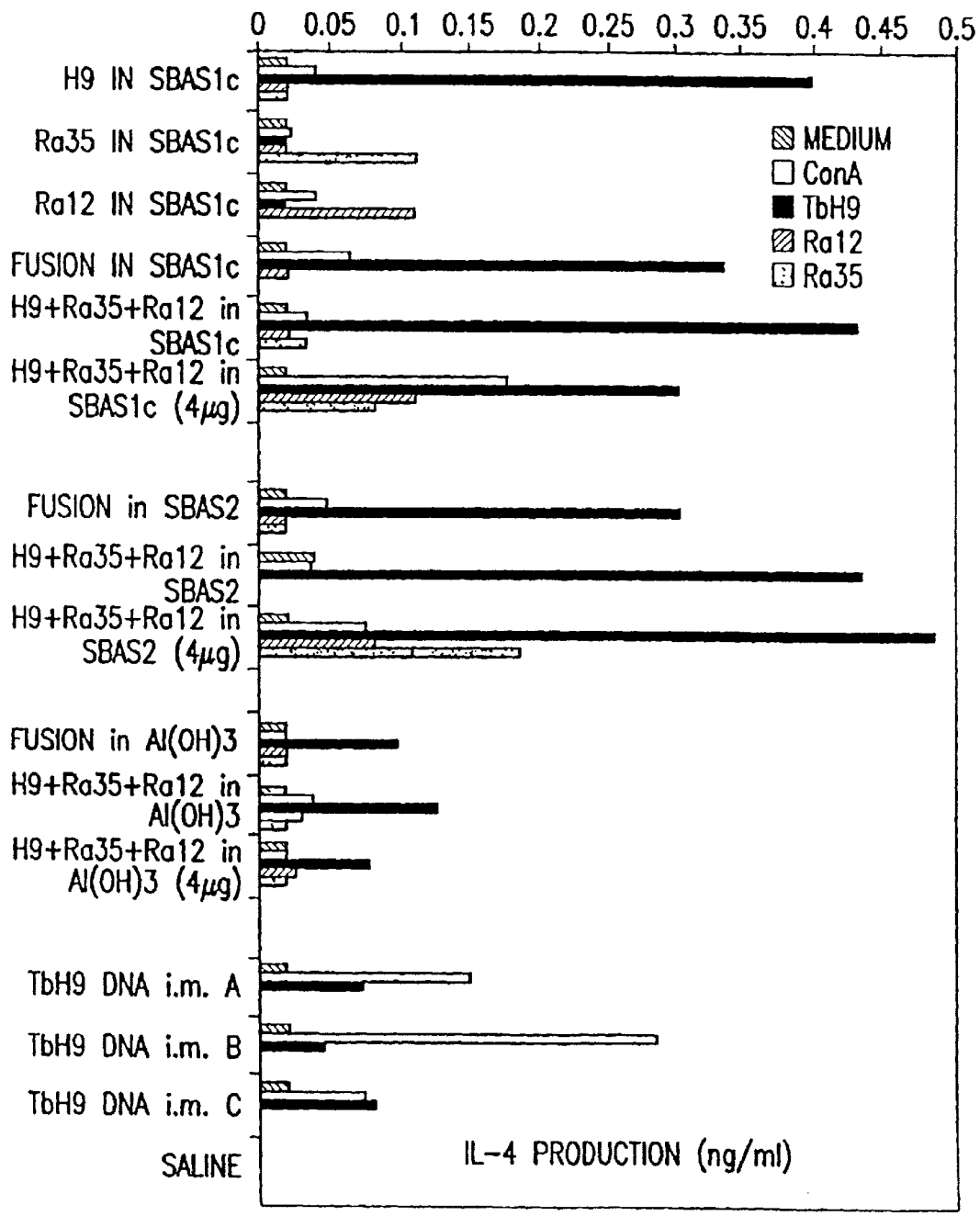
Figure 19A:
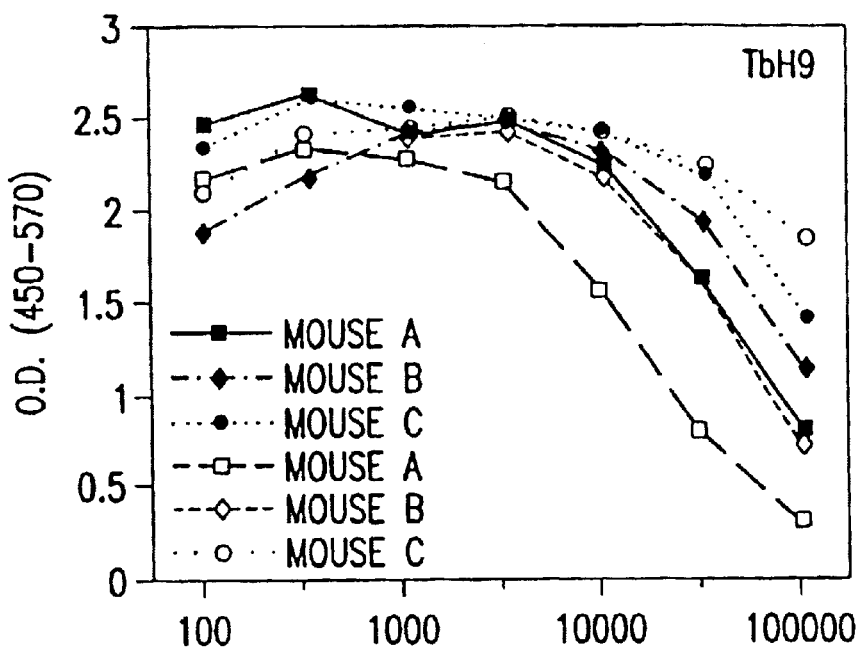
Figure 19B:
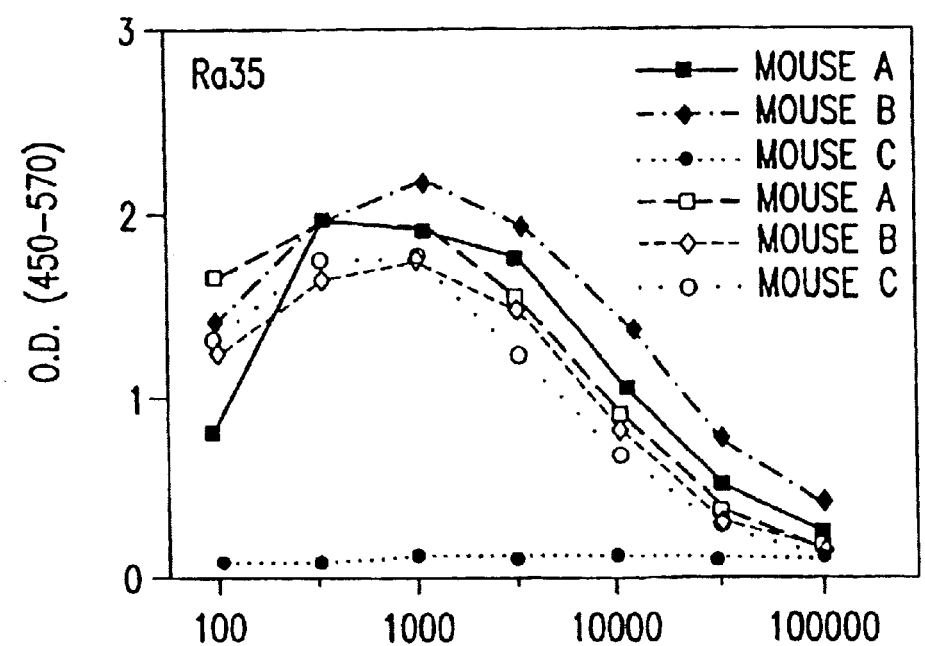
Figure 19C:
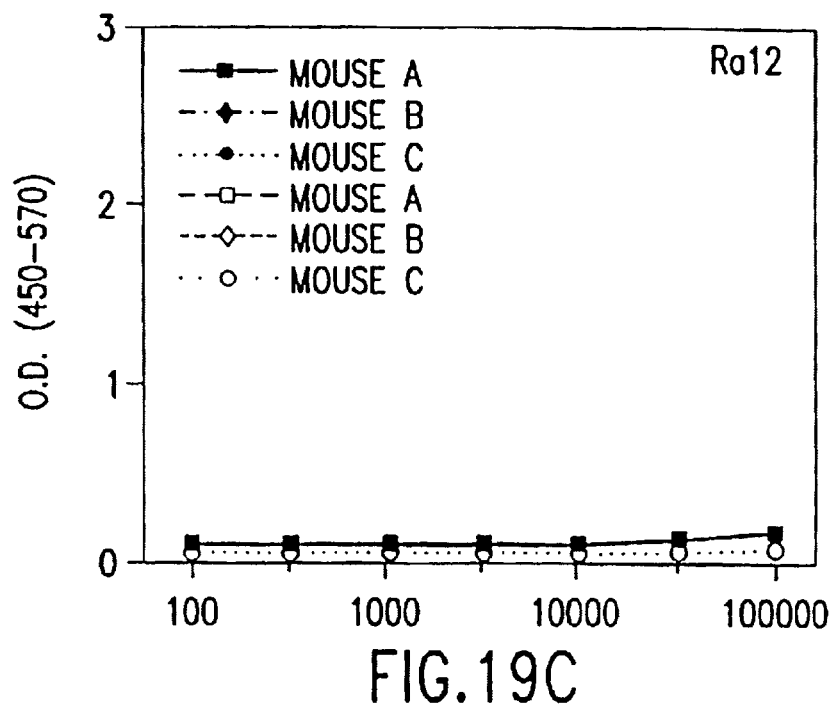
Figure 19D:
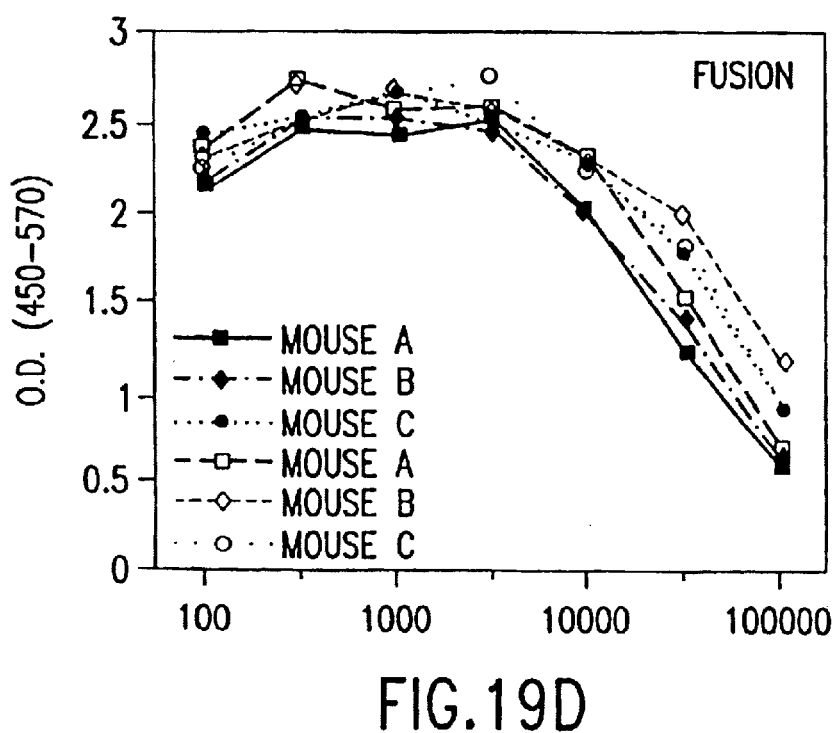
Figure 19E:
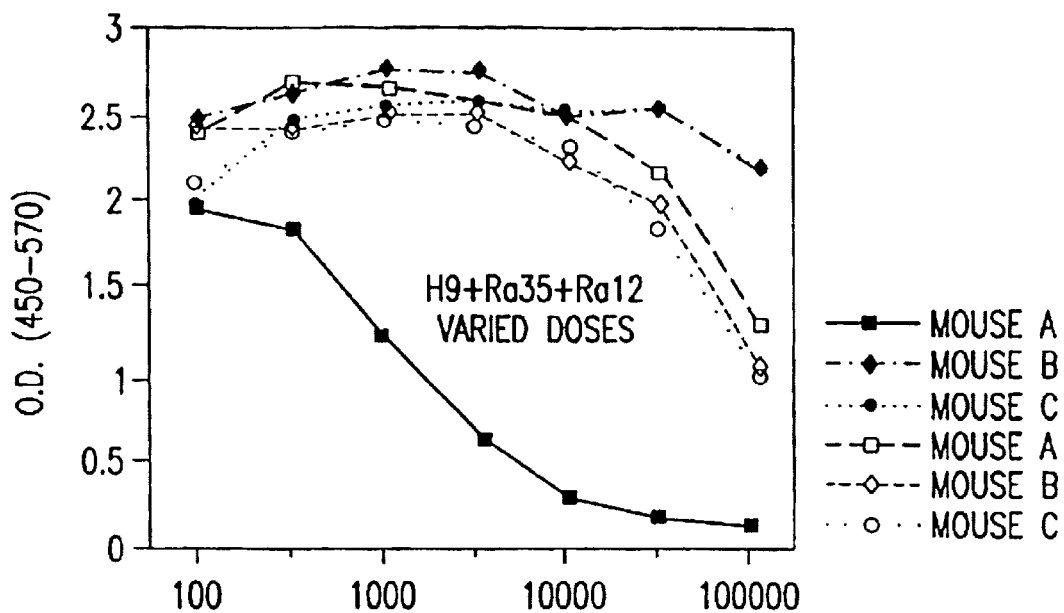
Figure 19F:
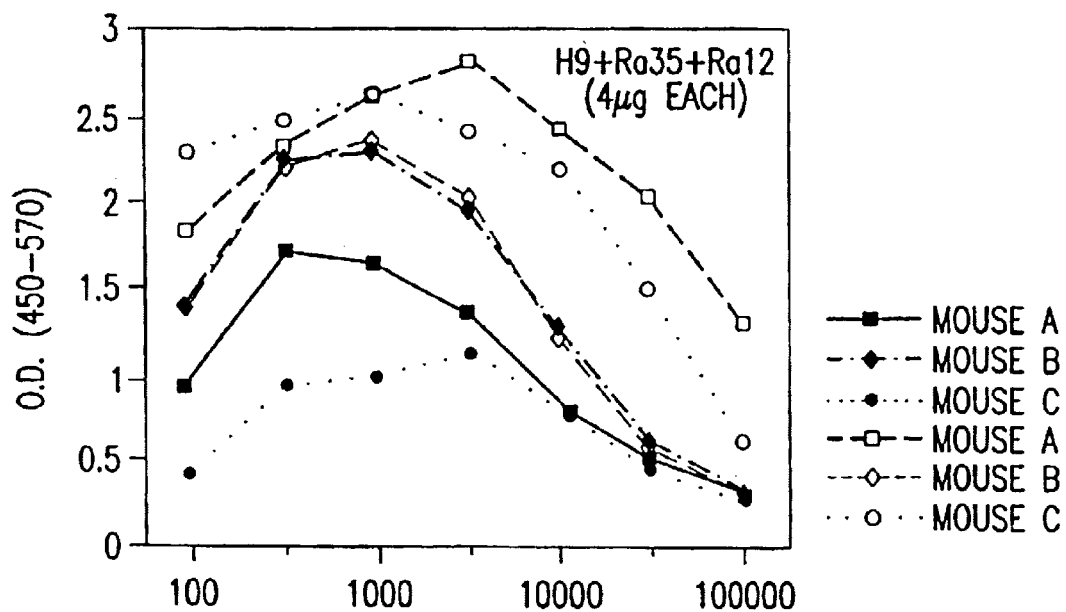

FIG. 18: IL-4 production of mice immunized with a fusion protein or its individual components and an adjuvant.

FIGS. 19A–19F: Serum antibody concentrations of mice immunized with a fusion protein or its individual components and an adjuvant.

Figure 20A:
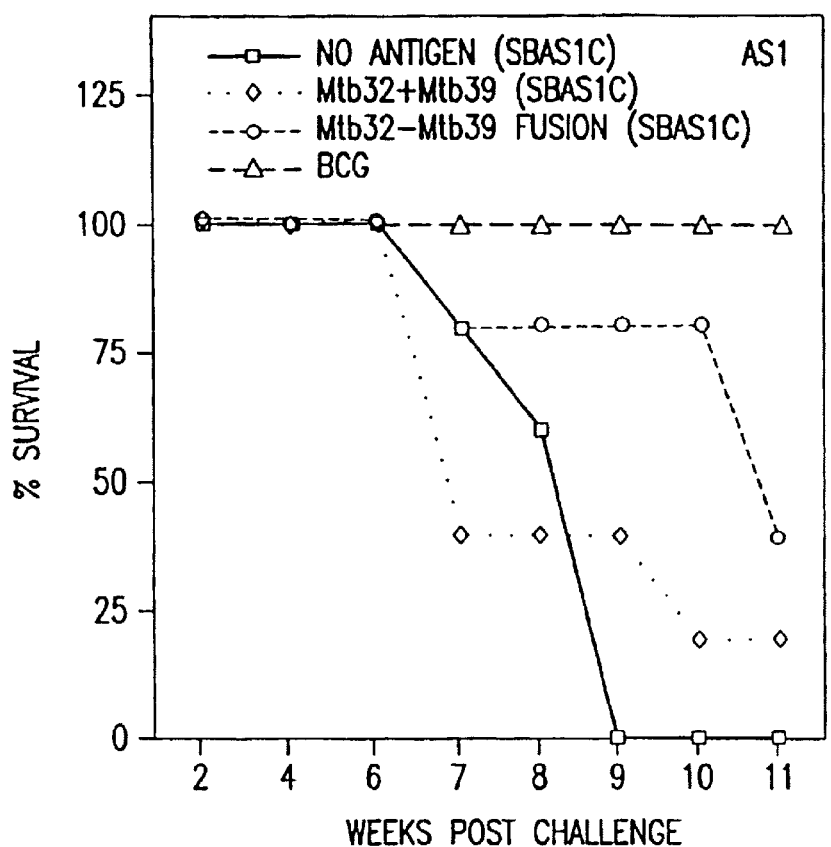
Figure 20B:
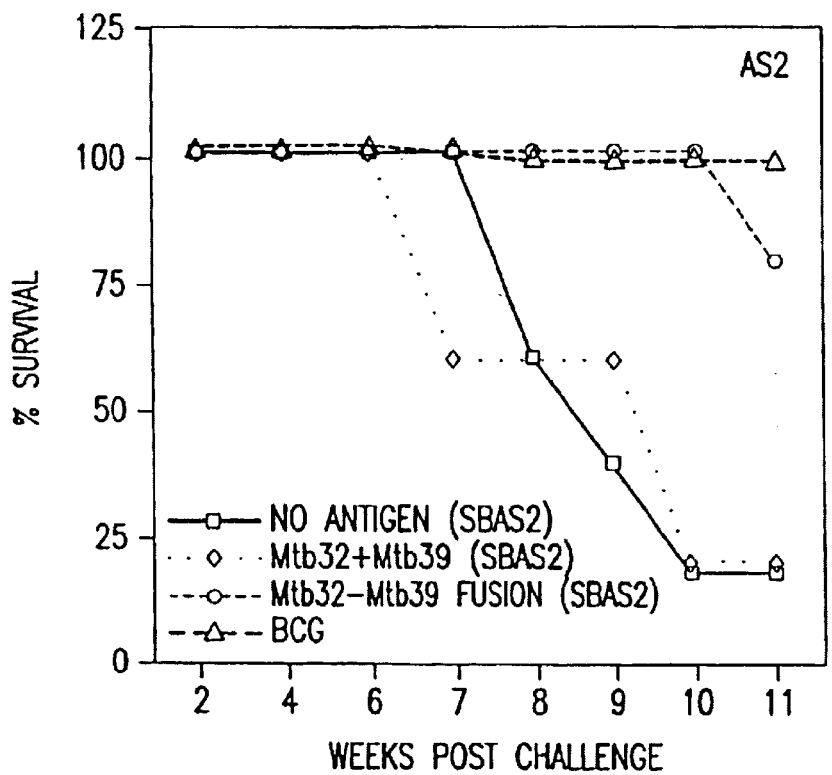
Figure 20C:
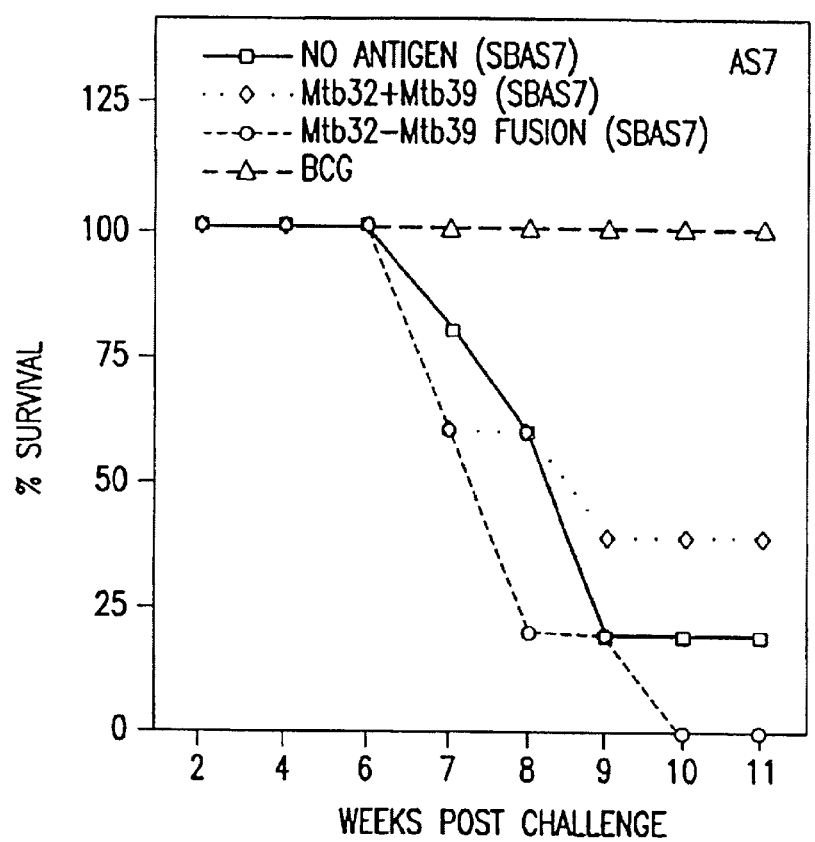

FIGS. 20A–20C: Survival of guinea pigs after aerosol challenge of *M. tuberculosis*. Fusion protein, Mtb32–Mtb39 fusion or a mixture of Mtb32A and Mtb39A, were formulated in adjuvant SBAS1c (20A), SBAS2 (20B) or SBAS7 (20C), and used as an immunogen in guinea pigs prior to challenge with bacteria. BCG is the positive control.

Figure 21A:
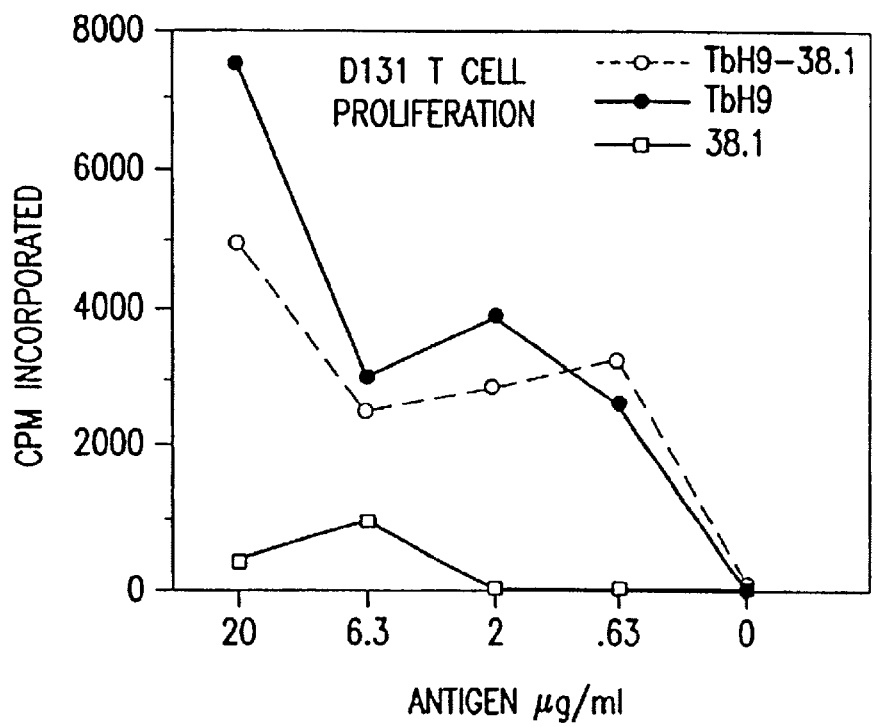
Figure 21B:
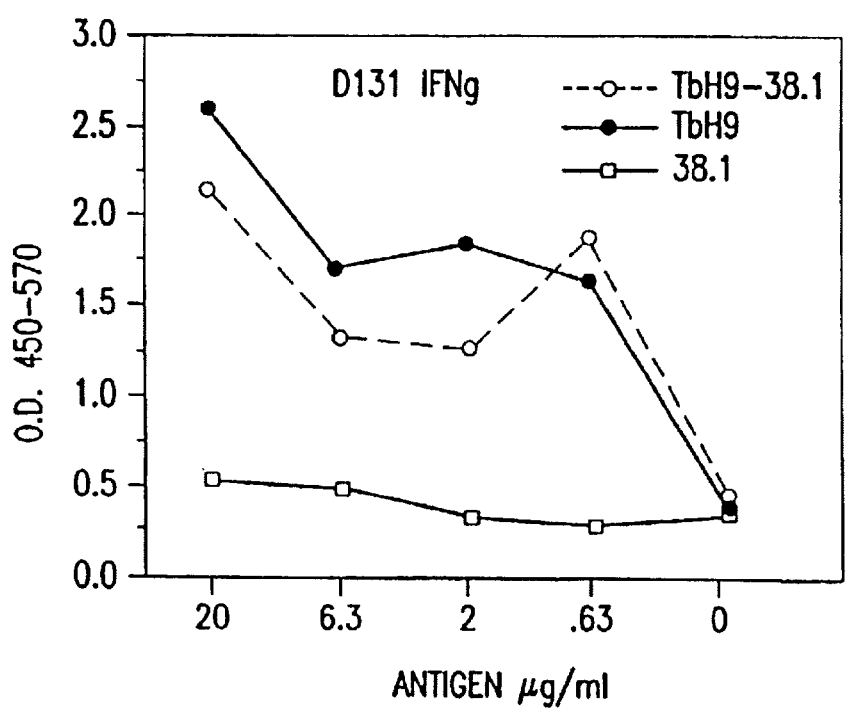

FIGS. 21A and 21B: Stimulation of proliferation and IFN-γ production in TbH9-specific T cells by the fusion protein TbH9-Tb38-1.

Figure 22A:
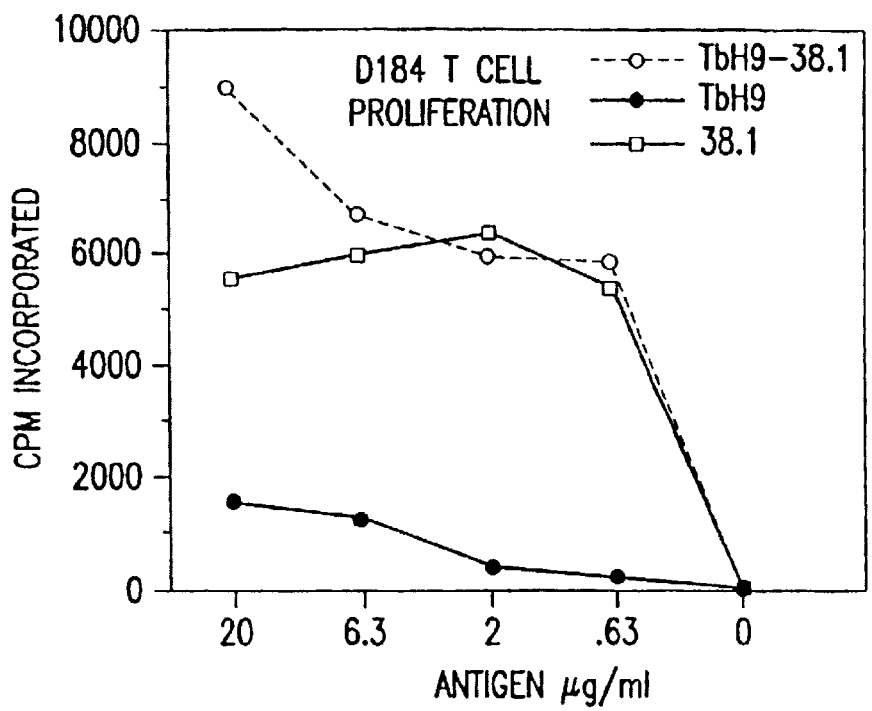
Figure 22B:
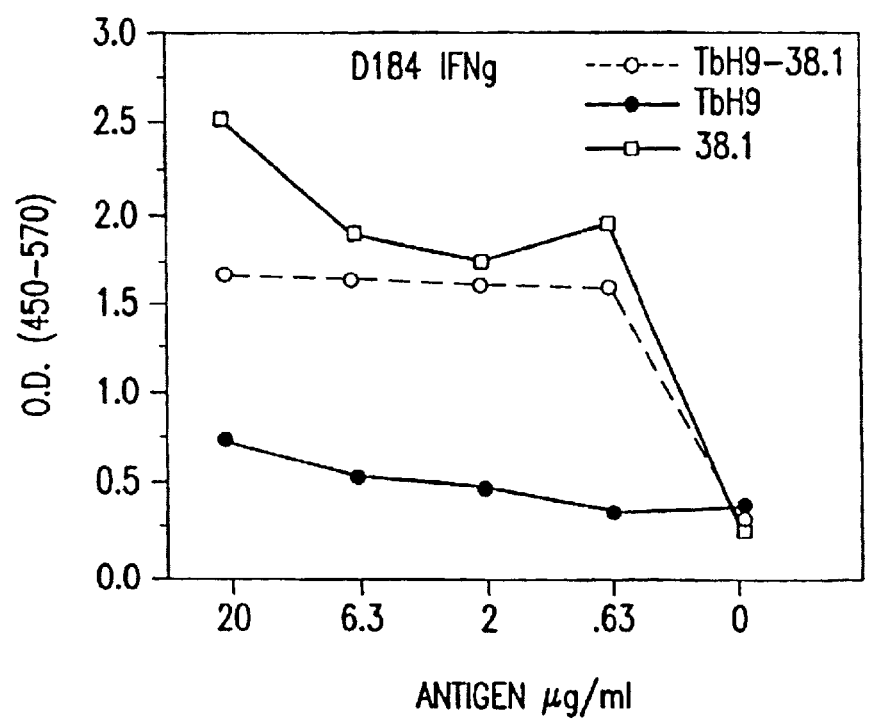

FIGS. 22A and 22B: Stimulation of proliferation and IFN-γ production in Tb38-1-specific T cells by the fusion protein TbH9-Tb38-1.

Figure 23A:
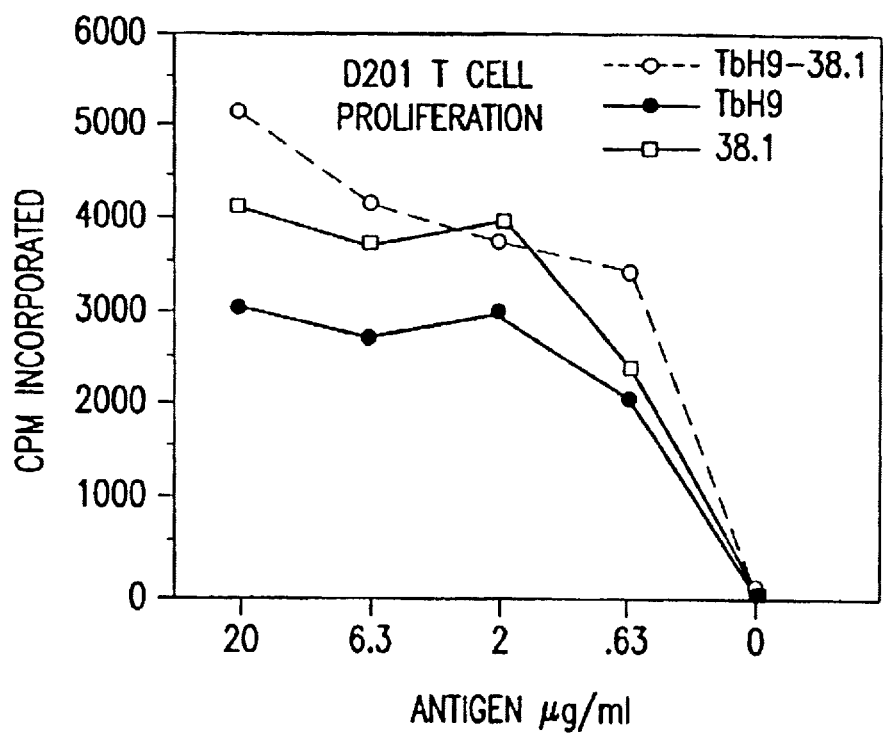
Figure 23B:
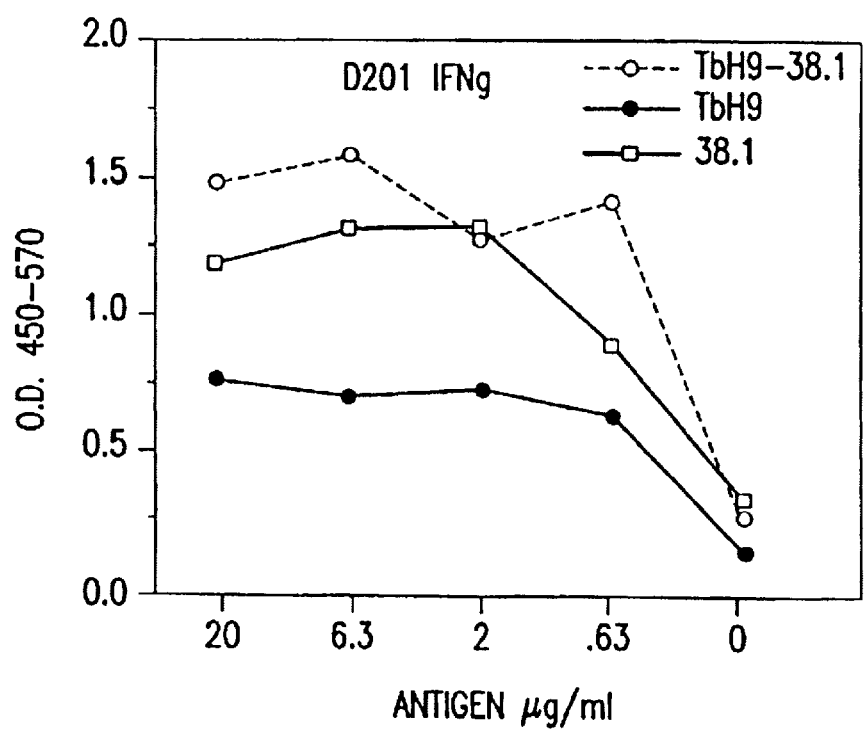

FIGS. 23A and 23B: Stimulation of proliferation and IFN-γ production in T cells previously shown to respond to both TbH-9 and Tb38-1 antigens by the fusion protein TbH9-Tb38-1.

5. DETAILED DESCRIPTION OF THE INVENTION

The present invention relates to antigens useful for the treatment and prevention of tuberculosis, polynucleotides encoding such antigens, and methods for their use. The antigens of the present invention are fusion polypeptides of *M. tuberculosis* antigens and variants thereof. More specifically, the antigens of the present invention comprise at least two polypeptides of *M. tuberculosis* that are fused into a larger fusion polypeptide molecule. The antigens of the present invention may further comprise other components designed to enhance the immunogenicity of the antigens or to improve these antigens in other aspects, for example, the isolation of these antigens through addition of a stretch of histidine residues at one end of the antigen.

5.1. *M. tuberculosis* Specific Antigens

The antigens of the present invention are exemplified in FIGS. 1A through 13B, including homologues and variants of those antigens. These antigens may be modified, for example, by adding linker peptide sequences as described below. These linker peptides may be inserted between one or more polypeptides which make up each of the fusion proteins presented in FIGS. 1A through 13B. Other antigens of the present invention are antigens described in FIGS. 1A through 13B which have been linked to a known antigen of *M. tuberculosis*, such as the previously described 38 kD (SEQ ID NO: 40) antigen (Andersen and Hansen, 1989, Infect. Immun. 57:2481–2488; Genbank Accession No. M30046).

5.2. Immunogenicity Assays

Antigens described herein, and immunogenic portions thereof, have the ability to induce an immunogenic response. More specifically, the antigens have the ability to induce proliferation and/or cytokine production (i.e., interferon-γ and/or interleukin-12 production) in T cells, NK cells, B cells and/or macrophages derived from an *M. tuberculosis*-immune individual. The selection of cell type for use in evaluating an immunogenic response to a antigen will depend on the desired response. For example, interleukin-12 production is most readily evaluated using preparations containing B cells and/or macrophages. An *M. tuberculosis*-immune individual is one who is considered to be resistant to the development of tuberculosis by virtue of having mounted an effective T cell response to M. tuberculosis (i.e., substantially free of disease symptoms). Such individuals may be identified based on a strongly positive (i.e., greater than about 10 mm diameter induration) intradermal skin test response to tuberculosis proteins (PPD) and an absence of any signs or symptoms of tuberculosis disease. T cells, NK cells, B cells and macrophages derived from M. tuberculosis-immune individuals may be prepared using methods known to those of ordinary skill in the art. For example, a preparation of PBMCs (i.e., peripheral blood mononuclear cells) may be employed without further separation of component cells. PBMCs may generally be prepared, for example, using density centrifugation through "FICOLL" (Winthrop Laboratories, N.Y). T cells for use in the assays described herein may also be purified directly from PBMCs. Alternatively, an enriched T cell line reactive against mycobacterial proteins, or T cell clones reactive to individual mycobacterial proteins, may be employed. Such T cell clones may be generated by, for example, culturing PBMCs from M. tuberculosis-immune individuals with mycobacterial proteins for a period of 2–4 weeks. This allows expansion of only the mycobacterial protein-specific T cells, resulting in a line composed solely of such cells. These cells may then be cloned and tested with individual proteins, using methods known to those of ordinary skill in the art, to more accurately define individual T cell specificity. In general, antigens that test positive in assays for proliferation and/or cytokine production (i.e., interferon-γ and/or interleukin-12 production) performed using T cells, NK cells, B cells and/or macrophages derived from an M. tuberculosis-immune individual are considered immunogenic. Such assays may be performed, for example, using the representative procedures described below. Immunogenic portions of such antigens may be identified using similar assays, and may be present within the polypeptides described herein.

The ability of a polypeptide (e.g., an immunogenic antigen, or a portion or other variant thereof) to induce cell proliferation is evaluated by contacting the cells (e.g., T cells and/or NK cells) with the polypeptide and measuring the proliferation of the cells. In general, the amount of polypeptide that is sufficient for evaluation of about $10^5$ cells ranges from about 10 ng/mL to about 100 μg/mL and preferably is about 10 μg/mL. The incubation of polypeptide with cells is typically performed at 37° C. for about six days. Following incubation with polypeptide, the cells are assayed for a proliferative response, which may be evaluated by methods known to those of ordinary skill in the art, such as exposing cells to a pulse of radiolabeled thymidine and measuring the incorporation of label into cellular DNA. In general, a polypeptide that results in at least a three fold increase in proliferation above background (i.e., the proliferation observed for cells cultured without polypeptide) is considered to be able to induce proliferation.

The ability of a polypeptide to stimulate the production of interferon-γ and/or interleukin-12 in cells may be evaluated by contacting the cells with the polypeptide and measuring the level of interferon-γ or interleukin-12 produced by the cells. In general, the amount of polypeptide that is sufficient for the evaluation of about $10^5$ cells ranges from about 10 ng/mL to about 100 μg/mL and preferably is about 10 μg/mL. The polypeptide may be, but need not be, immobilized on a solid support, such as a bead or a biodegradable microsphere, such as those described in U.S. Pat. Nos. 4,897,268 and 5,075,109. The incubation of polypeptide with the cells is typically performed at 37° C. for about six days. Following incubation with polypeptide, the cells are assayed for interferon-γ and/or interleukin-12 (or one or more subunits thereof), which may be evaluated by methods known to those of ordinary skill in the art, such as an enzyme-linked immunosorbent assay (ELISA) or, in the case of IL-12 P70 subunit, a bioassay such as an assay measuring proliferation of T cells. In general, a polypeptide that results in the production of at least 50 pg of interferon-γ per mL of cultured supernatant (containing $10^4$–$10^5$ T cells per mL) is considered able to stimulate the production of interferon-γ. A polypeptide that stimulates the production of at least 10 pg/mL of IL-12 P70 subunit, and/or at least 100 pg/mL of IL-12 P40 subunit, per $10^5$ macrophages or B cells (or per $3\times10^5$ PBMC) is considered able to stimulate the production of IL-12.

In general, immunogenic antigens are those antigens that stimulate proliferation and/or cytokine production (i.e., interferon-γ and/or interleukin-12 production) in T cells, NK cells, B cells and/or macrophages derived from at least about 25% of M. tuberculosis-immune individuals. Among these immunogenic antigens, polypeptides having superior therapeutic properties may be distinguished based on the magnitude of the responses in the above assays and based on the percentage of individuals for which a response is observed. In addition, antigens having superior therapeutic properties will not stimulate proliferation and/or cytokine production in vitro in cells derived from more than about 25% of individuals who are not M. tuberculosis-immune, thereby eliminating responses that are not specifically due to M. tuberculosis-responsive cells. Those antigens that induce a response in a high percentage of T cell, NK cell, B cell and/or macrophage preparations from M. tuberculosis-immune individuals (with a low incidence of responses in cell preparations from other individuals) have superior therapeutic properties.

Antigens with superior therapeutic properties may also be identified based on their ability to diminish the severity of M. tuberculosis infection in experimental animals, when administered as a vaccine. Suitable vaccine preparations for use on experimental animals are described in detail below. Efficacy may be determined based on the ability of the antigen to provide at least about a 50% reduction in bacterial numbers and/or at least about a 40% decrease in mortality following experimental infection. Suitable experimental animals include mice, guinea pigs and primates.

5.3. Isolation of Coding Sequences

The present invention also relates to nucleic acid molecules that encode fusion polypeptides of M. tuberculosis. In a specific embodiment by way of example in Section 6, infra, thirteen M. tuberculosis fusion coding sequences were constructed. In accordance with the invention, any nucleotide sequence which encodes the amino acid sequence of the fusion protein can be used to generate recombinant molecules which direct the expression of the coding sequence.

In order to clone full-length coding sequences or homologous variants to generate the fusion polynucleotides, labeled DNA probes designed from any portion of the nucleotide sequences or their complements disclosed herein may be used to screen a genomic or cDNA library made from various strains of M. tuberculosis to identify the coding sequence of each individual component. Isolation of coding sequences may also be carried out by the polymerase chain reactions (PCR) using two degenerate oligonucleotide primer pools designed on the basis of the coding sequences disclosed herein.

The invention also relates to isolated or purified polynucleotides complementary to the nucleotide sequences of SEQ ID NOS:1, 3, 5, 7, 9, 11, 13, 15, 18, 21, 23, 25 and 27, and polynucleotides that selectively hybridize to such complementary sequences. In a preferred embodiment, a polynucleotide which hybridizes to the sequence of SEQ ID NOS:1, 3, 5, 7, 9, 11, 13, 15, 18, 21, 23, 25 and 27 or its complementary sequence under conditions of low stringency and encodes a protein that retains the immunogenicity of the fusion proteins of SEQ ID NOS:2, 4, 6, 8, 10, 12, 14, 16, 19, 22, 24, 26 and 28 is provided. By way of example and not limitation, exemplary conditions of low stringency are as follows (see also Shilo and Weinberg, 1981, Proc. Natl. Acad. Sci. USA 78:6789–6792): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and re-exposed to film. Other conditions of low stringency which may be used are well known in the art (e.g., as employed for cross-species hybridizations).

In another preferred embodiment, a polynucleotide which hybridizes to the coding sequence of SEQ ID NOS:1, 3, 5, 7, 9, 11, 13, 15, 18, 21, 23, 25 and 27 or its complementary sequence under conditions of high stringency and encodes a protein that retains the immunogenicity of the fusion proteins of SEQ ID NOS:2, 4, 6, 8, 10, 12, 14, 16, 19, 22, 24, 26 and 28 is provided. By way of example and not limitation, exemplary conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/mL denatured salmon sperm DNA. Filters are hybridized for 48 h at 65° C. in prehybridization mixture containing 100 µg/mL denatured salmon sperm DNA and 5–20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

In yet another preferred embodiment, a polynucleotide which hybridizes to the coding sequence of SEQ ID NOS:1, 3, 5, 7, 9, 11, 13, 15, 18, 21, 23, 25 and 27 or its complementary sequence under conditions of moderate stringency and encodes a protein that retains the immunogenicity of the fusion proteins of SEQ ID NOS:2, 4, 6, 8, 10, 12, 14, 16, 19, 22, 24, 26 and 28 is provided. Exemplary conditions of moderate stringency are as follows: Filters containing DNA are pretreated for 6 h at 55° C. in a solution containing 6×SSC, 5× Denhart's solution, 0.5% SDS and 100 µg/mL denatured salmon sperm DNA. Hybridizations are carried out in the same solution and 5–20×10$^6$ cpm $^{32}$P-labeled probe is used. Filters are incubated in hybridization mixture for 18–20 h at 55° C., and then washed twice for 30 minutes at 60° C. in a solution containing 6×SSC and 0.1% SDS. Filters are blotted dry and exposed for autoradiography. Other conditions of moderate stringency which may be used are well-known in the art. Washing of filters is done at 37° C. for 1 h in a solution containing 2×SSC, 0.1% SDS.

5.4. Polypeptides Encoded by the Coding Sequences

In accordance with the invention, a polynucleotide of the invention which encodes a fusion protein, fragments thereof, or functional equivalents thereof may be used to generate recombinant nucleic acid molecules that direct the expression of the fusion protein, fragments thereof, or functional equivalents thereof, in appropriate host cells. The fusion polypeptide products encoded by such polynucleotides may be altered by molecular manipulation of the coding sequence.

Due to the inherent degeneracy of the genetic code, other DNA sequences which encode substantially the same or a functionally equivalent amino acid sequence, may be used in the practice of the invention for the expression of the fusion polypeptides. Such DNA sequences include those which are capable of hybridizing to the coding sequences or their complements disclosed herein under low, moderate or high stringency conditions described in Sections 5.3, supra.

Altered nucleotide sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues, which result in a silent change thus producing a functionally equivalent antigenic epitope. Such conservative amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine, histidine and arginine; amino acids with uncharged polar head groups having similar hydrophilicity values include the following: glycine, asparagine, glutamine, serine, threonine and tyrosine; and amino acids with nonpolar head groups include alanine, valine, isoleucine, leucine, phenylalanine, proline, methionine and tryptophan.

The nucleotide sequences of the invention may be engineered in order to alter the fusion protein coding sequence for a variety of ends, including but not limited to, alterations which modify processing and expression of the gene product. For example, mutations may be introduced using techniques which are well known in the art, e.g., site-directed mutagenesis, to insert new restriction sites, to alter glycosylation patterns, phosphorylation, etc.

In an alternate embodiment of the invention, the coding sequence of a fusion protein could be synthesized in whole or in part, using chemical methods well known in the art. See, e.g., Caruthers et al., 1980, Nuc. Acids Res. Symp. Ser. 7:215–233; Crea and Horn, 180, Nuc. Acids Res. 9(10):2331; Matteucci and Caruthers, 1980, Tetrahedron Letter 21:719; and Chow and Kempe, 1981, Nuc. Acids Res. 9(12):2807–2817. Alternatively, the polypeptide itself could be produced using chemical methods to synthesize an amino acid sequence in whole or in part. For example, peptides can be synthesized by solid phase techniques, cleaved from the resin, and purified by preparative high performance liquid chromatography. (See Creighton, 1983, Proteins Structures And Molecular Principles, W. H. Freeman and Co., N.Y. pp. 50–60). The composition of the synthetic polypeptides may be confirmed by amino acid analysis or sequencing (e.g., the Edman degradation procedure; see Creighton, 1983, *Proteins, Structures and Molecular Principles,* W. H. Freeman and Co., N.Y., pp. 34–49).

Additionally, the coding sequence of a fusion protein can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson, C., et al., 1978, J. Biol. Chem 253:6551), use of TAB® linkers (Pharmacia), and the like. It is important that the manipulations do not destroy immunogenicity of the fusion polypeptides.

In addition, nonclassical amino acids or chemical amino acid analogs can be introduced as a substitution or addition into the sequence. Non-classical amino acids include, but are not limited to, the D-isomers of the common amino acids, α-amino isobutyric acid, 4-aminobutyric acid, Abu, 2-amino butyric acid, γ-Abu, E-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In a specific embodiment, the coding sequences of each antigen in the fusion protein are joined at their amino- or carboxy-terminus via a peptide bond in any order. Alternatively, a peptide linker sequence may be employed to separate the individual polypeptides that make-up a fusion polypeptide by a distance sufficient to ensure that each polypeptide folds into a secondary and tertiary structure that maximizes its antigenic effectiveness for preventing and treating tuberculosis. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39–46, 1985; Murphy et al., Proc. Natl. Acad. Sci. USA 83:8258–8262, 1986; U.S. Pat. No. 4,935,233 and U.S. Pat. No. 4,751,10. The linker sequence may be from 1 to about 50 amino acids in length. Peptide sequences are not required when the first and second polypeptides have non-essential N-terminal amino acid regions that can be used to separate the functional domains and prevent steric interference. For example, the antigens in a fusion protein may be connected by a flexible polylinker such as Gly-Cys-Gly or Gly-Gly-Gly-Gly-Ser repeated 1 to 3 times (SEQ ID NOS:41–43 and 44–46, respectively) (Bird et al., 1988, Science 242:423–426; Chaudhary et al., 1990, Proc. Natl. Acad. Sci. U.S.A. 87:1066–1070).

In one embodiment, such a protein is produced by recombinant expression of a nucleic acid encoding the protein. Such a fusion product can be made by ligating the appropriate nucleic acid sequences encoding the desired amino acid sequences to each other by methods known in the art, in the proper coding frame, and expressing the product by methods known in the art. Alternatively, such a product may be made by protein synthetic techniques, e.g., by use of a peptide synthesizer. Coding sequences for other molecules such as a cytokine or an adjuvant can be added to the fusion polynucleotide as well.

5.5. Production of Fusion Proteins

In order to produce a *M. tuberculosis* fusion protein of the invention, the nucleotide sequence coding for the protein, or a functional equivalent, is inserted into an appropriate expression vector, i.e., a vector which contains the necessary elements for the transcription and translation of the inserted coding sequence. The host cells or cell lines transfected or transformed with recombinant expression vectors can be used for a variety of purposes. These include, but are not limited to, large scale production of the fusion protein.

Methods which are well known to those skilled in the art can be used to construct expression vectors containing a fusion coding sequence and appropriate transcriptional/translational control signals. These methods include in vitro recombinant DNA techniques, synthetic techniques and in vivo recombination/genetic recombination. (See, e.g., the techniques described in Sambrook et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.). RNA capable of encoding a polypeptide may also be chemically synthesized (Gait, 30 ed, 1984, Oligonucleoide Synthesis, IRL Press, Oxford).

5.5.1. Expression Systems

A variety of host-expression vector systems may be utilized to express a fusion protein coding sequence. These include, but are not limited to, microorganisms such as bacteria (e.g., *E. coli, B. subtilis*) transformed with recombinant bacteriophage DNA, plasmid DNA or cosmid DNA expression vectors containing a coding sequence; yeast (e.g., *Saccharomycdes, Pichia*) transformed with recombinant yeast expression vectors containing a coding sequence; insect cell systems infected with recombinant virus expression vectors (e.g., baculovirus) containing a coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a coding sequence; or mammalian cell systems (e.g., COS, CHO, BHK, 293, 3T3 cells). The expression elements of these systems vary in their strength and specificities.

Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter; cytomegalovirus promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll α/β binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of a the antigen coding sequence, SV40-, BPV- and EBV-based vectors may be used with an appropriate selectable marker.

Bacterial systems are preferred for the expression of *M. tuberculosis* antigens. For in vivo delivery, a bacterium such as Bacillus-Calmette-Guerrin may be engineered to express a fusion polypeptide of the invention on its cell surface. A number of other bacterial expression vectors may be advantageously selected depending upon the use intended for the expressed products. For example, when large quantities of the fusion protein are to be produced for formulation of pharmaceutical compositions, vectors which direct the expression of high levels of fusion protein products that are readily purified may be desirable. Such vectors include, but are not limited to, the *E. coli* expression vector pUR278 (Ruther et al., 1983, EMBO J. 2:1791), in which a coding sequence may be ligated into the vector in frame with the lacZ coding region so that a hybrid protein is produced; pIN vectors (Inouye and Inouye, 1985, Nucleic Acids Res. 13:3101–3109; Van Heeke and Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can be purified easily from lysed cells by adsorption to glutathione-agarose beads followed by elution in the presence of free glutathione. The pGEX vectors are designed to include thrombin or factor Xa protease cleavage sites so that the cloned fusion polypeptide of interest can be released from the GST moiety.

5.5.2. Protein Purification

Once a recombinant protein is expressed, it can be identified by assays based on the physical or functional properties of the product, including radioactive labeling of the product followed by analysis by gel electrophoresis, radioimmunoassay, ELISA, bioassays, etc.

Once the encoded protein is identified, it may be isolated and purified by standard methods including chromatography (e.g., high performance liquid chromatography, ion exchange, affinity, and sizing column chromatography), centrifugation, differential solubility, or by any other standard technique for the purification of proteins. The actual conditions used will depend, in part, on factors such as net charge, hydrophobicity, hydrophilicity, etc., and will be apparent to those having skill in the art. The functional properties may be evaluated using any suitable assay such as antibody binding, induction of T cell proliferation, stimulation of cytokine production such as IL2, IL-4 and IFN-γ. For the practice of the present invention, it is preferred that each fusion protein is at least 80% purified from other proteins. It is more preferred that they are at least 90% purified. For in vivo administration, it is preferred that the proteins are greater than 95% purified.

5.6. Uses of the Fusion Protein Coding Sequence

The fusion protein coding sequence of the invention may be used to encode a protein product for use as an immunogen to induce and/or enhance immune responses to *M. tuberculosis*. In addition, such coding sequence may be ligated with a coding sequence of another molecule such as cytokine or an adjuvant. Such polynucleotides may be used in vivo as a DNA vaccine (U.S. Pat. Nos. 5,589,466; 5,679,647; 5,703,055). In this embodiment of the invention, the polynucleotide expresses its encoded protein in a recipient to directly induce an immune response. The polynucleotide may be injected into a naive subject to prime an immune response to its encoded product, or administered to an infected or immunized subject to enhance the secondary immune responses.

In a preferred embodiment, a therapeutic composition comprises a fusion protein coding sequence or fragments thereof that is part of an expression vector. In particular, such a polynucleotide contains a promoter operably linked to the coding region, said promoter being inducible or constitutive, and, optionally, tissue-specific. In another embodiment, a polynucleotide contains a coding sequence flanked by regions that promote homologous recombination at a desired site in the genome, thus providing for intrachromosomal expression of the coding sequence (Koller and Smithies, 1989, Proc. Natl. Acad. Sci. USA 86:8932–8935; Zijlstra et al., 1989, Nature 342:435–438).

Delivery of the nucleic acid into a subject may be either direct, in which case the subject is directly exposed to the nucleic acid or nucleic acid-carrying vector, or indirect, in which case, cells are first transformed with the nucleic acid in vitro, then transplanted into the subject. These two approaches are known, respectively, as in vivo or ex vivo gene transfer.

In a specific embodiment, the nucleic acid is directly administered in vivo, where it is expressed to produce the encoded fusion protein product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see, U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules (U.S. Pat. Nos. 5,407,609; 5,853,763; 5,814,344 and 5,820,883), or by administering it in linkage to a peptide which is known to enter the nucleus, by administering it in linkage to a ligand subject to receptor-mediated endocytosis (see, e.g., Wu and Wu, 1987, J. Biol. Chem. 262:4429–4432) which can be used to target cell types specifically expressing the receptors, etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992; WO 92/22635 dated Dec. 23, 1992; WO92/20316 dated Nov. 26, 1992; WO93/14188 dated Jul. 22, 1993; WO 93/20221 dated Oct. 14, 1993). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342:435–438).

In a specific embodiment, a viral vector such as a retroviral vector can be used (see, Miller et al., 1993, Meth. Enzymol. 217:581–599). Retroviral vectors have been modified to delete retroviral sequences that are not necessary for packaging of the viral genome and integration into host cell DNA. A fusion coding sequence is cloned into the vector, which facilitates delivery of the nucleic acid into a recipient. More detail about retroviral vectors can be found in Boesen et al., 1994, Biotherapy 6:291–302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Adeno-associated virus (AAV) has also been proposed for use in in vivo gene transfer (Walsh et al., 1993, Proc. Soc. Exp. Biol. Med. 204:289–300.

Another approach involves transferring a construct to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599–618; Cohen et al., 1993, Meth. Enzymol. 217:618–644; Cline, 1985, Pharmac. Ther. 29:69–92) and may be used in accordance with the present invention.

The polynucleotides of the invention may also be used in the diagnosis of tuberculosis for detection of polynucleotide sequences specific to M. tuberculosis in a patient. Such detection may be accomplished, for example, by isolating polynucleotides from a biological sample obtained from a patient suspected of being infected with the bacteria. Upon isolation of polynucleotides from the biological sample, a labeled polynucleotide of the invention that is complementary to one or more of the polynucleotides, will be allowed to hybridize to polynucleotides in the biological sample using techniques of nucleic acid hybridization known to those of ordinary skill in the art. For example, such hybridization may be carried out in solution or with one hybridization partner on a solid support.

5.7. Therapeutic and Prophylactic Uses of the Fusion Protein

Purified or partially purified fusion proteins or fragments thereof may be formulated as a vaccine or therapeutic composition. Such composition may include adjuvants to enhance immune responses. In addition, such proteins may be further suspended in an oil emulsion to cause a slower release of the proteins in vivo upon injection. The optimal ratios of each component in the formulation may be determined by techniques well known to those skilled in the art.

Any of a variety of adjuvants may be employed in the vaccines of this invention to enhance the immune response. Most adjuvants contain a substance designed to protect the antigen from rapid catabolism, such as aluminum hydroxide or mineral oil, and a specific or nonspecific stimulator of immune responses, such as lipid A, *Bortadella pertussis* or *Mycobacterium tuberculosis.* Suitable adjuvants are commercially available and include, for example, Freund's Incomplete Adjuvant and Freund's Complete Adjuvant (Difco Laboratories) and Merck Adjuvant 65 (Merck and Company, Inc., Rahway, N.J.). Other suitable adjuvants include alum, biodegradable microspheres, monophosphoryl lipid A, quil A, SBAS1c, SBAS2 (Ling et al., 1997, Vaccine 15:1562–1567), SBAS7, $Al(OH)_3$ and CpG oligonucleotide (WO96/02555).

In the vaccines of the present invention, it is preferred that the adjuvant induces an immune response comprising Th1 aspects. Suitable adjuvant systems include, for example, a combination of monophosphoryl lipid A, preferably 3-de-O-acylated monophosphoryl lipid A (3D-MPL) together with an aluminum salt. An enhanced system involves the combination of a monophosphoryl lipid A and a saponin derivative, particularly the combination of 3D-MLP and the saponin QS21 as disclosed in WO 94/00153, or a less reactogenic composition where the QS21 is quenched with cholesterol as disclosed in WO 96/33739. Previous experiments have demonstrated a clear synergistic effect of combinations of 3D-MLP and QS21 in the induction of both humoral and Th1 type cellular immune responses. A particularly potent adjuvant formation involving QS21, 3D-MLP and tocopherol in an oil-in-water emulsion is described in WO 95/17210 and is a preferred formulation.

Formulations containing an antigen of the present invention may be administered to a subject per se or in the form of a pharmaceutical or therapeutic composition. Pharmaceutical compositions comprising the proteins may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the polypeptides into preparations which can be used pharmaceutically. Proper formulation is dependent upon the route of administration chosen.

For topical administration, the proteins may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injection, the proteins may be formulated in aqueous solutions, preferably in physiologically compatible buffers such as Hanks's solution, Ringer's solution, or physiological saline buffer. The solution may contain formulatory agents such as suspending, stabilizing and/or dispersing agents. Alternatively, the proteins may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, a composition can be readily formulated by combining the proteins with pharmaceutically acceptable carriers well known in the art. Such carriers enable the proteins to be formulated as tablets, pills, dragees, capsules, liquids, gels, syrups, slurries, suspensions and the like, for oral ingestion by a subject to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the proteins may take the form of tablets, lozenges, etc. formulated in conventional manner.

For administration by inhalation, the proteins for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the proteins and a suitable powder base such as lactose or starch.

The proteins may also be formulated in rectal or vaginal compositions such as suppositories or retention enemas, e.g., containing conventional suppository bases such as cocoa butter or other glycerides.

In addition to the formulations described previously, the proteins may also be formulated as a depot preparation. Such long acting formulations may be administered by implantation (for example subcutaneously or intramuscularly) or by intramuscular injection. Thus, for example, the proteins may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver an antigen. Certain organic solvents such as dimethylsulfoxide also may be employed, although usually at the cost of greater toxicity. The fusion proteins may also be encapsulated in microspheres (U.S. Pat. Nos. 5,407,609; 5,853,763; 5,814,344 and 5,820,883). Additionally, the proteins may be delivered using a sustained-release system, such as semipermeable matrices of solid polymers containing the therapeutic or vaccinating agent. Various sustained-release materials have been established and are well known by those skilled in the art. Sustained-release capsules may, depending on their chemical nature, release the proteins for a few weeks up to over 100 days. Depending on the chemical nature and the biological stability of the reagent, additional strategies for protein stabilization may be employed.

Determination of an effective amount of the fusion protein for inducing an immune response in a subject is well within the capabilities of those skilled in the art, especially in light of the detailed disclosure provided herein.

An effective dose can be estimated initially from in vitro assays. For example, a dose can be formulated in animal models to achieve an induction of an immune response using techniques that are well known in the art. One having ordinary skill in the art could readily optimize administration to humans based on animal data. Dosage amount and interval may be adjusted individually. For example, when used as a vaccine, the polypeptides and/or polynucleotides of the invention may be administered in about 1 to 3 doses for a 1–36 week period. Preferably, 3 doses are administered, at intervals of about 3–4 months, and booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from *M. tuberculosis* infection for at least 1–2 years. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 μg. Suitable dose range will vary with the size of the patient, but will typically range from about 0.1 mL to about 5 mL.

5.8 Diagnostic Uses of the Fusion Protein

The fusion polypeptides of the invention are useful in the diagnosis of tuberculosis infection in vitro and in vivo. The ability of a polypeptide of the invention to induce cell proliferation or cytokine production can be assayed by the methods disclosed in Section 5.2, supra.

In another aspect, this invention provides methods for using one or more of the fusion polypeptides to diagnose tuberculosis using a skin test in vivo. As used herein, a skin test is any assay performed directly on a patient in which a delayed-type hypersensitivity (DTH) reaction (such as swelling, reddening or dermatitis) is measured following intradermal injection of one or more polypeptides as described above. Such injection may be achieved using any suitable device sufficient to contact the polypeptide with dermal cells of the patient, such as, for example, a tuberculin syringe or 1 mL syringe. Preferably, the reaction is measured at least about 48 hours after injection, more preferably about 48 to about 72 hours after injection.

The DTH reaction is a cell-mediated immune response, which is greater in patients that have been exposed previously to the test antigen (i.e., the immunogenic portion of the polypeptide employed, or a variant thereof). The response may be measured visually, using a ruler. In general, a response that is greater than about 0.5 cm in diameter, preferably greater than about 1.0 cm in diameter, is a positive response, indicative of tuberculosis infection, which may or may not be manifested as an active disease.

The fusion polypeptides of this invention are preferably formulated, for use in a skin test, as pharmaceutical compositions containing a polypeptide and a physiologically acceptable carrier. Such compositions typically contain one or more of the above polypeptides in an amount ranging from about 1 μg to about 100 μg, preferably from about 10 μg to about 50 μg in a volume of 0.1 mL. Preferably, the carrier employed in such pharmaceutical compositions is a saline solution with appropriate preservatives, such as phenol and/or Tween 80™.

In another aspect, the present invention provides methods for using the polypeptides to diagnose tuberculosis. In this aspect, methods are provided for detecting *M. tuberculosis* infection in a biological sample using the fusion polypeptides alone or in combination. As used herein, a "biological sample" is any antibody-containing sample obtained from a patient. Preferably, the sample is whole blood, sputum, serum, plasma, saliva cerebrospinal fluid or urine. More preferably, the sample is a blood, serum or plasma sample obtained from a patient or a blood supply. The polypeptide (s) are used in an assay, as described below, to determine the presence or absence of antibodies to the polypeptide(s) in the sample relative to a predetermined cut-off value. The presence of such antibodies indicates previous sensitization to mycobacterial antigens which may be indicative of tuberculosis.

In embodiments in which more than one fusion polypeptide is employed, the polypeptides used are preferably complementary (i.e., one component polypeptide will tend to detect infection in samples where the infection would not be detected by another component polypeptide). Complementary polypeptides may generally be identified by using each polypeptide individually to evaluate serum samples obtained from a series of patients known to be infected with *M. tuberculosis*. After determining which samples test positive (as described below) with each polypeptide, combinations of two or more fusion polypeptides may be formulated that are capable of detecting infection in most, or all, of the samples tested. Such polypeptides are complementary. Approximately 25–30% of sera from tuberculosis-infected individuals are negative for antibodies to any single protein. Complementary polypeptides may, therefore, be used in combination to improve sensitivity of a diagnostic test.

There are a variety of assay formats known to those of ordinary skill in the art for using one or more polypeptides to detect antibodies in a sample. See, e.g., Harlow and Lane, *Antibodies: A Laboratory Manual*, Cold Spring Harbor Laboratory, 1988, which is incorporated herein by reference. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques known to those of ordinary skill in the art. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 $\mu$g, and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook. 1991, at A12–A13).

In certain embodiments, the assay is an enzyme linked immunosorbent 1 assay (ELISA). This assay may be performed by first contacting a fusion polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.) may be employed. The immobilized polypeptide is then incubated with the sample, and antibody is allowed to bind to the antigen. The sample may be diluted with a suitable diluent, such as phosphate-buffered saline (PBS) prior to incubation. In general, an appropriate contact time is that period of time that is sufficient to detect the presence of antibody within a *M. tuberculosis*-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (for example, Protein A, Protein G, lectin or free antigen) conjugated to a reporter group. Preferred reporter groups include enzymes (such as horseradish peroxidase), substrates, cofactors, inhibitors, dyes, radionuclides, luminescent groups, fluorescent groups, biotin and colloidal particles, such as colloidal gold and selenium. The conjugation of binding agent to reporter group may be achieved using standard methods known to those of ordinary skill in the art. Common binding agents may also be purchased conjugated to a variety of reporter groups from many commercial sources (e.g., Zymed Laboratories, San Francisco, Calif., and Pierce, Rockford. Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time). followed by spectroscopic or other analysis of the reaction products.

To determine the presence or absence of anti-*M. tuberculosis* antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In general, a sample generating a signal that is three standard deviations above the predetermined cut-off value is considered positive for tuberculosis. In an alternate preferred embodiment, the cut-off value is determined using a Receiver Operator Curve. according to the method of Sackett et al., 1985, *Clinical Epidemiology: A Basic Science for Clinical Medicine,* Little Brown and Co., pp. 106–107. Briefly, in this embodiment, the cut-off value may be determined from a plot of pairs of true positive rates (i e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for tuberculosis.

In a related embodiment, the assay is performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-*M. tuberculosis* antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 5 ng to about 1 $\mu$g, and more preferably from about 50 ng to about 500 ng. Such tests can typically be performed with a very small amount (e.g., one drop) of patient serum or blood.

The invention having been described, the following examples are offered by way of illustration and not limitation.

6. EXAMPLE

Fusion Proteins of *M. tuberculosis* Antigens Retain Immunogenicity of the Individual Components

6.1. Materials and Methods

6.1.1. Construction of Fusion Proteins

Coding sequences of *M. tuberculosis* antigens were modified by PCR in order to facilitate their fusion and subsequent expression of fusion protein. DNA amplification was performed using 10 $\mu$l 10× Pfu buffer, 2 $\mu$l 10 mM dNTPs, 2 $\mu$l each of the PCR primers at 10 $\mu$M concentration, 81.5 $\mu$l water, 1.5 $\mu$l Pfu DNA polymerase (Stratagene, La Jolla, Calif.) and 1 $\mu$l DNA at either 70 ng/$\mu$l (for TbRa3 antigen) or 50 ng/$\mu$l (for 38 kD and Tb38-1 antigens). For TbRa3 antigen, denaturation at 94° C. was performed for 2 min, followed by 40 cycles of 96° C. for 15 sec and 72° C. for 1 min, and lastly by 72° C. for 4 min. For 38 kD antigen, denaturation at 96° C. was performed for 2 min, followed by 40 cycles of 96° C. for 30 sec, 68° C. for 15 sec and 72° C. for 3 min, and finally by 72° C. for 4 min. For Tb38-1 antigen, denaturation at 94° C. for 2 min was followed by 10 cycles of 96° C. for 15 sec, 68° C. for 15 sec and 72° C. for 1.5 min, 30 cycles of 96° C. for 15 sec, 64° C. for 15 sec and 72° C. for 1.5, and finally by 72° C. for 4 min.

Following digestion with a restriction endonuclease to yield the desired cohesive or blunt ends, a polynucleotide specific for each fusion polypeptide was ligated into an expression plasmid. Each resulting plasmid contained the coding sequences of the individual antigens of each fusion polypeptide. The expression vectors used were pET-12b and pT7^L2 IL 1.

Figure 6B:
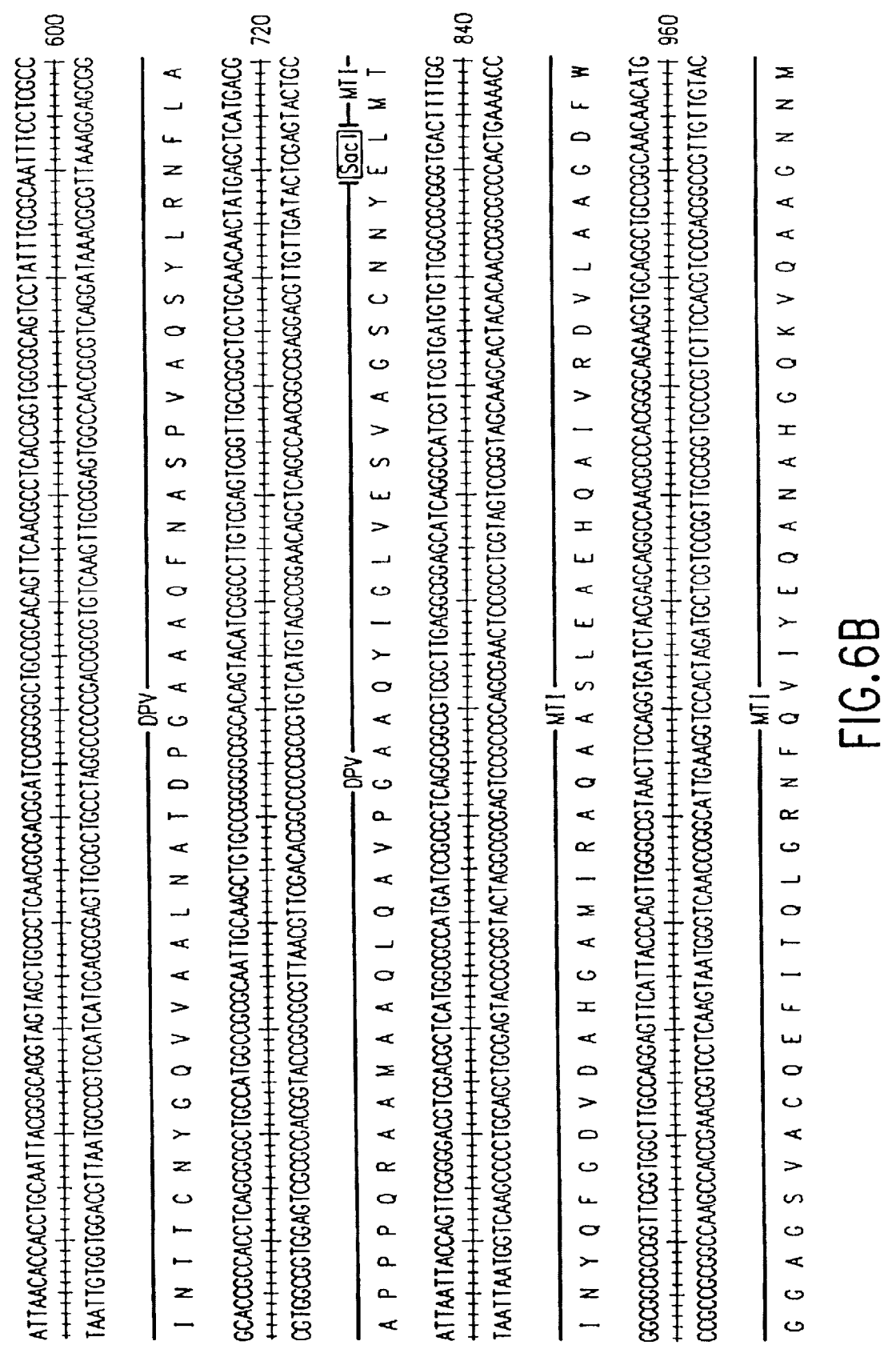
Figure 6C:
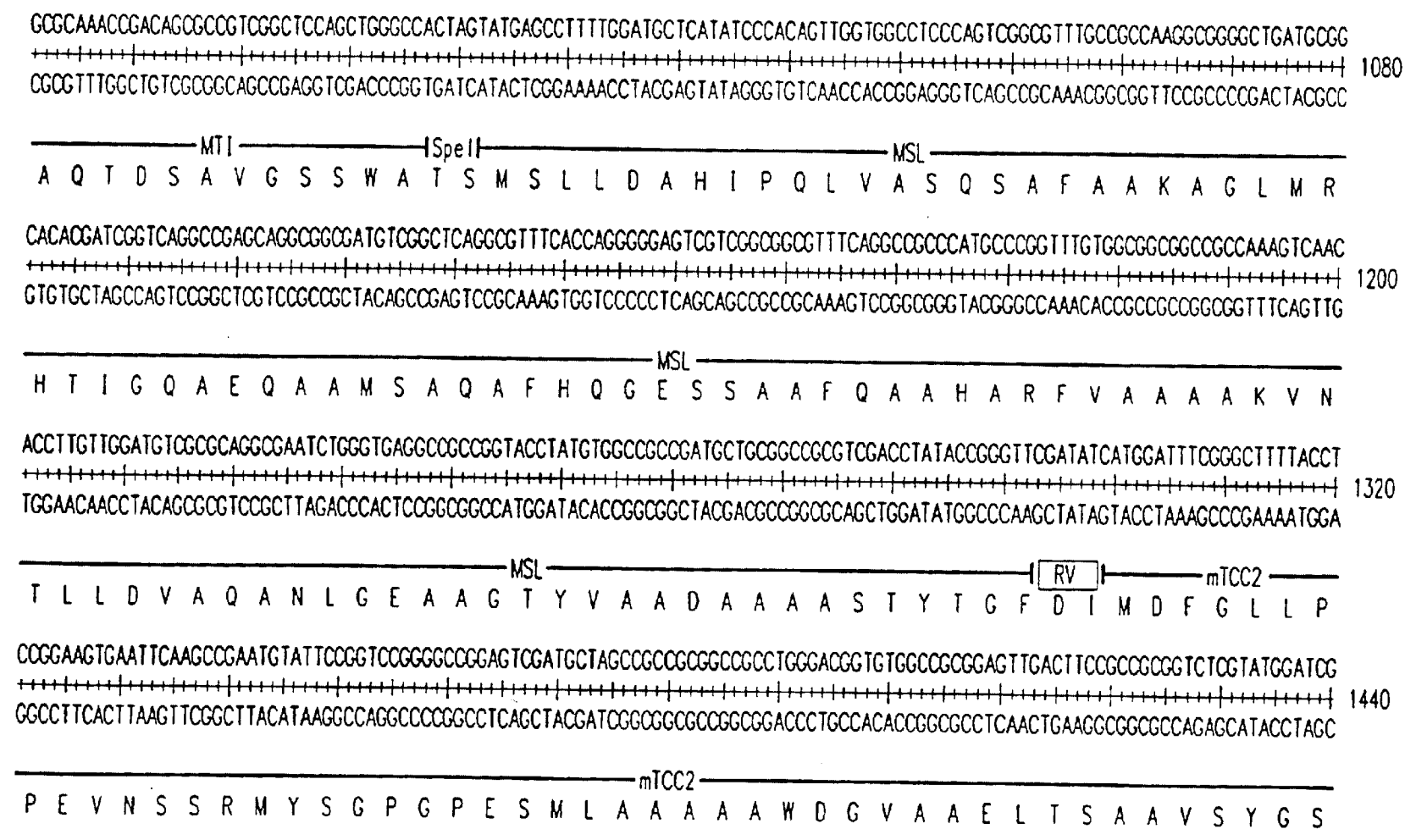
Figure 6D:
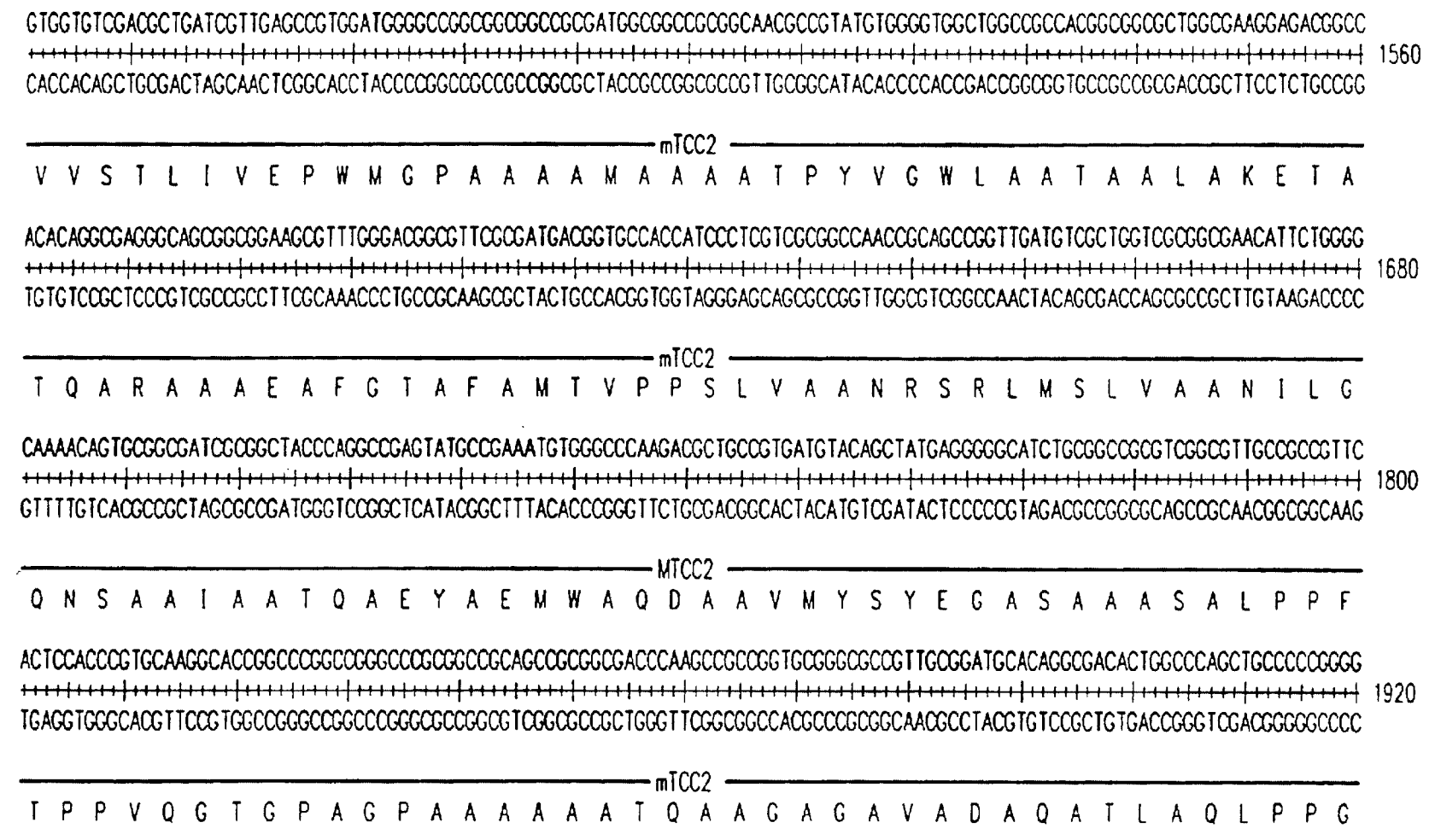
Figure 6E:
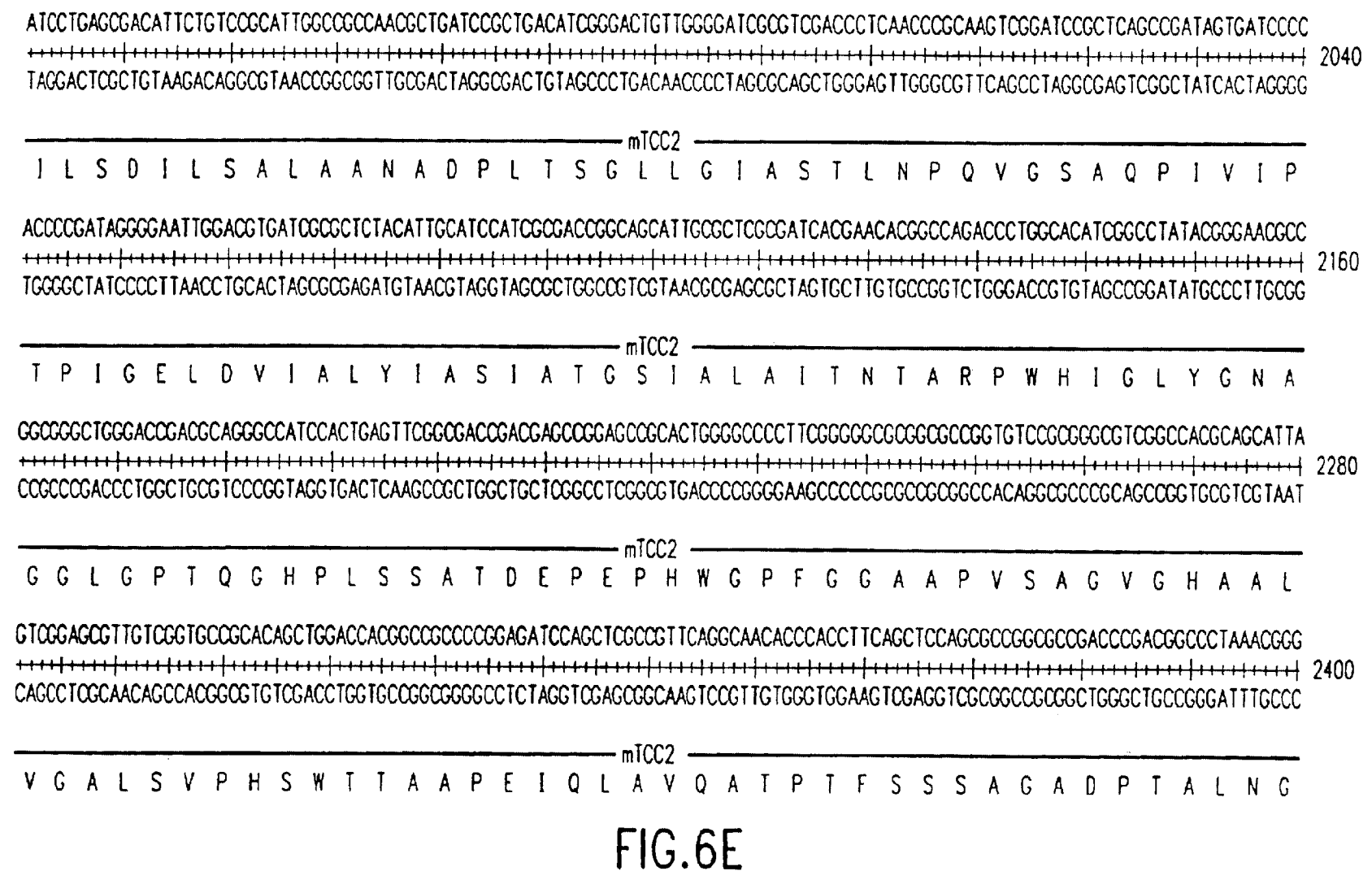

Three coding sequences for antigens Ra12, TbH9 and Ra35 were ligated to encode one fusion protein (SEQ ID NOS:1 and 2) (FIGS. 1A and 2B). Another three coding sequences for antigens Erd14, DPV and MTI were ligated to encode a second fusion protein (SEQ ID NOS:3 and 4) (FIG. 2). Three coding sequences for antigens TbRa3, 38 kD and Tb38-1 were ligated to encode one fusion protein (SEQ ID NOS:5 and 6) (FIGS. 3A–3D). Two coding sequences for antigens TbH9 and Tb38-1 were ligated to encode one fusion protein (SEQ ID NOS:7 and 8) (FIGS. 4A–4D). Four coding sequences for antigens TbRa3, 38 kD, Tb38-1 and DPEP were ligated to encode one fusion protein (SEQ ID NOS:9 and 10) (FIGS. 5A–5J). Five coding sequences for antigens Erd14, DPV, MTI, MSL and MTCC2 were ligated to encode one fusion protein (SEQ ID NOS:11 and 12) (FIGS. 6A and 6B). Four coding sequences for antigens Erd14, DPV, MTI and MSL were ligated to encode one fusion protein (SEQ ID NOS:13 and 14) (FIGS. 7A and 7B).

Figure 14B:
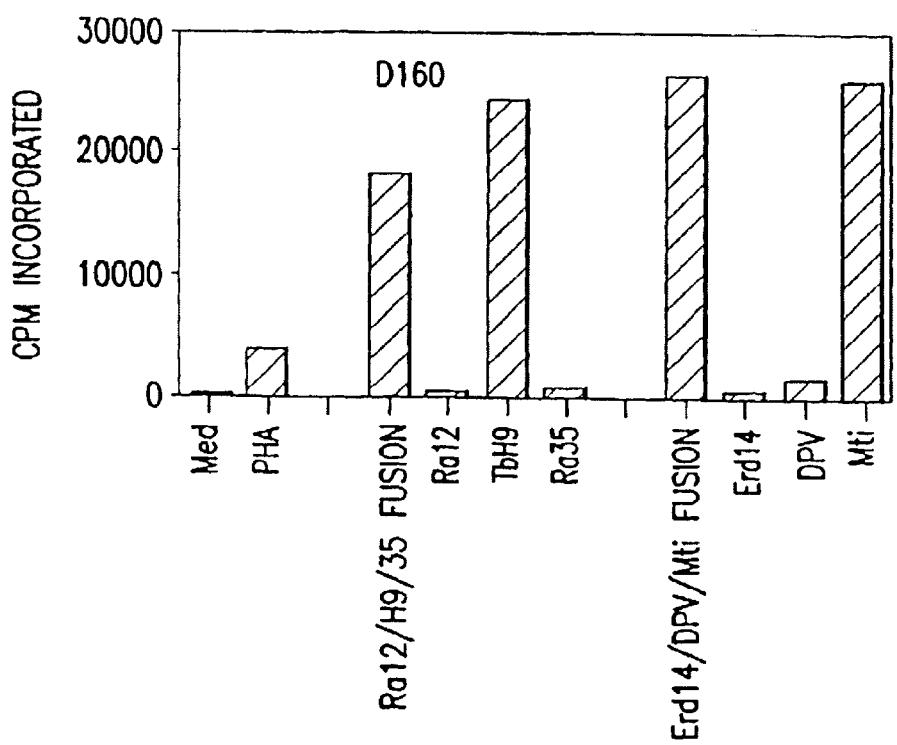
Figure 14C:
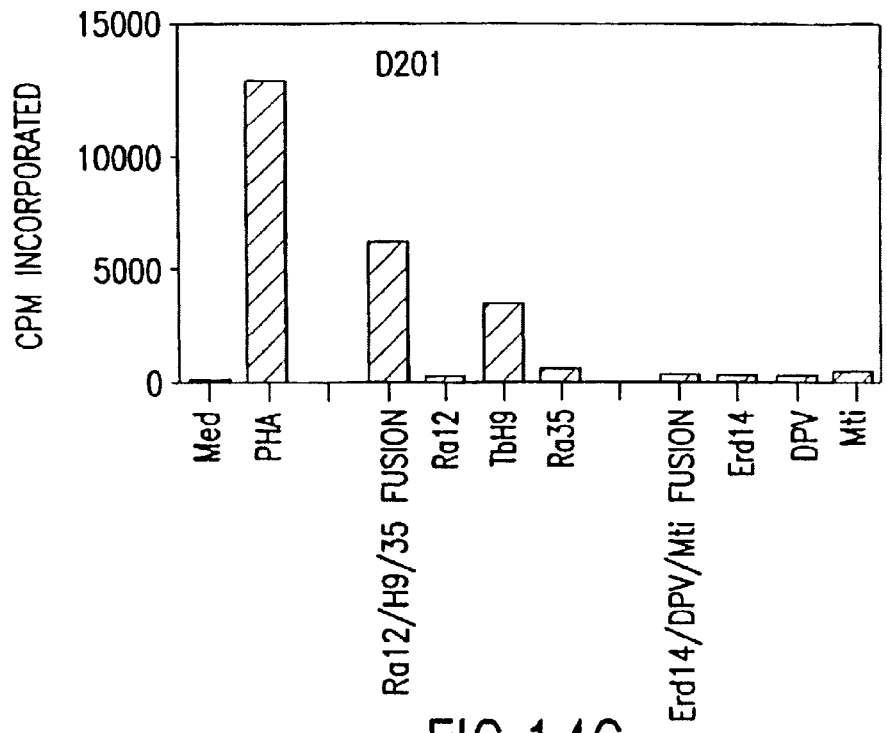
Figure 14D:
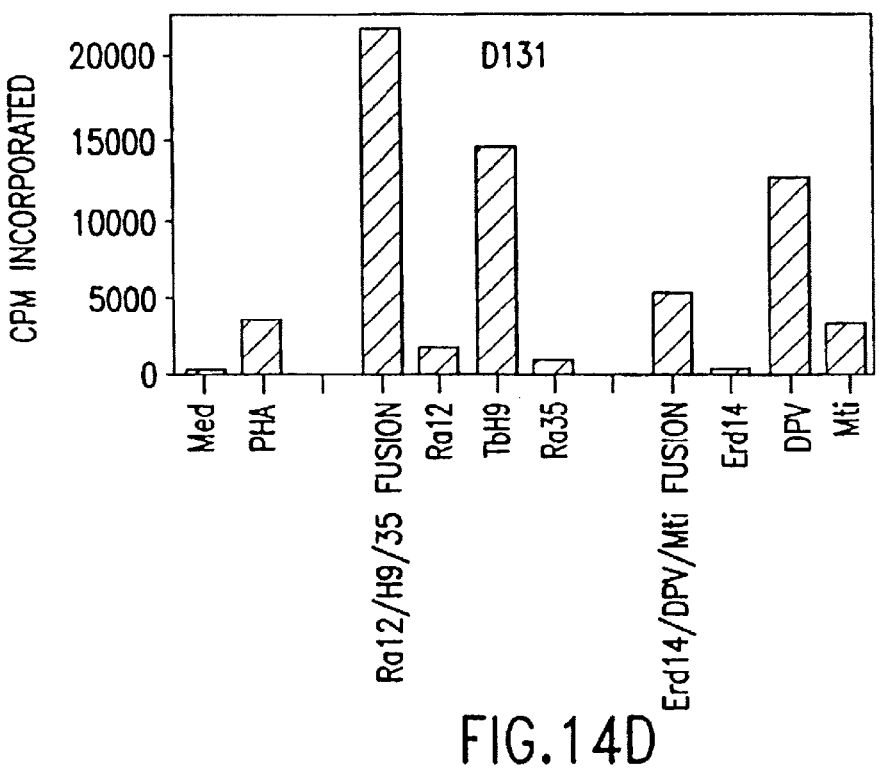
Figure 14E:
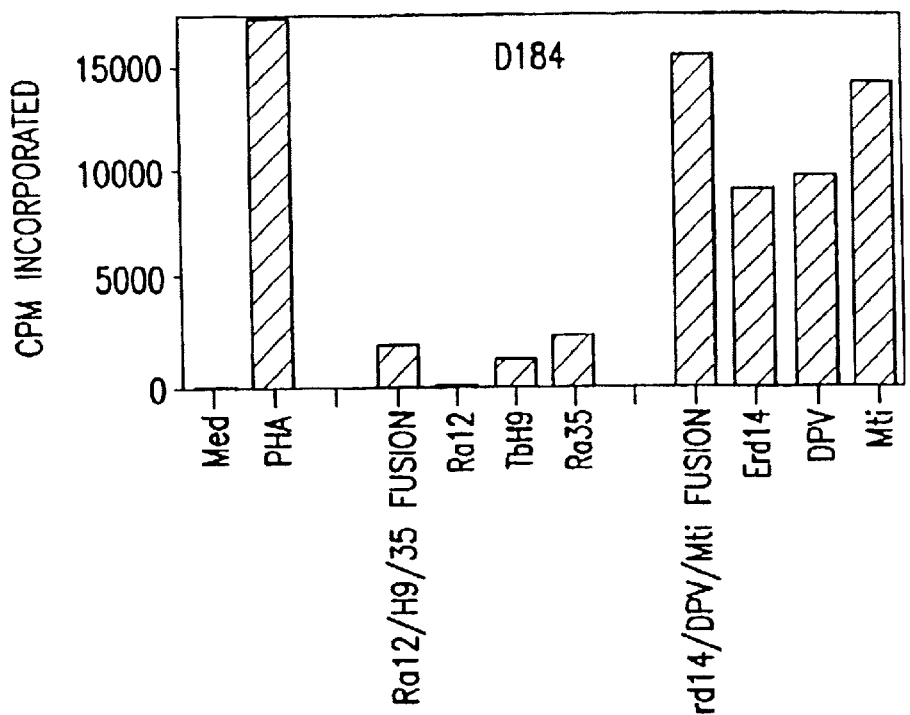
Figure 14F:
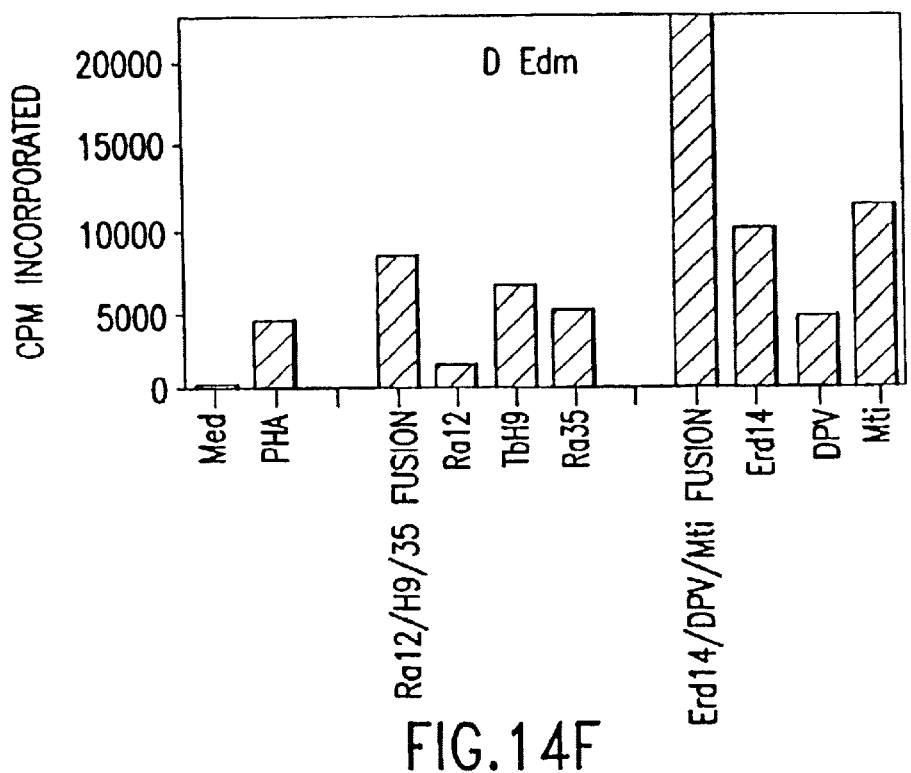
Figure 15A:
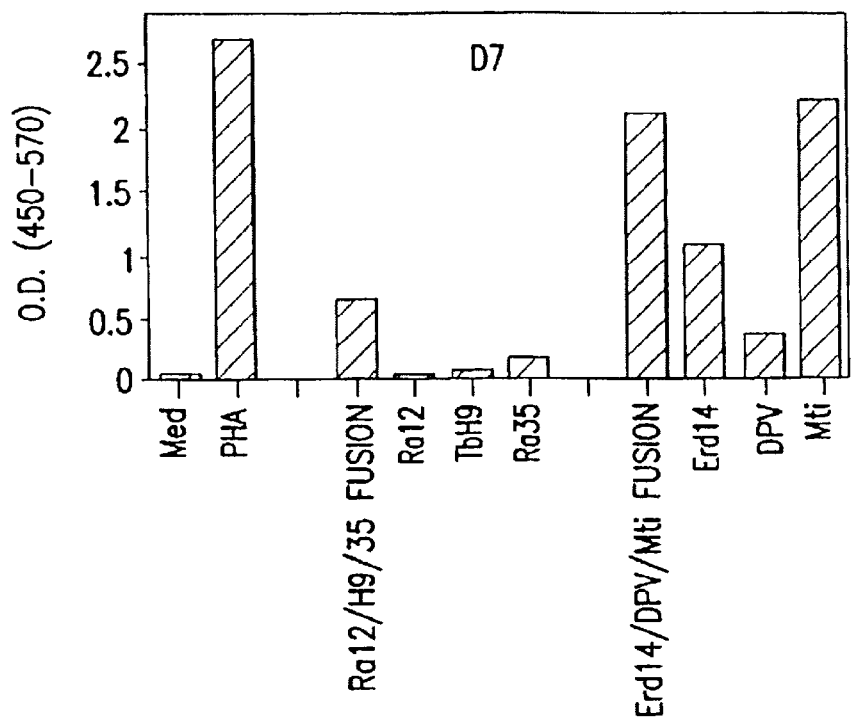
Figure 15B:
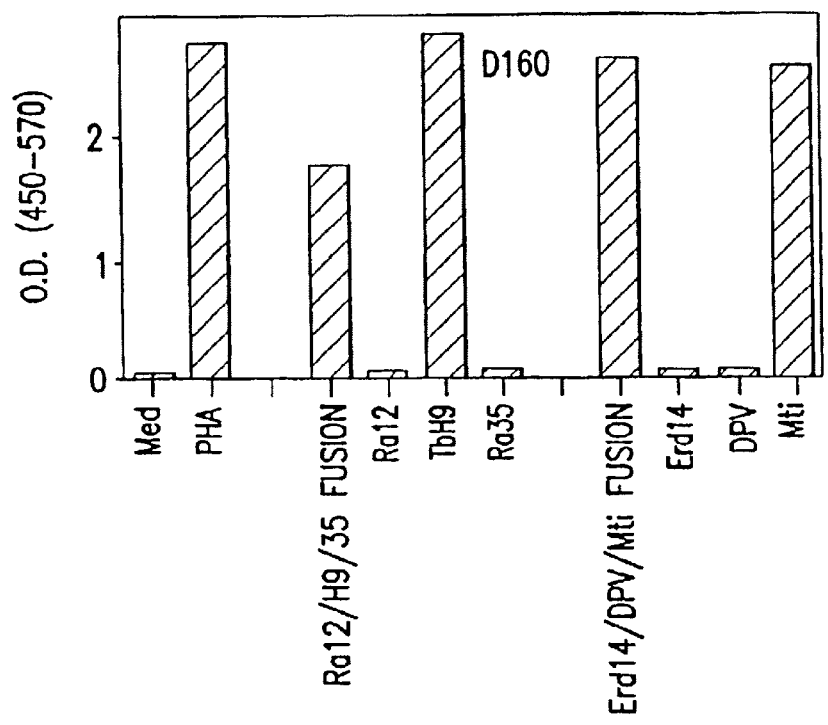
Figure 15C:
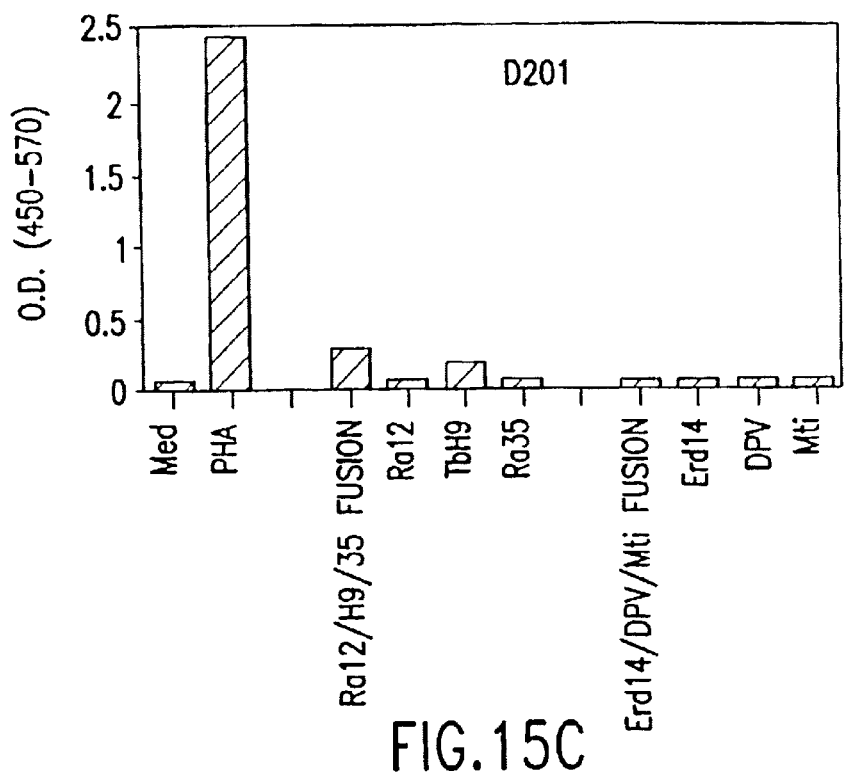
Figure 15D:
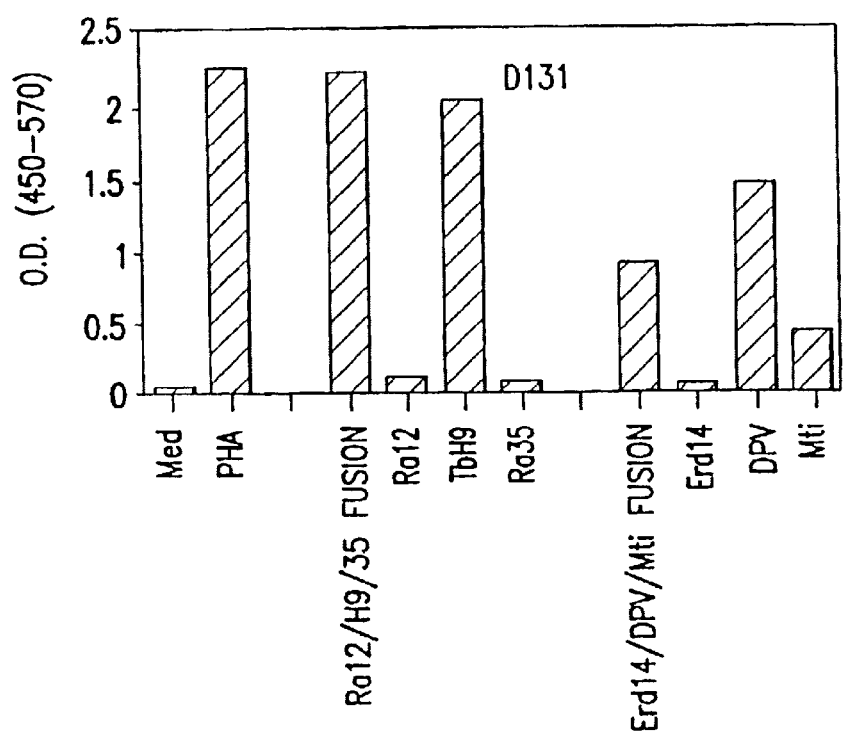
Figure 15E:
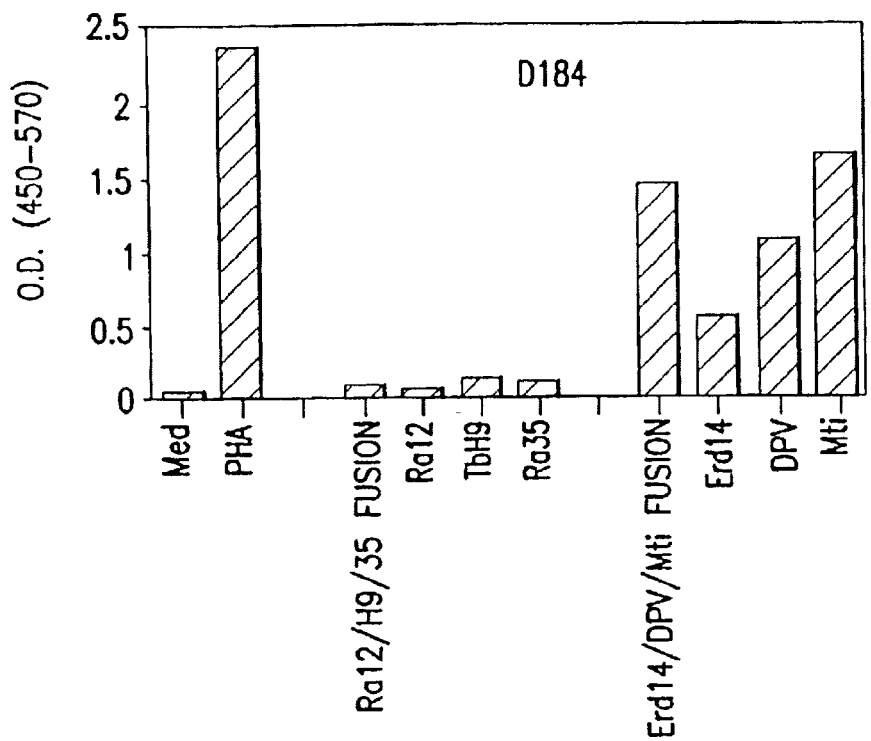
Figure 15F:
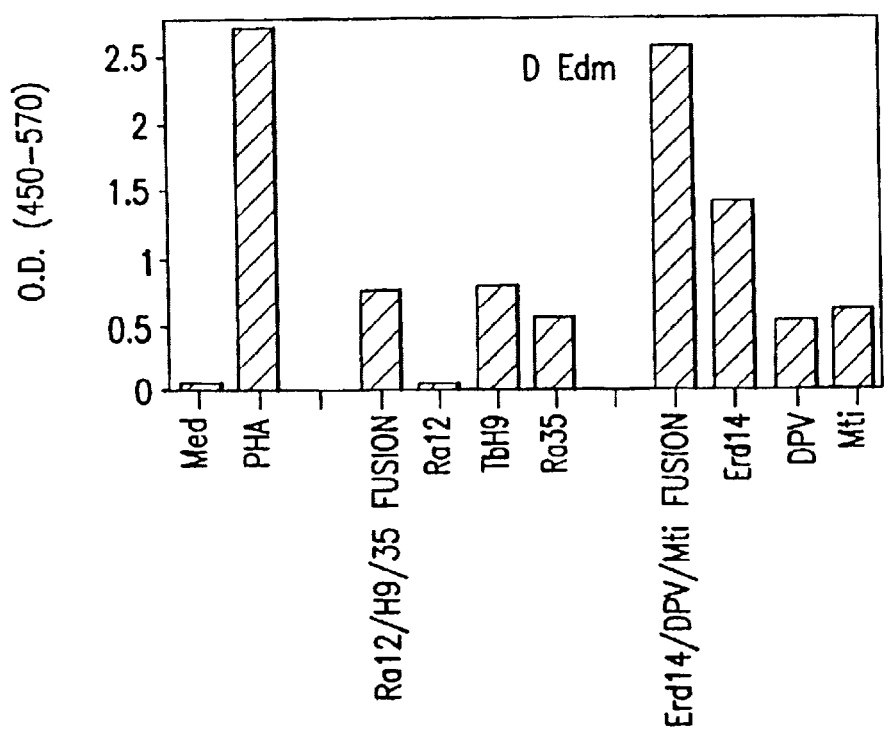

Four coding sequences for antigens DPV, MTI, MSL and MTCC2 were ligated to encode one fusion protein (SEQ ID NOS:15 and 16) (FIGS. 8A and 8B). Three coding sequences for antigens DPV, MTI and MSL were ligated to encode one fusion protein (SEQ ID NOS:18 and 19) (FIGS. 9A and 9B). Three coding sequences for antigens TbH9, DPV and MTI were ligated to encode one fusion protein (SEQ ID NOS:21 and 22) (FIGS. 10A and 10B). Three coding sequences for antigens Erd14, DPV and MTI were ligated to encode one fusion protein (SEQ ID NOS:23 and 24) (FIGS. 11A and 11B). Two coding sequences for antigens TbH9 and Ra35 were ligated to encode one fusion protein (SEQ ID NOS:25 and 26) (FIGS. 12A and 12B). Two coding sequences for antigens Ra12 and DPPD were ligated to encode one fusion protein (SEQ ID NOS:27 and 28) (FIGS. 13A and 13B).

The recombinant proteins were expressed in *E. coli* with six histidine residues at the amino-terminal portion using the pET plasmid vector (pET-17b) and a T7 RNA polymerase expression system (Novagen, Madison, Wis.). *E. coli* strain BL21 (DE3) pLysE (Novagen) was used for high level expression. The recombinant (His-Tag) fusion proteins were purified from the soluble supernatant or the insoluble inclusion body of 500 ml of IPTG induced batch cultures by affinity chromatography using the one step QIAexpress Ni-NTA Agarose matrix (QIAGEN, Chatsworth, Calif.) in the presence of 8M urea. Briefly, 20 ml of an overnight saturated culture of BL21 containing the pET construct was added into 500 ml of 2×YT media containing 50 μg/ml ampicillin and 34 μg/ml chloramphenicol, grown at 37° C. with shaking. The bacterial cultures were induced with 2 mM IPTG at an OD 560 of 0.3 and grown for an additional 3 h (OD=1.3 to 1.9). Cells were harvested from 500 ml batch cultures by centrifugation and resuspended in 20 ml of binding buffer (0.1 M sodium phosphate, pH 8.0; 10 mM Tris-HCl, pH 8.0) containing 2 mM PMSF and 20 μg/ml leupeptin plus one complete protease inhibitor tablet (Boehringer Mannheim) per 25 ml. *E. coli* was lysed by freeze-thaw followed by brief sonication, then spun at 12 k rpm for 30 min to pellet the inclusion bodies.

The inclusion bodies were washed three times in 1% CHAPS in 10 mM Tris-HCl (pH 8.0). This step greatly reduced the level of contaminating LPS. The inclusion body was finally solubilized in 20 ml of binding buffer containing 8 M urea or 8M urea was added directly into the soluble supernatant. Recombinant fusion proteins with His-Tag residues were batch bound to Ni-NTA agarose resin (5 ml resin per 500 ml inductions) by rocking at room temperature for 1 h and the complex passed over a column. The flow through was passed twice over the same column and the column washed three times with 30 ml each of wash buffer (0.1 M sodium phosphate and 10 mM Tris-HCL, pH 6.3) also containing 8 M urea. Bound protein was eluted with 30 ml of 150 mM immidazole in wash buffer and 5 ml fractions collected. Fractions containing each recombinant fusion protein were pooled, dialyzed against 10 mM TrisHCl (pH 8.0) bound one more time to the Ni-NTA matrix, eluted and dialyzed in 10 mM Tris-HCL (pH 7.8). The yield of recombinant protein varies from 25–150 mg per liter of induced bacterial culture with greater than 98% purity. Recombinant proteins were assayed for endotoxin contamination using the Limulus assay (BioWhittaker) and were shown to contain <10 E.U.Img.

6.1.2. T-Cell Proliferation Assay

Purified fusion polypeptides were tested for the ability to induce T-cell proliferation in peripheral blood mononuclear cell (PBMC) preparations. The PBMCs from donors known to be PPD skin test positive and whose T-cells were shown to proliferate in response to PPD and crude soluble proteins from *M. tuberculosis* were cultured in RPMI 1640 supplemented with 10% pooled human serum and 50 μg/ml gentamicin. Purified polypeptides were added in duplicate at concentrations of 0.5 to 10 μg/ml. After six days of culture in 96-well round-bottom plates in a volume of 200 μl, 50 μl of medium was removed from each well for determination of IFN-γ levels, as described below in Section 6.1.3. The plates were then pulsed with 1 μCi/well of tritiated thymidine for a further 18 hours, harvested and tritium uptake determined using a gas scintillation counter. Fractions that resulted in proliferation in both replicates three fold greater than the proliferation observed in cells cultured in medium alone were considered positive.

6.1.3. Interferon-γ Assay

Spleens from mice were removed asceptically and single cell suspension prepared in complete RPMI following lysis of red blood cells. 100 μl of cells ($2\times10^{-5}$ cells) were plated per well in a 96-well flat bottom microtiter plate. Cultures were stimulated with the indicated recombinant proteins for 24 h and the supernatant assayed for IFN-γ.

The levels of supernatant IFN-γ was analysed by sandwich ELISA, using antibody pairs and procedures available from PharMingen. Standard curves were generated using recombinant mouse cytokines. ELISA plates (Coming) were coated with 50 μl/well (1 μg/ml, in 0.1 M bicarbonate coating buffer, pH9.6) of a cytokine capture mAb (rat anti-mouse IFN-γ (PharMingen; Cat. #18181D)), and incubated for 4 h at room temp. Shake out plate contents and block with PBS-0.05% Tween, 1.0% BSA (200 μl/well) overnight at 4° C. and washed for 6× in PBS-0.1% Tween. Standards (mouse IFN-γ) and supernatant samples diluted in PBS-0.05% Tween, 0.1% BSA were then added for 2 hr at room temp. The plates were washed as above and then incubated for 2 hr at room temperature with 100 μl/well of a second Ab (biotin rat a mouse IFN-γ (Cat. #18112D; PharMingen) at 0.5 μg/ml diluted in PBS-0.05% Tween, 0.1% BSA. After washing, plates were incubated with 100 μl/well of streptavidin-HRP (Zymed) at a 1:2500 dilution in PBS-0.05% Tween, 0.1% BSA at room temp for 1 hr. The plates were washed one last time and developed with 100 μl/well TMB substrate (3,3',5,5'-tetramethylbenzidine, Kirkegaard and Perry, Gaithersburg, Md.) and the reaction stopped after color developed, with $H_2SO_4$, 50 μl/well. Absorbance (OD) were determined at 450 nm using 570 nm as a reference wavelength and the cytokine concentration evaluated using the standard curve.

6.2. Results 6.2.1. Tri-Fusion Proteins Induced Immune Responses

Three coding sequences for *M. tuberculosis* antigens were inserted into an expression vector for the production of a fusion protein. The antigens designated Ra12, TbH9 and Ra35 were produced as one recombinant fusion protein (FIGS. 1A and 1B). Antigens Erd14, DPV and MTI were produced as a second fusion protein (FIG. 2). The two fusion proteins were affinity purified for use in in vitro and in vivo assays.

The two fusion proteins were tested for their ability to stimulate T cell responses from six $PPD^+$ subjects. When T cell proliferation was measured, both fusion proteins exhibited a similar reactivity pattern as their individual components (FIGS. 14A–14F). A similar result was obtained when IFN-γ production was measured (FIGS. 15A–15F). For example, subject D160 responded to antigens TbH9 and MTI individually. Subject D160 also responded to the fusion proteins that contained these antigens (FIGS. 14B and 15B). In contrast, no T cell response from D160 was observed to other antigens individually. Another subject, D201, who did not react with antigens Erd14, DPV or MTI individually, was also unresponsive to the fusion protein containing these antigens. It should be noted that when the T cell responses to the individual components of the two fusion proteins were not particularly strong, the fusion proteins stimulated responses that were equal to or higher than that induced by the individual antigens in most cases.

The Ra12-TbH9-Ra35 tri-fusion protein was also tested as an immunogen in vivo. In these experiments, the fusion protein was injected into the footpads of mice for immunization. Each group of three mice received the protein in a different adjuvant formulation: SBAS1c, SBAS2 (Ling et al., 1997, Vaccine 15:1562–1567), SBAS7 and AL(OH)$_3$. After two subcutaneous immunizations at three week intervals, the animals were sacrificed one week later, and their draining lymph nodes were harvested for use as responder cells in T cell proliferation and cytokine production assays.

Figure 16A:
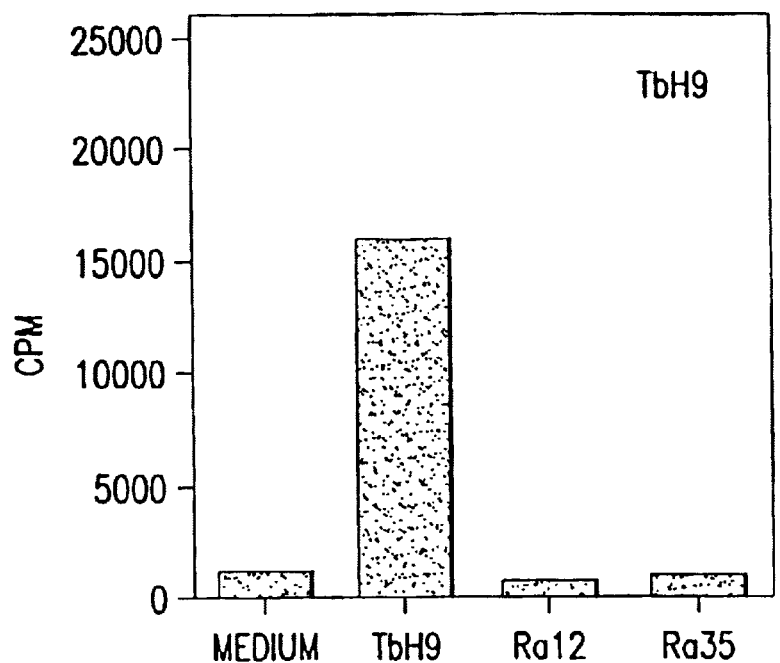
Figure 16B:
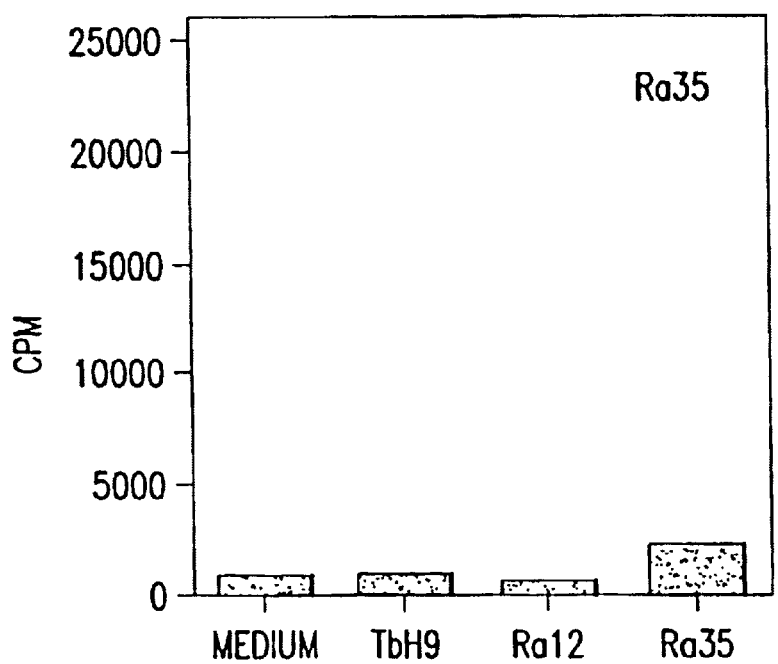
Figure 16C:
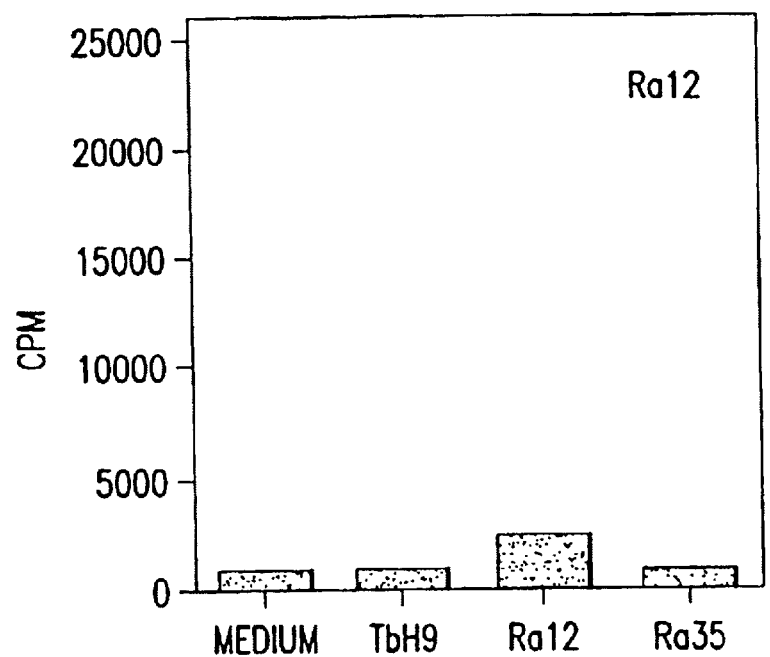
Figure 16D:
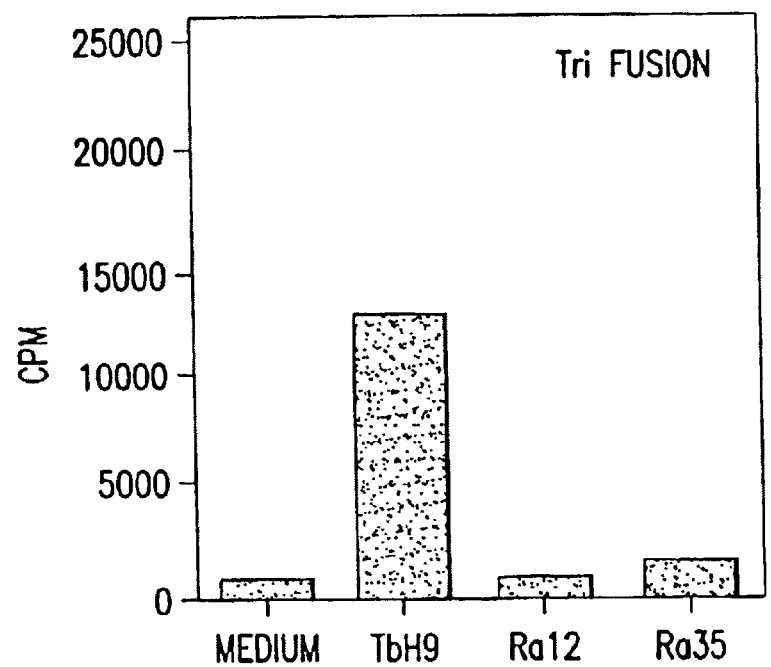
Figure 16E:
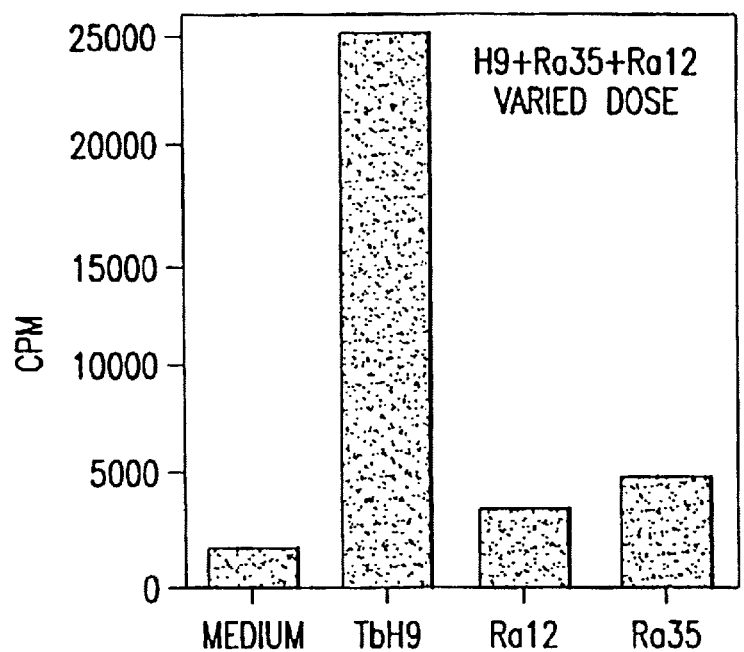
Figure 16F:
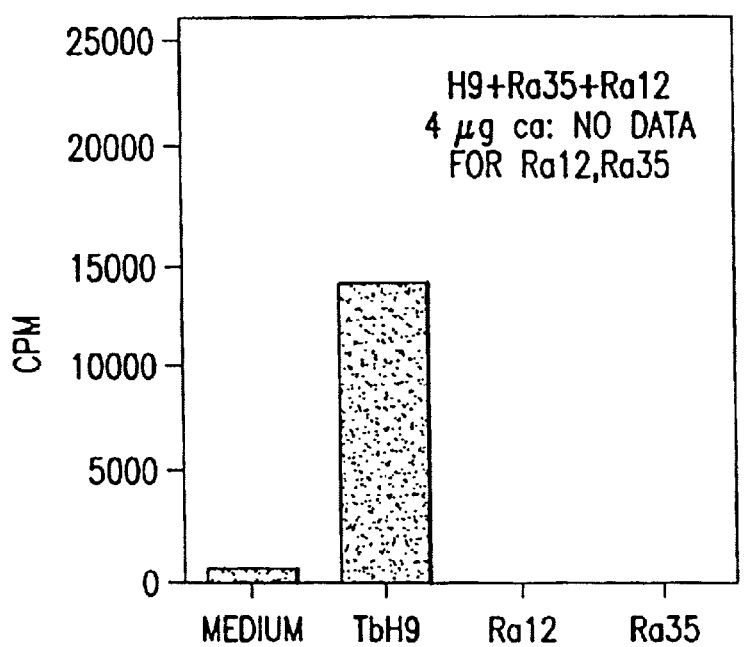

Regardless which adjuvant was used in the immunization, strong T cell proliferation responses were induced against TbH9 when it was used as an individual antigen (FIG. 16A). Weaker responses were induced against Ra35 and Ra12 (FIGS. 16B and 16C). When the Ra12-TbH9-Ra35 fusion protein was used as immunogen, a response similar to that against the individual components was observed.

When cytokine production was measured, adjuvants SBAS1c and SBAS2 produced similar IFN-γ (FIG. 17) and IL4 responses (FIG. 18). However, the combination of SBAS7 and aluminum hydroxide produced the strongest IFN-γ responses and the lowest level of IL-4 production for all three antigens. With respect to the humoral antibody response in vivo, FIGS. 19A–19F shows that the fusion protein elicited both IgG$_1$ and IgG$_{2a}$ antigen-specific responses when it was used with any of the three adjuvants.

Additionally, C57BL/6 mice were immunized with an expression construct containing Ra12-TbH9-Ra35 (Mtb32–Mtb39 fusion) coding sequence as DNA vaccine. The immunized animals exhibited significant protection against tuberculosis upon a subsequent aerosol challenge of live bacteria. Based on these results, a fusion construct of Mtb32–Mtb39 coding sequence was made, and its encoded product tested in a guinea pig long term protection model. In these studies, guinea pigs were immunized with a single recombinant fusion protein or a mixture of Mtb32A (Ra35) and Mtb39A (TbH9) proteins in formulations containing an adjuvant. FIGS. 20A–20C shows that guinea pigs immunized with the fusion protein in SBAS1c or SBAS2 were better protected against the development of tuberculosis upon subsequent challenge, as compared to animals immunized with the two antigens in a mixture in the same adjuvant formulation. The fusion proteins in SBAS2 formulation afforded the greatest protection in the animals. Thus, fusion proteins of various M. tuberculosis antigens may be used as more effective immunogens in vaccine formulations than a mixture of the individual components.

6.2.2. Bi-Fusion Protein Induced Immune Responses

A bi-fusion fusion protein containing the TbH-9 and Tb38-1 antigens without a hinge sequence was produced by recombinant methods. The ability of the TbH9-Tb38-1 fusion protein to induce T cell proliferation and IFN-γ production was examined. PBMC from three donors were employed: one donor had been previously shown to respond to TbH9 but not to Tb38-1 (donor 131); one had been shown to respond to Tb38-1 but not to TbH9 (donor 184); and one had been shown to respond to both antigens (donor 201). The results of these studies demonstrate the functional activity of both the antigens in the fusion protein (FIGS. 21A and 21B, 22A and 22B, and 23A and 23B).

6.2.3. A Tetra-Fusion Protein Reacted with tuberculosis Patient Sera

A fusion protein containing TbRa3, 38 KD antigen, Tb38-1 and DPEP was produced by recombinant methods. The reactivity of this tetra-fusion protein referred to as TbF-2 with sera from M. tuberculosis-infected patients was examined by ELISA. The results of these studies (Table 1) demonstrate that all four antigens function independently in the fusion protein.

One of skill in the art will appreciate that the order of the individual antigens within each fusion protein may be changed and that comparable activity would be expected provided that each of the epitopes is still functionally available. In addition, truncated forms of the proteins containing active epitopes may be used in the construction of fusion proteins.

The present invention is not to be limited in scope by the exemplified embodiments which are intended as illustrations of single aspects of the invention, and any clones, nucleotide or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims. It is also to be understood that all base pair sizes given for nucleotides are approximate and are used for purposes of description.

All publications cited herein are incorporated by reference in their entirety.

TABLE 1

REACTIVITY OF TBF-2 FUSION PROTEIN WITH TB AND NORMAL SERA

| | | TbF | | TbF-2 | | ELISA Reactivity | | | |
|---|---|---|---|---|---|---|---|---|---|
| Serum ID | Status | OD450 | Status | OD450 | Status | 38 kD | TbRa3 | Tb38-1 | DPEP |
| B931-40 | TB | 0.57 | + | 0.321 | + | − | + | − | + |
| B931-41 | TB | 0.601 | + | 0.396 | + | + | + | + | − |
| B931-109 | TB | 0.494 | + | 0.404 | + | + | + | ± | ±− |
| B931-132 | TB | 1.502 | + | 1.292 | + | + | + | + | ±± |
| 5004 | TB | 1.806 | + | 1.666 | + | ±± | ±± | + | − |
| 15004 | TB | 2.862 | + | 2.468 | + | + | + | + | − |
| 39004 | TB | 2.443 | + | 1.722 | + | + | + | + | − |

TABLE 1-continued

REACTIVITY OF TBF-2 FUSION PROTEIN WITH TB AND NORMAL SERA

| Serum ID | Status | TbF OD450 | Status | TbF-2 OD450 | Status | ELISA Reactivity 38 kD | TbRa3 | Tb38-1 | DPEP |
|---|---|---|---|---|---|---|---|---|---|
| 68004 | TB | 2.871 | + | 2.575 | + | + | + | + | − |
| 99004 | TB | 0.691 | + | 0.971 | + | − | ±± | + | − |
| 107004 | TB | 0.875 | + | 0.732 | + | − | ±± | + | − |
| 92004 | TB | 1.632 | + | 1.394 | + | + | ±± | ±± | − |
| 97004 | TB | 1.491 | + | 1.979 | + | + | ±± | − | + |
| 118004 | TB | 3.182 | + | 3.045 | + | + | ±± | − | − |
| 173004 | TB | 3.644 | + | 3.578 | + | + | + | + | − |
| 175004 | TB | 3.332 | + | 2.916 | + | + | + | − | − |
| 274004 | TB | 3.696 | + | 3.716 | + | − | + | − | + |
| 276004 | TB | 3.243 | + | 2.56 | + | − | − | + | − |
| 282004 | TB | 1.249 | + | 1.234 | + | + | − | − | − |
| 289004 | TB | 1.373 | + | 1.17 | + | − | + | − | − |
| 308004 | TB | 3.708 | + | 3.355 | + | − | − | + | − |
| 314004 | TB | 1.663 | + | 1.399 | + | − | − | + | − |
| 317004 | TB | 1.163 | + | 0.92 | + | + | − | − | − |
| 312004 | TB | 1.709 | + | 1.453 | + | − | + | − | − |
| 380004 | TB | 0.238 | − | 0.461 | + | − | ±± | − | + |
| 451004 | TB | 0.18 | − | 0.2 | − | − | − | − | ±± |
| 478004 | TB | 0.188 | − | 0.469 | + | − | − | − | ±± |
| 410004 | TB | 0.384 | + | 2.392 | + | ±± | − | − | + |
| 411004 | TB | 0.306 | + | 0.874 | + | − | + | − | + |
| 421004 | TB | 0.357 | + | 1.456 | + | − | + | − | + |
| 528004 | TB | 0.047 | − | 0.196 | − | − | − | − | + |
| A6-87 | Normal | 0.094 | − | 0.063 | − | − | − | − | − |
| A6-88 | Normal | 0.214 | − | 0.19 | − | − | − | − | − |
| A6-89 | Normal | 0.248 | − | 0.125 | − | − | − | − | − |
| A6-90 | Normal | 0.179 | − | 0.206 | − | − | − | − | − |
| A6-91 | Normal | 0.135 | − | 0.151 | − | − | − | − | − |
| A6-92 | Normal | 0.064 | − | 0.097 | − | − | − | − | − |
| A6-93 | Normal | 0.072 | − | 0.098 | − | − | − | − | − |
| A6-94 | Normal | 0.072 | − | 0.064 | − | − | − | − | − |
| A6-95 | Normal | 0.125 | − | 0.159 | − | − | − | − | − |
| A6-96 | Normal | 0.121 | − | 0.12 | − | − | − | − | − |
| Cut-off | | 0.284 | | 0.266 | | | | | |

What is claimed is:

1. A method of preventing tuberculosis, comprising administering effective amount of a purified polypeptide comprising the amino sequence of SEQ ID NO:2.

2. The method of claim 1, wherein the polypeptide is a soluble polypeptide.

3. The method of claim 1, wherein the polypeptide is produced by a recombinant DNA method.

4. The method of claim 1, wherein the polypeptide is produced by a chemical synthetic method.

5. The method of claim 1, wherein the polypeptide is fused with a second heterologous polypeptide.

6. The method of claim 1, wherein the administering of the polypeptide is by administering a pharmaceutical composition that comprises the polypeptide.

7. The method of claim 6, wherein the composition further comprises an adjuvant.

8. The method of claim 7, wherein the adjuvant is selected from the group consisting of Freund's incomplete adjuvant, Freund's complete adjuvant, alum, monophosphoryl lipid A, quil A, $Al(OH)_3$, CpG oligonucleotide, 3D-MPL, and QS21.

9. The method of claim 6, wherein the composition is formulated in an oil emulsion.

* * * * *

UNITED STATES PATENT AND TRADEMARK OFFICE
CERTIFICATE OF CORRECTION

PATENT NO. : 6,977,069 B2  Page 1 of 2
APPLICATION NO. : 10/359460
DATED : December 20, 2005
INVENTOR(S) : Reed et al.

It is certified that error appears in the above-identified patent and that said Letters Patent is hereby corrected as shown below:

In FIG. 1A, please delete the line directly below the line ending with 600,

"S A R M Y A G P G S A S L V A A A C M W D S V A S D L F S A A S A"

and insert,

--S A R M Y A G P G S A S L V A A A Q M W D S V A S D L F S A A S A--

In SEQ ID NO 1, Column 29, please delete the line ending with 1304,

"atg ttg aag ggc ttt gct ccg gcg gcg gcc cgc cag gcc gtg caa acc     1304
 Met Leu Lys Gly Phe Ala Pro Ala  Ala  Ala  Arg Gln  Ala  Val Gln Thr"

and insert,

--atg ttg aag ggc ttt gct ccg gcg gcg gcc gcc cag gcc gtg caa acc     1304
 Met Leu Lys Gly Phe Ala Pro Ala  Ala  Ala  Ala  Gln  Ala Val  Gln Thr--

In SEQ ID NO 1, Column 31, please delete the line ending with 2024,

"ggt ggc ggc gtc gcg gtt ggt gag ccc gtc gtc gcg atg ggc aac agc     2024
 Gly Gly Gly Val  Ala Val Gly Glu  Pro Val  Val Ala  Met Gly Asn Ser"

and insert,

--ggt ggc ggc gtc gcg gtt ggt gag ccc ttc gtc gcg atg ggc aac agc     2024
 Gly Gly Gly Val Ala Val Gly Glu  Pro Phe Val Ala  Met Gly Asn Ser--

In SEQ ID NO 2, Column 33, please delete the following line,

"Asn Thr Leu Ser Ser Met Leu Lys Gly Phe Ala Pro Ala Ala Ala Arg"
                405                            410                            415 and insert,

--Asn Thr Leu Ser Ser Met Leu Lys Gly Phe Ala Pro Ala Ala Ala Ala--
                405                            410                            415

UNITED STATES PATENT AND TRADEMARK OFFICE
CERTIFICATE OF CORRECTION

PATENT NO. : 6,977,069 B2
APPLICATION NO. : 10/359460
DATED : December 20, 2005
INVENTOR(S) : Reed et al.

It is certified that error appears in the above-identified patent and that said Letters Patent is hereby corrected as shown below:

In SEQ ID NO 2, Column 35, please delete the following line,

"Pro Ser Ala Ala Ile Gly Gly Gly Val Ala Val Gly Glu Pro Val Val"
               645                 650                 655 and insert,

--Pro Ser Ala Ala Ile Gly Gly Gly Val Ala Val Gly Glu Pro Phe Val--
               645                 650                 655

Signed and Sealed this

Twenty-fifth Day of November, 2008

JON W. DUDAS
*Director of the United States Patent and Trademark Office*

SEQUENCE LISTING

<160> NUMBER OF SEQ ID NOS: 46

<210> SEQ ID NO 1
<211> LENGTH: 2287
<212> TYPE: DNA
<213> ORGANISM: Artificial Sequence
<220> FEATURE:
<223> OTHER INFORMATION: Description of Artificial Sequence:tri-fusion
      protein Ra12-TbH9-Ra35 (designated Mtb32-Mtb39
      fusion)
<220> FEATURE:
<221> NAME/KEY: modified_base
<222> LOCATION: (30)
<223> OTHER INFORMATION: n = g, a, c or t
<220> FEATURE:
<221> NAME/KEY: modified_base
<222> LOCATION: (33)
<223> OTHER INFORMATION: n = g, a, c or t
<220> FEATURE:
<221> NAME/KEY: CDS
<222> LOCATION: (42)..(2231)
<220> FEATURE:
<221> NAME/KEY: modified_base
<222> LOCATION: (2270)
<223> OTHER INFORMATION: n = g, a, c or t

<400> SEQUENCE: 1
tctagaaata attttgttta ctttaagaan ganatataca t atg cat cac cat cac    56
                                              Met His His His His
                                                1               5

-continued

```
cat cac acg gcc gcg tcc gat aac ttc cag ctg tcc cag ggt ggg cag        104
His His Thr Ala Ala Ser Asp Asn Phe Gln Leu Ser Gln Gly Gly Gln
             10                  15                  20 gga ttc gcc att ccg atc ggg cag gcg atg gcg atc gcg ggc cag atc        152
Gly Phe Ala Ile Pro Ile Gly Gln Ala Met Ala Ile Ala Gly Gln Ile
                 25                  30                  35 cga tcg ggt ggg ggg tca ccc acc gtt cat atc ggg cct acc gcc ttc        200
Arg Ser Gly Gly Gly Ser Pro Thr Val His Ile Gly Pro Thr Ala Phe
         40                  45                  50 ctc ggc ttg ggt gtt gtc gac aac aac ggc aac ggc gca cga gtc caa        248
Leu Gly Leu Gly Val Val Asp Asn Asn Gly Asn Gly Ala Arg Val Gln
     55                  60                  65 cgc gtg gtc ggg agc gct ccg gcg gca agt ctc ggc atc tcc acc ggc        296
Arg Val Val Gly Ser Ala Pro Ala Ala Ser Leu Gly Ile Ser Thr Gly
 70                  75                  80                  85 gac gtg atc acc gcg gtc gac ggc gct ccg atc aac tcg gcc acc gcg        344
Asp Val Ile Thr Ala Val Asp Gly Ala Pro Ile Asn Ser Ala Thr Ala
                 90                  95                 100 atg gcg gac gcg ctt aac ggg cat cat ccc ggt gac gtc atc tcg gtg        392
Met Ala Asp Ala Leu Asn Gly His His Pro Gly Asp Val Ile Ser Val
             105                 110                 115 acc tgg caa acc aag tcg ggc ggc acg cgt aca ggg aac gtg aca ttg        440
Thr Trp Gln Thr Lys Ser Gly Gly Thr Arg Thr Gly Asn Val Thr Leu
         120                 125                 130 gcc gag gga ccc ccg gcc gaa ttc atg gtg gat ttc ggg gcg tta cca        488
Ala Glu Gly Pro Pro Ala Glu Phe Met Val Asp Phe Gly Ala Leu Pro
     135                 140                 145 ccg gag atc aac tcc gcg agg atg tac gcc ggc ccg ggt tcg gcc tcg        536
Pro Glu Ile Asn Ser Ala Arg Met Tyr Ala Gly Pro Gly Ser Ala Ser
150                 155                 160                 165 ctg gtg gcc gcg gct cag atg tgg gac agc gtg gcg agt gac ctg ttt        584
Leu Val Ala Ala Ala Gln Met Trp Asp Ser Val Ala Ser Asp Leu Phe
                 170                 175                 180 tcg gcc gcg tcg gcg ttt cag tcg gtg gtc tgg ggt ctg acg gtg ggg        632
Ser Ala Ala Ser Ala Phe Gln Ser Val Val Trp Gly Leu Thr Val Gly
             185                 190                 195 tcg tgg ata ggt tcg tcg gcg ggt ctg atg gtg gcg gcg gcc tcg ccg        680
Ser Trp Ile Gly Ser Ser Ala Gly Leu Met Val Ala Ala Ala Ser Pro
         200                 205                 210 tat gtg gcg tgg atg agc gtc acc gcg ggg cag gcc gag ctg acc gcc        728
Tyr Val Ala Trp Met Ser Val Thr Ala Gly Gln Ala Glu Leu Thr Ala
     215                 220                 225 gcc cag gtc cgg gtt gct gcg gcg gcc tac gag acg gcg tat ggg ctg        776
Ala Gln Val Arg Val Ala Ala Ala Ala Tyr Glu Thr Ala Tyr Gly Leu
230                 235                 240                 245 acg gtg ccc ccg ccg gtg atc gcc gag aac cgt gct gaa ctg atg att        824
Thr Val Pro Pro Pro Val Ile Ala Glu Asn Arg Ala Glu Leu Met Ile
                 250                 255                 260 ctg ata gcg acc aac ctc ttg ggg caa aac acc ccg gcg atc gcg gtc        872
Leu Ile Ala Thr Asn Leu Leu Gly Gln Asn Thr Pro Ala Ile Ala Val
             265                 270                 275 aac gag gcc gaa tac ggc gag atg tgg gcc caa gac gcc gcc gcg atg        920
Asn Glu Ala Glu Tyr Gly Glu Met Trp Ala Gln Asp Ala Ala Ala Met
         280                 285                 290 ttt ggc tac gcc gcg gcg acg gcg acg gcg acg gcg acg ttg ctg ccg        968
Phe Gly Tyr Ala Ala Ala Thr Ala Thr Ala Thr Ala Thr Leu Leu Pro
     295                 300                 305 ttc gag gag gcg ccg gag atg acc agc gcg ggt ggg ctc ctc gag cag       1016
Phe Glu Glu Ala Pro Glu Met Thr Ser Ala Gly Gly Leu Leu Glu Gln
```

-continued

| | | | | | | | | | | | | | | | |
|---|---|---|---|---|---|---|---|---|---|---|---|---|---|---|---|
| | Phe | Glu | Glu | Ala | Pro | Glu | Met | Thr | Ser | Ala | Gly | Gly | Leu | Leu | Glu | Gln |
| | 310 | | | | 315 | | | | 320 | | | | | 325 | |

| gcc gcg gtc gag gag gcc tcc gac acc gcc gcg aac cag ttg | 1064 |
|---|---|
| Ala Ala Val Glu Glu Ala Ser Asp Thr Ala Ala Asn Gln Leu | |
| 330 335 340 | |

| atg aac aat gtg ccc cag gcg ctg caa cag ctg gcc cag ccc acg cag | 1112 |
|---|---|
| Met Asn Asn Val Pro Gln Ala Leu Gln Gln Leu Ala Gln Pro Thr Gln | |
| 345 350 355 | |

| ggc acc acg cct tct tcc aag ctg ggt ggc ctg tgg aag acg gtc tcg | 1160 |
|---|---|
| Gly Thr Thr Pro Ser Ser Lys Leu Gly Gly Leu Trp Lys Thr Val Ser | |
| 360 365 370 | |

| ccg cat cgg tcg ccg atc agc aac atg gtg tcg atg gcc aac aac cac | 1208 |
|---|---|
| Pro His Arg Ser Pro Ile Ser Asn Met Val Ser Met Ala Asn Asn His | |
| 375 380 385 | |

| atg tcg atg acc aac tcg ggt gtg tcg atg acc aac acc ttg agc tcg | 1256 |
|---|---|
| Met Ser Met Thr Asn Ser Gly Val Ser Met Thr Asn Thr Leu Ser Ser | |
| 390 395 400 405 | |

| atg ttg aag ggc ttt gct ccg gcg gcg gcc cgc cag gcc gtg caa acc | 1304 |
|---|---|
| Met Leu Lys Gly Phe Ala Pro Ala Ala Ala Arg Gln Ala Val Gln Thr | |
| 410 415 420 | |

| gcg gcg caa aac ggg gtc cgg gcg atg agc tcg ctg ggc agc tcg ctg | 1352 |
|---|---|
| Ala Ala Gln Asn Gly Val Arg Ala Met Ser Ser Leu Gly Ser Ser Leu | |
| 425 430 435 | |

| ggt tct tcg ggt ctg ggc ggt ggg gtg gcc gcc aac ttg ggt cgg gcg | 1400 |
|---|---|
| Gly Ser Ser Gly Leu Gly Gly Gly Val Ala Ala Asn Leu Gly Arg Ala | |
| 440 445 450 | |

| gcc tcg gtc ggt tcg ttg tcg gtg ccg cag gcc tgg gcc gcg gcc aac | 1448 |
|---|---|
| Ala Ser Val Gly Ser Leu Ser Val Pro Gln Ala Trp Ala Ala Ala Asn | |
| 455 460 465 | |

| cag gca gtc acc ccg gcg gcg cgg gcg ctg ccg ctg acc agc ctg acc | 1496 |
|---|---|
| Gln Ala Val Thr Pro Ala Ala Arg Ala Leu Pro Leu Thr Ser Leu Thr | |
| 470 475 480 485 | |

| agc gcc gcg gaa aga ggg ccc ggg cag atg ctg ggc ggg ctg ccg gtg | 1544 |
|---|---|
| Ser Ala Ala Glu Arg Gly Pro Gly Gln Met Leu Gly Gly Leu Pro Val | |
| 490 495 500 | |

| ggg cag atg ggc gcc agg gcc ggt ggt ggg ctc agt ggt gtg ctg cgt | 1592 |
|---|---|
| Gly Gln Met Gly Ala Arg Ala Gly Gly Gly Leu Ser Gly Val Leu Arg | |
| 505 510 515 | |

| gtt ccg ccg cga ccc tat gtg atg ccg cat tct ccg gca gcc ggc gat | 1640 |
|---|---|
| Val Pro Pro Arg Pro Tyr Val Met Pro His Ser Pro Ala Ala Gly Asp | |
| 520 525 530 | |

| atc gcc ccg ccg gcc ttg tcg cag gac cgg ttc gcc gac ttc ccc gcg | 1688 |
|---|---|
| Ile Ala Pro Pro Ala Leu Ser Gln Asp Arg Phe Ala Asp Phe Pro Ala | |
| 535 540 545 | |

| ctg ccc ctc gac ccg tcc gcg atg gtc gcc caa gtg ggg cca cag gtg | 1736 |
|---|---|
| Leu Pro Leu Asp Pro Ser Ala Met Val Ala Gln Val Gly Pro Gln Val | |
| 550 555 560 565 | |

| gtc aac atc aac acc aaa ctg ggc tac aac aac gcc gtg ggc gcc ggg | 1784 |
|---|---|
| Val Asn Ile Asn Thr Lys Leu Gly Tyr Asn Asn Ala Val Gly Ala Gly | |
| 570 575 580 | |

| acc ggc atc gtc atc gat ccc aac ggt gtc gtg ctg acc aac aac cac | 1832 |
|---|---|
| Thr Gly Ile Val Ile Asp Pro Asn Gly Val Val Leu Thr Asn Asn His | |
| 585 590 595 | |

| gtg atc gcg ggc gcc acc gac atc aat gcg ttc agc gtc ggc tcc ggc | 1880 |
|---|---|
| Val Ile Ala Gly Ala Thr Asp Ile Asn Ala Phe Ser Val Gly Ser Gly | |
| 600 605 610 | |

| caa acc tac ggc gtc gat gtg gtc ggg tat gac cgc acc cag gat gtc | 1928 |
|---|---|
| Gln Thr Tyr Gly Val Asp Val Val Gly Tyr Asp Arg Thr Gln Asp Val | |
| 615 620 625 | |

-continued

```
gcg gtg ctg cag ctg cgc ggt gcc ggt ggc ctg ccg tcg gcg gcg atc    1976
Ala Val Leu Gln Leu Arg Gly Ala Gly Gly Leu Pro Ser Ala Ala Ile
630                 635                 640                 645 ggt ggc ggc gtc gcg gtt ggt gag ccc gtc gtc gcg atg ggc aac agc    2024
Gly Gly Gly Val Ala Val Gly Glu Pro Val Val Ala Met Gly Asn Ser
            650                 655                 660 ggt ggg cag ggc gga acg ccc cgt gcg gtg cct ggc agg gtg gtc gcg    2072
Gly Gly Gln Gly Gly Thr Pro Arg Ala Val Pro Gly Arg Val Val Ala
        665                 670                 675 ctc ggc caa acc gtg cag gcg tcg gat tcg ctg acc ggt gcc gaa gag    2120
Leu Gly Gln Thr Val Gln Ala Ser Asp Ser Leu Thr Gly Ala Glu Glu
    680                 685                 690 aca ttg aac ggg ttg atc cag ttc gat gcc gcg atc cag ccc ggt gat    2168
Thr Leu Asn Gly Leu Ile Gln Phe Asp Ala Ala Ile Gln Pro Gly Asp
695                 700                 705 tcg ggc ggg ccc gtc gtc aac ggc cta gga cag gtg gtc ggt atg aac    2216
Ser Gly Gly Pro Val Val Asn Gly Leu Gly Gln Val Val Gly Met Asn
710                 715                 720                 725 acg gcc gcg tcc taggatatcc atcacactgg cggccgctcg agcagatccg        2268
Thr Ala Ala Ser gntgtaacaa agcccgaaa                                               2287
```

<210> SEQ ID NO 2
<211> LENGTH: 729
<212> TYPE: PRT
<213> ORGANISM: Artificial Sequence
<220> FEATURE:
<223> OTHER INFORMATION: Description of Artificial Sequence:tri-fusion

<400> SEQUENCE: 2

```
Met His His His His His Thr Ala Ala Ser Asp Asn Phe Gln Leu
  1               5                  10                  15

Ser Gln Gly Gly Gln Gly Phe Ala Ile Pro Ile Gly Gln Ala Met Ala
                 20                  25                  30

Ile Ala Gly Gln Ile Arg Ser Gly Gly Gly Ser Pro Thr Val His Ile
             35                  40                  45

Gly Pro Thr Ala Phe Leu Gly Leu Gly Val Val Asp Asn Asn Gly Asn
         50                  55                  60

Gly Ala Arg Val Gln Arg Val Val Gly Ser Ala Pro Ala Ala Ser Leu
 65                  70                  75                  80

Gly Ile Ser Thr Gly Asp Val Ile Thr Ala Val Asp Gly Ala Pro Ile
                 85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
        115                 120                 125

Gly Asn Val Thr Leu Ala Glu Gly Pro Pro Ala Glu Phe Met Val Asp
    130                 135                 140

Phe Gly Ala Leu Pro Pro Glu Ile Asn Ser Ala Arg Met Tyr Ala Gly
145                 150                 155                 160

Pro Gly Ser Ala Ser Leu Val Ala Ala Ala Gln Met Trp Asp Ser Val
                165                 170                 175

Ala Ser Asp Leu Phe Ser Ala Ser Ala Phe Gln Ser Val Val Trp
            180                 185                 190

Gly Leu Thr Val Gly Ser Trp Ile Gly Ser Ser Ala Gly Leu Met Val
        195                 200                 205

Ala Ala Ala Ser Pro Tyr Val Ala Trp Met Ser Val Thr Ala Gly Gln
```

-continued

```
            210                 215                 220
Ala Glu Leu Thr Ala Ala Gln Val Arg Val Ala Ala Ala Tyr Glu
225                 230                 235                 240

Thr Ala Tyr Gly Leu Thr Val Pro Pro Val Ile Ala Glu Asn Arg
                245                 250                 255

Ala Glu Leu Met Ile Leu Ile Ala Thr Asn Leu Leu Gly Gln Asn Thr
                    260                 265                 270

Pro Ala Ile Ala Val Asn Glu Ala Glu Tyr Gly Glu Met Trp Ala Gln
                275                 280                 285

Asp Ala Ala Met Phe Gly Tyr Ala Ala Thr Ala Thr Ala Thr
290                 295                 300

Ala Thr Leu Leu Pro Phe Glu Glu Ala Pro Glu Met Thr Ser Ala Gly
305                 310                 315                 320

Gly Leu Leu Glu Gln Ala Ala Ala Val Glu Glu Ala Ser Asp Thr Ala
                325                 330                 335

Ala Ala Asn Gln Leu Met Asn Asn Val Pro Gln Ala Leu Gln Gln Leu
                340                 345                 350

Ala Gln Pro Thr Gln Gly Thr Thr Pro Ser Ser Lys Leu Gly Gly Leu
                355                 360                 365

Trp Lys Thr Val Ser Pro His Arg Ser Pro Ile Ser Asn Met Val Ser
370                 375                 380

Met Ala Asn Asn His Met Ser Met Thr Asn Ser Gly Val Ser Met Thr
385                 390                 395                 400

Asn Thr Leu Ser Ser Met Leu Lys Gly Phe Ala Pro Ala Ala Ala Arg
                405                 410                 415

Gln Ala Val Gln Thr Ala Ala Gln Asn Gly Val Arg Ala Met Ser Ser
                420                 425                 430

Leu Gly Ser Ser Leu Gly Ser Ser Gly Leu Gly Gly Val Ala Ala
                435                 440                 445

Asn Leu Gly Arg Ala Ala Ser Val Gly Ser Leu Ser Val Pro Gln Ala
450                 455                 460

Trp Ala Ala Ala Asn Gln Ala Val Thr Pro Ala Ala Arg Ala Leu Pro
465                 470                 475                 480

Leu Thr Ser Leu Thr Ser Ala Ala Glu Arg Gly Pro Gly Gln Met Leu
                485                 490                 495

Gly Gly Leu Pro Val Gly Gln Met Gly Ala Arg Ala Gly Gly Gly Leu
                500                 505                 510

Ser Gly Val Leu Arg Val Pro Pro Arg Pro Tyr Val Met Pro His Ser
                515                 520                 525

Pro Ala Ala Gly Asp Ile Ala Pro Pro Ala Leu Ser Gln Asp Arg Phe
                530                 535                 540

Ala Asp Phe Pro Ala Leu Pro Leu Asp Pro Ser Ala Met Val Ala Gln
545                 550                 555                 560

Val Gly Pro Gln Val Val Asn Ile Asn Thr Lys Leu Gly Tyr Asn Asn
                565                 570                 575

Ala Val Gly Ala Gly Thr Gly Ile Val Ile Asp Pro Asn Gly Val Val
                580                 585                 590

Leu Thr Asn Asn His Val Ile Ala Gly Ala Thr Asp Ile Asn Ala Phe
                595                 600                 605

Ser Val Gly Ser Gly Gln Thr Tyr Gly Val Asp Val Gly Tyr Asp
                610                 615                 620

Arg Thr Gln Asp Val Ala Val Leu Gln Leu Arg Gly Ala Gly Gly Leu
625                 630                 635                 640
```

```
Pro Ser Ala Ala Ile Gly Gly Val Ala Val Gly Glu Pro Val Val
            645                 650                 655

Ala Met Gly Asn Ser Gly Gly Gln Gly Gly Thr Pro Arg Ala Val Pro
                660                 665                 670

Gly Arg Val Val Ala Leu Gly Gln Thr Val Gln Ala Ser Asp Ser Leu
            675                 680                 685

Thr Gly Ala Glu Glu Thr Leu Asn Gly Leu Ile Gln Phe Asp Ala Ala
        690                 695                 700

Ile Gln Pro Gly Asp Ser Gly Gly Pro Val Val Asn Gly Leu Gly Gln
705                 710                 715                 720

Val Val Gly Met Asn Thr Ala Ala Ser
                725

<210> SEQ ID NO 3
<211> LENGTH: 1081
<212> TYPE: DNA
<213> ORGANISM: Artificial Sequence
<220> FEATURE:
<223> OTHER INFORMATION: Description of Artificial Sequence:tri-fusion
      protein Erd14-DPV-MTI
<220> FEATURE:
<221> NAME/KEY: CDS
<222> LOCATION: (10)..(1002)

<400> SEQUENCE: 3 gatatacat atg cat cac cat cac cat cac atg gcc acc acc ctt ccc gtt    51
          Met His His His His His His Met Ala Thr Thr Leu Pro Val
            1               5                   10 cag cgc cac ccg cgg tcc ctc ttc ccc gag ttt tct gag ctg ttc gcg    99
Gln Arg His Pro Arg Ser Leu Phe Pro Glu Phe Ser Glu Leu Phe Ala
 15                  20                  25                  30 gcc ttc ccg tca ttc gcc gga ctc cgg ccc acc ttc gac acc cgg ttg   147
Ala Phe Pro Ser Phe Ala Gly Leu Arg Pro Thr Phe Asp Thr Arg Leu
                 35                  40                  45 atg cgg ctg gaa gac gag atg aaa gag ggg cgc tac gag gta cgc gcg   195
Met Arg Leu Glu Asp Glu Met Lys Glu Gly Arg Tyr Glu Val Arg Ala
             50                  55                  60 gag ctt ccc ggg gtc gac ccc gac aag gac gtc gac att atg gtc cgc   243
Glu Leu Pro Gly Val Asp Pro Asp Lys Asp Val Asp Ile Met Val Arg
         65                  70                  75 gat ggt cag ctg acc atc aag gcc gag cgc acc gag cag aag gac ttc   291
Asp Gly Gln Leu Thr Ile Lys Ala Glu Arg Thr Glu Gln Lys Asp Phe
     80                  85                  90 gac ggt cgc tcg gaa ttc gcg tac ggt tcc ttc gtt cgc acg gtg tcg   339
Asp Gly Arg Ser Glu Phe Ala Tyr Gly Ser Phe Val Arg Thr Val Ser
 95                 100                 105                 110 ctg ccg gta ggt gct gac gag gac gac att aag gcc acc tac gac aag   387
Leu Pro Val Gly Ala Asp Glu Asp Asp Ile Lys Ala Thr Tyr Asp Lys
                115                 120                 125 ggc att ctt act gtg tcg gtg gcg gtt tcg gaa ggg aag cca acc gaa   435
Gly Ile Leu Thr Val Ser Val Ala Val Ser Glu Gly Lys Pro Thr Glu
            130                 135                 140 aag cac att cag atc cgg tcc acc aac aag ctt gat ccc gtg gac gcg   483
Lys His Ile Gln Ile Arg Ser Thr Asn Lys Leu Asp Pro Val Asp Ala
        145                 150                 155 gtc att aac acc acc tgc aat tac ggg cag gta gta gct gcg ctc aac   531
Val Ile Asn Thr Thr Cys Asn Tyr Gly Gln Val Val Ala Ala Leu Asn
    160                 165                 170 gcg acg gat ccg ggg gct gcc gca cag ttc aac gcc tca ccg gtg gcg   579
Ala Thr Asp Pro Gly Ala Ala Ala Gln Phe Asn Ala Ser Pro Val Ala
```

-continued

```
cag tcc tat ttg cgc aat ttc ctc gcc gca ccg cca cct cag cgc gct        627
Gln Ser Tyr Leu Arg Asn Phe Leu Ala Ala Pro Pro Pro Gln Arg Ala
            195                 200                 205 gcc atg gcc gcg caa ttg caa gct gtg ccg ggg gcg gca cag tac atc        675
Ala Met Ala Ala Gln Leu Gln Ala Val Pro Gly Ala Ala Gln Tyr Ile
        210                 215                 220 ggc ctt gtc gag tcg gtt gcc ggc tcc tgc aac aac tat gag ctc atg       723
Gly Leu Val Glu Ser Val Ala Gly Ser Cys Asn Asn Tyr Glu Leu Met
                225                 230                 235 acg att aat tac cag ttc ggg gac gtc gac gct cat ggc gcc atg atc       771
Thr Ile Asn Tyr Gln Phe Gly Asp Val Asp Ala His Gly Ala Met Ile
        240                 245                 250 cgc gct cag gcg gcg tcg ctt gag gcg gag cat cag gcc atc gtt cgt       819
Arg Ala Gln Ala Ala Ser Leu Glu Ala Glu His Gln Ala Ile Val Arg
255                 260                 265                 270 gat gtg ttg gcc gcg ggt gac ttt tgg ggc ggc gcc ggt tcg gtg gct       867
Asp Val Leu Ala Ala Gly Asp Phe Trp Gly Gly Ala Gly Ser Val Ala
                275                 280                 285 tgc cag gag ttc att acc cag ttg ggc cgt aac ttc cag gtg atc tac       915
Cys Gln Glu Phe Ile Thr Gln Leu Gly Arg Asn Phe Gln Val Ile Tyr
            290                 295                 300 gag cag gcc aac gcc cac ggg cag aag gtg cag gct gcc ggc aac aac       963
Glu Gln Ala Asn Ala His Gly Gln Lys Val Gln Ala Ala Gly Asn Asn
305                 310                 315 atg gcg caa acc gac agc gcc gtc ggc tcc agc tgg gcc actagtaacg        1012
Met Ala Gln Thr Asp Ser Ala Val Gly Ser Ser Trp Ala
                320                 325                 330 gccgccagtg tgctggaatt ctgcagatat ccatcacact ggcggccgct cgagcagatc    1072
cggctgcta                                                             1081
```

<210> SEQ ID NO 4
<211> LENGTH: 331
<212> TYPE: PRT
<213> ORGANISM: Artificial Sequence
<220> FEATURE:
<223> OTHER INFORMATION: Description of Artificial Sequence:tri-fusion

<400> SEQUENCE: 4

```
Met His His His His His Met Ala Thr Thr Leu Pro Val Gln Arg
 1               5                  10                  15

His Pro Arg Ser Leu Phe Pro Glu Phe Ser Glu Leu Phe Ala Ala Phe
                20                  25                  30

Pro Ser Phe Ala Gly Leu Arg Pro Thr Phe Asp Thr Arg Leu Met Arg
            35                  40                  45

Leu Glu Asp Glu Met Lys Glu Gly Arg Tyr Glu Val Arg Ala Glu Leu
        50                  55                  60

Pro Gly Val Asp Pro Asp Lys Asp Val Asp Ile Met Val Arg Asp Gly
65                  70                  75                  80

Gln Leu Thr Ile Lys Ala Glu Arg Thr Glu Gln Lys Asp Phe Asp Gly
                85                  90                  95

Arg Ser Glu Phe Ala Tyr Gly Ser Phe Val Arg Thr Val Ser Leu Pro
            100                 105                 110

Val Gly Ala Asp Glu Asp Asp Ile Lys Ala Thr Tyr Asp Lys Gly Ile
        115                 120                 125

Leu Thr Val Ser Val Ala Val Ser Glu Gly Lys Pro Thr Glu Lys His
    130                 135                 140
```

```
Ile Gln Ile Arg Ser Thr Asn Lys Leu Asp Pro Val Asp Ala Val Ile
145                 150                 155                 160

Asn Thr Thr Cys Asn Tyr Gly Gln Val Val Ala Ala Leu Asn Ala Thr
            165                 170                 175

Asp Pro Gly Ala Ala Gln Phe Asn Ala Ser Pro Val Ala Gln Ser
        180                 185                 190

Tyr Leu Arg Asn Phe Leu Ala Ala Pro Pro Gln Arg Ala Ala Met
    195                 200                 205

Ala Ala Gln Leu Gln Ala Val Pro Gly Ala Ala Gln Tyr Ile Gly Leu
    210                 215                 220

Val Glu Ser Val Ala Gly Ser Cys Asn Asn Tyr Glu Leu Met Thr Ile
225                 230                 235                 240

Asn Tyr Gln Phe Gly Asp Val Asp Ala His Gly Ala Met Ile Arg Ala
                245                 250                 255

Gln Ala Ala Ser Leu Glu Ala Glu His Gln Ala Ile Val Arg Asp Val
                260                 265                 270

Leu Ala Ala Gly Asp Phe Trp Gly Ala Gly Ser Val Ala Cys Gln
    275                 280                 285

Glu Phe Ile Thr Gln Leu Gly Arg Asn Phe Gln Val Ile Tyr Glu Gln
290                 295                 300

Ala Asn Ala His Gly Gln Lys Val Gln Ala Ala Gly Asn Asn Met Ala
305                 310                 315                 320

Gln Thr Asp Ser Ala Val Gly Ser Ser Trp Ala
                325                 330

<210> SEQ ID NO 5
<211> LENGTH: 1993
<212> TYPE: DNA
<213> ORGANISM: Artificial Sequence
<220> FEATURE:
<223> OTHER INFORMATION: Description of Artificial Sequence:tri-fusion
      protein TbRa3-38kD-Tb38-1
<220> FEATURE:
<221> NAME/KEY: CDS
<222> LOCATION: (152)..(1276)

<400> SEQUENCE: 5
tgttcttcga cggcaggctg gtggaggaag ggcccaccga acagctgttc tcctcgccga     60
agcatgcgga aaccgcccga tacgtcgccg gactgtcggg ggacgtcaag gacgccaagc    120
gcggaaattg aagagcacag aaaggtatgg c gtg aaa att cgt ttg cat acg       172
                                   Val Lys Ile Arg Leu His Thr
                                     1               5 ctg ttg gcc gtg ttg acc gct gcg ccg ctg ctg cta gca gcg gcg ggc      220
Leu Leu Ala Val Leu Thr Ala Ala Pro Leu Leu Leu Ala Ala Ala Gly
        10                  15                  20 tgt ggc tcg aaa cca ccg agc ggt tcg cct gaa acg ggc gcc ggc gcc      268
Cys Gly Ser Lys Pro Pro Ser Gly Ser Pro Glu Thr Gly Ala Gly Ala
    25                  30                  35 ggt act gtc gcg act acc ccc gcg tcg tcg ccg gtg acg ttg gcg gag      316
Gly Thr Val Ala Thr Thr Pro Ala Ser Ser Pro Val Thr Leu Ala Glu
40                  45                  50                  55 acc ggt agc acg ctg ctc tac ccg ctg ttc aac ctg tgg ggt ccg gcc      364
Thr Gly Ser Thr Leu Leu Tyr Pro Leu Phe Asn Leu Trp Gly Pro Ala
                60                  65                  70 ttt cac gag agg tat ccg aac gtc acg atc acc gct cag ggc acc ggt      412
Phe His Glu Arg Tyr Pro Asn Val Thr Ile Thr Ala Gln Gly Thr Gly
            75                  80                  85 tct ggt gcc ggg atc gcg cag gcc gcc gcc ggg acg gtc aac att ggg      460
```

-continued

| | | |
|---|---|---|
| Ser Gly Ala Gly Ile Ala Gln Ala Ala Gly Thr Val Asn Ile Gly<br>        90                        95                      100 | | |
| gcc tcc gac gcc tat ctg tcg gaa ggt gat atg gcc gcg cac aag ggg<br>Ala Ser Asp Ala Tyr Leu Ser Glu Gly Asp Met Ala Ala His Lys Gly<br>105                    110                    115 | 508 |
| ctg atg aac atc gcg cta gcc atc tcc gct cag cag gtc aac tac aac<br>Leu Met Asn Ile Ala Leu Ala Ile Ser Ala Gln Gln Val Asn Tyr Asn<br>120                    125                    130                    135 | 556 |
| ctg ccc gga gtg agc gag cac ctc aag ctg aac gga aaa gtc ctg gcg<br>Leu Pro Gly Val Ser Glu His Leu Lys Leu Asn Gly Lys Val Leu Ala<br>                  140                    145                    150 | 604 |
| gcc atg tac cag ggc acc atc aaa acc tgg gac gac ccg cag atc gct<br>Ala Met Tyr Gln Gly Thr Ile Lys Thr Trp Asp Asp Pro Gln Ile Ala<br>                  155                    160                    165 | 652 |
| gcg ctc aac ccc ggc gtg aac ctg ccc ggc acc gcg gta gtt ccg ctg<br>Ala Leu Asn Pro Gly Val Asn Leu Pro Gly Thr Ala Val Val Pro Leu<br>170                    175                    180 | 700 |
| cac cgc tcc gac ggg tcc ggt gac acc ttc ttg ttc acc cag tac ctg<br>His Arg Ser Asp Gly Ser Gly Asp Thr Phe Leu Phe Thr Gln Tyr Leu<br>                  185                    190                    195 | 748 |
| tcc aag caa gat ccc gag ggc tgg ggc aag tcg ccc ggc ttc ggc acc<br>Ser Lys Gln Asp Pro Glu Gly Trp Gly Lys Ser Pro Gly Phe Gly Thr<br>200                    205                    210                    215 | 796 |
| acc gtc gac ttc ccg gcg gtg ccg ggt gcg ctg ggt gag aac ggc aac<br>Thr Val Asp Phe Pro Ala Val Pro Gly Ala Leu Gly Glu Asn Gly Asn<br>                  220                    225                    230 | 844 |
| ggc ggc atg gtg acc ggt tgc gcc gag aca ccg ggc tgc gtg gcc tat<br>Gly Gly Met Val Thr Gly Cys Ala Glu Thr Pro Gly Cys Val Ala Tyr<br>                    235                    240                    245 | 892 |
| atc ggc atc agc ttc ctc gac cag gcc agt caa cgg gga ctc ggc gag<br>Ile Gly Ile Ser Phe Leu Asp Gln Ala Ser Gln Arg Gly Leu Gly Glu<br>                  250                    255                    260 | 940 |
| gcc caa cta ggc aat agc tct ggc aat ttc ttg ttg ccc gac gcg caa<br>Ala Gln Leu Gly Asn Ser Ser Gly Asn Phe Leu Leu Pro Asp Ala Gln<br>265                    270                    275 | 988 |
| agc att cag gcc gcg gcg gct ggc ttc gca tcg aaa acc ccg gcg aac<br>Ser Ile Gln Ala Ala Ala Ala Gly Phe Ala Ser Lys Thr Pro Ala Asn<br>280                    285                    290                    295 | 1036 |
| cag gcg att tcg atg atc gac ggg ccc gcc ccg gac ggc tac ccg atc<br>Gln Ala Ile Ser Met Ile Asp Gly Pro Ala Pro Asp Gly Tyr Pro Ile<br>                  300                    305                    310 | 1084 |
| atc aac tac gag tac gcc atc gtc aac aac cgg caa aag gac gcc gcc<br>Ile Asn Tyr Glu Tyr Ala Ile Val Asn Asn Arg Gln Lys Asp Ala Ala<br>                  315                    320                    325 | 1132 |
| acc gcg cag acc ttg cag gca ttt ctg cac tgg gcg atc acc gac ggc<br>Thr Ala Gln Thr Leu Gln Ala Phe Leu His Trp Ala Ile Thr Asp Gly<br>                  330                    335                    340 | 1180 |
| aac aag gcc tcg ttc ctc gac cag gtt cat ttc cag ccg ctg ccg ccc<br>Asn Lys Ala Ser Phe Leu Asp Gln Val His Phe Gln Pro Leu Pro Pro<br>345                    350                    355 | 1228 |
| gcg gtg gtg aag ttg tct gac gcg ttg atc gcg acg att tcc agc<br>Ala Val Val Lys Leu Ser Asp Ala Leu Ile Ala Thr Ile Ser Ser<br>360                    365                    370 | 1273 |
| tagcctcgtt gaccaccacg cgacagcaac ctccgtcggg ccatcgggct gctttgcgga | 1333 |
| gcatgctggc ccgtgccggt gaagtcggcc gcgctggccc ggccatccgg tggttgggtg | 1393 |
| ggataggtgc ggtgatcccg ctgcttgcgc tggtcttggt gctggtggtg ctggtcatcg | 1453 |
| aggcgatggg tgcgatcagg ctcaacgggt tgcatttctt caccgccacc gaatggaatc | 1513 |

```
caggcaacac ctacggcgaa accgttgtca ccgacgcgtc gcccatccgg tcggcgccta      1573
ctacggggcg ttgccgctga tcgtcgggac gctggcgacc tcggcaatcg ccctgatcat      1633
cgcggtgccg gtctctgtag gagcggcgct ggtgatcgtg gaacggctgc cgaaacggtt      1693
ggccgaggct gtgggaatag tcctggaatt gctcgccgga atccccagcg tggtcgtcgg      1753
tttgtggggg gcaatgacgt tcgggccgtt catcgctcat cacatcgctc cggtgatcgc      1813
tcacaacgct cccgatgtgc cggtgctgaa ctacttgcgc ggcgacccgg caacggggga      1873
gggcatgttg gtgtccggtc tggtgttggc ggtgatggtc gttcccatta cgccaccac       1933 cactcatgac ctgttccggc aggtgccggt gttgccccgg gagggcgcga tcgggaattc      1993
```

<210> SEQ ID NO 6
<211> LENGTH: 374
<212> TYPE: PRT
<213> ORGANISM: Artificial Sequence
<220> FEATURE:
<223> OTHER INFORMATION: Description of Artificial Sequence:tri-fusion

<400> SEQUENCE: 6

```
Val Lys Ile Arg Leu His Thr Leu Leu Ala Val Leu Thr Ala Ala Pro
 1               5                  10                  15

Leu Leu Leu Ala Ala Ala Gly Cys Gly Ser Lys Pro Pro Ser Gly Ser
                20                  25                  30

Pro Glu Thr Gly Ala Gly Ala Gly Thr Val Ala Thr Pro Ala Ser
            35                  40                  45

Ser Pro Val Thr Leu Ala Glu Thr Gly Ser Thr Leu Leu Tyr Pro Leu
        50                  55                  60

Phe Asn Leu Trp Gly Pro Ala Phe His Glu Arg Tyr Pro Asn Val Thr
65                  70                  75                  80

Ile Thr Ala Gln Gly Thr Gly Ser Gly Ala Gly Ile Ala Gln Ala Ala
                85                  90                  95

Ala Gly Thr Val Asn Ile Gly Ala Ser Asp Ala Tyr Leu Ser Glu Gly
            100                 105                 110

Asp Met Ala Ala His Lys Gly Leu Met Asn Ile Ala Leu Ala Ile Ser
        115                 120                 125

Ala Gln Gln Val Asn Tyr Asn Leu Pro Gly Val Ser Glu His Leu Lys
    130                 135                 140

Leu Asn Gly Lys Val Leu Ala Ala Met Tyr Gln Gly Thr Ile Lys Thr
145                 150                 155                 160

Trp Asp Asp Pro Gln Ile Ala Ala Leu Asn Pro Gly Val Asn Leu Pro
                165                 170                 175

Gly Thr Ala Val Val Pro Leu His Arg Ser Asp Gly Ser Gly Asp Thr
            180                 185                 190

Phe Leu Phe Thr Gln Tyr Leu Ser Lys Gln Asp Pro Glu Gly Trp Gly
        195                 200                 205

Lys Ser Pro Gly Phe Gly Thr Thr Val Asp Phe Pro Ala Val Pro Gly
    210                 215                 220

Ala Leu Gly Glu Asn Gly Asn Gly Gly Met Val Thr Gly Cys Ala Glu
225                 230                 235                 240

Thr Pro Gly Cys Val Ala Tyr Ile Gly Ile Ser Phe Leu Asp Gln Ala
                245                 250                 255

Ser Gln Arg Gly Leu Gly Glu Ala Gln Leu Gly Asn Ser Ser Gly Asn
            260                 265                 270

Phe Leu Leu Pro Asp Ala Gln Ser Ile Gln Ala Ala Ala Gly Phe
        275                 280                 285
```

```
Ala Ser Lys Thr Pro Ala Asn Gln Ala Ile Ser Met Ile Asp Gly Pro
    290                 295                 300

Ala Pro Asp Gly Tyr Pro Ile Ile Asn Tyr Glu Tyr Ala Ile Val Asn
305                 310                 315                 320

Asn Arg Gln Lys Asp Ala Ala Thr Ala Gln Thr Leu Gln Ala Phe Leu
            325                 330                 335

His Trp Ala Ile Thr Asp Gly Asn Lys Ala Ser Phe Leu Asp Gln Val
                340                 345                 350

His Phe Gln Pro Leu Pro Pro Ala Val Val Lys Leu Ser Asp Ala Leu
        355                 360                 365

Ile Ala Thr Ile Ser Ser
    370

<210> SEQ ID NO 7
<211> LENGTH: 1777
<212> TYPE: DNA
<213> ORGANISM: Artificial Sequence
<220> FEATURE:
<223> OTHER INFORMATION: Description of Artificial Sequence:bi-fusion
      protein TbH9-Tb38-1

<400> SEQUENCE: 7
ggtcttgacc accacctggg tgtcgaagtc ggtgcccgga ttgaagtcca ggtactcgtg      60
ggtggggcgg gcgaaacaat agcgacaagc atgcgagcag ccgcggtagc cgttgacggt     120
gtagcgaaac ggcaacgcgg ccgcgttggg caccttgttc agcgctgatt tgcacaacac     180
ctcgtggaag gtgatgccgt cgaattgtgg cgcgcgaacg ctgcggacca ggccgatccg     240
ctgcaacccg gcagcgcccg tcgtcaacgg catcccgtt caccgcgacg gcttgccggg      300
cccaacgcat accattattc gaacaaccgt tctatacttt gtcaacgctg gccgctaccg     360
agcgccgcac aggatgtgat atgccatctc tgcccgcaca gacaggagcc aggccttatg     420
acagcattcg gcgtcgagcc ctacgggcag ccgaagtacc tagaaatcgc cgggaagcgc     480
atggcgtata tcgacgaagg caaggggtgac gccatcgtct ttcagcacgg caaccccacg     540
tcgtcttact tgtggcgcaa catcatgccg cacttggaag gctgggccg ctggtggcc      600
tgcgatctga tcgggatggg cgcgtcggac aagctcagcc catcgggacc cgaccgctat     660
agctatggcg agcaacgaga ctttttgttc gcgctctggg atgcgctcga cctcggcgac     720
cacgtggtac tggtgctgca cgactggggc tcggcgctcg gcttcgactg gctaaccag     780
catcgcgacc gagtgcaggg gatcgcgttc atggaagcga tcgtcacccc gatgacgtgg     840
gcggactggc cgccggccgt gcggggtgtg ttccagggtt ccgatcgcc tcaaggcgag      900
ccaatggcgt tggagcacaa catctttgtc aacgggtgc tgcccggggc gatcctgcga     960
cagctcagcg acgaggaaat gaaccactat cggcggccat cgtgaacgg cggcgaggac    1020
cgtcgcccca cgttgtcgtg gccacgaaac cttccaatcg acggtgagcc cgccgaggtc    1080
gtcgcgttgg tcaacgagta ccggagctgg ctcgaggaaa ccgacatgcc gaaactgttc    1140
atcaacgccg agcccggcgc gatcatcacc ggccgcatcc gtgactatgt caggagctgg    1200
cccaaccaga ccgaaatcac agtgcccggc gtgcatttcg ttcaggagga cagcgatggc    1260
gtcgtatcgt gggcgggcgc tcggcagcat cggcgacctg ggagcgctct catttcacga    1320
gaccaagaat gtgatttccg gcgaaggcgg cgccctgctt gtcaactcat aagacttcct    1380
gctccgggca gagattctca gggaaaaggg caccaatcgc agccgcttcc ttcgcaacga    1440
ggtcgacaaa tatacgtggc aggacaaagg tcttcctatt tgcccagcga attagtcgct    1500
```

```
gcctttctat gggctcagtt cgaggaagcc gagcggatca cgcgtatccg attggaccta    1560
tggaaccggt atcatgaaag cttcgaatca ttggaacagc gggggctcct gcgccgtccg    1620
atcatcccac agggctgctc tcacaacgcc cacatgtact acgtgttact agcgcccagc    1680
gccgatcggg aggaggtgct ggcgcgtctg acgagcgaag gtataggcgc ggtctttcat    1740
tacgtgccgc ttcacgattc gccggccggg cgtcgct                             1777

<210> SEQ ID NO 8
<211> LENGTH: 358
<212> TYPE: PRT
<213> ORGANISM: Artificial Sequence
<220> FEATURE:
<223> OTHER INFORMATION: Description of Artificial Sequence:bi-fusion
      protein TbH9-Tb38-1
<220> FEATURE:
<221> NAME/KEY: MOD_RES
<222> LOCATION: (254)
<223> OTHER INFORMATION: Xaa = any amino acid

<400> SEQUENCE: 8
```

Val Ala Trp Met Ser Val Thr Ala Gly Gln Ala Glu Leu Thr Ala Ala
 1               5                  10                  15

Gln Val Arg Val Ala Ala Ala Tyr Glu Thr Ala Tyr Gly Leu Thr
            20                  25                  30

Val Pro Pro Val Ile Ala Glu Asn Arg Ala Glu Leu Met Ile Leu
        35                  40                  45

Ile Ala Thr Asn Leu Leu Gly Gln Asn Thr Pro Ala Ile Ala Val Asn
     50                  55                  60

Glu Ala Glu Tyr Gly Glu Met Trp Ala Gln Asp Ala Ala Ala Met Phe
 65                  70                  75                  80

Gly Tyr Ala Ala Ala Thr Ala Thr Ala Thr Ala Thr Leu Leu Pro Phe
                 85                  90                  95

Glu Glu Ala Pro Glu Met Thr Ser Ala Gly Leu Leu Glu Gln Ala
            100                 105                 110

Ala Ala Val Glu Glu Ala Ser Asp Thr Ala Ala Ala Asn Gln Leu Met
        115                 120                 125

Asn Asn Val Pro Gln Ala Leu Lys Gln Leu Ala Gln Pro Thr Gln Gly
    130                 135                 140

Thr Thr Pro Ser Ser Lys Leu Gly Gly Leu Trp Lys Thr Val Ser Pro
145                 150                 155                 160

His Arg Ser Pro Ile Ser Asn Met Val Ser Met Ala Asn Asn His Met
                165                 170                 175

Ser Met Thr Asn Ser Gly Val Ser Met Thr Asn Thr Leu Ser Ser Met
            180                 185                 190

Leu Lys Gly Phe Ala Pro Ala Ala Ala Ala Gln Ala Val Gln Thr Ala
        195                 200                 205

Ala Gln Asn Gly Val Arg Ala Met Ser Ser Leu Gly Ser Ser Leu Gly
    210                 215                 220

Ser Ser Gly Leu Gly Gly Gly Val Ala Ala Asn Leu Gly Arg Ala Ala
225                 230                 235                 240

Ser Val Arg Tyr Gly His Arg Asp Gly Gly Lys Tyr Ala Xaa Ser Gly
                245                 250                 255

Arg Arg Asn Gly Gly Pro Ala Thr Asp Ala Ala Thr Leu Ala Gln Glu
            260                 265                 270

Ala Gly Asn Phe Glu Arg Ile Ser Gly Asp Leu Lys Thr Gln Ile Asp
        275                 280                 285

-continued

```
Gln Val Glu Ser Thr Ala Gly Ser Leu Gln Gly Gln Trp Arg Gly Ala
    290                 295                 300

Ala Gly Thr Ala Ala Gln Ala Ala Val Val Arg Phe Gln Glu Ala Ala
305                 310                 315                 320

Asn Lys Gln Lys Gln Glu Leu Asp Glu Ile Ser Thr Asn Ile Arg Gln
                325                 330                 335

Ala Gly Val Gln Tyr Ser Arg Ala Asp Glu Glu Gln Gln Gln Ala Leu
            340                 345                 350

Ser Ser Gln Met Gly Phe
        355

<210> SEQ ID NO 9
<211> LENGTH: 7676
<212> TYPE: DNA
<213> ORGANISM: Artificial Sequence
<220> FEATURE:
<223> OTHER INFORMATION: Description of Artificial Sequence:tetra-fusion
      protein TbRa3-38kD-Tb38-1-DPEP (designated TbF-2)
<220> FEATURE:
<221> NAME/KEY: CDS
<222> LOCATION: (5072)..(7480)

<400> SEQUENCE: 9
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta aatcgggggc tccctttagg    180
gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta taagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
```

```
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccggggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt ttcctgtttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
```

```
                                                          -continued cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat tgattgcga gtgagatatt tatgccagcc agccagacgc agacgcgccg     4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg     4560 catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca t atg ggc cat cat cat cat cat      5092
                                   Met Gly His His His His His
                                    1               5 cac gtg atc gac atc atc ggg acc agc ccc aca tcc tgg gaa cag gcg      5140
His Val Ile Asp Ile Ile Gly Thr Ser Pro Thr Ser Trp Glu Gln Ala
        10                  15                  20 gcg gcg gag gcg gtc cag cgg gcg cgg gat agc gtc gat gac atc cgc      5188
Ala Ala Glu Ala Val Gln Arg Ala Arg Asp Ser Val Asp Asp Ile Arg
25                  30                  35 gtc gct cgg gtc att gag cag gac atg gcc gtg gac agc gcc ggc aag      5236
Val Ala Arg Val Ile Glu Gln Asp Met Ala Val Asp Ser Ala Gly Lys
    40                  45                  50                  55 atc acc tac cgc atc aag ctc gaa gtg tcg ttc aag atg agg ccg gcg      5284
Ile Thr Tyr Arg Ile Lys Leu Glu Val Ser Phe Lys Met Arg Pro Ala
                60                  65                  70 caa ccg agg ggc tcg aaa cca ccg agc ggt tcg cct gaa acg ggc gcc      5332
Gln Pro Arg Gly Ser Lys Pro Pro Ser Gly Ser Pro Glu Thr Gly Ala
            75                  80                  85 ggc gcc ggt act gtc gcg act acc ccc gcg tcg tcg ccg gtg acg ttg      5380
Gly Ala Gly Thr Val Ala Thr Thr Pro Ala Ser Ser Pro Val Thr Leu
        90                  95                  100 gcg gag acc ggt agc acg ctg ctc tac ccg ctg ttc aac ctg tgg ggt      5428
Ala Glu Thr Gly Ser Thr Leu Leu Tyr Pro Leu Phe Asn Leu Trp Gly
    105                 110                 115 ccg gcc ttt cac gag agg tat ccg aac gtc acg atc acc gct cag ggc      5476
Pro Ala Phe His Glu Arg Tyr Pro Asn Val Thr Ile Thr Ala Gln Gly
120                 125                 130                 135 acc ggt tct ggt gcc ggg atc gcg cag gcc gcc gcc ggg acg gtc aac      5524
Thr Gly Ser Gly Ala Gly Ile Ala Gln Ala Ala Ala Gly Thr Val Asn
                140                 145                 150
```

-continued

```
att ggg gcc tcc gac gcc tat ctg tcg gaa ggt gat atg gcc gcg cac        5572
Ile Gly Ala Ser Asp Ala Tyr Leu Ser Glu Gly Asp Met Ala Ala His
            155                 160                 165 aag ggg ctg atg aac atc gcg cta gcc atc tcc gct cag cag gtc aac        5620
Lys Gly Leu Met Asn Ile Ala Leu Ala Ile Ser Ala Gln Gln Val Asn
        170                 175                 180 tac aac ctg ccc gga gtg agc gag cac ctc aag ctg aac gga aaa gtc        5668
Tyr Asn Leu Pro Gly Val Ser Glu His Leu Lys Leu Asn Gly Lys Val
    185                 190                 195 ctg gcg gcc atg tac cag ggc acc atc aaa acc tgg gac gac ccg cag        5716
Leu Ala Ala Met Tyr Gln Gly Thr Ile Lys Thr Trp Asp Asp Pro Gln
200                 205                 210                 215 atc gct gcg ctc aac ccc ggc gtg aac ctg ccc ggc acc gcg gta gtt        5764
Ile Ala Ala Leu Asn Pro Gly Val Asn Leu Pro Gly Thr Ala Val Val
                220                 225                 230 ccg ctg cac cgc tcc gac ggg tcc ggt gac acc ttc ttg ttc acc cag        5812
Pro Leu His Arg Ser Asp Gly Ser Gly Asp Thr Phe Leu Phe Thr Gln
            235                 240                 245 tac ctg tcc aag caa gat ccc gag ggc tgg ggc aag tcg ccc ggc ttc        5860
Tyr Leu Ser Lys Gln Asp Pro Glu Gly Trp Gly Lys Ser Pro Gly Phe
        250                 255                 260 ggc acc acc gtc gac ttc ccg gcg gtg ccg ggt gcg ctg ggt gag aac        5908
Gly Thr Thr Val Asp Phe Pro Ala Val Pro Gly Ala Leu Gly Glu Asn
    265                 270                 275 ggc aac ggc ggc atg gtg acc ggt tgc gcc gag aca ccg ggc tgc gtg        5956
Gly Asn Gly Gly Met Val Thr Gly Cys Ala Glu Thr Pro Gly Cys Val
280                 285                 290                 295 gcc tat atc ggc atc agc ttc ctc gac cag gcc agt caa cgg gga ctc        6004
Ala Tyr Ile Gly Ile Ser Phe Leu Asp Gln Ala Ser Gln Arg Gly Leu
                300                 305                 310 ggc gag gcc caa cta ggc aat agc tct ggc aat ttc ttg ttg ccc gac        6052
Gly Glu Ala Gln Leu Gly Asn Ser Ser Gly Asn Phe Leu Leu Pro Asp
            315                 320                 325 gcg caa agc att cag gcc gcg gcg gct ggc ttc gca tcg aaa acc ccg        6100
Ala Gln Ser Ile Gln Ala Ala Ala Gly Phe Ala Ser Lys Thr Pro
        330                 335                 340 gcg aac cag gcg att tcg atg atc gac ggg ccc gcc ccg gac ggc tac        6148
Ala Asn Gln Ala Ile Ser Met Ile Asp Gly Pro Ala Pro Asp Gly Tyr
    345                 350                 355 ccg atc atc aac tac gag tac gcc atc gtc aac aac cgg caa aag gac        6196
Pro Ile Ile Asn Tyr Glu Tyr Ala Ile Val Asn Asn Arg Gln Lys Asp
360                 365                 370                 375 gcc gcc acc gcg cag acc ttg cag gca ttt ctg cac tgg gcg atc acc        6244
Ala Ala Thr Ala Gln Thr Leu Gln Ala Phe Leu His Trp Ala Ile Thr
                380                 385                 390 gac ggc aac aag gcc tcg ttc ctc gac cag gtt cat ttc cag ccg ctg        6292
Asp Gly Asn Lys Ala Ser Phe Leu Asp Gln Val His Phe Gln Pro Leu
            395                 400                 405 ccg ccc gcg gtg gtg aag ttg tct gac gcg ttg atc gcg acg att tcc        6340
Pro Pro Ala Val Val Lys Leu Ser Asp Ala Leu Ile Ala Thr Ile Ser
        410                 415                 420 agc gct gag atg aag acc gat gcc gct acc ctc gcg cag gag gca ggt        6388
Ser Ala Glu Met Lys Thr Asp Ala Ala Thr Leu Ala Gln Glu Ala Gly
    425                 430                 435 aat ttc gag cgg atc tcc ggc gac ctg aaa acc cag atc gac cag gtg        6436
Asn Phe Glu Arg Ile Ser Gly Asp Leu Lys Thr Gln Ile Asp Gln Val
440                 445                 450                 455 gag tcg acg gca ggt tcg ttg cag ggc cag tgg cgc ggc gcg gcg ggg        6484
Glu Ser Thr Ala Gly Ser Leu Gln Gly Gln Trp Arg Gly Ala Ala Gly
```

```
                     -continued
            460             465             470
acg gcc gcc cag gcc gcg gtg gtg cgc ttc caa gaa gca gcc aat aag    6532
Thr Ala Ala Gln Ala Ala Val Val Arg Phe Gln Glu Ala Ala Asn Lys
            475             480             485 cag aag cag gaa ctc gac gag atc tcg acg aat att cgt cag gcc ggc    6580
Gln Lys Gln Glu Leu Asp Glu Ile Ser Thr Asn Ile Arg Gln Ala Gly
        490             495             500 gtc caa tac tcg agg gcc gac gag gag cag cag cag gcg ctg tcc tcg    6628
Val Gln Tyr Ser Arg Ala Asp Glu Glu Gln Gln Gln Ala Leu Ser Ser
        505             510             515 caa atg ggc ttt gtg ccc aca acg gcc gcc tcg ccg ccg tcg acc gct    6676
Gln Met Gly Phe Val Pro Thr Thr Ala Ala Ser Pro Pro Ser Thr Ala
520             525             530             535 gca gcg cca ccc gca ccg gcg aca cct gtt gcc ccc cca cca ccg gcc    6724
Ala Ala Pro Pro Ala Pro Ala Thr Pro Val Ala Pro Pro Pro Pro Ala
            540             545             550 gcc gcc aac acg ccg aat gcc cag ccg ggc gat ccc aac gca gca cct    6772
Ala Ala Asn Thr Pro Asn Ala Gln Pro Gly Asp Pro Asn Ala Ala Pro
            555             560             565 ccg ccg gcc gac ccg aac gca ccg ccg cca cct gtc att gcc cca aac    6820
Pro Pro Ala Asp Pro Asn Ala Pro Pro Pro Val Ile Ala Pro Asn
        570             575             580 gca ccc caa cct gtc cgg atc gac aac ccg gtt gga gga ttc agc ttc    6868
Ala Pro Gln Pro Val Arg Ile Asp Asn Pro Val Gly Gly Phe Ser Phe
        585             590             595 gcg ctg cct gct ggc tgg gtg gag tct gac gcc gcc cac ttc gac tac    6916
Ala Leu Pro Ala Gly Trp Val Glu Ser Asp Ala Ala His Phe Asp Tyr
600             605             610             615 ggt tca gca ctc ctc agc aaa acc acc ggg gac ccg cca ttt ccc gga    6964
Gly Ser Ala Leu Leu Ser Lys Thr Thr Gly Asp Pro Pro Phe Pro Gly
            620             625             630 cag ccg ccg ccg gtg gcc aat gac acc cgt atc gtg ctc ggc cgg cta    7012
Gln Pro Pro Pro Val Ala Asn Asp Thr Arg Ile Val Leu Gly Arg Leu
            635             640             645 gac caa aag ctt tac gcc agc gcc gaa gcc acc gac tcc aag gcc gcg    7060
Asp Gln Lys Leu Tyr Ala Ser Ala Glu Ala Thr Asp Ser Lys Ala Ala
        650             655             660 gcc cgg ttg ggc tcg gac atg ggt gag ttc tat atg ccc tac ccg ggc    7108
Ala Arg Leu Gly Ser Asp Met Gly Glu Phe Tyr Met Pro Tyr Pro Gly
        665             670             675 acc cgg atc aac cag gaa acc gtc tcg ctt gac gcc aac ggg gtg tct    7156
Thr Arg Ile Asn Gln Glu Thr Val Ser Leu Asp Ala Asn Gly Val Ser
680             685             690             695 gga agc gcg tcg tat tac gaa gtc aag ttc agc gat ccg agt aag ccg    7204
Gly Ser Ala Ser Tyr Tyr Glu Val Lys Phe Ser Asp Pro Ser Lys Pro
            700             705             710 aac ggc cag atc tgg acg ggc gta atc ggc tcg ccc gcg gcg aac gca    7252
Asn Gly Gln Ile Trp Thr Gly Val Ile Gly Ser Pro Ala Ala Asn Ala
            715             720             725 ccg gac gcc ggg ccc cct cag cgc tgg ttt gtg gta tgg ctc ggg acc    7300
Pro Asp Ala Gly Pro Pro Gln Arg Trp Phe Val Val Trp Leu Gly Thr
            730             735             740 gcc aac aac ccg gtg gac aag ggc gcg gcc aag gcg ctg gcc gaa tcg    7348
Ala Asn Asn Pro Val Asp Lys Gly Ala Ala Lys Ala Leu Ala Glu Ser
745             750             755 atc cgg cct ttg gtc gcc ccg ccg gcg ccg gca ccg gct cct gca        7396
Ile Arg Pro Leu Val Ala Pro Pro Ala Pro Ala Pro Ala Pro Ala
760             765             770             775 gag ccc gct ccg gcg ccg gcg ccg gcc ggg gaa gtc gct cct acc ccg    7444
```

-continued

```
Glu Pro Ala Pro Ala Pro Ala Pro Ala Gly Glu Val Ala Pro Thr Pro
                780                 785                 790 acg aca ccg aca ccg cag cgg acc tta ccg gcc tgagaattct gcagatatcc    7497
Thr Thr Pro Thr Pro Gln Arg Thr Leu Pro Ala
        795                 800 atcacactgg cggccgctcg agcaccacca ccaccaccac tgagatccgg ctgctaacaa    7557
agcccgaaag gaagctgagt tggctgctgc caccgctgag caataactag cataaccoct    7617 tggggcctct aaacgggtct tgagggggttt tttgctgaaa ggaggaacta tatccggat    7676

<210> SEQ ID NO 10
<211> LENGTH: 802
<212> TYPE: PRT
<213> ORGANISM: Artificial Sequence
<220> FEATURE:
<223> OTHER INFORMATION: Description of Artificial Sequence:tetra-fusion

<400> SEQUENCE: 10

Met Gly His His His His His Val Ile Asp Ile Ile Gly Thr Ser
  1               5                  10                  15

Pro Thr Ser Trp Glu Gln Ala Ala Glu Ala Val Gln Arg Ala Arg
                 20                  25                  30

Asp Ser Val Asp Ile Arg Val Ala Arg Val Ile Glu Gln Asp Met
             35                  40                  45

Ala Val Asp Ser Ala Gly Lys Ile Thr Tyr Arg Ile Lys Leu Glu Val
         50                  55                  60

Ser Phe Lys Met Arg Pro Ala Gln Pro Arg Gly Ser Lys Pro Pro Ser
 65                  70                  75                  80

Gly Ser Pro Glu Thr Gly Ala Gly Ala Gly Thr Val Ala Thr Thr Pro
                 85                  90                  95

Ala Ser Ser Pro Val Thr Leu Ala Glu Thr Gly Ser Thr Leu Leu Tyr
                100                 105                 110

Pro Leu Phe Asn Leu Trp Gly Pro Ala Phe His Glu Arg Tyr Pro Asn
            115                 120                 125

Val Thr Ile Thr Ala Gln Gly Thr Gly Ser Gly Ala Gly Ile Ala Gln
        130                 135                 140

Ala Ala Ala Gly Thr Val Asn Ile Gly Ala Ser Asp Ala Tyr Leu Ser
145                 150                 155                 160

Glu Gly Asp Met Ala Ala His Lys Gly Leu Met Asn Ile Ala Leu Ala
                165                 170                 175

Ile Ser Ala Gln Gln Val Asn Tyr Asn Leu Pro Gly Val Ser Glu His
            180                 185                 190

Leu Lys Leu Asn Gly Lys Val Leu Ala Ala Met Tyr Gln Gly Thr Ile
        195                 200                 205

Lys Thr Trp Asp Asp Pro Gln Ile Ala Ala Leu Asn Pro Gly Val Asn
    210                 215                 220

Leu Pro Gly Thr Ala Val Val Pro Leu His Arg Ser Asp Gly Ser Gly
225                 230                 235                 240

Asp Thr Phe Leu Phe Thr Gln Tyr Leu Ser Lys Gln Asp Pro Glu Gly
                245                 250                 255

Trp Gly Lys Ser Pro Gly Phe Gly Thr Thr Val Asp Phe Pro Ala Val
            260                 265                 270

Pro Gly Ala Leu Gly Glu Asn Gly Asn Gly Gly Met Val Thr Gly Cys
        275                 280                 285

Ala Glu Thr Pro Gly Cys Val Ala Tyr Ile Gly Ile Ser Phe Leu Asp
    290                 295                 300
```

```
Gln Ala Ser Gln Arg Gly Leu Gly Glu Ala Gln Leu Gly Asn Ser Ser
305                 310                 315                 320

Gly Asn Phe Leu Leu Pro Asp Ala Gln Ser Ile Gln Ala Ala Ala Ala
                325                 330                 335

Gly Phe Ala Ser Lys Thr Pro Ala Asn Gln Ala Ile Ser Met Ile Asp
                340                 345                 350

Gly Pro Ala Pro Asp Gly Tyr Pro Ile Ile Asn Tyr Glu Tyr Ala Ile
                355                 360                 365

Val Asn Asn Arg Gln Lys Asp Ala Ala Thr Ala Gln Thr Leu Gln Ala
370                 375                 380

Phe Leu His Trp Ala Ile Thr Asp Gly Asn Lys Ala Ser Phe Leu Asp
385                 390                 395                 400

Gln Val His Phe Gln Pro Leu Pro Pro Ala Val Lys Leu Ser Asp
                405                 410                 415

Ala Leu Ile Ala Thr Ile Ser Ser Ala Glu Met Lys Thr Asp Ala Ala
                420                 425                 430

Thr Leu Ala Gln Glu Ala Gly Asn Phe Glu Arg Ile Ser Gly Asp Leu
                435                 440                 445

Lys Thr Gln Ile Asp Gln Val Glu Ser Thr Ala Gly Ser Leu Gln Gly
450                 455                 460

Gln Trp Arg Gly Ala Ala Gly Thr Ala Ala Gln Ala Ala Val Val Arg
465                 470                 475                 480

Phe Gln Glu Ala Ala Asn Lys Gln Lys Gln Glu Leu Asp Glu Ile Ser
                485                 490                 495

Thr Asn Ile Arg Gln Ala Gly Val Gln Tyr Ser Arg Ala Asp Glu Glu
                500                 505                 510

Gln Gln Gln Ala Leu Ser Ser Gln Met Gly Phe Val Pro Thr Thr Ala
                515                 520                 525

Ala Ser Pro Pro Ser Thr Ala Ala Pro Pro Ala Pro Ala Thr Pro
530                 535                 540

Val Ala Pro Pro Pro Ala Ala Ala Asn Thr Pro Asn Ala Gln Pro
545                 550                 555                 560

Gly Asp Pro Asn Ala Ala Pro Pro Ala Asp Pro Asn Ala Pro Pro
                565                 570                 575

Pro Pro Val Ile Ala Pro Asn Ala Pro Gln Pro Val Arg Ile Asp Asn
                580                 585                 590

Pro Val Gly Gly Phe Ser Phe Ala Leu Pro Ala Gly Trp Val Glu Ser
                595                 600                 605

Asp Ala Ala His Phe Asp Tyr Gly Ser Ala Leu Leu Ser Lys Thr Thr
610                 615                 620

Gly Asp Pro Pro Phe Pro Gly Gln Pro Pro Val Ala Asn Asp Thr
625                 630                 635                 640

Arg Ile Val Leu Gly Arg Leu Asp Gln Lys Leu Tyr Ala Ser Ala Glu
                645                 650                 655

Ala Thr Asp Ser Lys Ala Ala Arg Leu Gly Ser Asp Met Gly Glu
                660                 665                 670

Phe Tyr Met Pro Tyr Pro Gly Thr Arg Ile Asn Gln Glu Thr Val Ser
                675                 680                 685

Leu Asp Ala Asn Gly Val Ser Gly Ser Ala Ser Tyr Tyr Glu Val Lys
                690                 695                 700

Phe Ser Asp Pro Ser Lys Pro Asn Gly Gln Ile Trp Thr Gly Val Ile
705                 710                 715                 720
```

-continued

```
Gly Ser Pro Ala Ala Asn Ala Pro Asp Ala Gly Pro Pro Gln Arg Trp
            725                 730                 735

Phe Val Val Trp Leu Gly Thr Ala Asn Asn Pro Val Asp Lys Gly Ala
        740                 745                 750

Ala Lys Ala Leu Ala Glu Ser Ile Arg Pro Leu Val Ala Pro Pro Pro
    755                 760                 765

Ala Pro Ala Pro Ala Pro Ala Glu Pro Ala Pro Ala Pro Ala Pro Ala
    770                 775                 780

Gly Glu Val Ala Pro Thr Pro Thr Thr Pro Thr Pro Gln Arg Thr Leu
785                 790                 795                 800

Pro Ala

<210> SEQ ID NO 11
<211> LENGTH: 2577
<212> TYPE: DNA
<213> ORGANISM: Artificial Sequence
<220> FEATURE:
<223> OTHER INFORMATION: Description of Artificial Sequence:penta-fusion
      protein Erd14-DPV-MTI-MSL-MTCC2 (design

```
tcc tat ttg cgc aat ttc ctc gcc gca ccg cca cct cag cgc gct gcc      624
Ser Tyr Leu Arg Asn Phe Leu Ala Ala Pro Pro Pro Gln Arg Ala Ala
        195                 200                 205 atg gcc gcg caa ttg caa gct gtg ccg ggg gcg gca cag tac atc ggc      672
Met Ala Ala Gln Leu Gln Ala Val Pro Gly Ala Ala Gln Tyr Ile Gly
210                 215                 220 ctt gtc gag tcg gtt gcc ggc tcc tgc aac aac tat gag ctc atg acg      720
Leu Val Glu Ser Val Ala Gly Ser Cys Asn Asn Tyr Glu Leu Met Thr
225                 230                 235                 240 att aat tac cag ttc ggg gac gtc gac gct cat ggc gcc atg atc cgc      768
Ile Asn Tyr Gln Phe Gly Asp Val Asp Ala His Gly Ala Met Ile Arg
        245                 250                 255 gct cag gcg gcg tcg ctt gag gcg gag cat cag gcc atc gtt cgt gat      816
Ala Gln Ala Ala Ser Leu Glu Ala Glu His Gln Ala Ile Val Arg Asp
        260                 265                 270 gtg ttg gcc gcg ggt gac ttt tgg ggc ggc gcc ggt tcg gtg gct tgc      864
Val Leu Ala Ala Gly Asp Phe Trp Gly Gly Ala Gly Ser Val Ala Cys
        275                 280                 285 cag gag ttc att acc cag ttg ggc cgt aac ttc cag gtg atc tac gag      912
Gln Glu Phe Ile Thr Gln Leu Gly Arg Asn Phe Gln Val Ile Tyr Glu
290                 295                 300 cag gcc aac gcc cac ggg cag aag gtg cag gct gcc ggc aac aac atg      960
Gln Ala Asn Ala His Gly Gln Lys Val Gln Ala Ala Gly Asn Asn Met
305                 310                 315                 320 gcg caa acc gac agc gcc gtc ggc tcc agc tgg gcc act agt atg agc     1008
Ala Gln Thr Asp Ser Ala Val Gly Ser Ser Trp Ala Thr Ser Met Ser
        325                 330                 335 ctt ttg gat gct cat atc cca cag ttg gtg gcc tcc cag tcg gcg ttt     1056
Leu Leu Asp Ala His Ile Pro Gln Leu Val Ala Ser Gln Ser Ala Phe
        340                 345                 350 gcc gcc aag gcg ggg ctg atg cgg cac acg atc ggt cag gcc gag cag     1104
Ala Ala Lys Ala Gly Leu Met Arg His Thr Ile Gly Gln Ala Glu Gln
        355                 360                 365 gcg gcg atg tcg gct cag gcg ttt cac cag ggg gag tcg tcg gcg gcg     1152
Ala Ala Met Ser Ala Gln Ala Phe His Gln Gly Glu Ser Ser Ala Ala
370                 375                 380 ttt cag gcc gcc cat gcc cgg ttt gtg gcg gcg gcc gcc aaa gtc aac     1200
Phe Gln Ala Ala His Ala Arg Phe Val Ala Ala Ala Lys Val Asn
385                 390                 395                 400 acc ttg ttg gat gtc gcg cag gcg aat ctg ggt gag gcc gcc ggt acc     1248
Thr Leu Leu Asp Val Ala Gln Ala Asn Leu Gly Glu Ala Ala Gly Thr
        405                 410                 415 tat gtg gcc gcc gat gct gcg gcc gcg tcg acc tat acc ggg ttc gat     1296
Tyr Val Ala Ala Asp Ala Ala Ala Ala Ser Thr Tyr Thr Gly Phe Asp
        420                 425                 430 atc atg gat ttc ggg ctt tta cct ccg gaa gtg aat tca agc cga atg     1344
Ile Met Asp Phe Gly Leu Leu Pro Pro Glu Val Asn Ser Ser Arg Met
        435                 440                 445 tat tcc ggt ccg ggg ccg gag tcg atg cta gcc gcc gcg gcc gcc tgg     1392
Tyr Ser Gly Pro Gly Pro Glu Ser Met Leu Ala Ala Ala Ala Ala Trp
450                 455                 460 gac ggt gtg gcc gcg gag ttg act tcc gcc gcg gtc tcg tat gga tcg     1440
Asp Gly Val Ala Ala Glu Leu Thr Ser Ala Ala Val Ser Tyr Gly Ser
465                 470                 475                 480 gtg gtg tcg acg ctg atc gtt gag ccg tgg atg ggg ccg gcg gcg gcc     1488
Val Val Ser Thr Leu Ile Val Glu Pro Trp Met Gly Pro Ala Ala Ala
        485                 490                 495 gcg atg gcg gcc gcg gca acg ccg tat gtg ggg tgg ctg gcc gcc acg     1536
Ala Met Ala Ala Ala Ala Thr Pro Tyr Val Gly Trp Leu Ala Ala Thr
        500                 505                 510
```

-continued

```
gcg gcg ctg gcg aag gag acg gcc aca cag gcg agg gca gcg gcg gaa     1584
Ala Ala Leu Ala Lys Glu Thr Ala Thr Gln Ala Arg Ala Ala Ala Glu
        515                 520                 525 gcg ttt ggg acg gcg ttc gcg atg acg gtg cca cca tcc ctc gtc gcg     1632
Ala Phe Gly Thr Ala Phe Ala Met Thr Val Pro Pro Ser Leu Val Ala
530                 535                 540 gcc aac cgc agc cgg ttg atg tcg ctg gtc gcg gcg aac att ctg ggg     1680
Ala Asn Arg Ser Arg Leu Met Ser Leu Val Ala Ala Asn Ile Leu Gly
545                 550                 555                 560 caa aac agt gcg gcg atc gcg gct acc cag gcc gag tat gcc gaa atg     1728
Gln Asn Ser Ala Ala Ile Ala Ala Thr Gln Ala Glu Tyr Ala Glu Met
                565                 570                 575 tgg gcc caa gac gct gcc gtg atg tac agc tat gag ggg gca tct gcg     1776
Trp Ala Gln Asp Ala Ala Val Met Tyr Ser Tyr Glu Gly Ala Ser Ala
            580                 585                 590 gcc gcg tcg gcg ttg ccg ccg ttc act cca ccc gtg caa ggc acc ggc     1824
Ala Ala Ser Ala Leu Pro Pro Phe Thr Pro Pro Val Gln Gly Thr Gly
        595                 600                 605 ccg gcc ggg ccc gcg gcc gca gcc gcg gcg acc caa gcc gcc ggt gcg     1872
Pro Ala Gly Pro Ala Ala Ala Ala Ala Thr Gln Ala Ala Gly Ala
610                 615                 620 ggc gcc gtt gcg gat gca cag gcg aca ctg gcc cag ctg ccc ccg ggg     1920
Gly Ala Val Ala Asp Ala Gln Ala Thr Leu Ala Gln Leu Pro Pro Gly
625                 630                 635                 640 atc ctg agc gac att ctg tcc gca ttg gcc gcc aac gct gat ccg ctg     1968
Ile Leu Ser Asp Ile Leu Ser Ala Leu Ala Ala Asn Ala Asp Pro Leu
                645                 650                 655 aca tcg gga ctg ttg ggg atc gcg tcg acc ctc aac ccg caa gtc gga     2016
Thr Ser Gly Leu Leu Gly Ile Ala Ser Thr Leu Asn Pro Gln Val Gly
            660                 665                 670 tcc gct cag ccg ata gtg atc ccc acc ccg ata ggg gaa ttg gac gtg     2064
Ser Ala Gln Pro Ile Val Ile Pro Thr Pro Ile Gly Glu Leu Asp Val
        675                 680                 685 atc gcg ctc tac att gca tcc atc gcg acc ggc agc att gcg ctc gcg     2112
Ile Ala Leu Tyr Ile Ala Ser Ile Ala Thr Gly Ser Ile Ala Leu Ala
690                 695                 700 atc acg aac acg gcc aga ccc tgg cac atc ggc cta tac ggg aac gcc     2160
Ile Thr Asn Thr Ala Arg Pro Trp His Ile Gly Leu Tyr Gly Asn Ala
705                 710                 715                 720 ggc ggg ctg gga ccg acg cag ggc cat cca ctg agt tcg gcg acc gac     2208
Gly Gly Leu Gly Pro Thr Gln Gly His Pro Leu Ser Ser Ala Thr Asp
                725                 730                 735 gag ccg gag ccg cac tgg ggc ccc ttc ggg ggc gcg gcg ccg gtg tcc     2256
Glu Pro Glu Pro His Trp Gly Pro Phe Gly Gly Ala Ala Pro Val Ser
            740                 745                 750 gcg ggc gtc ggc cac gca gca tta gtc gga gcg ttg tcg gtg ccg cac     2304
Ala Gly Val Gly His Ala Ala Leu Val Gly Ala Leu Ser Val Pro His
        755                 760                 765 agc tgg acc acg gcc gcc ccg gag atc cag ctc gcc gtt cag gca aca     2352
Ser Trp Thr Thr Ala Ala Pro Glu Ile Gln Leu Ala Val Gln Ala Thr
770                 775                 780 ccc acc ttc agc tcc agc gcc ggc gcc gac ccg acg gcc cta aac ggg     2400
Pro Thr Phe Ser Ser Ser Ala Gly Ala Asp Pro Thr Ala Leu Asn Gly
785                 790                 795                 800 atg ccg gca ggc ctg ctc agc ggg atg gct ttg gcg agc ctg gcc gca     2448
Met Pro Ala Gly Leu Leu Ser Gly Met Ala Leu Ala Ser Leu Ala Ala
                805                 810                 815 cgc ggc acg acg ggc ggt ggc ggc acc cgt agc ggc acc agc act gac     2496
Arg Gly Thr Thr Gly Gly Gly Gly Thr Arg Ser Gly Thr Ser Thr Asp
```

-continued

```
                820                 825                 830
ggc caa gag gac ggc cgc aaa ccc ccg gta gtt gtg att aga gag cag        2544
Gly Gln Glu Asp Gly Arg Lys Pro Pro Val Val Val Ile Arg Glu Gln
        835                 840                 845 ccg ccg ccc gga aac ccc ccg cgg taagatatc                              2577
Pro Pro Pro Gly Asn Pro Pro Arg
    850                 855
```

<210> SEQ ID NO 12
<211> LENGTH: 856
<212> TYPE: PRT
<213> ORGANISM: Artificial Sequence
<220> FEATURE:
<223> OTHER INFORMATION: Description of Artificial Sequence:penta-fusion

<400> SEQUENCE: 12

```
His Met His His His His His Met Ala Thr Thr Leu Pro Val Gln
 1               5                  10                  15

Arg His Pro Arg Ser Leu Phe Pro Glu Phe Ser Glu Leu Phe Ala Ala
                20                  25                  30

Phe Pro Ser Phe Ala Gly Leu Arg Pro Thr Phe Asp Thr Arg Leu Met
            35                  40                  45

Arg Leu Glu Asp Glu Met Lys Glu Gly Arg Tyr Glu Val Arg Ala Glu
        50                  55                  60

Leu Pro Gly Val Asp Pro Asp Lys Asp Val Asp Ile Met Val Arg Asp
    65                  70                  75                  80

Gly Gln Leu Thr Ile Lys Ala Glu Arg Thr Glu Gln Lys Asp Phe Asp
                85                  90                  95

Gly Arg Ser Glu Phe Ala Tyr Gly Ser Phe Val Arg Thr Val Ser Leu
            100                 105                 110

Pro Val Gly Ala Asp Glu Asp Ile Lys Ala Thr Tyr Asp Lys Gly
        115                 120                 125

Ile Leu Thr Val Ser Val Ala Val Ser Glu Gly Lys Pro Thr Glu Lys
    130                 135                 140

His Ile Gln Ile Arg Ser Thr Asn Lys Leu Asp Pro Val Asp Ala Val
145                 150                 155                 160

Ile Asn Thr Thr Cys Asn Tyr Gly Gln Val Val Ala Ala Leu Asn Ala
                165                 170                 175

Thr Asp Pro Gly Ala Ala Ala Gln Phe Asn Ala Ser Pro Val Ala Gln
            180                 185                 190

Ser Tyr Leu Arg Asn Phe Leu Ala Ala Pro Pro Gln Arg Ala Ala
        195                 200                 205

Met Ala Ala Gln Leu Gln Ala Val Pro Gly Ala Ala Gln Tyr Ile Gly
    210                 215                 220

Leu Val Glu Ser Val Ala Gly Ser Cys Asn Asn Tyr Glu Leu Met Thr
225                 230                 235                 240

Ile Asn Tyr Gln Phe Gly Asp Val Asp Ala His Gly Ala Met Ile Arg
                245                 250                 255

Ala Gln Ala Ala Ser Leu Glu Ala Glu His Gln Ala Ile Val Arg Asp
            260                 265                 270

Val Leu Ala Ala Gly Asp Phe Trp Gly Gly Ala Gly Ser Val Ala Cys
        275                 280                 285

Gln Glu Phe Ile Thr Gln Leu Gly Arg Asn Phe Gln Val Ile Tyr Glu
    290                 295                 300

Gln Ala Asn Ala His Gly Gln Lys Val Gln Ala Ala Gly Asn Asn Met
305                 310                 315                 320
```

-continued

```
Ala Gln Thr Asp Ser Ala Val Gly Ser Ser Trp Ala Thr Ser Met Ser
                325                 330                 335

Leu Leu Asp Ala His Ile Pro Gln Leu Val Ala Ser Gln Ser Ala Phe
                340                 345                 350

Ala Ala Lys Ala Gly Leu Met Arg His Thr Ile Gly Gln Ala Glu Gln
                355                 360                 365

Ala Ala Met Ser Ala Gln Ala Phe His Gln Gly Glu Ser Ser Ala Ala
                370                 375                 380

Phe Gln Ala Ala His Ala Arg Phe Val Ala Ala Ala Lys Val Asn
385                 390                 395                 400

Thr Leu Leu Asp Val Ala Gln Ala Asn Leu Gly Glu Ala Ala Gly Thr
                405                 410                 415

Tyr Val Ala Ala Asp Ala Ala Ala Ser Thr Tyr Thr Gly Phe Asp
                420                 425                 430

Ile Met Asp Phe Gly Leu Leu Pro Pro Glu Val Asn Ser Ser Arg Met
                435                 440                 445

Tyr Ser Gly Pro Gly Pro Glu Ser Met Leu Ala Ala Ala Ala Trp
                450                 455                 460

Asp Gly Val Ala Ala Glu Leu Thr Ser Ala Ala Val Ser Tyr Gly Ser
465                 470                 475                 480

Val Val Ser Thr Leu Ile Val Glu Pro Trp Met Gly Pro Ala Ala Ala
                485                 490                 495

Ala Met Ala Ala Ala Thr Pro Tyr Val Gly Trp Leu Ala Ala Thr
                500                 505                 510

Ala Ala Leu Ala Lys Glu Thr Ala Thr Gln Ala Arg Ala Ala Ala Glu
                515                 520                 525

Ala Phe Gly Thr Ala Phe Ala Met Thr Val Pro Pro Ser Leu Val Ala
                530                 535                 540

Ala Asn Arg Ser Arg Leu Met Ser Leu Val Ala Ala Asn Ile Leu Gly
545                 550                 555                 560

Gln Asn Ser Ala Ala Ile Ala Ala Thr Gln Ala Glu Tyr Ala Glu Met
                565                 570                 575

Trp Ala Gln Asp Ala Ala Val Met Tyr Ser Tyr Glu Gly Ala Ser Ala
                580                 585                 590

Ala Ala Ser Ala Leu Pro Pro Phe Thr Pro Val Gln Gly Thr Gly
                595                 600                 605

Pro Ala Gly Pro Ala Ala Ala Ala Ala Thr Gln Ala Ala Gly Ala
                610                 615                 620

Gly Ala Val Ala Asp Ala Gln Ala Thr Leu Ala Gln Leu Pro Pro Gly
625                 630                 635                 640

Ile Leu Ser Asp Ile Leu Ser Ala Leu Ala Ala Asn Ala Asp Pro Leu
                645                 650                 655

Thr Ser Gly Leu Leu Gly Ile Ala Ser Thr Leu Asn Pro Gln Val Gly
                660                 665                 670

Ser Ala Gln Pro Ile Val Ile Pro Thr Pro Ile Gly Glu Leu Asp Val
                675                 680                 685

Ile Ala Leu Tyr Ile Ala Ser Ile Ala Thr Gly Ser Ile Ala Leu Ala
                690                 695                 700

Ile Thr Asn Thr Ala Arg Pro Trp His Ile Gly Leu Tyr Gly Asn Ala
705                 710                 715                 720

Gly Gly Leu Gly Pro Thr Gln Gly His Pro Leu Ser Ser Ala Thr Asp
                725                 730                 735
```

```
Glu Pro Glu Pro His Trp Gly Pro Phe Gly Ala Ala Pro Val Ser
            740                 745                 750

Ala Gly Val Gly His Ala Ala Leu Val Gly Ala Leu Ser Val Pro His
        755                 760                 765

Ser Trp Thr Thr Ala Ala Pro Glu Ile Gln Leu Ala Val Gln Ala Thr
    770                 775                 780

Pro Thr Phe Ser Ser Ser Ala Gly Ala Asp Pro Thr Ala Leu Asn Gly
785                 790                 795                 800

Met Pro Ala Gly Leu Leu Ser Gly Met Ala Leu Ala Ser Leu Ala Ala
                805                 810                 815

Arg Gly Thr Thr Gly Gly Gly Thr Arg Ser Gly Thr Ser Thr Asp
            820                 825                 830

Gly Gln Glu Asp Gly Arg Lys Pro Pro Val Val Val Ile Arg Glu Gln
        835                 840                 845

Pro Pro Pro Gly Asn Pro Pro Arg
    850                 855
```

<210> SEQ ID NO 13
<211> LENGTH: 1299
<212> TYPE: DNA
<213> ORGANISM: Artificial Sequence
<220> FEATURE:
<223> OTHER INFORMATION: Description of Artificial Sequence:tetra-fusion
      protein Erd14-DPV-MTI-MSL (designated Mtb46f)
<220> FEATURE:
<221> NAME/KEY: CDS
<222> LOCATION: (1)..(1299)

<400> SEQUENCE: 13

```
cat atg c

```
                Ile Asn Thr Thr Cys Asn Tyr Gly Gln Val Val Ala Ala Leu Asn Ala
                                165                 170                 175 acg gat ccg ggg gct gcc gca cag ttc aac gcc tca ccg gtg gcg cag              576
Thr Asp Pro Gly Ala Ala Ala Gln Phe Asn Ala Ser Pro Val Ala Gln
            180                 185                 190 tcc tat ttg cgc aat ttc ctc gcc gca ccg cca cct cag cgc gct gcc              624
Ser Tyr Leu Arg Asn Phe Leu Ala Ala Pro Pro Pro Gln Arg Ala Ala
            195                 200                 205 atg gcc gcg caa ttg caa gct gtg ccg ggg gcg gca cag tac atc ggc              672
Met Ala Ala Gln Leu Gln Ala Val Pro Gly Ala Ala Gln Tyr Ile Gly
210                 215                 220 ctt gtc gag tcg gtt gcc ggc tcc tgc aac aac tat gag ctc atg acg              720
Leu Val Glu Ser Val Ala Gly Ser Cys Asn Asn Tyr Glu Leu Met Thr
225                 230                 235                 240 att aat tac cag ttc ggg gac gtc gac gct cat ggc gcc atg atc cgc              768
Ile Asn Tyr Gln Phe Gly Asp Val Asp Ala His Gly Ala Met Ile Arg
                245                 250                 255 gct cag gcg gcg tcg ctt gag gcg gag cat cag gcc atc gtt cgt gat              816
Ala Gln Ala Ala Ser Leu Glu Ala Glu His Gln Ala Ile Val Arg Asp
            260                 265                 270 gtg ttg gcc gcg ggt gac ttt tgg ggc ggc gcc ggt tcg gtg gct tgc              864
Val Leu Ala Ala Gly Asp Phe Trp Gly Gly Ala Gly Ser Val Ala Cys
            275                 280                 285 cag gag ttc att acc cag ttg ggc cgt aac ttc cag gtg atc tac gag              912
Gln Glu Phe Ile Thr Gln Leu Gly Arg Asn Phe Gln Val Ile Tyr Glu
            290                 295                 300 cag gcc aac gcc cac ggg cag aag gtg cag gct gcc ggc aac aac atg              960
Gln Ala Asn Ala His Gly Gln Lys Val Gln Ala Ala Gly Asn Asn Met
305                 310                 315                 320 gcg caa acc gac agc gcc gtc ggc tcc agc tgg gcc act agt atg agc             1008
Ala Gln Thr Asp Ser Ala Val Gly Ser Ser Trp Ala Thr Ser Met Ser
                325                 330                 335 ctt ttg gat gct cat atc cca cag ttg gtg gcc tcc cag tcg gcg ttt             1056
Leu Leu Asp Ala His Ile Pro Gln Leu Val Ala Ser Gln Ser Ala Phe
            340                 345                 350 gcc gcc aag gcg ggg ctg atg cgg cac acg atc ggt cag gcc gag cag             1104
Ala Ala Lys Ala Gly Leu Met Arg His Thr Ile Gly Gln Ala Glu Gln
            355                 360                 365 gcg gcg atg tcg gct cag gcg ttt cac cag ggg gag tcg tcg gcg gcg             1152
Ala Ala Met Ser Ala Gln Ala Phe His Gln Gly Glu Ser Ser Ala Ala
            370                 375                 380 ttt cag gcc gcc cat gcc cgg ttt gtg gcg gcg gcc aaa gtc aac             1200
Phe Gln Ala Ala His Ala Arg Phe Val Ala Ala Ala Lys Val Asn
385                 390                 395                 400 acc ttg ttg gat gtc gcg cag gcg aat ctg ggt gag gcc gcc ggt acc             1248
Thr Leu Leu Asp Val Ala Gln Ala Asn Leu Gly Glu Ala Ala Gly Thr
                405                 410                 415 tat gtg gcc gcc gat gct gcg gcc gcg tcg acc tat acc ggg ttc gat             1296
Tyr Val Ala Ala Asp Ala Ala Ala Ala Ser Thr Tyr Thr Gly Phe Asp
            420                 425                 430 atc                                                                         1299
Ile <210> SEQ ID NO 14
<211> LENGTH: 433
<212> TYPE: PRT
<213> ORGANISM: Artificial Sequence
<220> FEATURE:
<223> OTHER INFORMATION: Description of Artificial Sequence:tetra-fusion

<400> SEQUENCE: 14
```

-continued

```
His Met His His His His His Met Ala Thr Thr Leu Pro Val Gln
 1               5                  10                  15

Arg His Pro Arg Ser Leu Phe Pro Glu Phe Ser Glu Leu Phe Ala Ala
                20                  25                  30

Phe Pro Ser Phe Ala Gly Leu Arg Pro Thr Phe Asp Thr Arg Leu Met
            35                  40                  45

Arg Leu Glu Asp Glu Met Lys Glu Gly Arg Tyr Glu Val Arg Ala Glu
        50                  55                  60

Leu Pro Gly Val Asp Pro Asp Lys Asp Val Asp Ile Met Val Arg Asp
65                  70                  75                  80

Gly Gln Leu Thr Ile Lys Ala Glu Arg Thr Glu Gln Lys Asp Phe Asp
                85                  90                  95

Gly Arg Ser Glu Phe Ala Tyr Gly Ser Phe Val Arg Thr Val Ser Leu
                100                 105                 110

Pro Val Gly Ala Asp Glu Asp Ile Lys Ala Thr Tyr Asp Lys Gly
            115                 120                 125

Ile Leu Thr Val Ser Val Ala Val Ser Glu Gly Lys Pro Thr Glu Lys
    130                 135                 140

His Ile Gln Ile Arg Ser Thr Asn Lys Leu Asp Pro Val Asp Ala Val
145                 150                 155                 160

Ile Asn Thr Thr Cys Asn Tyr Gly Gln Val Val Ala Ala Leu Asn Ala
                165                 170                 175

Thr Asp Pro Gly Ala Ala Ala Gln Phe Asn Ala Ser Pro Val Ala Gln
            180                 185                 190

Ser Tyr Leu Arg Asn Phe Leu Ala Ala Pro Pro Gln Arg Ala Ala
            195                 200                 205

Met Ala Ala Gln Leu Gln Ala Val Pro Gly Ala Ala Gln Tyr Ile Gly
    210                 215                 220

Leu Val Glu Ser Val Ala Gly Ser Cys Asn Asn Tyr Glu Leu Met Thr
225                 230                 235                 240

Ile Asn Tyr Gln Phe Gly Asp Val Asp Ala His Gly Ala Met Ile Arg
                245                 250                 255

Ala Gln Ala Ala Ser Leu Glu Ala Glu His Gln Ala Ile Val Arg Asp
            260                 265                 270

Val Leu Ala Ala Gly Asp Phe Trp Gly Ala Gly Ser Val Ala Cys
    275                 280                 285

Gln Glu Phe Ile Thr Gln Leu Gly Arg Asn Phe Gln Val Ile Tyr Glu
    290                 295                 300

Gln Ala Asn Ala His Gly Gln Lys Val Gln Ala Ala Gly Asn Asn Met
305                 310                 315                 320

Ala Gln Thr Asp Ser Ala Val Gly Ser Ser Trp Ala Thr Ser Met Ser
                325                 330                 335

Leu Leu Asp Ala His Ile Pro Gln Leu Val Ala Ser Gln Ser Ala Phe
            340                 345                 350

Ala Ala Lys Ala Gly Leu Met Arg His Thr Ile Gly Gln Ala Glu Gln
        355                 360                 365

Ala Ala Met Ser Ala Gln Ala Phe His Gln Gly Glu Ser Ser Ala Ala
    370                 375                 380

Phe Gln Ala Ala His Ala Arg Phe Val Ala Ala Ala Lys Val Asn
385                 390                 395                 400

Thr Leu Leu Asp Val Ala Gln Ala Asn Leu Gly Glu Ala Ala Gly Thr
                405                 410                 415
```

```
Tyr Val Ala Ala Asp Ala Ala Ala Ala Ser Thr Tyr Thr Gly Phe Asp
            420                 425                 430
Ile
```

<210> SEQ ID NO 15
<211> LENGTH: 2168
<212> TYPE: DNA
<213> ORGANISM: Artificial Sequence
<220> FEATURE:
<223> OTHER INFORMATION: Description of Artificial Sequence:tetra-fusion
      protein DPV-MTI-MSL-MTCC2 (designated Mtb71f)
<220> FEATURE:
<221> NAME/KEY: CDS
<222> LOCATION: (1)..(2133)

<400> SEQUENCE: 15 cat atg cat cac cat cac cat cac gat ccc gtg gac gcg gtc att aac 48
His Met His His His His His His Asp Pro Val Asp Ala Val Ile Asn
1 5 10 15 acc acc tgc aat tac ggg cag gta gta gct gcg ctc aac gcg acg gat 96
Thr Thr Cys Asn Tyr Gly Gln Val Val Ala Ala Leu Asn Ala Thr Asp
20 25 30 ccg ggg gct gcc gca cag ttc aac gcc tca ccg gtg gcg cag tcc tat 144
Pro Gly Ala Ala Ala Gln Phe Asn Ala Ser Pro Val Ala Gln Ser Tyr
35 40 45 ttg cgc aat ttc ctc gcc gca ccg cca cct cag cgc gct gcc atg gcc 192
Leu Arg Asn Phe Leu Ala Ala Pro Pro Pro Gln Arg Ala Ala Met Ala
50 55 60 gcg caa ttg caa gct gtg ccg ggg gcg gca cag tac atc ggc ctt gtc 240
Ala Gln Leu Gln Ala Val Pro Gly Ala Ala Gln Tyr Ile Gly Leu Val
65 70 75 80 gag tcg gtt gcc ggc tcc tgc aac aac tat gag ctc atg acg att aat 288
Glu Ser Val Ala Gly Ser Cys Asn Asn Tyr Glu Leu Met Thr Ile Asn
85 90 95 tac cag ttc ggg gac gtc gac gct cat ggc gcc atg atc cgc gct cag 336
Tyr Gln Phe Gly Asp Val Asp Ala His Gly Ala Met Ile Arg Ala Gln
100 105 110 gcg gcg tcg ctt gag gcg gag cat cag gcc atc gtt cgt gat gtg ttg 384
Ala Ala Ser Leu Glu Ala Glu His Gln Ala Ile Val Arg Asp Val Leu
115 120 125 gcc gcg ggt gac ttt tgg ggc ggc gcc ggt tcg gtg gct tgc cag gag 432
Ala Ala Gly Asp Phe Trp Gly Gly Ala Gly Ser Val Ala Cys Gln Glu
130 135 140 ttc att acc cag ttg ggc cgt aac ttc cag gtg atc tac gag cag gcc 480
Phe Ile Thr Gln Leu Gly Arg Asn Phe Gln Val Ile Tyr Glu Gln Ala
145 150 155 160 aac gcc cac ggg cag aag gtg cag gct gcc ggc aac aac atg gcg caa 528
Asn Ala His Gly Gln Lys Val Gln Ala Ala Gly Asn Asn Met Ala Gln
165 170 175 acc gac agc gcc gtc ggc tcc agc tgg gcc act agt atg agc ctt ttg 576
Thr Asp Ser Ala Val Gly Ser Ser Trp Ala Thr Ser Met Ser Leu Leu
180 185 190 gat gct cat atc cca cag ttg gtg gcc tcc cag tcg gcg ttt gcc gcc 624
Asp Ala His Ile Pro Gln Leu Val Ala Ser Gln Ser Ala Phe Ala Ala
195 200 205 aag gcg ggg ctg atg cgg cac acg atc ggt cag gcc gag cag gcg gcg 672
Lys Ala Gly Leu Met Arg His Thr Ile Gly Gln Ala Glu Gln Ala Ala
210 215 220 atg tcg gct cag gcg ttt cac cag ggg gag tcg tcg gcg gcg ttt cag 720
Met Ser Ala Gln Ala Phe His Gln Gly Glu Ser Ser Ala Ala Phe Gln
225 230 235 240

-continued

| | | |
|---|---|---|
| gcc gcc cat gcc cgg ttt gtg gcg gcg gcc gcc aaa gtc aac acc ttg<br>Ala Ala His Ala Arg Phe Val Ala Ala Ala Ala Lys Val Asn Thr Leu<br>                  245                              250                        255 | 768 |
| ttg gat gtc gcg cag gcg aat ctg ggt gag gcc gcc ggt acc tat gtg<br>Leu Asp Val Ala Gln Ala Asn Leu Gly Glu Ala Ala Gly Thr Tyr Val<br>                  260                              265                        270 | 816 |
| gcc gcc gat gct gcg gcc gcg tcg acc tat acc ggg ttc gat atc atg<br>Ala Ala Asp Ala Ala Ala Ala Ser Thr Tyr Thr Gly Phe Asp Ile Met<br>                  275                              280                        285 | 864 |
| gat ttc ggg ctt tta cct ccg gaa gtg aat tca agc cga atg tat tcc<br>Asp Phe Gly Leu Leu Pro Pro Glu Val Asn Ser Ser Arg Met Tyr Ser<br>        290                              295                              300 | 912 |
| ggt ccg ggg ccg gag tcg atg cta gcc gcc gcg gcc gcc tgg gac ggt<br>Gly Pro Gly Pro Glu Ser Met Leu Ala Ala Ala Ala Ala Trp Asp Gly<br>305                              310                              315                        320 | 960 |
| gtg gcc gcg gag ttg act tcc gcc gcg gtc tcg tat gga tcg gtg gtg<br>Val Ala Ala Glu Leu Thr Ser Ala Ala Val Ser Tyr Gly Ser Val Val<br>                  325                              330                        335 | 1008 |
| tcg acg ctg atc gtt gag ccg tgg atg ggg ccg gcg gcg gcc gcg atg<br>Ser Thr Leu Ile Val Glu Pro Trp Met Gly Pro Ala Ala Ala Ala Met<br>                  340                              345                        350 | 1056 |
| gcg gcc gcg gca acg ccg tat gtg ggg tgg ctg gcc gcc acg gcg gcg<br>Ala Ala Ala Ala Thr Pro Tyr Val Gly Trp Leu Ala Ala Thr Ala Ala<br>                    355                              360                        365 | 1104 |
| ctg gcg aag gag acg gcc aca cag gcg agg gca gcg gaa gcg ttt<br>Leu Ala Lys Glu Thr Ala Thr Gln Ala Arg Ala Ala Ala Glu Ala Phe<br>370                              375                              380 | 1152 |
| ggg acg gcg ttc gcg atg acg gtg cca cca tcc ctc gtc gcg gcc aac<br>Gly Thr Ala Phe Ala Met Thr Val Pro Pro Ser Leu Val Ala Ala Asn<br>385                              390                              395                        400 | 1200 |
| cgc agc cgg ttg atg tcg ctg gtc gcg gcg aac att ctg ggg caa aac<br>Arg Ser Arg Leu Met Ser Leu Val Ala Ala Asn Ile Leu Gly Gln Asn<br>                  405                              410                        415 | 1248 |
| agt gcg gcg atc gcg gct acc cag gcc gag tat gcc gaa atg tgg gcc<br>Ser Ala Ala Ile Ala Ala Thr Gln Ala Glu Tyr Ala Glu Met Trp Ala<br>                    420                              425                        430 | 1296 |
| caa gac gct gcc gtg atg tac agc tat gag ggg gca tct gcg gcc gcg<br>Gln Asp Ala Ala Val Met Tyr Ser Tyr Glu Gly Ala Ser Ala Ala Ala<br>                  435                              440                        445 | 1344 |
| tcg gcg ttg ccg ccg ttc act cca ccc gtg caa ggc acc ggc ccg gcc<br>Ser Ala Leu Pro Pro Phe Thr Pro Pro Val Gln Gly Thr Gly Pro Ala<br>        450                              455                              460 | 1392 |
| ggg ccc gcg gcc gca gcc gcg gcg acc caa gcc gcc ggt gcg ggc gcc<br>Gly Pro Ala Ala Ala Ala Ala Ala Thr Gln Ala Ala Gly Ala Gly Ala<br>465                              470                              475                        480 | 1440 |
| gtt gcg gat gca cag gcg aca ctg gcc cag ctg ccc ccg ggg atc ctg<br>Val Ala Asp Ala Gln Ala Thr Leu Ala Gln Leu Pro Pro Gly Ile Leu<br>                    485                              490                        495 | 1488 |
| agc gac att ctg tcc gca ttg gcc gcc aac gct gat ccg ctg aca tcg<br>Ser Asp Ile Leu Ser Ala Leu Ala Ala Asn Ala Asp Pro Leu Thr Ser<br>                  500                              505                        510 | 1536 |
| gga ctg ttg ggg atc gcg tcg acc ctc aac ccg caa gtc gga tcc gct<br>Gly Leu Leu Gly Ile Ala Ser Thr Leu Asn Pro Gln Val Gly Ser Ala<br>                  515                              520                        525 | 1584 |
| cag ccg ata gtg atc ccc acc ccg ata ggg gaa ttg gac gtg atc gcg<br>Gln Pro Ile Val Ile Pro Thr Pro Ile Gly Glu Leu Asp Val Ile Ala<br>                  530                              535                        540 | 1632 |
| ctc tac att gca tcc atc gcg acc ggc agc att gcg ctc gcg atc acg<br>Leu Tyr Ile Ala Ser Ile Ala Thr Gly Ser Ile Ala Leu Ala Ile Thr<br>545                              550                              555                        560 | 1680 |

```
aac acg gcc aga ccc tgg cac atc ggc cta tac ggg aac gcc ggc ggg      1728
Asn Thr Ala Arg Pro Trp His Ile Gly Leu Tyr Gly Asn Ala Gly Gly
            565                 570                 575 ctg gga ccg acg cag ggc cat cca ctg agt tcg gcg acc gac gag ccg      1776
Leu Gly Pro Thr Gln Gly His Pro Leu Ser Ser Ala Thr Asp Glu Pro
        580                 585                 590 gag ccg cac tgg ggc ccc ttc ggg ggc gcg gcg ccg gtg tcc gcg ggc      1824
Glu Pro His Trp Gly Pro Phe Gly Gly Ala Ala Pro Val Ser Ala Gly
    595                 600                 605 gtc ggc cac gca gca tta gtc gga gcg ttg tcg gtg ccg cac agc tgg      1872
Val Gly His Ala Ala Leu Val Gly Ala Leu Ser Val Pro His Ser Trp
610                 615                 620 acc acg gcc gcc ccg gag atc cag ctc gcc gtt cag gca aca ccc acc      1920
Thr Thr Ala Ala Pro Glu Ile Gln Leu Ala Val Gln Ala Thr Pro Thr
625                 630                 635                 640 ttc agc tcc agc gcc ggc gcc gac ccg acg gcc cta aac ggg atg ccg      1968
Phe Ser Ser Ser Ala Gly Ala Asp Pro Thr Ala Leu Asn Gly Met Pro
            645                 650                 655 gca ggc ctg ctc agc ggg atg gct ttg gcg agc ctg gcc gca cgc ggc      2016
Ala Gly Leu Leu Ser Gly Met Ala Leu Ala Ser Leu Ala Ala Arg Gly
        660                 665                 670 acg acg ggc ggt ggc ggc acc cgt agc ggc acc agc act gac ggc caa      2064
Thr Thr Gly Gly Gly Gly Thr Arg Ser Gly Thr Ser Thr Asp Gly Gln
    675                 680                 685 gag gac ggc cgc aaa ccc ccg gta gtt gtg att aga gag cag ccg ccg      2112
Glu Asp Gly Arg Lys Pro Pro Val Val Val Ile Arg Glu Gln Pro Pro
690                 695                 700 ccc gga aac ccc ccg cgg taagatttct aaatccatca cactggcggc cgctcgag    2168
Pro Gly Asn Pro Pro Arg
705                 710

<210> SEQ ID NO 16
<211> LENGTH: 710
<212> TYPE: PRT
<213> ORGANISM: Artificial Sequence
<220> FEATURE:
<223> OTHER INFORMATION: Description of Artificial Sequence:tetra-fusion

<400> SEQUENCE: 16

His Met His His His His His Asp Pro Val Asp Ala Val Ile Asn
 1               5                  10                  15

Thr Thr Cys Asn Tyr Gly Gln Val Val Ala Ala Leu Asn Ala Thr Asp
                20                  25                  30

Pro Gly Ala Ala Ala Gln Phe Asn Ala Ser Pro Val Ala Gln Ser Tyr
            35                  40                  45

Leu Arg Asn Phe Leu Ala Ala Pro Pro Gln Arg Ala Ala Met Ala
    50                  55                  60

Ala Gln Leu Gln Ala Val Pro Gly Ala Ala Gln Tyr Ile Gly Leu Val
65                  70                  75                  80

Glu Ser Val Ala Gly Ser Cys Asn Asn Tyr Glu Leu Met Thr Ile Asn
                85                  90                  95

Tyr Gln Phe Gly Asp Val Asp Ala His Gly Ala Met Ile Arg Ala Gln
            100                 105                 110

Ala Ala Ser Leu Glu Ala Glu His Gln Ala Ile Val Arg Asp Val Leu
        115                 120                 125

Ala Ala Gly Asp Phe Trp Gly Gly Ala Gly Ser Val Ala Cys Gln Glu
    130                 135                 140

Phe Ile Thr Gln Leu Gly Arg Asn Phe Gln Val Ile Tyr Glu Gln Ala
```

-continued

```
            145                 150                 155                 160
Asn Ala His Gly Gln Lys Val Gln Ala Ala Gly Asn Asn Met Ala Gln
                165                 170                 175
Thr Asp Ser Ala Val Gly Ser Ser Trp Ala Thr Ser Met Ser Leu Leu
            180                 185                 190
Asp Ala His Ile Pro Gln Leu Val Ala Ser Gln Ser Ala Phe Ala Ala
        195                 200                 205
Lys Ala Gly Leu Met Arg His Thr Ile Gly Gln Ala Glu Gln Ala Ala
    210                 215                 220
Met Ser Ala Gln Ala Phe His Gln Gly Glu Ser Ser Ala Ala Phe Gln
225                 230                 235                 240
Ala Ala His Ala Arg Phe Val Ala Ala Ala Lys Val Asn Thr Leu
                245                 250                 255
Leu Asp Val Ala Gln Ala Asn Leu Gly Glu Ala Ala Gly Thr Tyr Val
                260                 265                 270
Ala Ala Asp Ala Ala Ala Ser Thr Tyr Thr Gly Phe Asp Ile Met
            275                 280                 285
Asp Phe Gly Leu Leu Pro Pro Glu Val Asn Ser Ser Arg Met Tyr Ser
    290                 295                 300
Gly Pro Gly Pro Glu Ser Met Leu Ala Ala Ala Ala Trp Asp Gly
305                 310                 315                 320
Val Ala Ala Glu Leu Thr Ser Ala Ala Val Ser Tyr Gly Ser Val Val
                325                 330                 335
Ser Thr Leu Ile Val Glu Pro Trp Met Gly Pro Ala Ala Ala Met
            340                 345                 350
Ala Ala Ala Ala Thr Pro Tyr Val Gly Trp Leu Ala Ala Thr Ala Ala
            355                 360                 365
Leu Ala Lys Glu Thr Ala Thr Gln Ala Arg Ala Ala Ala Glu Ala Phe
    370                 375                 380
Gly Thr Ala Phe Ala Met Thr Val Pro Pro Ser Leu Val Ala Ala Asn
385                 390                 395                 400
Arg Ser Arg Leu Met Ser Leu Val Ala Ala Asn Ile Leu Gly Gln Asn
                405                 410                 415
Ser Ala Ala Ile Ala Ala Thr Gln Ala Glu Tyr Ala Glu Met Trp Ala
                420                 425                 430
Gln Asp Ala Ala Val Met Tyr Ser Tyr Glu Gly Ala Ser Ala Ala Ala
        435                 440                 445
Ser Ala Leu Pro Pro Phe Thr Pro Pro Val Gln Gly Thr Gly Pro Ala
    450                 455                 460
Gly Pro Ala Ala Ala Ala Ala Thr Gln Ala Ala Gly Ala Gly Ala
465                 470                 475                 480
Val Ala Asp Ala Gln Ala Thr Leu Ala Gln Leu Pro Pro Gly Ile Leu
                485                 490                 495
Ser Asp Ile Leu Ser Ala Leu Ala Ala Asn Ala Asp Pro Leu Thr Ser
            500                 505                 510
Gly Leu Leu Gly Ile Ala Ser Thr Leu Asn Pro Gln Val Gly Ser Ala
            515                 520                 525
Gln Pro Ile Val Ile Pro Thr Pro Ile Gly Glu Leu Asp Val Ile Ala
        530                 535                 540
Leu Tyr Ile Ala Ser Ile Ala Thr Gly Ser Ile Ala Leu Ala Ile Thr
545                 550                 555                 560
Asn Thr Ala Arg Pro Trp His Ile Gly Leu Tyr Gly Asn Ala Gly Gly
                565                 570                 575
```

```
Leu Gly Pro Thr Gln Gly His Pro Leu Ser Ser Ala Thr Asp Glu Pro
            580                 585                 590

Glu Pro His Trp Gly Pro Phe Gly Gly Ala Ala Pro Val Ser Ala Gly
        595                 600                 605

Val Gly His Ala Ala Leu Val Gly Ala Leu Ser Val Pro His Ser Trp
    610                 615                 620

Thr Thr Ala Ala Pro Glu Ile Gln Leu Ala Val Gln Ala Thr Pro Thr
625                 630                 635                 640

Phe Ser Ser Ser Ala Gly Ala Asp Pro Thr Ala Leu Asn Gly Met Pro
                645                 650                 655

Ala Gly Leu Leu Ser Gly Met Ala Leu Ala Ser Leu Ala Ala Arg Gly
            660                 665                 670

Thr Thr Gly Gly Gly Thr Arg Ser Gly Thr Ser Thr Asp Gly Gln
        675                 680                 685

Glu Asp Gly Arg Lys Pro Pro Val Val Val Ile Arg Glu Gln Pro Pro
    690                 695                 700

Pro Gly Asn Pro Pro Arg
705             710

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence:peptide from
      transcription of pET polylinker and XhoI
      restriction site at positions 2143-2168 of
      SEQ ID NO:15

<400> SEQUENCE: 17

Ile His His Thr Gly Gly Arg Ser Ser
  1               5

<210> SEQ ID NO 18
<211> LENGTH: 921
<212> TYPE: DNA
<213> ORGANISM: Artificial Sequence
<220> FEATURE:
<223> OTHER INFORMATION: Description of Artificial Sequence:tri-fusion
      protein DPV-MTI-MSL (designated Mtb31f)
<220> FEATURE:
<221> NAME/

-continued

```
            Glu Ser Val Ala Gly Ser Cys Asn Asn Tyr Glu Leu Met Thr Ile Asn
                         85                  90                  95 tac cag ttc ggg gac gtc gac gct cat ggc gcc atg atc cgc gct cag         336
Tyr Gln Phe Gly Asp Val Asp Ala His Gly Ala Met Ile Arg Ala Gln
                100                 105                 110 gcg gcg tcg ctt gag gcg gag cat cag gcc atc gtt cgt gat gtg ttg         384
Ala Ala Ser Leu Glu Ala Glu His Gln Ala Ile Val Arg Asp Val Leu
            115                 120                 125 gcc gcg ggt gac ttt tgg ggc ggc gcc ggt tcg gtg gct tgc cag gag         432
Ala Ala Gly Asp Phe Trp Gly Gly Ala Gly Ser Val Ala Cys Gln Glu
        130                 135                 140 ttc att acc cag ttg ggc cgt aac ttc cag gtg atc tac gag cag gcc         480
Phe Ile Thr Gln Leu Gly Arg Asn Phe Gln Val Ile Tyr Glu Gln Ala
145                 150                 155                 160 aac gcc cac ggg cag aag gtg cag gct gcc ggc aac aac atg gcg caa         528
Asn Ala His Gly Gln Lys Val Gln Ala Ala Gly Asn Asn Met Ala Gln
                165                 170                 175 acc gac agc gcc gtc ggc tcc agc tgg gcc act agt atg agc ctt ttg         576
Thr Asp Ser Ala Val Gly Ser Ser Trp Ala Thr Ser Met Ser Leu Leu
            180                 185                 190 gat gct cat atc cca cag ttg gtg gcc tcc cag tcg gcg ttt gcc gcc         624
Asp Ala His Ile Pro Gln Leu Val Ala Ser Gln Ser Ala Phe Ala Ala
        195                 200                 205 aag gcg ggg ctg atg cgg cac acg atc ggt cag gcc gag cag gcg gcg         672
Lys Ala Gly Leu Met Arg His Thr Ile Gly Gln Ala Glu Gln Ala Ala
    210                 215                 220 atg tcg gct cag gcg ttt cac cag ggg gag tcg tcg gcg gcg ttt cag         720
Met Ser Ala Gln Ala Phe His Gln Gly Glu Ser Ser Ala Ala Phe Gln
225                 230                 235                 240 gcc gcc cat gcc cgg ttt gtg gcg gcg gcc gcc aaa gtc aac acc ttg         768
Ala Ala His Ala Arg Phe Val Ala Ala Ala Lys Val Asn Thr Leu
                245                 250                 255 ttg gat gtc gcg cag gcg aat ctg ggt gag gcc gcc ggt acc tat gtg         816
Leu Asp Val Ala Gln Ala Asn Leu Gly Glu Ala Ala Gly Thr Tyr Val
            260                 265                 270 gcc gcc gat gct gcg gcc gcg tcg acc tat acc ggg ttc gat atc cat         864
Ala Ala Asp Ala Ala Ala Ala Ser Thr Tyr Thr Gly Phe Asp Ile His
        275                 280                 285 cac act ggc ggc cgc tcg agc aga tcc ggc tgc taacaaagcc cgaaggaag        917
His Thr Gly Gly Arg Ser Ser Arg Ser Gly Cys
    290                 295 ctga                                                                    921

<210> SEQ ID NO 19
<211> LENGTH: 299
<212> TYPE: PRT
<213> ORGANISM: Artificial Sequence
<220> FEATURE:
<223> OTHER INFORMATION: Description of Artificial Sequence:tri-fusion

<400> SEQUENCE: 19

His Met His His His His His His Asp Pro Val Asp Ala Val Ile Asn
 1               5                  10                  15

Thr Thr Cys Asn Tyr Gly Gln Val Val Ala Ala Leu Asn Ala Thr Asp
                20                  25                  30

Pro Gly Ala Ala Ala Gln Phe Asn Ala Ser Pro Val Ala Gln Ser Tyr
            35                  40                  45

Leu Arg Asn Phe Leu Ala Ala Pro Pro Gln Arg Ala Ala Met Ala
        50                  55                  60
```

-continued

```
Ala Gln Leu Gln Ala Val Pro Gly Ala Ala Gln Tyr Ile Gly Leu Val
 65                  70                  75                  80

Glu Ser Val Ala Gly Ser Cys Asn Asn Tyr Glu Leu Met Thr Ile Asn
                 85                  90                  95

Tyr Gln Phe Gly Asp Val Asp Ala His Gly Ala Met Ile Arg Ala Gln
            100                 105                 110

Ala Ala Ser Leu Glu Ala Glu His Gln Ala Ile Val Arg Asp Val Leu
        115                 120                 125

Ala Ala Gly Asp Phe Trp Gly Gly Ala Gly Ser Val Ala Cys Gln Glu
    130                 135                 140

Phe Ile Thr Gln Leu Gly Arg Asn Phe Gln Val Ile Tyr Glu Gln Ala
145                 150                 155                 160

Asn Ala His Gly Gln Lys Val Gln Ala Ala Gly Asn Asn Met Ala Gln
                165                 170                 175

Thr Asp Ser Ala Val Gly Ser Ser Trp Ala Thr Ser Met Ser Leu Leu
            180                 185                 190

Asp Ala His Ile Pro Gln Leu Val Ala Ser Gln Ser Ala Phe Ala Ala
        195                 200                 205

Lys Ala Gly Leu Met Arg His Thr Ile Gly Gln Ala Glu Gln Ala Ala
    210                 215                 220

Met Ser Ala Gln Ala Phe His Gln Gly Glu Ser Ser Ala Ala Phe Gln
225                 230                 235                 240

Ala Ala His Ala Arg Phe Val Ala Ala Ala Ala Lys Val Asn Thr Leu
                245                 250                 255

Leu Asp Val Ala Gln Ala Asn Leu Gly Glu Ala Ala Gly Thr Tyr Val
            260                 265                 270

Ala Ala Asp Ala Ala Ala Ala Ser Thr Tyr Thr Gly Phe Asp Ile His
        275                 280                 285

His Thr Gly Gly Arg Ser Ser Arg Ser Gly Cys
    290                 295

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence:peptide
      transcribed from positions 901-918 of
      SEQ ID NO:18

<400> SEQUENCE: 20

Gln Ser Pro Lys Gly Ser
  1               5

<210> SEQ ID NO 21
<211> LENGTH: 1801
<212> TYPE: DNA
<213> ORGANISM: Artificial Sequence
<220> FEATURE:
<223> OTHER INFORMATION: Description of Artificial Sequence:tri-fusion
      protein TbH9-DPV-MTI (designated Mtb61f)
<220> FEATURE:
<221> NAME/KEY: CDS
<222> LOCATION: (1)..(1800)

<400> SEQUENCE: 21 cat atg cat cac cat cac cat cac atg gtg gat ttc ggg gcg tta cca       48
His Met His His His His His His Met Val Asp Phe Gly Ala Leu Pro
  1               5                  10                  15 ccg gag atc aac tcc gcg agg atg tac gcc ggc ccg ggt tcg gcc tcg       96
```

```
Pro Glu Ile Asn Ser Ala Arg Met Tyr Ala Gly Pro Gly Ser Ala Ser
         20                  25                  30 ctg gtg gcc gcg gct cag atg tgg gac agc gtg gcg agt gac ctg ttt     144
Leu Val Ala Ala Ala Gln Met Trp Asp Ser Val Ala Ser Asp Leu Phe
         35                  40                  45 tcg gcc gcg tcg gcg ttt cag tcg gtg gtc tgg ggt ctg acg gtg ggg     192
Ser Ala Ala Ser Ala Phe Gln Ser Val Val Trp Gly Leu Thr Val Gly
 50                  55                  60 tcg tgg ata ggt tcg tcg gcg ggt ctg atg gtg gcg gcg gcc tcg ccg     240
Ser Trp Ile Gly Ser Ser Ala Gly Leu Met Val Ala Ala Ala Ser Pro
 65                  70                  75                  80 tat gtg gcg tgg atg agc gtc acc gcg ggg cag gcc gag ctg acc gcc     288
Tyr Val Ala Trp Met Ser Val Thr Ala Gly Gln Ala Glu Leu Thr Ala
                 85                  90                  95 gcc cag gtc cgg gtt gct gcg gcg gcc tac gag acg gcg tat ggg ctg     336
Ala Gln Val Arg Val Ala Ala Ala Ala Tyr Glu Thr Ala Tyr Gly Leu
                100                 105                 110 acg gtg ccc ccg ccg gtg atc gcc gag aac cgt gct gaa ctg atg att     384
Thr Val Pro Pro Pro Val Ile Ala Glu Asn Arg Ala Glu Leu Met Ile
            115                 120                 125 ctg ata gcg acc aac ctc ttg ggg caa aac acc ccg gcg atc gcg gtc     432
Leu Ile Ala Thr Asn Leu Leu Gly Gln Asn Thr Pro Ala Ile Ala Val
        130                 135                 140 aac gag gcc gaa tac ggc gag atg tgg gcc caa gac gcc gcc gcg atg     480
Asn Glu Ala Glu Tyr Gly Glu Met Trp Ala Gln Asp Ala Ala Ala Met
145                 150                 155                 160 ttt ggc tac gcc gcg gcg acg gcg acg gcg acg gcg acg ttg ctg ccg     528
Phe Gly Tyr Ala Ala Ala Thr Ala Thr Ala Thr Ala Thr Leu Leu Pro
                165                 170                 175 ttc gag gag gcg ccg gag atg acc agc gcg ggt ggg ctc ctc gag cag     576
Phe Glu Glu Ala Pro Glu Met Thr Ser Ala Gly Gly Leu Leu Glu Gln
                180                 185                 190 gcc gcc gcg gtc gag gag gcc tcc gac acc gcc gcg gcg aac cag ttg     624
Ala Ala Ala Val Glu Glu Ala Ser Asp Thr Ala Ala Ala Asn Gln Leu
            195                 200                 205 atg aac aat gtg ccc cag gcg ctg caa cag ctg gcc cag ccc acg cag     672
Met Asn Asn Val Pro Gln Ala Leu Gln Gln Leu Ala Gln Pro Thr Gln
        210                 215                 220 ggc acc acg cct tct tcc aag ctg ggt ggc ctg tgg aag acg gtc tcg     720
Gly Thr Thr Pro Ser Ser Lys Leu Gly Gly Leu Trp Lys Thr Val Ser
225                 230                 235                 240 ccg cat cgg tcg ccg atc agc aac atg gtg tcg atg gcc aac aac cac     768
Pro His Arg Ser Pro Ile Ser Asn Met Val Ser Met Ala Asn Asn His
                245                 250                 255 atg tcg atg acc aac tcg ggt gtg tcg atg acc aac acc ttg agc tcg     816
Met Ser Met Thr Asn Ser Gly Val Ser Met Thr Asn Thr Leu Ser Ser
                260                 265                 270 atg ttg aag ggc ttt gct ccg gcg gcg gcc gcc cag gcc gtg caa acc     864
Met Leu Lys Gly Phe Ala Pro Ala Ala Ala Ala Gln Ala Val Gln Thr
            275                 280                 285 gcg gcg caa aac ggg gtc cgg gcg atg agc tcg ctg ggc agc tcg ctg     912
Ala Ala Gln Asn Gly Val Arg Ala Met Ser Ser Leu Gly Ser Ser Leu
        290                 295                 300 ggt tct tcg ggt ctg ggc ggt ggg gtg gcc gcc aac ttg ggt cgg gcg     960
Gly Ser Ser Gly Leu Gly Gly Gly Val Ala Ala Asn Leu Gly Arg Ala
305                 310                 315                 320 gcc tcg gtc ggt tcg ttg tcg gtg ccg cag gcc tgg gcc gcg gcc aac    1008
Ala Ser Val Gly Ser Leu Ser Val Pro Gln Ala Trp Ala Ala Ala Asn
                325                 330                 335
```

```
cag gca gtc acc ccg gcg gcg cgg gcg ctg ccg ctg acc agc ctg acc        1056
Gln Ala Val Thr Pro Ala Ala Arg Ala Leu Pro Leu Thr Ser Leu Thr
            340                 345                 350 agc gcc gcg gaa aga ggg ccc ggg cag atg ctg ggc ggg ctg ccg gtg        1104
Ser Ala Ala Glu Arg Gly Pro Gly Gln Met Leu Gly Gly Leu Pro Val
355                 360                 365 ggg cag atg ggc gcc agg gcc ggt ggt ggg ctc agt ggt gtg ctg cgt        1152
Gly Gln Met Gly Ala Arg Ala Gly Gly Gly Leu Ser Gly Val Leu Arg
    370                 375                 380 gtt ccg ccg cga ccc tat gtg atg ccg cat tct ccg gca gcc ggc aag        1200
Val Pro Pro Arg Pro Tyr Val Met Pro His Ser Pro Ala Ala Gly Lys
385                 390                 395                 400 ctt gat ccc gtg gac gcg gtc att aac acc acc tgc aat tac ggg cag        1248
Leu Asp Pro Val Asp Ala Val Ile Asn Thr Thr Cys Asn Tyr Gly Gln
                405                 410                 415 gta gta gct gcg ctc aac gcg acg gat ccg ggg gct gcc gca cag ttc        1296
Val Val Ala Ala Leu Asn Ala Thr Asp Pro Gly Ala Ala Ala Gln Phe
            420                 425                 430 aac gcc tca ccg gtg gcg cag tcc tat ttg cgc aat ttc ctc gcc gca        1344
Asn Ala Ser Pro Val Ala Gln Ser Tyr Leu Arg Asn Phe Leu Ala Ala
        435                 440                 445 ccg cca cct cag cgc gct gcc atg gcc gcg caa ttg caa gct gtg ccg        1392
Pro Pro Pro Gln Arg Ala Ala Met Ala Ala Gln Leu Gln Ala Val Pro
    450                 455                 460 ggg gcg gca cag tac atc ggc ctt gtc gag tcg gtt gcc ggc tcc tgc        1440
Gly Ala Ala Gln Tyr Ile Gly Leu Val Glu Ser Val Ala Gly Ser Cys
465                 470                 475                 480 aac aac tat gag ctc atg acg att aat tac cag ttc ggg gac gtc gac        1488
Asn Asn Tyr Glu Leu Met Thr Ile Asn Tyr Gln Phe Gly Asp Val Asp
                485                 490                 495 gct cat ggc gcc atg atc cgc gct cag gcg gcg tcg ctt gag gcg gag        1536
Ala His Gly Ala Met Ile Arg Ala Gln Ala Ala Ser Leu Glu Ala Glu
            500                 505                 510 cat cag gcc atc gtt cgt gat gtg ttg gcc gcg ggt gac ttt tgg ggc        1584
His Gln Ala Ile Val Arg Asp Val Leu Ala Ala Gly Asp Phe Trp Gly
        515                 520                 525 ggc gcc ggt tcg gtg gct tgc cag gag ttc att acc cag ttg ggc cgt        1632
Gly Ala Gly Ser Val Ala Cys Gln Glu Phe Ile Thr Gln Leu Gly Arg
    530                 535                 540 aac ttc cag gtg atc tac gag cag gcc aac gcc cac ggg cag aag gtg        1680
Asn Phe Gln Val Ile Tyr Glu Gln Ala Asn Ala His Gly Gln Lys Val
545                 550                 555                 560 cag gct gcc ggc aac aac atg gcg caa acc gac agc gcc gtc ggc tcc        1728
Gln Ala Ala Gly Asn Asn Met Ala Gln Thr Asp Ser Ala Val Gly Ser
                565                 570                 575 agc tgg gcc act agt aac ggc cgc cag tgt gct gga att ctg cag ata        1776
Ser Trp Ala Thr Ser Asn Gly Arg Gln Cys Ala Gly Ile Leu Gln Ile
            580                 585                 590 tcc atc aca ctg gcg gcc gct cga g                                      1801
Ser Ile Thr Leu Ala Ala Ala Arg
        595                 600

<210> SEQ ID NO 22
<211> LENGTH: 600
<212> TYPE: PRT
<213> ORGANISM: Artificial Sequence
<220> FEATURE:
<223> OTHER INFORMATION: Description of Artificial Sequence:tri-fusion

<400> SEQUENCE: 22

His Met His His His His His Met Val Asp Phe Gly Ala Leu Pro
```

```
  1               5              10              15
Pro Glu Ile Asn Ser Ala Arg Met Tyr Ala Gly Pro Gly Ser Ala Ser
             20                  25                  30
Leu Val Ala Ala Ala Gln Met Trp Asp Ser Val Ala Ser Asp Leu Phe
             35                  40                  45
Ser Ala Ala Ser Ala Phe Gln Ser Val Val Trp Gly Leu Thr Val Gly
             50                  55                  60
Ser Trp Ile Gly Ser Ser Ala Gly Leu Met Val Ala Ala Ser Pro
 65                  70                  75                  80
Tyr Val Ala Trp Met Ser Val Thr Ala Gly Gln Ala Glu Leu Thr Ala
                 85                  90                  95
Ala Gln Val Arg Val Ala Ala Ala Tyr Glu Thr Ala Tyr Gly Leu
                100                 105                 110
Thr Val Pro Pro Pro Val Ile Ala Glu Asn Arg Ala Glu Leu Met Ile
                115                 120                 125
Leu Ile Ala Thr Asn Leu Leu Gly Gln Asn Thr Pro Ala Ile Ala Val
                130                 135                 140
Asn Glu Ala Glu Tyr Gly Glu Met Trp Ala Gln Asp Ala Ala Ala Met
145                 150                 155                 160
Phe Gly Tyr Ala Ala Ala Thr Ala Thr Ala Thr Ala Thr Leu Leu Pro
                165                 170                 175
Phe Glu Glu Ala Pro Glu Met Thr Ser Ala Gly Gly Leu Leu Glu Gln
                180                 185                 190
Ala Ala Ala Val Glu Glu Ala Ser Asp Thr Ala Ala Ala Asn Gln Leu
                195                 200                 205
Met Asn Asn Val Pro Gln Ala Leu Gln Gln Leu Ala Gln Pro Thr Gln
210                 215                 220
Gly Thr Thr Pro Ser Ser Lys Leu Gly Gly Leu Trp Lys Thr Val Ser
225                 230                 235                 240
Pro His Arg Ser Pro Ile Ser Asn Met Val Ser Met Ala Asn Asn His
                245                 250                 255
Met Ser Met Thr Asn Ser Gly Val Ser Met Thr Asn Thr Leu Ser Ser
                260                 265                 270
Met Leu Lys Gly Phe Ala Pro Ala Ala Ala Gln Ala Val Gln Thr
                275                 280                 285
Ala Ala Gln Asn Gly Val Arg Ala Met Ser Ser Leu Gly Ser Ser Leu
                290                 295                 300
Gly Ser Ser Gly Leu Gly Gly Val Ala Ala Asn Leu Gly Arg Ala
305                 310                 315                 320
Ala Ser Val Gly Ser Leu Ser Val Pro Gln Ala Trp Ala Ala Ala Asn
                325                 330                 335
Gln Ala Val Thr Pro Ala Ala Arg Ala Leu Pro Leu Thr Ser Leu Thr
                340                 345                 350
Ser Ala Ala Glu Arg Gly Pro Gly Gln Met Leu Gly Gly Leu Pro Val
                355                 360                 365
Gly Gln Met Gly Ala Arg Ala Gly Gly Leu Ser Gly Val Leu Arg
                370                 375                 380
Val Pro Pro Arg Pro Tyr Val Met Pro His Ser Pro Ala Ala Gly Lys
385                 390                 395                 400
Leu Asp Pro Val Asp Ala Val Ile Asn Thr Thr Cys Asn Tyr Gly Gln
                405                 410                 415
Val Val Ala Ala Leu Asn Ala Thr Asp Pro Gly Ala Ala Ala Gln Phe
                420                 425                 430
```

```
Asn Ala Ser Pro Val Ala Gln Ser Tyr Leu Arg Asn Phe Leu Ala Ala
        435                 440                 445

Pro Pro Pro Gln Arg Ala Ala Met Ala Ala Gln Leu Gln Ala Val Pro
        450                 455                 460

Gly Ala Ala Gln Tyr Ile Gly Leu Val Glu Ser Val Ala Gly Ser Cys
465                 470                 475                 480

Asn Asn Tyr Glu Leu Met Thr Ile Asn Tyr Gln Phe Gly Asp Val Asp
                    485                 490                 495

Ala His Gly Ala Met Ile Arg Ala Gln Ala Ala Ser Leu Glu Ala Glu
                500                 505                 510

His Gln Ala Ile Val Arg Asp Val Leu Ala Ala Gly Asp Phe Trp Gly
                515                 520                 525

Gly Ala Gly Ser Val Ala Cys Gln Glu Phe Ile Thr Gln Leu Gly Arg
            530                 535                 540

Asn Phe Gln Val Ile Tyr Glu Gln Ala Asn Ala His Gly Gln Lys Val
545                 550                 555                 560

Gln Ala Ala Gly Asn Asn Met Ala Gln Thr Asp Ser Ala Val Gly Ser
                565                 570                 575

Ser Trp Ala Thr Ser Asn Gly Arg Gln Cys Ala Gly Ile Leu Gln Ile
                580                 585                 590

Ser Ile Thr Leu Ala Ala Arg
            595                 600

<210> SEQ ID NO 23
<211> LENGTH: 1104
<212> TYPE: DNA
<213> ORGANISM: Artificial Sequence
<220> FEATURE:
<223> OTHER INFORMATION: Description of Artificial Sequence:tri-fusion
      Erd14-DPV-MTI (designated Mtb36f)
<220> FEATURE:
<221> NAME/KEY: CDS
<222> LO

```
att ctt act gtg tcg gtg gcg gtt tcg gaa ggg aag cca acc gaa aag     432
Ile Leu Thr Val Ser Val Ala Val Ser Glu Gly Lys Pro Thr Glu Lys
    130                 135                 140 cac att cag atc cgg tcc acc aac aag ctt gat ccc gtg gac gcg gtc     480
His Ile Gln Ile Arg Ser Thr Asn Lys Leu Asp Pro Val Asp Ala Val
145                 150                 155                 160 att aac acc acc tgc aat tac ggg cag gta gta gct gcg ctc aac gcg     528
Ile Asn Thr Thr Cys Asn Tyr Gly Gln Val Val Ala Ala Leu Asn Ala
                165                 170                 175 acg gat ccg ggg gct gcc gca cag ttc aac gcc tca ccg gtg gcg cag     576
Thr Asp Pro Gly Ala Ala Ala Gln Phe Asn Ala Ser Pro Val Ala Gln
            180                 185                 190 tcc tat ttg cgc aat ttc ctc gcc gca ccg cca cct cag cgc gct gcc     624
Ser Tyr Leu Arg Asn Phe Leu Ala Ala Pro Pro Pro Gln Arg Ala Ala
        195                 200                 205 atg gcc gcg caa ttg caa gct gtg ccg ggg gcg gca cag tac atc ggc     672
Met Ala Ala Gln Leu Gln Ala Val Pro Gly Ala Ala Gln Tyr Ile Gly
    210                 215                 220 ctt gtc gag tcg gtt gcc ggc tcc tgc aac aac tat gag ctc atg acg     720
Leu Val Glu Ser Val Ala Gly Ser Cys Asn Asn Tyr Glu Leu Met Thr
225                 230                 235                 240 att aat tac cag ttc ggg gac gtc gac gct cat ggc gcc atg atc cgc     768
Ile Asn Tyr Gln Phe Gly Asp Val Asp Ala His Gly Ala Met Ile Arg
                245                 250                 255 gct cag gcg gcg tcg ctt gag gcg gag cat cag gcc atc gtt cgt gat     816
Ala Gln Ala Ala Ser Leu Glu Ala Glu His Gln Ala Ile Val Arg Asp
            260                 265                 270 gtg ttg gcc gcg ggt gac ttt tgg ggc ggc gcc ggt tcg gtg gct tgc     864
Val Leu Ala Ala Gly Asp Phe Trp Gly Gly Ala Gly Ser Val Ala Cys
        275                 280                 285 cag gag ttc att acc cag ttg ggc cgt aac ttc cag gtg atc tac gag     912
Gln Glu Phe Ile Thr Gln Leu Gly Arg Asn Phe Gln Val Ile Tyr Glu
    290                 295                 300 cag gcc aac gcc cac ggg cag aag gtg cag gct gcc ggc aac aac atg     960
Gln Ala Asn Ala His Gly Gln Lys Val Gln Ala Ala Gly Asn Asn Met
305                 310                 315                 320 gcg caa acc gac agc gcc gtc ggc tcc agc tgg gcc act agt aac ggc     1008
Ala Gln Thr Asp Ser Ala Val Gly Ser Ser Trp Ala Thr Ser Asn Gly
                325                 330                 335 cgc cag tgt gct gga att ctg cag ata tcc atc aca ctg gcg gcc gct     1056
Arg Gln Cys Ala Gly Ile Leu Gln Ile Ser Ile Thr Leu Ala Ala Ala
            340                 345                 350 cga gca gat ccg gct gct aac aaa gcc cga aag gaa gct gag ttg gct     1104
Arg Ala Asp Pro Ala Ala Asn Lys Ala Arg Lys Glu Ala Glu Leu Ala
        355                 360                 365
```

<210> SEQ ID NO 24
<211> LENGTH: 368
<212> TYPE: PRT
<213> ORGANISM: Artificial Sequence
<220> FEATURE:
<223> OTHER INFORMATION: Description of Artificial Sequence:tri-fusion

<400> SEQUENCE: 24

```
His Met His His His His His His Met Ala Thr Thr Leu Pro Val Gln
  1               5                  10                  15

Arg His Pro Arg Ser Leu Phe Pro Glu Phe Ser Glu Leu Phe Ala Ala
             20                  25                  30

Phe Pro Ser Phe Ala Gly Leu Arg Pro Thr Phe Asp Thr Arg Leu Met
         35                  40                  45
```

```
Arg Leu Glu Asp Glu Met Lys Glu Gly Arg Tyr Glu Val Arg Ala Glu
 50                  55                  60

Leu Pro Gly Val Asp Pro Asp Lys Asp Val Asp Ile Met Val Arg Asp
 65                  70                  75                  80

Gly Gln Leu Thr Ile Lys Ala Glu Arg Thr Glu Gln Lys Asp Phe Asp
                 85                  90                  95

Gly Arg Ser Glu Phe Ala Tyr Gly Ser Phe Val Arg Thr Val Ser Leu
            100                 105                 110

Pro Val Gly Ala Asp Glu Asp Ile Lys Ala Thr Tyr Asp Lys Gly
        115                 120                 125

Ile Leu Thr Val Ser Val Ala Val Ser Glu Gly Lys Pro Thr Glu Lys
130                 135                 140

His Ile Gln Ile Arg Ser Thr Asn Lys Leu Asp Pro Val Asp Ala Val
145                 150                 155                 160

Ile Asn Thr Thr Cys Asn Tyr Gly Gln Val Val Ala Ala Leu Asn Ala
                165                 170                 175

Thr Asp Pro Gly Ala Ala Gln Phe Asn Ala Ser Pro Val Ala Gln
            180                 185                 190

Ser Tyr Leu Arg Asn Phe Leu Ala Ala Pro Pro Gln Arg Ala Ala
        195                 200                 205

Met Ala Ala Gln Leu Gln Ala Val Pro Gly Ala Ala Gln Tyr Ile Gly
210                 215                 220

Leu Val Glu Ser Val Ala Gly Ser Cys Asn Asn Tyr Glu Leu Met Thr
225                 230                 235                 240

Ile Asn Tyr Gln Phe Gly Asp Val Asp Ala His Gly Ala Met Ile Arg
                245                 250                 255

Ala Gln Ala Ala Ser Leu Glu Ala Glu His Gln Ala Ile Val Arg Asp
            260                 265                 270

Val Leu Ala Ala Gly Asp Phe Trp Gly Gly Ala Gly Ser Val Ala Cys
        275                 280                 285

Gln Glu Phe Ile Thr Gln Leu Gly Arg Asn Phe Gln Val Ile Tyr Glu
290                 295                 300

Gln Ala Asn Ala His Gly Gln Lys Val Gln Ala Ala Gly Asn Asn Met
305                 310                 315                 320

Ala Gln Thr Asp Ser Ala Val Gly Ser Ser Trp Ala Thr Ser Asn Gly
                325                 330                 335

Arg Gln Cys Ala Gly Ile Leu Gln Ile Ser Ile Thr Leu Ala Ala Ala
            340                 345                 350

Arg Ala Asp Pro Ala Ala Asn Lys Ala Arg Lys Glu Ala Glu Leu Ala
        355                 360                 365

<210> SEQ ID NO 25
<211> LENGTH: 1797
<212> TYPE: DNA
<213> ORGANISM: Artificial Sequence
<220> FEATURE:
<223> OTHER INFORMATION: Description of Artificial Sequence:bi-fusion
      protein TbH9-Ra35 (designated Mtb59f)
<220> FEATURE:
<221> NAME/KEY: CDS
<222> LOCATION: (1)..(1791)

<400> SEQUENCE: 25 cat atg cat cac cat cac cat cac atg gtg gat ttc ggg gcg tta cca      48
His Met His His His His His His Met Val Asp Phe Gly Ala Leu Pro
 1               5                  10                  15
```

-continued

```
ccg gag atc aac tcc gcg agg atg tac gcc ggc ccg ggt tcg gcc tcg      96
Pro Glu Ile Asn Ser Ala Arg Met Tyr Ala Gly Pro Gly Ser Ala Ser
            20                  25                  30 ctg gtg gcc gcg gct cag atg tgg gac agc gtg gcg agt gac ctg ttt     144
Leu Val Ala Ala Ala Gln Met Trp Asp Ser Val Ala Ser Asp Leu Phe
     35                  40                  45 tcg gcc gcg tcg gcg ttt cag tcg gtg gtc tgg ggt ctg acg gtg ggg     192
Ser Ala Ala Ser Ala Phe Gln Ser Val Val Trp Gly Leu Thr Val Gly
 50                  55                  60 tcg tgg ata ggt tcg tcg gcg ggt ctg atg gtg gcg gcg tcg ccg         240
Ser Trp Ile Gly Ser Ser Ala Gly Leu Met Val Ala Ala Ser Pro
 65                  70                  75                  80 tat gtg gcg tgg atg agc gtc acc gcg ggg cag gcc gag ctg acc gcc     288
Tyr Val Ala Trp Met Ser Val Thr Ala Gly Gln Ala Glu Leu Thr Ala
                 85                  90                  95 gcc cag gtc cgg gtt gct gcg gcg gcc tac gag acg gcg tat ggg ctg     336
Ala Gln Val Arg Val Ala Ala Ala Ala Tyr Glu Thr Ala Tyr Gly Leu
         100                 105                 110 acg gtg ccc ccg ccg gtg atc gcc gag aac cgt gct gaa ctg atg att     384
Thr Val Pro Pro Pro Val Ile Ala Glu Asn Arg Ala Glu Leu Met Ile
     115                 120                 125 ctg ata gcg acc aac ctc ttg ggg caa aac acc ccg gcg atc gcg gtc     432
Leu Ile Ala Thr Asn Leu Leu Gly Gln Asn Thr Pro Ala Ile Ala Val
 130                 135                 140 aac gag gcc gaa tac ggc gag atg tgg gcc caa gac gcc gcc gcg atg     480
Asn Glu Ala Glu Tyr Gly Glu Met Trp Ala Gln Asp Ala Ala Ala Met
145                 150                 155                 160 ttt ggc tac gcc gcg gcg acg gcg acg gcg acg gcg acg ttg ctg ccg     528
Phe Gly Tyr Ala Ala Ala Thr Ala Thr Ala Thr Ala Thr Leu Leu Pro
                 165                 170                 175 ttc gag gag gcg ccg gag atg acc agc gcg ggt ggg ctc ctc gag cag     576
Phe Glu Glu Ala Pro Glu Met Thr Ser Ala Gly Gly Leu Leu Glu Gln
         180                 185                 190 gcc gcc gcg gtc gag gag gcc tcc gac acc gcc gcg gcg aac cag ttg     624
Ala Ala Ala Val Glu Glu Ala Ser Asp Thr Ala Ala Ala Asn Gln Leu
     195                 200                 205 atg aac aat gtg ccc cag gcg ctg caa cag ctg gcc cag ccc acg cag     672
Met Asn Asn Val Pro Gln Ala Leu Gln Gln Leu Ala Gln Pro Thr Gln
 210                 215                 220 ggc acc acg cct tct tcc aag ctg ggt ggc ctg tgg aag acg gtc tcg     720
Gly Thr Thr Pro Ser Ser Lys Leu Gly Gly Leu Trp Lys Thr Val Ser
225                 230                 235                 240 ccg cat cgg tcg ccg atc agc aac atg gtg tcg atg gcc aac aac cac     768
Pro His Arg Ser Pro Ile Ser Asn Met Val Ser Met Ala Asn Asn His
                 245                 250                 255 atg tcg atg acc aac tcg ggt gtg tcg atg acc aac acc ttg agc tcg     816
Met Ser Met Thr Asn Ser Gly Val Ser Met Thr Asn Thr Leu Ser Ser
         260                 265                 270 atg ttg aag ggc ttt gct ccg gcg gcg gcc gcc cag gcc gtg caa acc     864
Met Leu Lys Gly Phe Ala Pro Ala Ala Ala Ala Gln Ala Val Gln Thr
     275                 280                 285 gcg gcg caa aac ggg gtc cgg gcg atg agc tcg ctg ggc agc tcg ctg     912
Ala Ala Gln Asn Gly Val Arg Ala Met Ser Ser Leu Gly Ser Ser Leu
 290                 295                 300 ggt tct tcg ggt ctg ggc ggt ggg gtg gcc gcc aac ttg ggt cgg gcg     960
Gly Ser Ser Gly Leu Gly Gly Gly Val Ala Ala Asn Leu Gly Arg Ala
305                 310                 315                 320 gcc tcg gtc ggt tcg ttg tcg gtg ccg cag gcc tgg gcc gcg gcc aac    1008
Ala Ser Val Gly Ser Leu Ser Val Pro Gln Ala Trp Ala Ala Ala Asn
                 325                 330                 335
```

```
cag gca gtc acc ccg gcg gcg cgg gcg ctg ccg ctg acc agc ctg acc       1056
Gln Ala Val Thr Pro Ala Ala Arg Ala Leu Pro Leu Thr Ser Leu Thr
        340                 345                 350 agc gcc gcg gaa aga ggg ccc ggg cag atg ctg ggc ggg ctg ccg gtg       1104
Ser Ala Ala Glu Arg Gly Pro Gly Gln Met Leu Gly Gly Leu Pro Val
    355                 360                 365 ggg cag atg ggc gcc agg gcc ggt ggt ggg ctc agt ggt gtg ctg cgt       1152
Gly Gln Met Gly Ala Arg Ala Gly Gly Gly Leu Ser Gly Val Leu Arg
370                 375                 380 gtt ccg ccg cga ccc tat gtg atg ccg cat tct ccg gca gcc ggc gat       1200
Val Pro Pro Arg Pro Tyr Val Met Pro His Ser Pro Ala Ala Gly Asp
385                 390                 395                 400 atc gcc ccg ccg gcc ttg tcg cag gac cgg ttc gcc gac ttc ccc gcg       1248
Ile Ala Pro Pro Ala Leu Ser Gln Asp Arg Phe Ala Asp Phe Pro Ala
            405                 410                 415 ctg ccc ctc gac ccg tcc gcg atg gtc gcc caa gtg ggg cca cag gtg       1296
Leu Pro Leu Asp Pro Ser Ala Met Val Ala Gln Val Gly Pro Gln Val
        420                 425                 430 gtc aac atc aac acc aaa ctg ggc tac aac aac gcc gtg ggc gcc ggg       1344
Val Asn Ile Asn Thr Lys Leu Gly Tyr Asn Asn Ala Val Gly Ala Gly
    435                 440                 445 acc ggc atc gtc atc gat ccc aac ggt gtc gtg ctg acc aac aac cac       1392
Thr Gly Ile Val Ile Asp Pro Asn Gly Val Val Leu Thr Asn Asn His
450                 455                 460 gtg atc gcg ggc gcc acc gac atc aat gcg ttc agc gtc ggc tcc ggc       1440
Val Ile Ala Gly Ala Thr Asp Ile Asn Ala Phe Ser Val Gly Ser Gly
465                 470                 475                 480 caa acc tac ggc gtc gat gtg gtc ggg tat gac cgc acc cag gat gtc       1488
Gln Thr Tyr Gly Val Asp Val Val Gly Tyr Asp Arg Thr Gln Asp Val
            485                 490                 495 gcg gtg ctg cag ctg cgc ggt gcc ggt ggc ctg ccg tcg gcg gcg atc       1536
Ala Val Leu Gln Leu Arg Gly Ala Gly Gly Leu Pro Ser Ala Ala Ile
        500                 505                 510 ggt ggc ggc gtc gcg gtt ggt gag ccc gtc gtc gcg atg ggc aac agc       1584
Gly Gly Gly Val Ala Val Gly Glu Pro Val Val Ala Met Gly Asn Ser
    515                 520                 525 ggt ggg cag ggc gga acg ccc cgt gcg gtg cct ggc agg gtg gtc gcg       1632
Gly Gly Gln Gly Gly Thr Pro Arg Ala Val Pro Gly Arg Val Val Ala
530                 535                 540 ctc ggc caa acc gtg cag gcg tcg gat tcg ctg acc ggt gcc gaa gag       1680
Leu Gly Gln Thr Val Gln Ala Ser Asp Ser Leu Thr Gly Ala Glu Glu
545                 550                 555                 560 aca ttg aac ggg ttg atc cag ttc gat gcc gcg atc cag ccc ggt gat       1728
Thr Leu Asn Gly Leu Ile Gln Phe Asp Ala Ala Ile Gln Pro Gly Asp
            565                 570                 575 tcg ggc ggg ccc gtc gtc aac ggc cta gga cag gtg gtc ggt atg aac       1776
Ser Gly Gly Pro Val Val Asn Gly Leu Gly Gln Val Val Gly Met Asn
        580                 585                 590 acg gcc gcg tcc taggatatc                                             1797
Thr Ala Ala Ser
        595

<210> SEQ ID NO 26
<211> LENGTH: 596
<212> TYPE: PRT
<213> ORGANISM: Artificial Sequence
<220> FEATURE:
<223> OTHER INFORMATION: Description of Artificial Sequence:bi-fusion

<400> SEQUENCE: 26
```

-continued

```
His Met His His His His His Met Val Asp Phe Gly Ala Leu Pro
 1               5              10               15

Pro Glu Ile Asn Ser Ala Arg Met Tyr Ala Gly Pro Gly Ser Ala Ser
             20                  25                  30

Leu Val Ala Ala Ala Gln Met Trp Asp Ser Val Ala Ser Asp Leu Phe
             35                  40                  45

Ser Ala Ala Ser Ala Phe Gln Ser Val Val Trp Gly Leu Thr Val Gly
 50                  55                  60

Ser Trp Ile Gly Ser Ser Ala Gly Leu Met Val Ala Ala Ser Pro
 65                  70                  75                  80

Tyr Val Ala Trp Met Ser Val Thr Ala Gly Gln Ala Glu Leu Thr Ala
                 85                  90                  95

Ala Gln Val Arg Val Ala Ala Ala Tyr Glu Thr Ala Tyr Gly Leu
                100                 105                 110

Thr Val Pro Pro Pro Val Ile Ala Glu Asn Arg Ala Glu Leu Met Ile
             115                 120                 125

Leu Ile Ala Thr Asn Leu Leu Gly Gln Asn Thr Pro Ala Ile Ala Val
             130                 135                 140

Asn Glu Ala Glu Tyr Gly Glu Met Trp Ala Gln Asp Ala Ala Met
145                 150                 155                 160

Phe Gly Tyr Ala Ala Thr Ala Thr Ala Thr Ala Thr Leu Leu Pro
                165                 170                 175

Phe Glu Glu Ala Pro Glu Met Thr Ser Ala Gly Gly Leu Leu Glu Gln
             180                 185                 190

Ala Ala Ala Val Glu Glu Ala Ser Asp Thr Ala Ala Ala Asn Gln Leu
             195                 200                 205

Met Asn Asn Val Pro Gln Ala Leu Gln Gln Leu Ala Gln Pro Thr Gln
210                 215                 220

Gly Thr Thr Pro Ser Ser Lys Leu Gly Gly Leu Trp Lys Thr Val Ser
225                 230                 235                 240

Pro His Arg Ser Pro Ile Ser Asn Met Val Ser Met Ala Asn Asn His
                245                 250                 255

Met Ser Met Thr Asn Ser Gly Val Ser Met Thr Asn Thr Leu Ser Ser
             260                 265                 270

Met Leu Lys Gly Phe Ala Pro Ala Ala Ala Gln Ala Val Gln Thr
             275                 280                 285

Ala Ala Gln Asn Gly Val Arg Ala Met Ser Ser Leu Gly Ser Ser Leu
             290                 295                 300

Gly Ser Ser Gly Leu Gly Gly Val Ala Ala Asn Leu Gly Arg Ala
305                 310                 315                 320

Ala Ser Val Gly Ser Leu Ser Val Pro Gln Ala Trp Ala Ala Ala Asn
                325                 330                 335
Gln Ala Val Thr Pro Ala Ala Arg Ala Leu Pro Leu Thr Ser Leu Thr
             340                 345                 350

Ser Ala Ala Glu Arg Gly Pro Gly Gln Met Leu Gly Gly Leu Pro Val
             355                 360                 365

Gly Gln Met Gly Ala Arg Ala Gly Gly Leu Ser Gly Val Leu Arg
             370                 375                 380

Val Pro Pro Arg Pro Tyr Val Met Pro His Ser Pro Ala Ala Gly Asp
385                 390                 395                 400

Ile Ala Pro Pro Ala Leu Ser Gln Asp Arg Phe Ala Asp Phe Pro Ala
                405                 410                 415

Leu Pro Leu Asp Pro Ser Ala Met Val Ala Gln Val Gly Pro Gln Val
             420                 425                 430
```

```
Val Asn Ile Asn Thr Lys Leu Gly Tyr Asn Asn Ala Val Gly Ala Gly
        435                 440                 445

Thr Gly Ile Val Ile Asp Pro Asn Gly Val Val Leu Thr Asn Asn His
    450                 455                 460

Val Ile Ala Gly Ala Thr Asp Ile Asn Ala Phe Ser Val Gly Ser Gly
465                 470                 475                 480

Gln Thr Tyr Gly Val Asp Val Val Gly Tyr Asp Arg Thr Gln Asp Val
                485                 490                 495

Ala Val Leu Gln Leu Arg Gly Ala Gly Gly Leu Pro Ser Ala Ala Ile
            500                 505                 510

Gly Gly Gly Val Ala Val Gly Glu Pro Val Val Ala Met Gly Asn Ser
        515                 520                 525

Gly Gly Gln Gly Gly Thr Pro Arg Ala Val Pro Gly Arg Val Val Ala
        530                 535                 540

Leu Gly Gln Thr Val Gln Ala Ser Asp Ser Leu Thr Gly Ala Glu Glu
545                 550                 555                 560

Thr Leu Asn Gly Leu Ile Gln Phe Asp Ala Ala Ile Gln Pro Gly Asp
                565                 570                 575

Ser Gly Gly Pro Val Val Asn Gly Leu Gly Gln Val Val Gly Met Asn
                580                 585                 590

Thr Ala Ala Ser
            595

<210> SEQ ID NO 27
<211> LENGTH: 702
<212> TYPE: DNA
<213> ORGANISM: Artificial Sequence
<220> FEATURE:
<223> OTHER INFORMATION: Description of Artificial Sequence:bi-fusion
      protein Ra12-DPPD (designated Mtb24), reading
      frame 1
<220> FEATURE:
<221> NAME/KEY: CDS
<222> LOCATION: (1)..(693)
<223> OTHER INFORMATION: bi-fusion protein Ra12-DPPD (designated Mtb24),
      reading frame 1
<220> FEATURE:
<221> NAME/KEY: CDS
<222> LOCATION: (2)..(700)
<223> OTHER INFORMATION: reading frame 2
<220> FEATURE:
<221> NAME/KEY: CDS
<222> LOCATION: (3)..(701)
<223> OTHER INFORMATION: reading frame 3

<400> SEQUENCE: 27 cat atg cat cac cat cac cat cac acg gcc gcg tcc gat aac ttc cag        48
His Met His His His His His His Thr Ala Ala Ser Asp Asn Phe Gln
 1               5                  10                  15 ctg tcc cag ggt ggg cag gga ttc gcc att ccg atc ggg cag gcg atg        96
Leu Ser Gln Gly Gly Gln Gly Phe Ala Ile Pro Ile Gly Gln Ala Met
            20                  25                  30 gcg atc gcg ggc cag atc cga tcg ggt ggg ggg tca ccc acc gtt cat       144
Ala Ile Ala Gly Gln Ile Arg Ser Gly Gly Gly Ser Pro Thr Val His
        35                  40                  45 atc ggg cct acc gcc ttc ctc ggc ttg ggt gtt gtc gac aac aac ggc       192
Ile Gly Pro Thr Ala Phe Leu Gly Leu Gly Val Val Asp Asn Asn Gly
    50                  55                  60 aac ggc gca cga gtc caa cgc gtg gtc ggg agc gct ccg gcg gca agt       240
Asn Gly Ala Arg Val Gln Arg Val Val Gly Ser Ala Pro Ala Ala Ser
65                  70                  75                  80
```

-continued

| | | | | | | | | | | | | | | | |
|---|---|---|---|---|---|---|---|---|---|---|---|---|---|---|---|
| ctc | ggc | atc | tcc | acc | ggc | gac | gtg | atc | acc | gcg | gtc | gac | ggc | gct | ccg | 288
| Leu | Gly | Ile | Ser | Thr | Gly | Asp | Val | Ile | Thr | Ala | Val | Asp | Gly | Ala | Pro |
| | | | | 85 | | | | | 90 | | | | | 95 | |
| atc | aac | tcg | gcc | acc | gcg | atg | gcg | gac | gcg | ctt | aac | ggg | cat | cat | ccc | 336
| Ile | Asn | Ser | Ala | Thr | Ala | Met | Ala | Asp | Ala | Leu | Asn | Gly | His | His | Pro |
| | | | 100 | | | | | 105 | | | | | 110 | | |
| ggt | gac | gtc | atc | tcg | gtg | acc | tgg | caa | acc | aag | tcg | ggc | ggc | acg | cgt | 384
| Gly | Asp | Val | Ile | Ser | Val | Thr | Trp | Gln | Thr | Lys | Ser | Gly | Gly | Thr | Arg |
| | | | 115 | | | | | 120 | | | | | 125 | | |
| aca | ggg | aac | gtg | aca | ttg | gcc | gag | gga | ccc | ccg | gcc | gaa | ttc | gac | gac | 432
| Thr | Gly | Asn | Val | Thr | Leu | Ala | Glu | Gly | Pro | Pro | Ala | Glu | Phe | Asp | Asp |
| | 130 | | | | | 135 | | | | | 140 | | | | |
| gac | gac | aag | gat | cca | cct | gac | ccg | cat | cag | ccg | gac | atg | acg | aaa | ggc | 480
| Asp | Asp | Lys | Asp | Pro | Pro | Asp | Pro | His | Gln | Pro | Asp | Met | Thr | Lys | Gly |
| 145 | | | | | 150 | | | | | 155 | | | | | 160 |
| tat | tgc | ccg | ggt | ggc | cga | tgg | ggt | ttt | ggc | gac | ttg | gcc | gtg | tgc | gac | 528
| Tyr | Cys | Pro | Gly | Gly | Arg | Trp | Gly | Phe | Gly | Asp | Leu | Ala | Val | Cys | Asp |
| | | | | 165 | | | | | 170 | | | | | 175 | |
| ggc | gag | aag | tac | ccc | gac | ggc | tcg | ttt | tgg | cac | cag | tgg | atg | caa | acg | 576
| Gly | Glu | Lys | Tyr | Pro | Asp | Gly | Ser | Phe | Trp | His | Gln | Trp | Met | Gln | Thr |
| | | | 180 | | | | | 185 | | | | | 190 | | |
| tgg | ttt | acc | ggc | cca | cag | ttt | tac | ttc | gat | tgt | gtc | agc | ggc | ggt | gag | 624
| Trp | Phe | Thr | Gly | Pro | Gln | Phe | Tyr | Phe | Asp | Cys | Val | Ser | Gly | Gly | Glu |
| | | | 195 | | | | | 200 | | | | | 205 | | |
| ccc | ctc | ccc | ggc | ccg | ccg | cca | ccg | ggt | ggt | tgc | ggt | ggg | gca | att | ccg | 672
| Pro | Leu | Pro | Gly | Pro | Pro | Pro | Pro | Gly | Gly | Cys | Gly | Gly | Ala | Ile | Pro |
| | 210 | | | | | 215 | | | | | 220 | | | | |
| tcc | gag | cag | ccc | aac | gct | ccc | tgagaattc | | | | | | | | | 702
| Ser | Glu | Gln | Pro | Asn | Ala | Pro | | | | | | | | | |
| 225 | | | | | 230 | | | | | | | | | | |

<210> SEQ ID NO 28
<211> LENGTH: 231
<212> TYPE: PRT
<213> ORGANISM: Artificial Sequence
<220> FEATURE:
<223> OTHER INFORMATION: Description of Artificial Sequence:bi-fusion

<400> SEQUENCE: 28

His Met His His His His His Thr Ala Ala Ser Asp Asn Phe Gln
 1               5                  10                  15

Leu Ser Gln Gly Gly Gln Gly Phe Ala Ile Pro Ile Gly Gln Ala Met
             20                  25                  30

Ala Ile Ala Gly Gln Ile Arg Ser Gly Gly Ser Pro Thr Val His
         35                  40                  45

Ile Gly Pro Thr Ala Phe Leu Gly Leu Gly Val Val Asp Asn Asn Gly
     50                  55                  60

Asn Gly Ala Arg Val Gln Arg Val Val Gly Ser Ala Pro Ala Ala Ser
 65                  70                  75                  80

Leu Gly Ile Ser Thr Gly Asp Val Ile Thr Ala Val Asp Gly Ala Pro
                 85                  90                  95

Ile Asn Ser Ala Thr Ala Met Ala Asp Ala Leu Asn Gly His His Pro
            100                 105                 110

Gly Asp Val Ile Ser Val Thr Trp Gln Thr Lys Ser Gly Gly Thr Arg
        115                 120                 125

Thr Gly Asn Val Thr Leu Ala Glu Gly Pro Pro Ala Glu Phe Asp Asp
    130                 135                 140

Asp Asp Lys Asp Pro Pro Asp Pro His Gln Pro Asp Met Thr Lys Gly
145                 150                 155                 160

```
Tyr Cys Pro Gly Gly Arg Trp Gly Phe Gly Asp Leu Ala Val Cys Asp
                165                 170                 175

Gly Glu Lys Tyr Pro Asp Gly Ser Phe Trp His Gln Trp Met Gln Thr
            180                 185                 190

Trp Phe Thr Gly Pro Gln Phe Tyr Phe Asp Cys Val Ser Gly Gly Glu
        195                 200                 205

Pro Leu Pro Gly Pro Pro Pro Gly Gly Cys Gly Gly Ala Ile Pro
    210                 215                 220

Ser Glu Gln Pro Asn Ala Pro
225                 230

<210> SEQ ID NO 29
<211> LENGTH: 87
<212> TYPE: PRT
<213> ORGANISM: Artificial Sequence
<220> FEATURE:
<223> OTHER INFORMATION: Description of Artificial Sequence:peptide of

<400> SEQUENCE: 29

Ile Cys Ile Thr Ile Thr Ile Thr Arg Pro Arg Pro Ile Thr Ser Ser
1               5                   10                  15

Cys Pro Arg Val Gly Arg Asp Ser Pro Phe Arg Ser Gly Arg Arg Trp
            20                  25                  30

Arg Ser Arg Ala Arg Ser Asp Arg Val Gly Gly His Pro Pro Phe Ile
        35                  40                  45

Ser Gly Leu Pro Pro Ser Ser Ala Trp Val Leu Ser Thr Thr Thr Ala
    50                  55                  60

Thr Ala His Glu Ser Asn Ala Trp Ser Gly Ala Leu Arg Arg Gln Val
65                  70                  75                  80

Ser Ala Ser Pro Pro Ala Thr
                85

<210> SEQ ID NO 30
<211> LENGTH: 29
<212> TYPE: PRT
<213> ORGANISM: Artificial Sequence
<220> FEATURE:
<223> OTHER INFORMATION: Description of Artificial Sequence:peptide of

<400> SEQUENCE: 30

Ser Pro Arg Ser Thr Ala Leu Arg Ser Thr Arg Pro Pro Arg Trp Arg
1               5                   10                  15

Thr Arg Leu Thr Gly Ile Ile Pro Val Thr Ser Ser Arg
            20                  25

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence:peptide of

<400> SEQUENCE: 31

Pro Gly Lys Pro Ser Arg Ala Ala Arg Val Gln Gly Thr
1               5                   10

<210> SEQ ID NO 32
<211> LENGTH: 24
<212> TYPE: PRT
<213> ORGANISM: Artificial Sequence
<220> FEATURE:
```

<223> OTHER INFORMATION: Description of Artificial Sequence:peptide of

<400> SEQUENCE: 32

His Trp Pro Arg Asp Pro Arg Pro Asn Ser Thr Thr Thr Arg Ile
 1               5                  10                  15

His Leu Thr Arg Ile Ser Arg Thr
            20

<210> SEQ ID NO 33
<211> LENGTH: 77
<212> TYPE: PRT
<213> ORGANISM: Artificial Sequence
<220> FEATURE:
<223> OTHER INFORMATION: Description of Artificial Sequence:peptide of

<400> SEQUENCE: 33

Arg Lys Ala Ile Ala Arg Val Ala Asp Gly Val Leu Ala Thr Trp Pro
 1               5                  10                  15

Cys Ala Thr Ala Arg Ser Thr Pro Thr Ala Arg Phe Gly Thr Ser Gly
            20                  25                  30

Cys Lys Arg Gly Leu Pro Ala His Ser Phe Thr Ser Ile Val Ser Ala
        35                  40                  45

Ala Val Ser Pro Ser Pro Ala Arg Arg His Arg Val Val Ala Val Gly
    50                  55                  60

Gln Phe Arg Pro Ser Ser Pro Thr Leu Pro Glu Asn Ser
65                  70                  75

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence:peptide of

<400> SEQUENCE: 34

Pro Tyr Ala Ser Pro Ser Pro Ser His Gly Arg Val Arg
 1               5                  10

<210> SEQ ID NO 35
<211> LENGTH: 93
<212> TYPE: PRT
<213> ORGANISM: Artificial Sequence
<220> FEATURE:
<223> OTHER INFORMATION: Description of Artificial Sequence:peptide of

<400> SEQUENCE: 35

Leu Pro Ala Val Pro Gly Trp Ala Gly Ile Arg His Ser Asp Arg Ala
 1               5                  10                  15

Gly Asp Gly Asp Arg Gly Pro Asp Pro Ile Gly Trp Gly Val Thr His
            20                  25                  30

Arg Ser Tyr Arg Ala Tyr Arg Leu Pro Arg Leu Gly Cys Cys Arg Gln
        35                  40                  45

Gln Arg Gln Arg Arg Thr Ser Pro Thr Arg Gly Arg Glu Arg Ser Gly
    50                  55                  60

Gly Lys Ser Arg His Leu His Arg Arg Asp His Arg Gly Arg Arg
65                  70                  75                  80

Arg Ser Asp Gln Leu Gly His Arg Asp Gly Gly Arg Ala
                85                  90

<210> SEQ ID NO 36
<211> LENGTH: 5

```
<212> TYPE: PRT
<213> ORGANISM: Artificial Sequence
<220> FEATURE:
<223> OTHER INFORMATION: Description of Artificial Sequence:peptide of

<400> SEQUENCE: 36

Arg Ala Ser Ser Arg
 1               5

<210> SEQ ID NO 37
<211> LENGTH: 36
<212> TYPE: PRT
<213> ORGANISM: Artificial Sequence
<220> FEATURE:
<223> OTHER INFORMATION: Description of Artificial Sequence:peptide of

<400> SEQUENCE: 37

Arg His Leu Gly Asp Leu Ala Asn Gln Val Gly Arg His Ala Tyr Arg
 1               5                  10                  15

Glu Arg Asp Ile Gly Arg Gly Thr Pro Gly Arg Ile Arg Arg Arg Arg
                20                  25                  30

Gln Gly Ser Thr
        35

<210> SEQ ID NO 38
<211> LENGTH: 56
<212> TYPE: PRT
<213> ORGANISM: Artificial Sequence
<220> FEATURE:
<223> OTHER INFORMATION: Description of Artificial Sequence:peptide of

<400> SEQUENCE: 38

Pro Ala Ser Ala Gly His Asp Glu Arg Leu Leu Pro Gly Trp Pro Met
 1               5                  10                  15

Gly Phe Trp Arg Leu Gly Arg Val Arg Arg Glu Val Pro Arg Arg
                20                  25                  30

Leu Val Leu Ala Pro Val Asp Ala Asn Val Val Tyr Arg Pro Thr Val
            35                  40                  45

Leu Leu Arg Leu Cys Gln Arg Arg
        50                  55

<210> SEQ ID NO 39
<211> LENGTH: 26
<212> TYPE: PRT
<213> ORGANISM: Artificial Sequence
<220> FEATURE:
<223> OTHER INFORMATION: Description of Artificial Sequence:peptide of

<400> SEQUENCE: 39

Ala Pro Pro Arg Pro Ala Ala Thr Gly Trp Leu Arg Trp Gly Asn Ser
 1               5                  10                  15

Val Arg Ala Ala Gln Arg Ser Leu Arg Ile
                20                  25

<210> SEQ ID NO 40
<211> LENGTH: 374
<212> TYPE: PRT
<213> ORGANISM: Mycobacterium tuberculosis
<220> FEATURE:
<223> OTHER INFORMATION: 38 kD antigen

<400> SEQUENCE: 40

Met Lys Ile Arg Leu His Thr Leu Leu Ala Val Leu Thr Ala Ala Pro
 1               5                  10                  15
```

Leu Leu Leu Ala Ala Ala Gly Cys Gly Ser Lys Pro Pro Ser Gly Ser
            20                  25                  30

Pro Glu Thr Gly Ala Gly Ala Gly Thr Val Ala Thr Thr Pro Ala Ser
            35                  40                  45

Ser Pro Val Thr Leu Ala Glu Thr Gly Ser Thr Leu Leu Tyr Pro Leu
            50                  55                  60

Phe Asn Leu Trp Gly Pro Ala Phe His Glu Arg Tyr Pro Asn Val Thr
 65                  70                  75                  80

Ile Thr Ala Gln Gly Thr Gly Ser Gly Ala Gly Ile Ala Gln Ala Ala
            85                  90                  95

Ala Gly Thr Val Asn Ile Gly Ala Ser Asp Ala Tyr Leu Ser Glu Gly
            100                 105                 110

Asp Met Ala Ala His Lys Gly Leu Met Asn Ile Ala Leu Ala Ile Ser
            115                 120                 125

Ala Gln Gln Val Asn Tyr Asn Leu Pro Gly Val Ser Glu His Leu Lys
            130                 135                 140

Leu Asn Gly Lys Val Leu Ala Ala Met Tyr Gln Gly Thr Ile Lys Thr
145                 150                 155                 160

Trp Asp Asp Pro Gln Ile Ala Ala Leu Asn Pro Gly Val Asn Leu Pro
            165                 170                 175

Gly Thr Ala Val Val Pro Leu His Arg Ser Asp Gly Ser Gly Asp Thr
            180                 185                 190

Phe Leu Phe Thr Gln Tyr Leu Ser Lys Gln Asp Pro Glu Gly Trp Gly
            195                 200                 205

Lys Ser Pro Gly Phe Gly Thr Thr Val Asp Phe Pro Ala Val Pro Gly
            210                 215                 220

Ala Leu Gly Glu Asn Gly Asn Gly Gly Met Val Thr Gly Cys Ala Glu
225                 230                 235                 240

Thr Pro Gly Cys Val Ala Tyr Ile Gly Ile Ser Phe Leu Asp Gln Ala
            245                 250                 255

Ser Gln Arg Gly Leu Gly Glu Ala Gln Leu Gly Asn Ser Ser Gly Asn
            260                 265                 270

Phe Leu Leu Pro Asp Ala Gln Ser Ile Gln Ala Ala Ala Gly Phe
            275                 280                 285

Ala Ser Lys Thr Pro Ala Asn Gln Ala Ile Ser Met Ile Asp Gly Pro
            290                 295                 300

Ala Pro Asp Gly Tyr Pro Ile Ile Asn Tyr Glu Tyr Ala Ile Val Asn
305                 310                 315                 320

Asn Arg Gln Lys Asp Ala Ala Thr Ala Gln Thr Leu Gln Ala Phe Leu
            325                 330                 335

His Trp Ala Ile Thr Asp Gly Asn Lys Ala Ser Phe Leu Asp Gln Val
            340                 345                 350

His Phe Gln Pro Leu Pro Pro Ala Val Val Lys Leu Ser Asp Ala Leu
            355                 360                 365

Ile Ala Thr Ile Ser Ser
    370

<210> SEQ ID NO 41
<211> LENGTH: 3
<212> TYPE: PRT
<213> ORGANISM: Artificial Sequence
<220> FEATURE:
<223> OTHER INFORMATION: Description of Artificial Sequence:flexible
      polylinker

```
<400> SEQUENCE: 41

Gly Cys Gly
 1

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence:flexible
      polylinker

<400> SEQUENCE: 42

Gly Cys Gly Gly Cys Gly
 1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence:flexible
      polylinker

<400> SEQUENCE: 43

Gly Cys Gly Gly Cys Gly Gly Cys Gly
 1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence:flexible
      polylinker

<400> SEQUENCE: 44

Gly Gly Gly Gly Ser
 1               5

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence:flexible
      polylinker

<400> SEQUENCE: 45

Gly Gly Gly Gly Ser Gly Gly Gly Gly Ser
 1               5                  10

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence:flexible
      polylinker

<400> SEQUENCE: 46

Gly Gly Gly Gly Ser Gly Gly Gly Gly Ser Gly Gly Gly Gly Ser
 1               5                  10                  15
```